(12) United States Patent
Langley et al.

(10) Patent No.: US 12,734,300 B2
(45) Date of Patent: Sep. 15, 2026

(54) DEVICES AND METHODS FOR PRECISION DOSE DELIVERY

(71) Applicant: Regeneron Pharmaceuticals, Inc., Tarrytown, NY (US)

(72) Inventors: Trevor Langley, Rensselaer, NY (US); Justin Bechstein, Philadelphia, PA (US); Jeremy Odegard, Hudson, WI (US); Sibgat Ulla, Rensselaer, NY (US); Daniel Halbig, Rensselaer, NY (US); Bryan Grygus, Clifton Park, NY (US); Prithvi Singh, Rensselaer, NY (US); Andrew Dumont, Rensselaer, NY (US); David Nett, Rensselaer, NY (US); Tasha Gillum, Rensselaer, NY (US); Ryan Ainsworth, Rensselaer, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 8 days.

(21) Appl. No.: 17/816,615

(22) Filed: Aug. 1, 2022

(65) Prior Publication Data

US 2022/0370721 A1 Nov. 24, 2022

Related U.S. Application Data

(63) Continuation of application No. 17/457,526, filed on Dec. 3, 2021, and a continuation of application No.
(Continued)

(51) Int. Cl.

| | |
|---|---|
| ***A61M 5/315*** | (2006.01) |
| ***A61M 5/31*** | (2006.01) |
| *A61F 9/00* | (2006.01) |

(52) U.S. Cl.
CPC ...... *A61M 5/31505* (2013.01); *A61M 5/3135* (2013.01); *A61M 5/3146* (2013.01);
(Continued)

(58) Field of Classification Search
CPC ........ A61M 2005/3139; A61M 5/3135; A61M 5/3137; A61M 5/31501
See application file for complete search history.

(56) References Cited

U.S. PATENT DOCUMENTS

| | | | |
|---|---|---|---|
| 2,129,675 | A | 9/1938 | Cole |
| 2,375,711 | A | 5/1945 | Joseph |

(Continued)

FOREIGN PATENT DOCUMENTS

| | | | |
|---|---|---|---|
| AU | 54957/69 | | 11/1970 |
| AU | 40517/85 | A | 10/1985 |

(Continued)

OTHER PUBLICATIONS

Taiwanese Search Report for Application No. 112302459, mailed on Oct. 26, 2023, 4 pages.

(Continued)

*Primary Examiner* — Deanna K Hall
(74) *Attorney, Agent, or Firm* — Bookoff McAndrews, PLLC

(57) ABSTRACT

Disclosed herein are devices and methods for delivering a predetermined volume of a drug substance or other product including a fluid. An exemplary device may include a body configured to receive a drug substance therein, and a plunger rod disposed at least partially inside the body to distally move a stopper in the body. The device may include a component configured to regulate distal movement of the plunger rod in a priming step and in a subsequent delivery
(Continued)

step, so that the device may be accurately primed and may accurately dispense a predetermined volume of a drug substance.

25 Claims, 84 Drawing Sheets

Related U.S. Application Data

17/354,850, filed on Jun. 22, 2021, now Pat. No. 11,439,758, which is a continuation of application No. PCT/US2020/036200, filed on Jun. 4, 2020, said application No. 17/457,526 is a continuation of application No. PCT/US2020/036200, filed on Jun. 4, 2020.

(60) Provisional application No. 62/860,481, filed on Jun. 12, 2019, provisional application No. 62/857,678, filed on Jun. 5, 2019.

(52) U.S. Cl.
CPC .... *A61M 5/31536* (2013.01); *A61M 5/31583* (2013.01); *A61F 9/0008* (2013.01); *A61M 2005/3139* (2013.01); *A61M 2005/31508* (2013.01); *A61M 2005/3154* (2013.01); *A61M 2205/584* (2013.01)

(56) References Cited

U.S. PATENT DOCUMENTS 2,739,590 A 3/1956 Yochem
2,792,834 A 5/1957 Leon
3,122,280 A 2/1964 Goda
3,128,765 A 4/1964 Tint
3,236,423 A 2/1966 Marbach et al.
3,236,434 A 2/1966 Taddeau
3,337,095 A 8/1967 Marbach et al.
3,608,550 A 9/1971 Becton
3,610,241 A 10/1971 Lemarie
3,797,487 A 3/1974 Schmidt
3,934,586 A 1/1976 Easton et al.
3,965,945 A 6/1976 Ross
4,117,728 A 10/1978 Johnson
4,152,939 A 5/1979 Renshaw
4,357,971 A 11/1982 Friedman
4,391,272 A 7/1983 Staempfli
4,444,335 A 4/1984 Wood et al.
4,475,905 A 10/1984 Himmelstrup
4,654,035 A 3/1987 Ando
4,840,616 A 6/1989 Banks
4,852,768 A 8/1989 Bartsch
4,871,094 A 10/1989 Gall et al.
4,915,692 A 4/1990 Verlier
4,915,695 A 4/1990 Koobs
5,009,645 A 4/1991 Silver et al.
5,080,649 A 1/1992 Vetter
5,084,017 A 1/1992 Maffetone
RE33,821 E 2/1992 Banks
5,092,842 A 3/1992 Bechtold et al.
5,114,406 A 5/1992 Gabriel et al.
5,284,132 A 2/1994 Geier
5,295,976 A 3/1994 Harris
5,318,544 A 6/1994 Drypen et al.
5,358,497 A 10/1994 Dorsey et al.
5,364,374 A 11/1994 Morrison et al.
5,370,620 A 12/1994 Shonfeld
5,380,295 A 1/1995 Vacca
5,439,643 A 8/1995 Liebert
5,485,853 A 1/1996 Stubbs
5,507,727 A 4/1996 Crainich
5,533,970 A 7/1996 Berger et al.
5,545,147 A 8/1996 Harris
5,554,122 A 9/1996 Emanuel
5,593,391 A 1/1997 Stanners
5,688,251 A 11/1997 Chanoch
5,700,247 A 12/1997 Grimard et al.
5,795,337 A 8/1998 Grimard
5,801,156 A 9/1998 Robinson et al.
5,807,343 A 9/1998 Tucker et al.
5,807,345 A 9/1998 Grabenkort
5,820,603 A 10/1998 Tucker et al.
5,827,233 A 10/1998 Futagawa et al.
5,833,669 A 11/1998 Wyrick
5,834,313 A 11/1998 Lin
5,843,034 A 12/1998 Redfern et al.
5,904,897 A 5/1999 Kendall et al.
5,911,950 A 6/1999 Chen et al.
5,919,418 A 7/1999 Kendall et al.
5,925,316 A 7/1999 Kendall et al.
5,951,526 A 9/1999 Korisch et al.
5,961,495 A 10/1999 Walters et al.
5,961,921 A 10/1999 Addy et al.
5,971,956 A 10/1999 Epstein
5,976,113 A 11/1999 Morigi et al.
5,980,487 A 11/1999 Jones et al.
5,980,825 A 11/1999 Addy et al.
5,988,452 A 11/1999 Dent et al.
6,030,579 A 2/2000 Addy et al.
6,042,571 A 3/2000 Hjertman et al.
6,066,294 A 5/2000 Lin et al.
6,068,817 A 5/2000 Addy et al.
6,077,480 A 6/2000 Edwards et al.
6,096,010 A 8/2000 Walters et al.
6,096,266 A 8/2000 Duroselle
6,120,730 A 9/2000 Palaniappan et al.
6,126,640 A 10/2000 Tucker et al.
6,132,679 A 10/2000 Conviser
6,132,680 A 10/2000 Addy et al.
6,142,976 A 11/2000 Kubo
6,142,977 A 11/2000 Kolberg et al.
6,164,044 A 12/2000 Porfano et al.
6,174,502 B1 1/2001 Addy et al.
6,187,265 B1 2/2001 Wu et al.
6,189,195 B1 2/2001 Reilly et al.
6,189,292 B1 2/2001 Odell et al.
6,193,931 B1 2/2001 Lin et al.
6,203,756 B1 3/2001 Lin et al.
6,224,828 B1 5/2001 Lin et al.
6,228,324 B1 5/2001 Hasegawa et al.
6,250,052 B1 6/2001 Porfano et al.
6,263,641 B1 7/2001 Odell et al.
6,264,629 B1 7/2001 Landau
6,273,152 B1 8/2001 Buehler et al.
6,279,622 B1 8/2001 Nguyen et al.
6,319,235 B1 11/2001 Yoshino
6,319,480 B1 11/2001 Addy et al.
6,325,972 B1 12/2001 Jacobs et al.
6,349,850 B1 2/2002 Cheikh
6,378,526 B1 4/2002 Bowman et al.
6,390,155 B1 5/2002 Nguyen
6,391,008 B1 5/2002 Tsai
6,394,111 B1 5/2002 Jacobs et al.
6,397,849 B1 6/2002 Bowman et al.
6,398,762 B1 6/2002 Vetter et al.
6,406,666 B1 6/2002 Cicha et al.
6,419,656 B1 7/2002 Vetter et al.
6,450,993 B1 9/2002 Lin
6,451,254 B1 9/2002 Wang et al.
6,451,255 B1 9/2002 Williams et al.
6,451,272 B1 9/2002 Fryer et al.
6,454,874 B1 9/2002 Jacobs et al.
6,491,881 B2 12/2002 Fryer et al.
6,494,964 B1 12/2002 Jacobs et al.
6,495,100 B1 12/2002 Lin et al.
6,511,457 B2 1/2003 Thompson
D470,234 S 2/2003 Mahurkar
6,516,817 B2 2/2003 Jacobs et al.
6,516,818 B2 2/2003 Jacobs et al.
6,528,015 B1 3/2003 Lin et al.
6,528,016 B1 3/2003 Kohler et al.
6,528,017 B2 3/2003 Jacobs et al.

(56) References Cited

U.S. PATENT DOCUMENTS 6,530,399 B2 3/2003 Nguyen et al.
6,530,906 B2 3/2003 Hu
6,562,006 B1 5/2003 Hjertman et al.
6,589,481 B1 7/2003 Lin et al.
6,627,150 B1 9/2003 Wang et al.
6,645,429 B1 11/2003 Raniwala
6,656,426 B1 12/2003 Wang et al.
6,656,427 B2 12/2003 Lin et al.
6,673,313 B2 1/2004 Wang et al.
6,682,696 B1 1/2004 Bjerborn
D489,819 S 5/2004 Ford
6,734,405 B2 5/2004 Centanni et al.
6,746,647 B2 6/2004 Kohler et al.
6,746,652 B2 6/2004 Khorzad et al.
6,790,410 B2 9/2004 Metzner et al.
6,792,743 B2 9/2004 Odell et al.
6,807,797 B2 10/2004 Forsberg et al.
6,808,681 B2 10/2004 Bjerborn
6,815,206 B2 11/2004 Lin et al.
6,852,279 B2 2/2005 Williams et al.
6,906,296 B2 6/2005 Centanni et al.
6,942,638 B1 9/2005 Quinn
6,945,962 B2 9/2005 Koenig et al.
6,967,315 B2 11/2005 Centanni et al.
6,977,061 B2 12/2005 Lin et al.
6,996,952 B2 2/2006 Gupta et al.
7,014,813 B1 3/2006 Watling et al.
7,040,485 B2 5/2006 Gupta et al.
7,048,887 B2 5/2006 Frost et al.
7,108,832 B2 9/2006 Christensen et al.
7,146,746 B2 12/2006 Kawasaki
7,169,133 B2 1/2007 Broennimann et al.
7,179,419 B2 2/2007 Lin et al.
7,201,869 B2 4/2007 Williams et al.
D543,625 S 5/2007 Numata et al.
7,229,590 B2 6/2007 Awakowicz et al.
7,229,591 B2 6/2007 Wu et al.
7,246,627 B2 7/2007 Jacobs et al.
7,252,800 B2 8/2007 Jacobs et al.
7,267,806 B2 9/2007 Kendall et al.
7,273,594 B2 9/2007 Lin et al.
7,285,254 B2 10/2007 Lin et al.
7,294,305 B2 11/2007 Lin et al.
7,303,748 B2 12/2007 Wiegand et al.
7,329,241 B2 2/2008 Horvath et al.
7,354,581 B2 4/2008 Cedarbaum et al.
7,396,347 B2 7/2008 Hjertman et al.
7,407,494 B2 8/2008 Boström et al.
7,452,504 B2 11/2008 Wu et al.
7,459,133 B2 12/2008 Swank
7,468,159 B2 12/2008 Lin et al.
7,481,974 B2 1/2009 Sizer
7,491,371 B2 2/2009 Moller et al.
7,517,334 B2 4/2009 Jacobs et al.
7,531,172 B2 5/2009 Stahl et al.
7,531,173 B2 5/2009 Wiegand et al.
7,534,233 B2 5/2009 Schiller et al.
7,553,486 B2 6/2009 Finger
7,556,767 B2 7/2009 Lin et al.
7,564,983 B2 7/2009 Ibuka et al.
7,569,180 B2 8/2009 Kohler et al.
7,575,716 B2 8/2009 Wu et al.
7,582,257 B2 9/2009 Bedard et al.
7,604,773 B2 10/2009 Ekstrom et al.
7,608,218 B2 10/2009 Fryer et al.
7,611,495 B1 11/2009 Gianturco
7,638,090 B2 12/2009 Hyde et al.
7,640,782 B2 1/2010 Hill
7,645,267 B2 1/2010 Vetter et al.
7,666,369 B2 2/2010 Bondar
7,670,550 B2 3/2010 Lin et al.
7,704,237 B2 4/2010 Fisher et al.
7,704,238 B2 4/2010 Diller et al.
7,704,426 B2 4/2010 Earhart et al.
7,713,473 B2 5/2010 Kendall et al.
7,727,195 B2 6/2010 Norton
7,727,201 B2 6/2010 Kirchhofer
7,727,464 B2 6/2010 Frost
7,749,200 B2 7/2010 Graf et al.
7,754,156 B2 7/2010 Hyde et al.
7,803,316 B2 9/2010 Lin et al.
7,807,100 B2 10/2010 Choperena et al.
7,807,164 B2 10/2010 Furfine et al.
7,811,263 B2 10/2010 Burren et al.
7,824,610 B2 11/2010 Ko
7,850,906 B2 12/2010 Watling et al.
D631,153 S 1/2011 McGlothlin et al.
7,880,887 B2 2/2011 Olson et al.
7,892,486 B2 2/2011 Mizuno et al.
7,910,055 B2 3/2011 Bondar
7,918,824 B2 4/2011 Bishop et al.
7,954,521 B2 6/2011 Py et al.
7,954,672 B2 6/2011 Keller
7,976,506 B2 7/2011 Vitullo et al.
7,981,361 B2 7/2011 Bacik
8,017,074 B2 9/2011 Arnold et al.
8,029,725 B2 10/2011 Olsson et al.
8,034,288 B2 10/2011 Burns et al.
8,039,022 B2 10/2011 Minamikawa et al.
8,062,590 B1 11/2011 Ricciardi et al.
8,071,021 B2 12/2011 Hill
8,075,533 B2 12/2011 Lee
8,075,547 B2 12/2011 Lee
8,105,293 B2 1/2012 Pickhard
8,110,156 B2 2/2012 Ricciardi et al.
8,114,342 B2 2/2012 Jung et al.
8,118,788 B2 2/2012 Frezza
8,124,127 B2 2/2012 Faucher et al.
8,132,600 B2 3/2012 Py et al.
8,147,752 B2 4/2012 Iwashita et al.
8,147,771 B2 4/2012 Yokoi et al.
8,163,234 B2 4/2012 Fedegari
8,178,042 B2 5/2012 Jung et al.
8,187,597 B2 5/2012 Shima et al.
8,196,741 B2 6/2012 Finke et al.
8,205,416 B2 6/2012 Hansen
8,216,575 B2 7/2012 Yu
8,221,679 B2 7/2012 Golkowski
8,230,616 B2 7/2012 McLaren et al.
8,246,577 B2 8/2012 Schrul et al.
8,246,949 B2 8/2012 Higuchi et al.
8,263,016 B2 9/2012 Kanner
8,263,102 B2 9/2012 Labrecque et al.
8,268,238 B2 9/2012 Bondar et al.
8,268,257 B2 9/2012 Frost
8,276,583 B2 10/2012 Farieta et al.
8,277,724 B2 10/2012 Jung et al.
8,312,836 B2 11/2012 Corbeil et al.
8,323,582 B2 12/2012 Ko
8,329,098 B2 12/2012 Kanner
8,329,113 B2 12/2012 Kanner
8,329,119 B2 12/2012 Pearcy et al.
8,333,931 B2 12/2012 Kanner
8,337,772 B2 12/2012 Laumer et al.
8,343,435 B2 1/2013 Kanner
8,348,905 B2 1/2013 Radmer et al.
8,349,272 B2 1/2013 Hill
8,357,331 B2 1/2013 McVey et al.
8,366,680 B2 2/2013 Raab
8,366,995 B2 2/2013 McLaren et al.
8,367,099 B2 2/2013 Herweck et al.
8,388,761 B2 3/2013 Iwashita et al.
8,394,068 B2 3/2013 Kosinski et al.
8,399,006 B2 3/2013 De Juan, Jr. et al.
8,414,912 B2 4/2013 Ciolino et al.
8,425,837 B2 4/2013 Carbone et al.
8,428,447 B2 4/2013 Von Stenglin
8,431,076 B2 4/2013 Fraundorfer
8,431,077 B2 4/2013 Goncalves
8,435,459 B2 5/2013 Reddy et al.
8,444,919 B2 5/2013 Erickson
8,486,332 B1 7/2013 Ricciardi et al.
8,497,004 B2 7/2013 Davis et al.
8,506,900 B1 8/2013 Ricciardi et al.

(56) References Cited

U.S. PATENT DOCUMENTS 8,521,273 B2 8/2013 Kliman
8,529,832 B2 9/2013 Lee
8,574,618 B2 11/2013 Herweck et al.
8,574,627 B2 11/2013 Martakos et al.
8,591,807 B2 11/2013 Berentsveig et al.
8,591,808 B2 11/2013 Berentsveig et al.
8,597,680 B2 12/2013 Coppeta et al.
8,617,109 B2 12/2013 Kronestedt et al.
8,621,824 B2 1/2014 Mielnik et al.
8,623,395 B2 1/2014 De Juan, Jr et al.
8,628,501 B2 1/2014 Hadden
8,636,713 B2 1/2014 Prausnitz et al.
8,641,982 B2 2/2014 Burgmeier et al.
8,652,403 B2 2/2014 Reddy et al.
8,657,804 B2 2/2014 Horne et al.
8,658,089 B2 2/2014 Berentsveig et al.
8,658,092 B2 2/2014 Kohler et al.
8,663,555 B2 3/2014 Shiosawa
8,663,639 B2 3/2014 Dor et al.
8,685,336 B2 4/2014 Bondar
8,685,337 B2 4/2014 Beckmann et al.
8,696,986 B2 4/2014 Rovison, Jr. et al.
8,703,066 B2 4/2014 Vaughn et al.
8,715,570 B2 5/2014 Lindblad et al.
8,721,601 B2 5/2014 Burren et al.
8,721,983 B2 5/2014 Yokoi et al.
8,721,984 B2 5/2014 Carbone et al.
8,722,077 B2 5/2014 Labrecque et al.
8,722,132 B2 5/2014 Labrecque et al.
8,727,117 B2 5/2014 Maasarani
8,741,227 B2 6/2014 Yokoi et al.
8,758,679 B2 6/2014 Hyde et al.
8,758,681 B2 6/2014 Golkowski
8,765,064 B2 7/2014 Yokoi et al.
8,771,595 B2 7/2014 Paskalov
8,790,576 B2 7/2014 Bauer et al.
8,808,225 B2 8/2014 Prausnitz et al.
8,808,622 B2 8/2014 Arnold et al.
8,808,631 B2 8/2014 Hill et al.
8,821,807 B2 9/2014 Schwartz et al.
8,821,943 B2 9/2014 Kompella et al.
8,834,790 B2 9/2014 Boschi et al.
8,834,808 B2 9/2014 Drenguis
8,834,884 B2 9/2014 Trogden et al.
8,840,836 B2 9/2014 Olson
8,858,978 B2 10/2014 Labrecque et al.
8,865,066 B2 10/2014 Rovison et al.
8,871,145 B2 10/2014 Paskalov
8,894,926 B2 11/2014 Hanada et al.
8,900,201 B2 12/2014 Edhouse et al.
8,911,402 B2 12/2014 Veasey et al.
8,911,426 B2 12/2014 Coppeta et al.
8,911,768 B2 12/2014 Whitcup et al.
8,915,404 B2 12/2014 Farne'et al.
8,919,359 B2 12/2014 Iwashita et al.
8,932,535 B2 1/2015 Hyde et al.
8,936,577 B2 1/2015 Lee et al.
8,940,245 B2 1/2015 Reddy et al.
8,945,048 B2 2/2015 Thorley et al.
8,945,468 B2 2/2015 Reddy et al.
8,948,863 B2 2/2015 Kraft et al.
8,956,655 B2 2/2015 Lyons et al.
8,956,830 B2 2/2015 Prentice et al.
8,961,872 B2 2/2015 Fehr et al.
8,962,023 B2 2/2015 Labrecque et al.
8,974,730 B2 3/2015 Burns et al.
8,974,737 B2 3/2015 Erickson
8,979,807 B2 3/2015 Grunhut et al.
8,992,484 B2 3/2015 Radmer et al.
8,992,837 B2 3/2015 Jung et al.
8,992,853 B2 3/2015 Stratman et al.
D729,931 S 5/2015 Takeuchi et al.
9,022,001 B2 5/2015 Shafto
9,022,079 B2 5/2015 Py et al.
9,023,350 B2 5/2015 Gallo Barraco
9,028,749 B2 5/2015 Ryu et al.
9,033,934 B2 5/2015 Karlsson et al.
9,034,249 B2 5/2015 Foreman et al.
9,044,548 B2 6/2015 Miller et al.
9,050,385 B2 6/2015 Weinberger et al.
9,078,435 B2 7/2015 Dunn
9,078,943 B2 7/2015 Herold et al.
9,101,679 B2 8/2015 Robitaille et al.
9,108,835 B2 8/2015 Hayakawa et al.
9,114,212 B2 8/2015 Enggaard et al.
9,120,660 B2 9/2015 Sangi et al.
9,120,661 B2 9/2015 Sangi et al.
9,125,960 B2 9/2015 Stratman et al.
9,125,988 B2 9/2015 Karlsson
9,138,005 B2 9/2015 Berentsveig et al.
9,144,648 B2 9/2015 Lesch, Jr. et al.
D741,476 S 10/2015 Hiraoka et al.
9,156,576 B2 10/2015 Pjanic et al.
9,173,968 B2 11/2015 Hanada
9,180,047 B2 11/2015 Andino et al.
9,180,217 B2 11/2015 Arnold et al.
9,186,460 B2 11/2015 MacDonald et al.
9,192,164 B2 11/2015 Berentsveig et al.
9,192,567 B2 11/2015 Rabinovich-Guilatt et al.
9,192,725 B2 11/2015 Kawamura
9,213,341 B2 12/2015 Hill
9,217,168 B2 12/2015 Prentice
9,220,631 B2 12/2015 Sigg et al.
9,220,820 B2 12/2015 Faucher et al.
D747,796 S 1/2016 Romao
9,238,106 B2 1/2016 Jones
9,241,491 B2 1/2016 Berentsveig et al.
9,242,053 B2 1/2016 Wozencroft
9,242,753 B2 1/2016 Gay et al.
9,248,229 B2 2/2016 Devouassoux et al.
9,254,338 B2 2/2016 Yancopoulos
9,254,343 B2 2/2016 Herold et al.
9,265,604 B2 2/2016 Woods
9,265,814 B2 2/2016 Kauper et al.
9,265,827 B2 2/2016 Wiegand et al.
9,271,866 B2 3/2016 Humayun et al.
9,284,369 B2 3/2016 Ferrara et al.
9,289,560 B2 3/2016 Raab et al.
9,295,744 B2 3/2016 Rovison et al.
9,302,021 B2 4/2016 Klobusnik
9,308,124 B2 4/2016 Humayun et al.
9,320,647 B2 4/2016 Lerner et al.
9,320,819 B2 4/2016 Koyama
9,320,820 B2 4/2016 Rovison, Jr. et al.
9,339,573 B2 5/2016 Seidenberg et al.
9,340,594 B2 5/2016 Furfine et al.
9,345,838 B2 5/2016 Plumptre
9,345,866 B2 5/2016 Kubo et al.
9,352,104 B2 5/2016 Thorley et al.
9,358,301 B2 6/2016 Friberg et al.
9,364,571 B2 6/2016 Ahiska
9,388,239 B2 7/2016 Baldi et al.
D765,241 S 8/2016 Holland
9,402,928 B2 8/2016 Tremblay et al.
9,403,330 B2 8/2016 Laumer et al.
9,408,746 B2 8/2016 Lerner et al.
9,408,931 B1 8/2016 Ricciardi et al.
9,408,965 B2 8/2016 Christensen
9,410,191 B2 8/2016 Alvarez, Jr. et al.
9,414,960 B2 8/2016 Woods
9,421,129 B2 8/2016 Lerner
9,427,485 B2 8/2016 Tremblay et al.
9,439,991 B2 9/2016 Schwartz et al.
9,452,138 B2 9/2016 Trollsas et al.
9,452,231 B2 9/2016 Nonnenmacher
9,457,114 B2 10/2016 Loy
9,463,259 B2 10/2016 Hanada
9,474,688 B2 10/2016 Weeks et al.
9,474,815 B2 10/2016 Dufresne et al.
9,475,225 B2 10/2016 Giraud et al.
D770,612 S 11/2016 Green et al.
9,480,763 B2 11/2016 Dufresne et al.
9,480,764 B2 11/2016 Tremblay et al.
9,480,765 B2 11/2016 Tremblay et al.

(56) References Cited

U.S. PATENT DOCUMENTS 9,487,810 B2 11/2016 Prentice et al.
9,498,549 B2 11/2016 Kanno et al.
9,504,603 B2 11/2016 Lerner
9,505,598 B2 11/2016 Niehr et al.
9,505,830 B2 11/2016 Ordas et al.
9,522,202 B1 12/2016 Ahiska et al.
9,522,205 B2 12/2016 Ahiska
9,526,837 B2 12/2016 Carrel et al.
9,526,841 B2 12/2016 Kubo et al.
9,533,065 B2 1/2017 Foreman et al.
9,533,100 B2 1/2017 Jones
9,539,352 B2 1/2017 Keener et al.
9,539,391 B2 1/2017 Lee et al.
9,541,487 B2 1/2017 Saito et al.
9,545,473 B2 1/2017 Devouassoux et al.
9,545,481 B1 1/2017 Rafaat
9,554,968 B2 1/2017 Weikart et al.
9,555,146 B2 1/2017 Fehr et al.
D778,174 S 2/2017 Zhang et al.
9,561,297 B2 2/2017 Kreber
9,566,360 B2 2/2017 Morikawa et al.
9,566,361 B2 2/2017 Morikawa et al.
9,572,800 B2 2/2017 Zarnitsyn et al.
9,572,932 B2 2/2017 Eggert et al.
9,572,940 B2 2/2017 Horlock
9,592,324 B2 3/2017 Herweck et al.
9,593,004 B2 3/2017 Hayakawa et al.
9,597,377 B2 3/2017 Fan
9,603,739 B2 3/2017 Lerner
9,604,015 B2 3/2017 Pina
9,604,740 B2 3/2017 Py
9,616,368 B2 4/2017 Turbett et al.
9,617,135 B2 4/2017 Hayakawa et al.
9,617,136 B2 4/2017 Hayakawa et al.
9,629,936 B2 4/2017 Salmisuo
9,636,253 B1 5/2017 Andino et al.
9,636,332 B2 5/2017 Zarnitsyn et al.
9,637,604 B2 5/2017 Ito et al.
9,650,444 B2 5/2017 Wiegand et al.
9,662,244 B2 5/2017 Hatta et al.
9,662,412 B2 5/2017 Ferrell et al.
9,662,450 B2 5/2017 Jones et al.
9,663,810 B2 5/2017 Prentice
D790,691 S 6/2017 Davis et al.
9,668,915 B2 6/2017 Haffner et al.
9,669,069 B2 6/2017 Yancopoulos
9,669,988 B2 6/2017 Kojima et al.
9,675,763 B2 6/2017 Huet
9,677,105 B2 6/2017 Collins et al.
9,682,154 B2 6/2017 Leubitz et al.
9,682,163 B2 6/2017 Loy et al.
9,682,175 B2 6/2017 Labrecque et al.
9,694,095 B2 7/2017 Paskalov
9,708,390 B2 7/2017 Sivakumar et al.
RE46,510 E 8/2017 Odell et al.
D794,185 S 8/2017 Dolk et al.
D794,187 S 8/2017 Dolk et al.
9,717,854 B2 8/2017 Evans et al.
9,724,438 B2 8/2017 Turbett
9,737,667 B2 8/2017 Holmqvist et al.
9,750,832 B2 9/2017 Paver, Jr.
9,750,887 B2 9/2017 Hirschel et al.
9,750,888 B2 9/2017 Raab et al.
9,757,452 B2 9/2017 Pham
9,766,012 B2 9/2017 McLaren et al.
9,770,361 B2 9/2017 Andino et al.
9,770,559 B2 9/2017 Armstrong
D800,900 S 10/2017 Darras et al.
9,775,924 B2 10/2017 Tanimoto et al.
9,788,995 B2 10/2017 Prausnitz et al.
9,802,726 B2 10/2017 Mielnik et al.
9,814,795 B2 11/2017 Dufresne et al.
9,814,796 B2 11/2017 Dunn
9,814,840 B2 11/2017 Cowe et al.
9,827,341 B2 11/2017 Fehr et al.
9,833,523 B2 12/2017 Christoforidis et al.
9,849,244 B2 12/2017 Plumptre et al.
9,867,948 B2 1/2018 Selz et al.
9,872,961 B2 1/2018 Fourt et al.
D810,282 S 2/2018 Ratjen
9,895,259 B2 2/2018 Lerner
9,896,480 B2 2/2018 Mackel et al.
D812,223 S 3/2018 Evans et al.
D814,026 S 3/2018 Darras et al.
9,907,913 B2 3/2018 Kosinski et al.
9,913,750 B2 3/2018 Lerner
9,919,057 B2 3/2018 Kim et al.
9,925,340 B2 3/2018 Glocker
D815,279 S 4/2018 Darras et al.
9,931,330 B2 4/2018 Zarnitsyn et al.
9,932,630 B2 4/2018 Alvarez, Jr. et al.
9,937,099 B2 4/2018 Weikart et al.
9,937,335 B2 4/2018 Moss et al.
9,943,573 B2 4/2018 Constable et al.
9,950,116 B2 4/2018 Plumptre et al.
9,956,114 B2 5/2018 Andino et al.
9,957,324 B2 5/2018 Josiah et al.
9,962,333 B2 5/2018 Gaillard et al.
9,962,493 B2 5/2018 Guthart
9,968,603 B2 5/2018 Astafieva et al.
9,968,743 B2 5/2018 Kuwahara et al.
9,982,032 B2 5/2018 Park et al.
D819,805 S 6/2018 Knight et al.
9,993,568 B2 6/2018 Kim et al.
9,995,706 B2 6/2018 Schenk et al.
9,999,595 B2 6/2018 Rakic et al.
10,004,788 B2 6/2018 Constable et al.
10,010,447 B2 7/2018 Kashani et al.
10,016,338 B2 7/2018 Weikart et al.
10,022,502 B2 7/2018 Wong et al.
10,034,922 B2 7/2018 Kim
10,035,850 B2 7/2018 Gekkieva et al.
10,046,027 B2 8/2018 Jensen et al.
10,058,106 B2 8/2018 Itarashiki et al.
10,064,997 B2 9/2018 Evans et al.
10,065,784 B2 9/2018 Tanoguchi
10,073,949 B2 9/2018 Ballou, Jr. et al.
10,080,682 B2 9/2018 Horvath et al.
D830,540 S 10/2018 Rolfs et al.
D830,543 S 10/2018 Walker et al.
10,092,708 B2 10/2018 Thorley et al.
10,106,605 B2 10/2018 Ghosh et al.
10,111,975 B2 10/2018 Laflamme et al.
10,117,774 B2 11/2018 Humayun et al.
10,130,681 B2 11/2018 Yancopoulos
10,137,249 B2 11/2018 Oakley et al.
D838,363 S 1/2019 Katagiri et al.
10,166,142 B2 1/2019 De Juan, Jr. et al.
10,172,682 B2 1/2019 Van Der Raad-Meijer et al.
10,179,206 B2 1/2019 Bendek et al.
10,195,348 B2 2/2019 Komann
10,196,685 B2 2/2019 Alvarez, Jr. et al.
10,206,813 B2 2/2019 Haffner et al.
10,213,556 B2 2/2019 Young et al.
10,213,557 B2 2/2019 Eggert et al.
10,213,558 B2 2/2019 Raghuveer et al.
10,214,338 B2 2/2019 Devouassoux et al.
10,226,728 B2 3/2019 Turbett et al.
10,232,119 B2 3/2019 Raab et al.
D845,476 S 4/2019 Evans et al.
10,245,178 B1 4/2019 Heitzmann et al.
10,245,335 B2 4/2019 Turbett et al.
D849,935 S 5/2019 Rolfs et al.
10,293,068 B2 5/2019 Ruley et al.
10,293,965 B2 5/2019 Lu et al.
D851,753 S 6/2019 Green
10,329,073 B2 6/2019 Tanoguchi
10,350,306 B2 7/2019 Sieving et al.
10,350,346 B2 7/2019 Kerschbaumer et al.
10,363,214 B2 7/2019 Whitcup et al.
10,369,107 B2 8/2019 McDonnell et al.
10,370,442 B2 8/2019 Portugal et al.
10,376,582 B2 8/2019 Cini et al.
10,383,954 B2 8/2019 Leubitz et al.

(56) References Cited

U.S. PATENT DOCUMENTS 10,383,966 B2 8/2019 Dufresne et al.
10,385,842 B2 8/2019 Kuczek et al.
10,391,259 B2 8/2019 Tran et al.
10,420,724 B2 9/2019 Jarrett et al.
10,426,659 B2 10/2019 Myung et al.
10,426,817 B2 10/2019 Rudolf et al.
D865,946 S 11/2019 Horlock
10,471,212 B2 11/2019 Ashmead et al.
10,478,335 B2 11/2019 Lerner
10,517,756 B2 12/2019 Andino et al.
10,519,226 B2 12/2019 Rau et al.
10,524,957 B2 1/2020 Lerner
10,537,494 B2 1/2020 Weikart et al.
10,537,563 B2 1/2020 Adams et al.
10,556,008 B2 2/2020 Pham
10,568,934 B2 2/2020 Hohman
10,568,951 B2 2/2020 Sigl
D878,569 S 3/2020 Reynolds et al.
D878,576 S 3/2020 Johnson
10,576,128 B2 3/2020 Sigl
10,588,855 B2 3/2020 Ambati et al.
10,603,427 B2 3/2020 Hasumi
10,617,557 B2 4/2020 De Juan et al.
10,632,013 B2 4/2020 Prausnitz et al.
10,653,621 B2 5/2020 Wu et al.
10,656,152 B2 5/2020 De Juan, Jr. et al.
10,683,345 B2 6/2020 Duerr et al.
D889,639 S 7/2020 Johnson et al.
D891,611 S 7/2020 Valentin et al.
10,709,803 B2 7/2020 Laflamme et al.
10,710,759 B2 7/2020 Lu et al.
10,722,396 B2 7/2020 Andino et al.
D892,313 S 8/2020 Lin
D892,321 S 8/2020 Newton
10,730,825 B2 8/2020 Bavik et al.
10,730,944 B2 8/2020 Giurleo et al.
10,751,417 B2 8/2020 Adams et al.
10,752,901 B2 8/2020 Corson et al.
D895,110 S 9/2020 Takada et al.
10,765,759 B2 9/2020 Healy et al.
10,773,014 B2 9/2020 Maasarani
10,781,027 B2 9/2020 Devouassoux et al.
10,786,462 B2 9/2020 Jarrett et al.
10,799,639 B2 10/2020 Wei
10,799,642 B2 10/2020 Wong et al.
10,806,630 B2 10/2020 Price et al.
10,813,788 B2 10/2020 De Juan, Jr. et al.
10,813,789 B2 10/2020 Haffner et al.
10,821,221 B2 11/2020 Takahashi et al.
10,828,345 B2 11/2020 Yancopoulos
10,839,960 B2 11/2020 Ballou, Jr. et al.
10,851,165 B2 12/2020 Freeman et al.
10,857,205 B2 12/2020 Yancopoulos
10,888,601 B2 1/2021 Yancopoulos
10,905,586 B2 2/2021 Prausnitz et al.
10,905,587 B2 2/2021 Lerner
10,905,784 B2 2/2021 Kelly et al.
10,906,969 B2 2/2021 Lee et al.
10,912,714 B2 2/2021 Weikart et al.
10,925,927 B2 2/2021 Brockmeyer et al.
10,961,304 B2 3/2021 Eriksson et al.
10,973,681 B2 4/2021 Andino et al.
10,973,879 B2 4/2021 Vitti et al.
10,980,766 B2 4/2021 Huang et al.
10,980,890 B2 4/2021 Kim et al.
10,993,834 B2 5/2021 Kahook
11,007,259 B2 5/2021 Murakami et al.
11,020,530 B2 6/2021 Takeuchi et al.
11,020,531 B2 6/2021 Ashmead et al.
11,026,885 B2 6/2021 Ashton et al.
11,028,448 B2 6/2021 Innocenti et al.
11,052,094 B2 7/2021 Ostrow et al.
11,052,095 B2 7/2021 Ostrow et al.
11,052,130 B2 7/2021 Kim et al.
11,065,151 B2 7/2021 De Juan, Jr. et al.
11,077,188 B2 8/2021 Kauvar et al.
11,078,262 B2 8/2021 Hughes et al.
11,090,445 B2 8/2021 Diaz et al.
11,096,822 B2 8/2021 Yamamoto et al.
11,098,110 B2 8/2021 Gekkieva et al.
11,103,552 B2 8/2021 Graham et al.
11,103,644 B2 8/2021 Bryant et al.
11,110,001 B2 9/2021 Bachelder et al.
11,110,226 B2 9/2021 Bryant et al.
11,111,291 B2 9/2021 Famili et al.
11,116,695 B2 9/2021 Weikart et al.
11,135,266 B2 10/2021 Kerwin et al.
11,147,925 B2 10/2021 Bryant et al.
11,154,420 B2 10/2021 Yamamoto et al.
11,160,918 B2 11/2021 Cook et al.
11,161,916 B2 11/2021 Gschwind et al.
11,179,521 B2 11/2021 Bryant et al.
11,185,499 B2 11/2021 Desai et al.
11,185,635 B2 11/2021 Bryant et al.
11,202,762 B2 12/2021 Mihov et al.
11,209,444 B2 12/2021 Baldwin et al.
D940,302 S 1/2022 Wu
D940,306 S 1/2022 Osypka et al.
11,214,426 B2 1/2022 Devouassoux et al.
11,219,552 B2 1/2022 Olson
11,241,380 B2 2/2022 Freeman et al.
11,253,572 B2 2/2022 Yancopoulos
11,253,620 B2 2/2022 Golkowski et al.
11,266,608 B2 3/2022 Kang-Mieler et al.
11,266,743 B2 3/2022 Wimley et al.
11,291,636 B2 4/2022 Chen et al.
11,298,405 B2 4/2022 Brockmeyer et al.
11,298,437 B2 4/2022 Conseil et al.
D950,721 S 5/2022 Howes et al.
D953,089 S 5/2022 Scheinert
11,331,430 B2 5/2022 Dobson
D954,258 S 6/2022 Hang et al.
D954,942 S 6/2022 Lee
D956,205 S 6/2022 Nimkar et al.
11,351,347 B2 6/2022 Myung et al.
11,369,591 B2 6/2022 Jarrett et al.
D957,630 S 7/2022 Punim
11,382,955 B2 7/2022 Ferrara
11,383,006 B2 7/2022 Hughes et al.
11,389,594 B2 7/2022 Smith et al.
D961,067 S 8/2022 Schootstra et al.
11,400,080 B2 8/2022 Maturi
11,406,592 B2 8/2022 De Juan, Jr. et al.
11,419,985 B2 8/2022 Wei
11,426,306 B2 8/2022 Haffner et al.
D965,141 S 9/2022 Oldfield et al.
11,433,118 B2 9/2022 Ferrara
11,452,811 B2 9/2022 Kerschbaumer et al.
D967,414 S 10/2022 Cebadera Miranda
11,458,199 B2 10/2022 Santos et al.
11,459,374 B2 10/2022 Tustian et al.
11,478,465 B2 10/2022 Eriksson et al.
D969,992 S 11/2022 Espinoza
11,504,431 B2 11/2022 Prausnitz et al.
11,505,593 B2 11/2022 Wang et al.
11,510,869 B2 11/2022 Doshi
D973,203 S 12/2022 Tyrsing et al.
D973,873 S 12/2022 Tyrsing et al.
11,518,984 B2 12/2022 Her et al.
11,524,998 B2 12/2022 Bigelow et al.
11,525,001 B2 12/2022 Giurleo et al.
11,534,396 B2 12/2022 Blizzard et al.
11,541,139 B2 1/2023 Eveland
11,542,317 B1 1/2023 Wang et al.
11,554,215 B2 1/2023 Hawson et al.
11,559,428 B2 1/2023 Andino et al.
11,559,520 B2 1/2023 Surber
11,559,564 B2 1/2023 Yancopoulos
11,564,834 B2 1/2023 Bley et al.
11,564,907 B2 1/2023 Muller et al.
D979,054 S 2/2023 Lee-Sepsick et al.
D979,750 S 2/2023 Dyk
11,576,948 B2 2/2023 Ferrara
11,584,774 B2 2/2023 Iyer et al.

(56) References Cited

U.S. PATENT DOCUMENTS 11,596,545 B2 3/2023 Andino et al.
11,596,667 B2 3/2023 Rezaei
D983,965 S 4/2023 Siddiqui
11,618,782 B2 4/2023 Ziegelaar et al.
11,622,884 B2 4/2023 Bley et al.
11,633,300 B2 4/2023 Lazar
11,633,545 B2 4/2023 Vedrine et al.
D986,413 S 5/2023 Atterbury et al.
D987,820 S 5/2023 Yabe
11,642,214 B2 5/2023 Loria
11,642,310 B2 5/2023 De Juan, Jr. et al.
11,654,046 B2 5/2023 Weikart et al.
11,660,266 B2 5/2023 Jiang et al.
D989,302 S 6/2023 Hang et al.
D989,951 S 6/2023 Renou et al.
11,666,632 B2 6/2023 Brockmeyer et al.
11,672,800 B2 6/2023 Campbell et al.
11,679,027 B2 6/2023 De Juan, Jr. et al.
11,680,266 B2 6/2023 D'Amore et al.
11,692,027 B2 7/2023 Kraft et al.
11,707,506 B2 7/2023 Yancopoulos
11,707,531 B2 7/2023 Iyer
11,707,577 B2 7/2023 Shetty et al.
11,723,982 B2 8/2023 Healy et al.
11,725,246 B2 8/2023 Ghosh et al.
11,730,794 B2 8/2023 Yancopoulos
11,738,007 B2 8/2023 Gurkan et al.
11,738,064 B2 8/2023 Kim et al.
11,739,294 B2 8/2023 Klassen et al.
D998,146 S 9/2023 Kelleher et al.
11,752,101 B2 9/2023 Yamamoto et al.
11,752,225 B2 9/2023 Shieu et al.
11,759,577 B2 9/2023 Shanley et al.
11,766,489 B2 9/2023 Kirn et al.
11,786,396 B2 10/2023 De Juan, Jr. et al.
11,793,926 B2 10/2023 Cook et al.
11,795,136 B2 10/2023 Bavik et al.
11,806,513 B2 11/2023 Bowman et al.
11,813,196 B2 11/2023 Erickson et al.
11,819,454 B2 11/2023 Nazzaro
11,826,431 B2 11/2023 Wei et al.
D1,025,354 S 4/2024 Ullsten et al.
D1,028,225 S 5/2024 Kubo et al.
D1,037,440 S 7/2024 Suzuki et al.
12,048,837 B2 7/2024 Bryant et al.
12,059,555 B2 8/2024 Mismar et al.
D1,048,392 S 10/2024 Hang et al.
2001/0021382 A1 9/2001 Ferrara et al.
2002/0098187 A1 7/2002 Ferrara et al.
2002/0161334 A1 10/2002 Castellano et al.
2002/0177819 A1 11/2002 Barker et al.
2002/0194630 A1 12/2002 Manning et al.
2003/0004467 A1 1/2003 Musick et al.
2003/0032928 A1 2/2003 Sudo et al.
2003/0139707 A1 7/2003 Hommann et al.
2003/0236503 A1 12/2003 Koenig et al.
2004/0064105 A1 4/2004 Capes et al.
2004/0097883 A1 5/2004 Roe
2004/0122359 A1 6/2004 Wenz et al.
2004/0162528 A1 8/2004 Horvath et al.
2004/0199113 A1 10/2004 Capes et al.
2004/0220524 A1 11/2004 Sadowski et al.
2004/0236285 A1 11/2004 Fisher et al.
2005/0004530 A1 1/2005 Grabenkort et al.
2005/0027255 A1 2/2005 Lavi et al.
2005/0090782 A1 4/2005 Marshall et al.
2005/0131354 A1 6/2005 Tachikawa et al.
2005/0182370 A1 8/2005 Hato
2005/0215957 A1 9/2005 Hynes
2006/0153693 A1 7/2006 Fiechter et al.
2006/0193862 A1 8/2006 Ferrara et al.
2006/0223027 A1 10/2006 Smith et al.
2006/0258988 A1 11/2006 Keitel et al.
2006/0264815 A1 11/2006 Hommann et al.
2006/0270984 A1 11/2006 Hommann
2006/0270985 A1 11/2006 Hommann et al.
2007/0016142 A1 1/2007 Burren et al.
2007/0027101 A1 2/2007 Guyer et al.
2007/0059302 A1 3/2007 Baca et al.
2007/0088268 A1 4/2007 Edwards et al.
2007/0190058 A1 8/2007 Shams
2007/0203144 A1 8/2007 Kusari et al.
2007/0233001 A1 10/2007 Burroughs et al.
2007/0233009 A1 10/2007 Kirchhofer
2007/0253959 A1 11/2007 Ferrara et al.
2007/0265580 A1 11/2007 Tachikawa et al.
2007/0280902 A1 12/2007 Rabinovich-Guilatt et al.
2007/0281913 A1 12/2007 Rabinovich-Guilatt et al.
2007/0281914 A1 12/2007 Rabinovich-Guilatt et al.
2008/0019977 A1 1/2008 Adamis
2008/0065027 A1 3/2008 Sharp
2008/0071227 A1 3/2008 Moser et al.
2008/0082044 A1 4/2008 Sharon et al.
2008/0135130 A1 6/2008 Py et al.
2008/0160019 A1 7/2008 Wood et al.
2008/0181900 A1 7/2008 Ferrara et al.
2008/0183138 A1 7/2008 Moser et al.
2008/0202961 A1 8/2008 Sharp
2008/0208123 A1 8/2008 Hommann
2008/0269692 A1 10/2008 James et al.
2009/0005735 A1 1/2009 Wikner et al.
2009/0062746 A1 3/2009 Heffernan et al.
2009/0074786 A1 3/2009 Dor et al.
2009/0087424 A1 4/2009 Miyamoto et al.
2009/0098139 A1 4/2009 Katz et al.
2009/0149743 A1 6/2009 Barron et al.
2009/0169556 A1 7/2009 Ferrara et al.
2009/0196903 A1 8/2009 Kliman
2009/0254036 A1 10/2009 Asmussen et al.
2009/0275914 A1 11/2009 Harms et al.
2009/0299278 A1 12/2009 Lesch, Jr. et al.
2010/0010472 A1 1/2010 Moore
2010/0016807 A1 1/2010 Thilly
2010/0036320 A1 2/2010 Cox et al.
2010/0111963 A1 5/2010 Shams
2010/0119523 A1 5/2010 Ferrara et al.
2010/0152671 A1 6/2010 Raab et al.
2010/0160894 A1 6/2010 Julian et al.
2010/0175779 A1 7/2010 Ogawa et al.
2010/0185205 A1 7/2010 Novakovic et al.
2010/0186739 A1 7/2010 Kronestedt et al.
2010/0292672 A1 11/2010 Lee
2010/0298779 A1 11/2010 Hetzler et al.
2010/0305514 A1 12/2010 Valenti et al.
2010/0316652 A1 12/2010 Ferrara et al.
2010/0318063 A1 12/2010 Soll
2011/0009829 A1 1/2011 Kosinski et al.
2011/0009830 A1 1/2011 Kosinski et al.
2011/0092915 A1 4/2011 Olson et al.
2011/0098640 A1 4/2011 Horne et al.
2011/0110932 A1 5/2011 Patel
2011/0190709 A1 8/2011 Mitsuno et al.
2011/0276026 A1 11/2011 Dowds
2011/0287024 A1 11/2011 Ferrara et al.
2012/0009185 A1 1/2012 Shams
2012/0035528 A1 2/2012 Coppeta et al.
2012/0070428 A1 3/2012 Chan et al.
2012/0104045 A1 5/2012 Chang
2012/0114524 A1 5/2012 Sigg
2012/0128670 A1 5/2012 Barr et al.
2012/0143146 A1 6/2012 Strehl et al.
2012/0197211 A1 8/2012 Brister et al.
2012/0203184 A1 8/2012 Selz et al.
2012/0226240 A1 9/2012 Bedford et al.
2012/0232492 A1 9/2012 Hato
2012/0245530 A1 9/2012 Oden et al.
2012/0283654 A1 11/2012 MacDonald et al.
2012/0316509 A1 12/2012 Kayser et al.
2013/0004384 A1 1/2013 Yoo
2013/0004486 A1 1/2013 Chan et al.
2013/0006192 A1 1/2013 Teucher et al.
2013/0028911 A1 1/2013 Ferrara et al.
2013/0060232 A1 3/2013 Adlon et al.
2013/0082057 A1 4/2013 Schiff et al.

(56) References Cited

U.S. PATENT DOCUMENTS

2013/0085452 A1 4/2013 Schiff et al.
2013/0085455 A1 4/2013 Manke et al.
2013/0085458 A1 4/2013 Manke et al.
2013/0110054 A1 5/2013 Raab et al.
2013/0136697 A1 5/2013 Kannan et al.
2013/0150803 A1 6/2013 Shetty et al.
2013/0195806 A1 8/2013 Gay et al.
2013/0197016 A1 8/2013 Brigell et al.
2013/0218081 A1 8/2013 Roth
2013/0218130 A1 8/2013 Plumptre et al.
2013/0224110 A1 8/2013 Bynoe
2013/0289491 A1 10/2013 Kramer et al.
2013/0296779 A1 11/2013 Kuehne et al.
2013/0303985 A1 11/2013 Wotton et al.
2013/0310744 A1 11/2013 Brereton et al.
2013/0317431 A1 11/2013 Kramer et al.
2013/0317477 A1 11/2013 Edwards et al.
2013/0323242 A1 12/2013 Everett et al.
2013/0324924 A1 12/2013 Brereton et al.
2014/0005610 A1 1/2014 Kakiuchi et al.
2014/0012227 A1 1/2014 Sigg et al.
2014/0058335 A1 2/2014 Mudd
2014/0086934 A1 3/2014 Shams
2014/0093499 A1 4/2014 Gschwind et al.
2014/0114208 A1 4/2014 Smith et al.
2014/0135712 A1 5/2014 Horne et al.
2014/0148792 A1 5/2014 Coppeta et al.
2014/0179621 A1 6/2014 Patel et al.
2014/0180217 A1 6/2014 Kuczek et al.
2014/0221934 A1 8/2014 Janvier et al.
2014/0223862 A1 8/2014 Nicoletti et al.
2014/0271622 A1 9/2014 Prentice
2014/0288507 A1 9/2014 Samuel
2014/0294816 A1 10/2014 Shima et al.
2014/0303556 A1 10/2014 Travanty
2014/0336589 A1 11/2014 Sund et al.
2014/0350516 A1 11/2014 Schwab et al.
2014/0377276 A1 12/2014 Ferrara et al.
2015/0017163 A1 1/2015 Patel et al.
2015/0018771 A1 1/2015 Schenker et al.
2015/0037422 A1 2/2015 Kaplan et al.
2015/0051551 A1 2/2015 Hirschel et al.
2015/0073355 A1 3/2015 Hirschel et al.
2015/0078961 A1 3/2015 Opie
2015/0105734 A1 4/2015 Bryant et al.
2015/0119810 A1 4/2015 Jakob et al.
2015/0126458 A1 5/2015 Hohman et al.
2015/0152503 A1 6/2015 Boisen et al.
2015/0157709 A1 6/2015 Everett et al.
2015/0157801 A1 6/2015 Tran et al.
2015/0182623 A1 7/2015 Everett et al.
2015/0190566 A1 7/2015 Okihara
2015/0202289 A1 7/2015 Shima et al.
2015/0224266 A1 8/2015 Plumptre et al.
2015/0297453 A1 10/2015 Kim et al.
2015/0297454 A1 10/2015 Sanders et al.
2015/0297675 A1 10/2015 Osborne
2015/0297839 A1 10/2015 Sanders et al.
2015/0320782 A1 11/2015 Panjwani et al.
2015/0328151 A1 11/2015 Ballou, Jr. et al.
2015/0335826 A1 11/2015 Huet
2015/0352298 A1 12/2015 Egerström et al.
2015/0374924 A1 12/2015 Keitel et al.
2016/0008540 A1 1/2016 Fourt et al.
2016/0022919 A1 1/2016 Cammish et al.
2016/0038589 A1 2/2016 Patel
2016/0106928 A1 4/2016 Davis et al.
2016/0129080 A1 5/2016 Osborne
2016/0130321 A1 5/2016 Burian
2016/0137717 A1 5/2016 Burian
2016/0144122 A1 5/2016 Locati et al.
2016/0144128 A1 5/2016 Oakley et al.
2016/0151578 A1 6/2016 Oakley et al.
2016/0159893 A1 6/2016 Burian et al.
2016/0168240 A1 6/2016 Burian et al.
2016/0193421 A1 7/2016 Bayer et al.
2016/0213852 A1 7/2016 Harms et al.
2016/0220540 A1 8/2016 Peters et al.
2016/0220759 A1 8/2016 Enggaard et al.
2016/0220761 A1 8/2016 Shetty et al.
2016/0220762 A1 8/2016 Goral et al.
2016/0228642 A1 8/2016 Cowe
2016/0264969 A1 9/2016 Patel et al.
2016/0279339 A1 9/2016 Schenker et al.
2016/0296550 A1 10/2016 Patel et al.
2016/0310417 A1 10/2016 Prausnitz et al.
2016/0317752 A1 11/2016 Cowe
2016/0325047 A1 11/2016 Genentech
2016/0347492 A1 12/2016 Lu et al.
2017/0042816 A1 2/2017 Trollsas et al.
2017/0056469 A1 3/2017 Iezzi
2017/0056923 A1 3/2017 Hioki et al.
2017/0057635 A1 3/2017 Strayer
2017/0080086 A1 3/2017 Vitti et al.
2017/0080159 A1 3/2017 Wei
2017/0100284 A1 4/2017 Lerner
2017/0100306 A1 4/2017 Weikart et al.
2017/0100542 A1 4/2017 Norton et al.
2017/0100543 A1 4/2017 Cabiri et al.
2017/0157207 A1 6/2017 Hohman et al.
2017/0157316 A1 6/2017 Browne
2017/0173161 A1 6/2017 Kaplan et al.
2017/0173267 A1 6/2017 Ashmead et al.
2017/0182253 A1 6/2017 Folk et al.
2017/0182259 A1 6/2017 Fukushi et al.
2017/0189619 A1 7/2017 Constantineau et al.
2017/0197024 A1 7/2017 Kiminami et al.
2017/0203043 A1 7/2017 Rusch et al.
2017/0203052 A1 7/2017 Abe et al.
2017/0224435 A1 8/2017 Godfrey et al.
2017/0232199 A1 8/2017 Fiedler
2017/0233782 A1 8/2017 Collins et al.
2017/0246401 A1 8/2017 Keenan
2017/0258633 A1 9/2017 Vure et al.
2017/0274147 A1 9/2017 Raghuveer et al.
2017/0281872 A1 10/2017 Guthart
2017/0290987 A1 10/2017 Mandaroux et al.
2017/0296756 A1 10/2017 Giraud et al.
2017/0340830 A1 11/2017 Wieselblad et al.
2018/0036488 A1 2/2018 Wei
2018/0042765 A1 2/2018 Noronha et al.
2018/0057602 A1 3/2018 Theuer et al.
2018/0126085 A1 5/2018 Bowman et al.
2018/0126086 A1 5/2018 Kosinski et al.
2018/0133288 A1 5/2018 Kim et al.
2018/0147214 A1 5/2018 Ostrow et al.
2018/0171004 A1 6/2018 Gokarn et al.
2018/0177948 A1 6/2018 Raab et al.
2018/0177949 A1 6/2018 Malefijt et al.
2018/0194835 A1 7/2018 Burian et al.
2018/0207091 A1 7/2018 Brown
2018/0221483 A1 8/2018 Gaillard et al.
2018/0221584 A1 8/2018 Grimoldby et al.
2018/0228649 A1 8/2018 Lerner
2018/0237430 A1 8/2018 Peters et al.
2018/0243513 A1 8/2018 Rolfs et al.
2018/0250474 A1* 9/2018 Wei .................. A61M 5/31505
2018/0251457 A1 9/2018 Peters et al.
2018/0256747 A1 9/2018 Hawthorne et al.
2018/0263816 A1 9/2018 Lerner
2018/0264111 A1 9/2018 Pedrussio et al.
2018/0280622 A1 10/2018 Li et al.
2018/0280623 A1 10/2018 Pilkington
2018/0311319 A1 11/2018 Constable et al.
2018/0326126 A1 11/2018 Fiedler
2018/0333296 A1 11/2018 Heitzmann et al.
2018/0333300 A1 11/2018 Lerner
2018/0361080 A1 12/2018 Diaz et al.
2019/0001065 A1 1/2019 Daniel
2019/0015597 A1 1/2019 Holmqvist et al.
2019/0016817 A1 1/2019 Taddei et al.
2019/0030253 A1 1/2019 Barbour
2019/0076603 A1 3/2019 Thorley et al.
2019/0111212 A1 4/2019 Schiff et al.

(56) References Cited

U.S. PATENT DOCUMENTS

2019/0143049 A1 5/2019 Bilgic
2019/0183842 A1 6/2019 Huang et al.
2019/0201430 A1 7/2019 Vavvas et al.
2019/0231986 A1 8/2019 Devaraneni et al.
2019/0290485 A1 9/2019 Andino et al.
2019/0343918 A1 11/2019 Graham et al.
2019/0358123 A1 11/2019 Weikart et al.
2019/0365565 A1 12/2019 Bryant et al.
2019/0381008 A1 12/2019 Zeitz et al.
2019/0381087 A1 12/2019 Patel et al.
2019/0388522 A1 12/2019 Burian et al.
2020/0000635 A1 1/2020 Lerner
2020/0001062 A1 1/2020 Moss et al.
2020/0002411 A1 1/2020 Famili et al.
2020/0023076 A1 1/2020 Fotin-Mleczek et al.
2020/0031917 A1 1/2020 Kraft et al.
2020/0048341 A1 2/2020 Ghosh et al.
2020/0054635 A1 2/2020 Campbell et al.
2020/0069770 A1 3/2020 Rudolf et al.
2020/0069814 A1 3/2020 Zhao et al.
2020/0069816 A1 3/2020 Kim et al.
2020/0085735 A1 3/2020 Brown
2020/0093852 A1 3/2020 Nelms et al.
2020/0129435 A1 4/2020 Akbari et al.
2020/0147056 A1 5/2020 Maturi
2020/0155764 A1 5/2020 Kakiuchi et al.
2020/0163877 A1 5/2020 Santos et al.
2020/0171244 A1 6/2020 Weikart et al.
2020/0179167 A1 6/2020 Bryant et al.
2020/0188405 A1 6/2020 Kaushal
2020/0188589 A1 6/2020 Hawson et al.
2020/0188590 A1 6/2020 Hamlin
2020/0188593 A1 6/2020 Carrel et al.
2020/0190179 A1 6/2020 Sigg et al.
2020/0206025 A1 7/2020 Chalberg, Jr. et al.
2020/0214888 A1 7/2020 Bryant et al.
2020/0214889 A1 7/2020 Lerner
2020/0215079 A1 7/2020 Yang et al.
2020/0222233 A1 7/2020 Rotenstreich
2020/0222547 A1 7/2020 Stark et al.
2020/0230237 A1 7/2020 Kauvar et al.
2020/0237862 A1 7/2020 Sigl
2020/0237997 A1 7/2020 Brockmeyer et al.
2020/0261266 A1 8/2020 Bley et al.
2020/0268899 A1 8/2020 Iyer
2020/0270299 A1 8/2020 Iyer et al.
2020/0276261 A1 9/2020 Zhao et al.
2020/0276322 A1 9/2020 Wimley et al.
2020/0277364 A1 9/2020 Yoo et al.
2020/0297869 A1 9/2020 Cepeda et al.
2020/0297919 A1 9/2020 Hemminger et al.
2020/0368331 A1 11/2020 Borodic
2020/0368445 A1 11/2020 Weber et al.
2020/0375889 A1 12/2020 Hughes et al.
2020/0384203 A1 12/2020 Wong et al.
2020/0390724 A1 12/2020 Arkin et al.
2020/0390725 A1 12/2020 Arkin et al.
2020/0390907 A1 12/2020 Sieving et al.
2020/0399656 A1 12/2020 Neitz et al.
2020/0405808 A1 12/2020 Hohman
2020/0405898 A1 12/2020 Laflamme et al.
2021/0000758 A1 1/2021 Arkin et al.
2021/0008158 A1 1/2021 Hohman et al.
2021/0008284 A1 1/2021 Fiedler
2021/0015662 A1 1/2021 Haffner et al.
2021/0017266 A1 1/2021 Racine et al.
2021/0022918 A1 1/2021 Prausnitz et al.
2021/0023173 A1 1/2021 Yancopoulos
2021/0030945 A1 2/2021 Cook et al.
2021/0047692 A1 2/2021 Ghosh et al.
2021/0060258 A1 3/2021 Mismar et al.
2021/0077645 A1 3/2021 Mismar et al.
2021/0085745 A1 3/2021 Innocenti et al.
2021/0100856 A1 4/2021 Gasmi et al.
2021/0107999 A1 4/2021 Ehrlich et al.
2021/0113660 A1 4/2021 Park et al.
2021/0115124 A1 4/2021 Koenig et al.
2021/0121524 A1 4/2021 Yancopoulos
2021/0128840 A1 5/2021 Lilly et al.
2021/0138034 A1 5/2021 Rudolf et al.
2021/0139576 A1 5/2021 Osborne et al.
2021/0147542 A1 5/2021 Giurleo et al.
2021/0161706 A1 6/2021 Bryant et al.
2021/0161971 A1 6/2021 Nagy et al.
2021/0169689 A1 6/2021 Bley et al.
2021/0169896 A1 6/2021 Zhao et al.
2021/0169975 A1 6/2021 Rezaei
2021/0170029 A1 6/2021 Gillespie et al.
2021/0177951 A1 6/2021 Clube
2021/0178080 A1 6/2021 Shetty et al.
2021/0196510 A1 7/2021 De Juan, Jr. et al.
2021/0205410 A1 7/2021 Vitti et al.
2021/0207166 A1 7/2021 Layton et al.
2021/0212940 A1 7/2021 Yamamoto et al.
2021/0220173 A1 7/2021 Andino et al.
2021/0220435 A1 7/2021 Brockmeyer et al.
2021/0220436 A1 7/2021 Kim et al.
2021/0228539 A1 7/2021 Corson et al.
2021/0228574 A1 7/2021 Whitcup et al.
2021/0230261 A1 7/2021 Yonan et al.
2021/0236649 A1 8/2021 Burian et al.
2021/0260047 A1 8/2021 Zarnitsyn et al.
2021/0260297 A1 8/2021 Sawaguchi
2021/0275447 A1 9/2021 Hong et al.
2021/0283142 A1 9/2021 Ostrow et al.
2021/0283336 A1 9/2021 Bryant et al.
2021/0292402 A1 9/2021 Sawaguchi
2021/0315776 A1 10/2021 Hang et al.
2021/0322213 A1 10/2021 Kahook
2021/0322400 A1 10/2021 Eriksson et al.
2021/0324062 A1 10/2021 Freichel et al.
2021/0332142 A1 10/2021 Yan et al.
2021/0338678 A1 11/2021 Zablow
2021/0340242 A1 11/2021 Gekkieva et al.
2021/0347852 A1 11/2021 Olson et al.
2021/0353456 A1 11/2021 Rotenstreich
2021/0353714 A1 11/2021 Graham et al.
2021/0355206 A1 11/2021 Ghosh et al.
2021/0361769 A1 11/2021 Kauvar et al.
2021/0363231 A1 11/2021 Famili et al.
2021/0363270 A1 11/2021 Park et al.
2021/0379012 A1 12/2021 Corson et al.
2021/0379161 A1 12/2021 Buice et al.
2021/0393436 A1 12/2021 Prausnitz et al.
2021/0393649 A1 12/2021 Ostrow et al.
2021/0393738 A1 12/2021 Ke
2021/0393883 A1 12/2021 Shluzas
2021/0395833 A1 12/2021 Innocenti et al.
2022/0015945 A1 1/2022 Lerner
2022/0023245 A1 1/2022 Snyder et al.
2022/0023529 A1 1/2022 Cook et al.
2022/0025032 A1 1/2022 Bigelow et al.
2022/0031952 A1 2/2022 Bryant et al.
2022/0054586 A1 2/2022 Kim et al.
2022/0071924 A1 3/2022 Arkin et al.
2022/0079876 A1 3/2022 Blizzard et al.
2022/0079889 A1 3/2022 Panigrahi
2022/0087863 A1 3/2022 Bachelder et al.
2022/0096596 A1 3/2022 Hohman
2022/0111015 A1 4/2022 Constable et al.
2022/0112278 A1 4/2022 Li et al.
2022/0117888 A1 4/2022 Jiang et al.
2022/0133866 A1 5/2022 Schraermeyer
2022/0133889 A1 5/2022 Dranoff et al.
2022/0133908 A1 5/2022 Rejman et al.
2022/0133981 A1 5/2022 Dumont et al.
2022/0142924 A1 5/2022 McDonnell et al.
2022/0143137 A1 5/2022 Witt et al.
2022/0162296 A1 5/2022 Lin et al.
2022/0168142 A1 6/2022 Saim et al.
2022/0175881 A1 6/2022 Hohman et al.
2022/0175883 A1 6/2022 Brockmeyer et al.
2022/0220194 A1 7/2022 Ziegelaar et al.
2022/0226270 A1 7/2022 Bazan et al.

(56) References Cited

U.S. PATENT DOCUMENTS

2022/0227855 A1 7/2022 Tsiros et al.
2022/0249594 A1 8/2022 Zhao et al.
2022/0274976 A1 9/2022 Peters et al.
2022/0280341 A1 9/2022 Prausnitz et al.
2022/0280608 A1 9/2022 Pakola et al.
2022/0306732 A1 9/2022 Bakhle et al.
2022/0331345 A1 10/2022 Klier et al.
2022/0339108 A1 10/2022 Jarrett et al.
2022/0339148 A1 10/2022 DeVries et al.
2022/0339360 A1 10/2022 Young et al.
2022/0347094 A1 11/2022 Blizzard et al.
2022/0348646 A1 11/2022 Bigelow et al.
2022/0348678 A1 11/2022 Kolesnick et al.
2022/0354968 A1 11/2022 Calias et al.
2022/0356236 A1 11/2022 Bigelow et al.
2022/0362441 A1 11/2022 Fiedler
2022/0378962 A1 12/2022 Sias et al.
2022/0379044 A1 12/2022 Chitnis et al.
2022/0380478 A1 12/2022 Lederman
2022/0387554 A1 12/2022 Nelson
2022/0395557 A1 12/2022 McLaughlin et al.
2022/0401390 A1 12/2022 Feener et al.
2023/0010108 A1 1/2023 Zhao et al.
2023/0029307 A1 1/2023 Ferrara
2023/0047299 A1 2/2023 Sawaguchi
2023/0052782 A1 2/2023 Hamlin et al.
2023/0054032 A1 2/2023 Pandey
2023/0056821 A1 2/2023 Lu et al.
2023/0063116 A1 3/2023 Martin et al.
2023/0066364 A1 3/2023 Eriksson et al.
2023/0078528 A1 3/2023 Lerner
2023/0080971 A1 3/2023 Miller
2023/0089914 A1 3/2023 Kansara et al.
2023/0090539 A1 3/2023 Haffner et al.
2023/0091723 A1 3/2023 Weikart et al.
2023/0097413 A1 3/2023 Behar-Cohen et al.
2023/0103552 A1 4/2023 Goldberg et al.
2023/0104800 A1 4/2023 Li et al.
2023/0113993 A1 4/2023 Bryant et al.
2023/0115871 A1 4/2023 Zhao et al.
2023/0118774 A1 4/2023 Blizzard et al.
2023/0126239 A1 4/2023 Drenser et al.
2023/0126447 A1 4/2023 Huang et al.
2023/0128124 A1 4/2023 Yoshida
2023/0130754 A1 4/2023 Kim et al.
2023/0135092 A1 5/2023 Eaton et al.
2023/0136844 A1 5/2023 Lindblad et al.
2023/0149629 A1 5/2023 Hawson et al.
2023/0157533 A1 5/2023 Chang et al.
2023/0157869 A1 5/2023 Andino et al.
2023/0165931 A1 6/2023 Zhao et al.
2023/0166092 A1 6/2023 Unger et al.
2023/0167170 A1 6/2023 Pham et al.
2023/0181357 A1 6/2023 Pinchuk et al.
2023/0181686 A1 6/2023 Fu et al.
2023/0201371 A1 6/2023 Ciulla et al.
2023/0201387 A1 6/2023 Shieu et al.
2023/0226280 A1 7/2023 Lerner
2023/0233373 A1 7/2023 Chang
2023/0233375 A1 7/2023 Patel et al.
2023/0248806 A1 8/2023 Sigl
2023/0248855 A1 8/2023 Ludwig et al.
2023/0248898 A1 8/2023 Cook et al.
2023/0256107 A1 8/2023 Kelley, Jr. et al.
2023/0263957 A1 8/2023 Taha et al.
2023/0265199 A1 8/2023 Sapieha et al.
2023/0270670 A1 8/2023 Yoon et al.
2023/0271871 A1 8/2023 Chillon et al.
2023/0271999 A1 8/2023 Iyer et al.
2023/0277375 A1 9/2023 Egloff et al.
2023/0279090 A1 9/2023 Dengl et al.
2023/0285282 A1 9/2023 Blizzard et al.
2023/0285678 A1 9/2023 Sakhrani et al.
2023/0293731 A1 9/2023 Fotin-Mleczek et al.
2023/0295266 A1 9/2023 Vitti et al.
2023/0302085 A1 9/2023 Vitti et al.
2023/0302156 A1 9/2023 Jiang et al.
2023/0303305 A1 9/2023 Abrams et al.
2023/0310734 A1 10/2023 Tono et al.
2023/0312697 A1 10/2023 Sikorski et al.
2023/0317288 A1 10/2023 Li et al.
2023/0322911 A1 10/2023 Blumenkranz et al.
2023/0330323 A1 10/2023 Dominguez et al.
2023/0338483 A1 10/2023 Schraermeyer
2023/0338599 A1 10/2023 Olson et al.
2023/0355544 A1 11/2023 Gong et al.
2023/0355885 A1 11/2023 Shetty et al.
2023/0363941 A1 11/2023 Andino et al.
2023/0364086 A1 11/2023 Campbell et al.
2023/0364349 A1 11/2023 Huang et al.
2023/0372538 A1 11/2023 Bee et al.
2023/0381183 A1 11/2023 Zhan et al.
2023/0398233 A1 12/2023 Ni et al.
2023/0414602 A1 12/2023 Park
2023/0414677 A1 12/2023 Nagy et al.
2023/0414770 A1 12/2023 Stark et al.
2023/0414788 A1 12/2023 Bee et al.
2023/0414800 A1 12/2023 Shieu et al.
2023/0414859 A1 12/2023 Cook et al.
2023/0416351 A1 12/2023 Clemens et al.
2023/0416353 A1 12/2023 Osborne et al.
2024/0000889 A1 1/2024 Rezaei
2024/0002489 A1 1/2024 Ziegelaar et al.
2024/0058461 A1 2/2024 Iyer

FOREIGN PATENT DOCUMENTS

AU 2006251769 B2 7/2009
AU 2010320885 A1 5/2012
AU 201616239 12/2016
BE 853718 A 10/1977
CA 87137 7/1999
CA 2680335 A1 9/2008
CA 2773015 A1 4/2011
CA 2781483 A1 5/2011
CA 167018 2/2017
CA 170630 2/2017
CA 175995 9/2018
CA 180221 S 4/2019
CA 3096847 A1 10/2019
CL 199501972 12/1995
CL 20003263 11/2000
CL 200003263 11/2000
CL 20022008 9/2002
CL 20022009 9/2002
CL 20022010 9/2002
CL 20022012 9/2002
CL 20022013 9/2002
CL 200400771 4/2004
CL 200403345 12/2004
CL 50273 B1 1/2005
CL 47361 B1 7/2005
CL 200703300 6/2008
CL 200703301 6/2008
CL 201000322 4/2010
CL 201102772 2/2012
CL 201300288 1/2013
CL 201300289 1/2013
CL 201800652 3/2018
CL 202103018 4/2020
CL 202001590 8/2020
CL 202002325 8/2020
CL 202002869 11/2020
CL 202003174 12/2020
CL 202103017 12/2020
CL 202103019 11/2021
CL 202103227 12/2021
CL 202401553 11/2022
CL 202401555 11/2022
CL 202301422 5/2023
CL 202302511 2/2024
CL 202302512 2/2024
CL 202302513 2/2024
CL 202302514 2/2024

(56) References Cited

FOREIGN PATENT DOCUMENTS

| | | | |
|---|---|---|---|
| CL | 202302515 | | 2/2024 |
| CL | 202302516 | | 2/2024 |
| CL | 202302517 | | 2/2024 |
| CN | 1186699 | A | 7/1998 |
| CN | 1197398 | A | 10/1998 |
| CN | 1649638 | A | 8/2005 |
| CN | 2748094 | Y | 12/2005 |
| CN | 100540077 | C | 9/2009 |
| CN | 201356870 | Y | 12/2009 |
| CN | 202113444 | U | 1/2012 |
| CN | 102481418 | A | 5/2012 |
| CN | 102946930 | A | 2/2013 |
| CN | 203227124 | U | 10/2013 |
| CN | 204501944 | U | 7/2015 |
| CN | 204972542 | U | 1/2016 |
| CN | 105381520 | A | 3/2016 |
| CN | 105709308 | A | 6/2016 |
| CN | 205434581 | U | 8/2016 |
| CN | 106215286 | A | 12/2016 |
| CN | 106975125 | A | 7/2017 |
| CN | 107205843 | A | 9/2017 |
| CN | 108025137 | A | 5/2018 |
| CN | 304679488 | | 6/2018 |
| CN | 109172952 | A | 1/2019 |
| CN | 109310821 | A | 2/2019 |
| CN | 109641107 | A | 4/2019 |
| CN | 110115657 | | 8/2019 |
| CN | 110913926 | A | 3/2020 |
| CN | 111249062 | | 6/2020 |
| CN | 213099452 | | 5/2021 |
| CN | 112972828 | | 6/2021 |
| CN | 306672665 | S | 7/2021 |
| CN | 306732751 | S | 8/2021 |
| CN | 306748066 | S | 8/2021 |
| CN | 215350708 | | 12/2021 |
| CN | 215350709 | | 12/2021 |
| CN | 215350710 | | 12/2021 |
| CN | 109310815 | | 6/2022 |
| CN | 110913926 | | 7/2022 |
| CN | 115054777 | | 9/2022 |
| CN | 109172952 | | 9/2023 |
| CN | 116710137 | | 9/2023 |
| CO | 11784-0001 | | 12/2020 |
| DE | 68509572 | | 9/1985 |
| DE | 19856167 | C1 | 5/2000 |
| DE | 10110126 | A1 | 9/2002 |
| DE | 202005020468 | U1 | 2/2006 |
| DE | 102005008065 | A1 | 8/2006 |
| DK | 172984 | B1 | 11/1999 |
| DM | DM212509 | | 4/2020 |
| EP | 0208975 | A2 | 1/1987 |
| EP | 0901380 | A1 | 3/1999 |
| EP | 0904792 | A2 | 3/1999 |
| EP | 1019120 | A1 | 7/2000 |
| EP | 1061974 | A1 | 12/2000 |
| EP | 0846072 | B1 | 5/2001 |
| EP | 1061975 | B1 | 2/2004 |
| EP | 0971749 | B1 | 7/2004 |
| EP | 000221551-0001 | | 9/2004 |
| EP | 0937477 | B1 | 11/2004 |
| EP | 1409046 | B1 | 3/2005 |
| EP | 0976415 | B1 | 5/2005 |
| EP | 1559443 | A1 | 8/2005 |
| EP | 1568389 | A1 | 8/2005 |
| EP | 000494356-0001 | | 3/2006 |
| EP | 000494356-0002 | | 3/2006 |
| EP | 000494356-0003 | | 3/2006 |
| EP | 000508049-0001 | | 3/2006 |
| EP | 1702636 | A1 | 9/2006 |
| EP | 1675632 | B1 | 9/2007 |
| EP | 1829577 | A2 | 9/2007 |
| EP | 1525015 | B1 | 10/2007 |
| EP | 1855742 | A1 | 11/2007 |
| EP | 1885414 | A1 | 2/2008 |
| EP | 1071487 | B1 | 3/2008 |
| EP | 1924309 | A1 | 5/2008 |
| EP | 1728529 | B1 | 7/2008 |
| EP | 1818069 | B1 | 9/2008 |
| EP | 1704887 | B1 | 10/2008 |
| EP | 1973592 | A2 | 10/2008 |
| EP | 1730999 | | 12/2008 |
| EP | 1855742 | B1 | 12/2008 |
| EP | 1605847 | B1 | 9/2009 |
| EP | 2121085 | A1 | 11/2009 |
| EP | 2134391 | A2 | 12/2009 |
| EP | 1488818 | B1 | 3/2010 |
| EP | 1735014 | B1 | 8/2010 |
| EP | 2253548 | A1 | 11/2010 |
| EP | 2253549 | A1 | 11/2010 |
| EP | 2292286 | A1 | 3/2011 |
| EP | 2371406 | | 10/2011 |
| EP | 2397174 | A2 | 12/2011 |
| EP | 1885414 | A4 | 4/2012 |
| EP | 2453928 | A1 | 5/2012 |
| EP | 1885414 | B1 | 11/2012 |
| EP | 2524693 | A1 | 11/2012 |
| EP | 2552349 | A1 | 2/2013 |
| EP | 2593369 | A1 | 5/2013 |
| EP | 2627377 | A1 | 8/2013 |
| EP | 1647285 | | 11/2013 |
| EP | 002416487-0001 | | 3/2014 |
| EP | 2482890 | B1 | 12/2014 |
| EP | 2253549 | B1 | 3/2015 |
| EP | 2555820 | B1 | 3/2015 |
| EP | 2846754 | A1 | 3/2015 |
| EP | 2854762 | A1 | 4/2015 |
| EP | 2862587 | A1 | 4/2015 |
| EP | 1940476 | B1 | 5/2015 |
| EP | 2869813 | A1 | 5/2015 |
| EP | 2436407 | B1 | 6/2015 |
| EP | 2436408 | B1 | 6/2015 |
| EP | 1433705 | B1 | 7/2015 |
| EP | 2445552 | | 10/2015 |
| EP | 2939649 | A1 | 11/2015 |
| EP | 2488232 | B1 | 1/2016 |
| EP | 2601979 | | 5/2016 |
| EP | 3021900 | A1 | 5/2016 |
| EP | 1728529 | B2 | 7/2016 |
| EP | 1019120 | B1 | 8/2016 |
| EP | 3056223 | | 8/2016 |
| EP | 3057633 | A1 | 8/2016 |
| EP | 2925392 | B1 | 4/2017 |
| EP | 3160471 | A1 | 5/2017 |
| EP | 3162401 | A2 | 5/2017 |
| EP | 1973592 | B1 | 6/2017 |
| EP | 3192549 | A1 | 7/2017 |
| EP | 2944583 | B1 | 8/2017 |
| EP | 3199189 | A1 | 8/2017 |
| EP | 3202389 | A1 | 8/2017 |
| EP | 3202447 | A1 | 8/2017 |
| EP | 3213786 | A1 | 9/2017 |
| EP | 2550043 | B1 | 10/2017 |
| EP | 2666510 | B1 | 10/2017 |
| EP | 2134391 | B1 | 12/2017 |
| EP | 3108902 | | 7/2018 |
| EP | 2968729 | | 8/2018 |
| EP | 3377040 | | 9/2018 |
| EP | 2869813 | B1 | 11/2018 |
| EP | 3056224 | | 11/2018 |
| EP | 2451511 | B1 | 1/2019 |
| EP | 3424547 | | 1/2019 |
| EP | 2701773 | B1 | 2/2019 |
| EP | 3437678 | | 2/2019 |
| EP | 3452103 | A1 | 3/2019 |
| EP | 3470058 | | 4/2019 |
| EP | 2627377 | B1 | 8/2019 |
| EP | 3539597 | A1 | 9/2019 |
| EP | 3124005 | | 12/2019 |
| EP | 3581185 | A1 | 12/2019 |
| EP | 3065761 | B1 | 1/2020 |
| EP | 3600442 | A1 | 2/2020 |
| EP | 3630043 | | 4/2020 |
| EP | 3630062 | A2 | 4/2020 |
| EP | 3057633 | B1 | 5/2020 |

(56) References Cited

FOREIGN PATENT DOCUMENTS

| | | | |
|---|---|---|---|
| EP | 3403622 | B1 | 5/2020 |
| EP | 3656373 | A1 | 5/2020 |
| EP | 2701778 | B1 | 7/2020 |
| EP | 3226895 | | 7/2020 |
| EP | 3687464 | A1 | 8/2020 |
| EP | 3687599 | | 8/2020 |
| EP | 3471780 | B1 | 10/2020 |
| EP | 3738580 | A1 | 11/2020 |
| EP | 3763384 | | 1/2021 |
| EP | 3452013 | B1 | 2/2021 |
| EP | 3536310 | | 4/2021 |
| EP | 3381444 | | 5/2021 |
| EP | 2991706 | B1 | 6/2021 |
| EP | 3782807 | | 6/2021 |
| EP | 3679922 | | 7/2021 |
| EP | 3291812 | B1 | 9/2021 |
| EP | 3484531 | | 11/2021 |
| EP | 3685826 | | 11/2021 |
| EP | 3193829 | B1 | 12/2021 |
| EP | 3656373 | | 2/2022 |
| EP | 3777834 | | 2/2022 |
| EP | 3472317 | B1 | 3/2022 |
| EP | 4025272 | | 7/2022 |
| EP | 4028128 | A1 | 7/2022 |
| EP | 4031208 | | 7/2022 |
| EP | 2604295 | | 9/2022 |
| EP | 3116553 | | 9/2022 |
| EP | 4065150 | A1 | 10/2022 |
| EP | 2887982 | B1 | 11/2022 |
| EP | 3897595 | B1 | 3/2023 |
| EP | 4153494 | | 3/2023 |
| EP | 2760509 | | 4/2023 |
| EP | 3380040 | B1 | 4/2023 |
| EP | 3685828 | B1 | 4/2023 |
| EP | 3858405 | | 4/2023 |
| EP | 4159220 | A1 | 4/2023 |
| EP | 4201441 | | 6/2023 |
| EP | 3384049 | B1 | 8/2023 |
| EP | 4218862 | | 8/2023 |
| EP | 4225235 | A1 | 8/2023 |
| EP | 4245312 | A1 | 9/2023 |
| EP | 4245336 | A1 | 9/2023 |
| EP | 4251204 | A1 | 10/2023 |
| EP | 4255530 | A1 | 10/2023 |
| EP | 4257509 | | 10/2023 |
| EP | 4262894 | | 10/2023 |
| EP | 3233056 | B1 | 11/2023 |
| EP | 3681448 | B1 | 11/2023 |
| EP | 3634543 | | 6/2024 |
| FR | 711644 | A | 9/1931 |
| FR | 1216753 | A | 4/1960 |
| FR | 1412547 | A | 10/1965 |
| FR | 2536285 | A1 | 5/1984 |
| FR | 2561925 | A3 | 10/1985 |
| FR | D053933-0001 | | 10/2000 |
| GB | 1230522 | A | 5/1971 |
| GB | 1550308 | A | 8/1979 |
| IL | 70802 | | 6/2023 |
| IN | 342357001 | | 4/2021 |
| IN | 342359001 | | 4/2021 |
| IN | 356804001 | | 1/2022 |
| IN | 356808001 | | 1/2022 |
| IN | 342358001 | | 4/2022 |
| IT | MI20102322 | A1 | 6/2012 |
| JP | S4824842 | U | 3/1973 |
| JP | S54-117736 | A | 9/1978 |
| JP | 55-107113 | A | 8/1980 |
| JP | 60-175249 | A | 9/1985 |
| JP | 7-7650 | | 2/1995 |
| JP | H07244442 | A | 9/1995 |
| JP | 8-164206 | A | 6/1996 |
| JP | H11151301 | A | 6/1999 |
| JP | 2000-197700 | A | 7/2000 |
| JP | 2000202027 | A | 7/2000 |
| JP | 2001-218843 | A | 8/2001 |
| JP | 2001-526097 | | 12/2001 |
| JP | 2003-199828 | A | 7/2003 |
| JP | 2004-500201 | A | 1/2004 |
| JP | 2004-49726 | A | 2/2004 |
| JP | 2005-312699 | A | 11/2005 |
| JP | 2006-26280 | A | 2/2006 |
| JP | 4191409 | B2 | 12/2008 |
| JP | 2008307237 | A | 12/2008 |
| JP | 2009011481 | A | 1/2009 |
| JP | 2012-85813 | A | 5/2012 |
| JP | 2012179240 | A | 9/2012 |
| JP | 2012528642 | A | 11/2012 |
| JP | 2012-245180 | A | 12/2012 |
| JP | 5163882 | | 3/2013 |
| JP | 2013511309 | A | 4/2013 |
| JP | 2014-4041 | A | 1/2014 |
| JP | 2014515683 | A | 7/2014 |
| JP | 5718157 | B2 | 5/2015 |
| JP | 2015-123296 | A | 7/2015 |
| JP | 5744927 | | 7/2015 |
| JP | 2015-523867 | A | 8/2015 |
| JP | D1531421 | S | 8/2015 |
| JP | 2015-171514 | | 10/2015 |
| JP | 5801314 | B2 | 10/2015 |
| JP | 5907874 | B2 | 4/2016 |
| JP | D1552403 | S | 6/2016 |
| JP | 2016124594 | A | 7/2016 |
| JP | 5978742 | B2 | 8/2016 |
| JP | 2016-538960 | A | 12/2016 |
| JP | 2017-60837 | | 3/2017 |
| JP | 6144264 | | 6/2017 |
| JP | 6313038 | | 4/2018 |
| JP | D1646523 | S | 11/2019 |
| JP | 2020522351 | A | 7/2020 |
| JP | 6781546 | | 11/2020 |
| JP | 6920269 | | 8/2021 |
| JP | D1700933 | S | 11/2021 |
| JP | D1701001 | S | 11/2021 |
| JP | 2023506180 | | 2/2023 |
| JP | 7244442 | | 3/2023 |
| JP | 2023071962 | | 5/2023 |
| JP | 2023550458 | | 12/2023 |
| KR | 20050004800 | A | 1/2005 |
| KR | 100721549 | B1 | 5/2007 |
| KR | 1020110022607 | A | 2/2014 |
| KR | 10-1510680 | | 4/2015 |
| KR | 20150119092 | A | 10/2015 |
| KR | 101774823 | | 9/2017 |
| KR | 102232708 | | 3/2021 |
| KR | 102288287 | | 8/2021 |
| KR | 102299177 | | 9/2021 |
| KR | 102341670 | | 12/2021 |
| KR | 20220085906 | | 6/2022 |
| MX | PA03007940 | A | 10/2004 |
| RU | 2488410 | C2 | 7/2013 |
| RU | 2012125349 | A | 12/2013 |
| SE | D060555-0002 | | 1/2002 |
| SG | 30202008659 | T | 12/2020 |
| SG | 30202008662 | P | 12/2020 |
| SG | 30202008663 | | 12/2020 |
| TW | M261222 | U | 4/2005 |
| TW | 201215424 | A | 4/2012 |
| TW | 201600133 | A | 1/2016 |
| TW | D187080 | S | 12/2017 |
| TW | I632920 | | 8/2018 |
| TW | 201831212 | A | 9/2018 |
| TW | 201900234 | A | 1/2019 |
| TW | I720632 | | 3/2021 |
| TW | D215156 | S | 11/2021 |
| TW | 202144033 | A | 12/2021 |
| TW | D215855 | S | 12/2021 |
| TW | D216479 | S | 1/2022 |
| TW | D216480 | S | 1/2022 |
| TW | 202237181 | | 10/2022 |
| VN | 3-0028936-000 | | 12/2017 |
| VN | 3-0028632-000 | | 7/2018 |
| WO | 8601728 | A2 | 3/1986 |
| WO | WO-9320784 | A1 | 10/1993 |
| WO | 9504563 | A1 | 2/1995 |

(56) References Cited

FOREIGN PATENT DOCUMENTS

| | | | |
|---|---|---|---|
| WO | 9512418 | A1 | 5/1995 |
| WO | 9530444 | | 11/1995 |
| WO | 9626754 | A2 | 9/1996 |
| WO | WO-9630046 | A1 | 10/1996 |
| WO | 9701362 | A2 | 1/1997 |
| WO | 9708054 | A1 | 3/1997 |
| WO | 9709080 | A1 | 3/1997 |
| WO | 9744068 | A1 | 11/1997 |
| WO | 9805366 | | 2/1998 |
| WO | 9819715 | A1 | 5/1998 |
| WO | 9856438 | A1 | 12/1998 |
| WO | 9856439 | A1 | 12/1998 |
| WO | 9915215 | A1 | 4/1999 |
| WO | 9927971 | A2 | 6/1999 |
| WO | 9945984 | A1 | 9/1999 |
| WO | 9945985 | A1 | 9/1999 |
| WO | 0154756 | | 8/2001 |
| WO | 0178812 | A1 | 10/2001 |
| WO | 0195959 | A1 | 12/2001 |
| WO | 02072157 | A1 | 9/2002 |
| WO | 03004080 | A1 | 1/2003 |
| WO | 03057285 | A2 | 7/2003 |
| WO | 03077976 | A1 | 9/2003 |
| WO | 03080160 | A1 | 10/2003 |
| WO | 03097133 | A1 | 11/2003 |
| WO | 03057285 | A3 | 12/2003 |
| WO | 2004032996 | A2 | 4/2004 |
| WO | 2004035113 | A2 | 4/2004 |
| WO | 2004032996 | A3 | 7/2004 |
| WO | 2005032627 | A1 | 4/2005 |
| WO | 2005067984 | A1 | 7/2005 |
| WO | 2006047325 | A1 | 5/2006 |
| WO | 2006089734 | A1 | 8/2006 |
| WO | 2006130098 | A1 | 12/2006 |
| WO | 2006130100 | A1 | 12/2006 |
| WO | 2007002052 | A2 | 1/2007 |
| WO | WO-2007011873 | A2 | 1/2007 |
| WO | 2007024957 | A1 | 3/2007 |
| WO | 2007035621 | A1 | 3/2007 |
| WO | 2007083034 | A2 | 7/2007 |
| WO | WO-2007084765 | A2 | 7/2007 |
| WO | WO-2007087457 | A2 | 8/2007 |
| WO | WO-2007112675 | A1 | 10/2007 |
| WO | 2008051561 | A2 | 5/2008 |
| WO | 2008058666 | A1 | 5/2008 |
| WO | 2008058668 | A1 | 5/2008 |
| WO | WO-2008063932 | A2 | 5/2008 |
| WO | 2008083875 | A1 | 7/2008 |
| WO | WO-2008101985 | A2 | 8/2008 |
| WO | 2008110890 | A1 | 9/2008 |
| WO | 2008112472 | A2 | 9/2008 |
| WO | 2008112472 | A3 | 11/2008 |
| WO | 2009007997 | A2 | 1/2009 |
| WO | 2009092430 | A1 | 7/2009 |
| WO | WO-2009086112 | A2 | 7/2009 |
| WO | WO-2009089409 | A2 | 7/2009 |
| WO | WO-2009155724 | A2 | 12/2009 |
| WO | WO-2010081838 | A2 | 7/2010 |
| WO | WO-2010085542 | A2 | 7/2010 |
| WO | WO-2010088548 | A1 | 8/2010 |
| WO | 2010127449 | A1 | 11/2010 |
| WO | WO-2010127029 | A1 | 11/2010 |
| WO | 2010149466 | A2 | 12/2010 |
| WO | 2011006877 | A1 | 1/2011 |
| WO | 2011032513 | A1 | 3/2011 |
| WO | 2011037437 | A2 | 3/2011 |
| WO | 2011038487 | A1 | 4/2011 |
| WO | 2011039211 | A1 | 4/2011 |
| WO | 2011057335 | | 5/2011 |
| WO | 2011061313 | A1 | 5/2011 |
| WO | 2011073174 | A1 | 6/2011 |
| WO | 2011073176 | A1 | 6/2011 |
| WO | 2011081867 | A2 | 7/2011 |
| WO | WO-2011085288 | A2 | 7/2011 |
| WO | 2011115428 | A2 | 9/2011 |
| WO | 2011117878 | A1 | 9/2011 |
| WO | 2011125133 | A1 | 10/2011 |
| WO | 2011133097 | A1 | 10/2011 |
| WO | 2011137437 | A2 | 11/2011 |
| WO | 2012007056 | A1 | 1/2012 |
| WO | WO-2012003437 | A1 | 1/2012 |
| WO | WO-2012019176 | A2 | 2/2012 |
| WO | 2012049141 | A1 | 4/2012 |
| WO | WO-2012055884 | A1 | 5/2012 |
| WO | WO-2012097019 | A1 | 7/2012 |
| WO | 2012118687 | A1 | 9/2012 |
| WO | 2012125132 | A1 | 9/2012 |
| WO | 2012148717 | A1 | 11/2012 |
| WO | 2012158095 | A1 | 11/2012 |
| WO | WO-2012149040 | A2 | 11/2012 |
| WO | 2012/166287 | A1 | 12/2012 |
| WO | 2013028537 | A2 | 2/2013 |
| WO | 2013034986 | A2 | 3/2013 |
| WO | WO-2012019139 | A9 | 3/2013 |
| WO | 2013048310 | A1 | 4/2013 |
| WO | WO-2013126799 | A1 | 8/2013 |
| WO | WO-2013151904 | A1 | 10/2013 |
| WO | 2013178771 | A1 | 12/2013 |
| WO | 2013184270 | A1 | 12/2013 |
| WO | 2014005728 | A1 | 1/2014 |
| WO | 2014/033184 | A1 | 3/2014 |
| WO | WO-2014036009 | A1 | 3/2014 |
| WO | 2014049712 | A1 | 4/2014 |
| WO | 2014049714 | A1 | 4/2014 |
| WO | 2014068283 | A2 | 5/2014 |
| WO | 2014073618 | A1 | 5/2014 |
| WO | WO-2014074823 | A1 | 5/2014 |
| WO | 2014102987 | A1 | 7/2014 |
| WO | WO-2014105978 | A1 | 7/2014 |
| WO | 2014162551 | A1 | 10/2014 |
| WO | 2014187779 | A1 | 11/2014 |
| WO | WO-2014179698 | A2 | 11/2014 |
| WO | 2014/203181 | A1 | 12/2014 |
| WO | WO-2014203182 | A1 | 12/2014 |
| WO | WO-2014203183 | A1 | 12/2014 |
| WO | 2015007808 | A1 | 1/2015 |
| WO | 2015007811 | A1 | 1/2015 |
| WO | WO-2015006734 | A1 | 1/2015 |
| WO | 2015/032800 | A2 | 3/2015 |
| WO | 2015033280 | A1 | 3/2015 |
| WO | 2015045180 | A1 | 4/2015 |
| WO | 2015047758 | A2 | 4/2015 |
| WO | 2015055608 | A1 | 4/2015 |
| WO | WO-2015069668 | A1 | 5/2015 |
| WO | WO-2015073895 | A1 | 5/2015 |
| WO | 2015047758 | A3 | 7/2015 |
| WO | 2015157484 | A1 | 10/2015 |
| WO | 2015164413 | A1 | 10/2015 |
| WO | WO-2015164626 | A2 | 10/2015 |
| WO | WO-2015168619 | A1 | 11/2015 |
| WO | WO-2015195842 | A1 | 12/2015 |
| WO | WO-2015196085 | A2 | 12/2015 |
| WO | 2016033701 | A1 | 3/2016 |
| WO | WO-2016042162 | A1 | 3/2016 |
| WO | 2016052037 | A1 | 4/2016 |
| WO | 2016068333 | A1 | 5/2016 |
| WO | WO-2016073918 | A1 | 5/2016 |
| WO | 2016094387 | A2 | 6/2016 |
| WO | 2016169718 | A1 | 10/2016 |
| WO | 2016191535 | A2 | 12/2016 |
| WO | 2016193620 | A1 | 12/2016 |
| WO | 2016193624 | A1 | 12/2016 |
| WO | 2016199133 | A1 | 12/2016 |
| WO | 2017012789 | A1 | 1/2017 |
| WO | WO-2017014630 | A1 | 1/2017 |
| WO | 2017027876 | A1 | 2/2017 |
| WO | 2017030195 | A1 | 2/2017 |
| WO | WO-2017025928 | A2 | 2/2017 |
| WO | WO-2017046358 | A1 | 3/2017 |
| WO | 2017055462 | A1 | 4/2017 |
| WO | 2017057477 | A1 | 4/2017 |
| WO | 2017062304 | A1 | 4/2017 |
| WO | 2017062407 | A1 | 4/2017 |
| WO | 2017062930 | A1 | 4/2017 |

(56) References Cited

FOREIGN PATENT DOCUMENTS

| | | | |
|---|---|---|---|
| WO | 2017062931 | A1 | 4/2017 |
| WO | 2017062933 | A1 | 4/2017 |
| WO | 2017087798 | A1 | 5/2017 |
| WO | 2017087871 | A1 | 5/2017 |
| WO | 2017103954 | A1 | 6/2017 |
| WO | 2017126550 | A1 | 7/2017 |
| WO | WO-2017120601 | A1 | 7/2017 |
| WO | 2017129685 | A1 | 8/2017 |
| WO | 2017139375 | A1 | 8/2017 |
| WO | 2017139573 | A1 | 8/2017 |
| WO | 2017158805 | A1 | 9/2017 |
| WO | WO-2017158366 | A2 | 9/2017 |
| WO | 2017180480 | A1 | 10/2017 |
| WO | 2017191306 | A1 | 11/2017 |
| WO | 2017204787 | A1 | 11/2017 |
| WO | WO-2018031913 | A1 | 2/2018 |
| WO | 2018085759 | A1 | 5/2018 |
| WO | 2018085768 | A2 | 5/2018 |
| WO | WO-2018111862 | A1 | 6/2018 |
| WO | 2018141634 | A1 | 8/2018 |
| WO | 2018204140 | A1 | 11/2018 |
| WO | 2018215580 | A1 | 11/2018 |
| WO | 2018217995 | A1 | 11/2018 |
| WO | 2018218013 | A2 | 11/2018 |
| WO | 2018224640 | A1 | 12/2018 |
| WO | 2018224644 | A1 | 12/2018 |
| WO | 2018232408 | A1 | 12/2018 |
| WO | WO-2019040397 | A1 | 2/2019 |
| WO | WO-2019108770 | A1 | 6/2019 |
| WO | WO-2019175727 | A1 | 9/2019 |
| WO | 2019197361 | A1 | 10/2019 |
| WO | WO-2019217927 | A1 | 11/2019 |
| WO | WO-2020160256 | A1 | 8/2020 |
| WO | WO-2020180951 | A1 | 9/2020 |
| WO | 2020247686 | | 12/2020 |
| WO | WO-2021046070 | A1 | 3/2021 |
| WO | WO-2021048779 | A2 | 3/2021 |
| WO | WO-2021050649 | A1 | 3/2021 |
| WO | WO-2021072265 | A1 | 4/2021 |
| WO | WO-2021108255 | A1 | 6/2021 |
| WO | WO-2021119544 | A1 | 6/2021 |
| WO | WO-2021168218 | A1 | 8/2021 |
| WO | WO-2021178899 | A1 | 9/2021 |
| WO | WO-2021183555 | A1 | 9/2021 |
| WO | WO-2021195163 | A1 | 9/2021 |
| WO | WO-2021240488 | A1 | 12/2021 |
| WO | WO-2021252647 | A1 | 12/2021 |
| WO | WO-2021252962 | A1 | 12/2021 |
| WO | WO-2022005100 | A1 | 1/2022 |
| WO | WO-2022011323 | A1 | 1/2022 |
| WO | WO-2022013172 | A1 | 1/2022 |
| WO | WO-2022056326 | A1 | 3/2022 |
| WO | WO-2022066788 | A1 | 3/2022 |
| WO | WO-2022067330 | A1 | 3/2022 |
| WO | WO-2022076549 | A1 | 4/2022 |
| WO | WO-2022076591 | A1 | 4/2022 |
| WO | WO-2022076938 | A1 | 4/2022 |
| WO | WO-2022093818 | A1 | 5/2022 |
| WO | WO-2022094340 | A1 | 5/2022 |
| WO | WO-2022111379 | A1 | 6/2022 |
| WO | WO-2022112957 | A1 | 6/2022 |
| WO | WO-2022131789 | A1 | 6/2022 |
| WO | WO-2022175601 | A1 | 8/2022 |
| WO | WO-2022183418 | A1 | 9/2022 |
| WO | WO-2022201084 | A1 | 9/2022 |
| WO | WO-2022204374 | A1 | 9/2022 |
| WO | WO-2022212360 | A1 | 10/2022 |
| WO | WO-2022217110 | A1 | 10/2022 |
| WO | WO-2022220602 | A1 | 10/2022 |
| WO | WO-2022221315 | A1 | 10/2022 |
| WO | WO-2022221395 | A1 | 10/2022 |
| WO | WO-2022221537 | A1 | 10/2022 |
| WO | WO-2022223140 | A1 | 10/2022 |
| WO | WO-2022226347 | A1 | 10/2022 |
| WO | WO-2022229932 | A1 | 11/2022 |
| WO | WO-2022232790 | A1 | 11/2022 |
| WO | WO-2022246476 | A1 | 11/2022 |
| WO | 2022272257 | | 12/2022 |
| WO | WO-2022251710 | A2 | 12/2022 |
| WO | WO-2022268048 | A1 | 12/2022 |
| WO | WO-2023014892 | A1 | 2/2023 |
| WO | WO-2023039458 | A1 | 3/2023 |
| WO | WO-2023041697 | A1 | 3/2023 |
| WO | WO-2023047375 | A2 | 3/2023 |
| WO | WO-2023054503 | A1 | 4/2023 |
| WO | WO-2023081528 | A1 | 5/2023 |
| WO | WO-2023091955 | A1 | 5/2023 |
| WO | 2023114123 | | 6/2023 |
| WO | WO-2023130081 | A1 | 7/2023 |
| WO | WO-2023133058 | A2 | 7/2023 |
| WO | WO-2023150566 | A1 | 8/2023 |
| WO | WO-2023153535 | A1 | 8/2023 |
| WO | WO-2023158990 | A1 | 8/2023 |
| WO | WO-2023171360 | A1 | 9/2023 |
| WO | WO-2023172585 | A1 | 9/2023 |
| WO | WO-2023173055 | A2 | 9/2023 |
| WO | WO-2023173088 | A1 | 9/2023 |
| WO | WO-2023173093 | A1 | 9/2023 |
| WO | WO-2023175549 | A1 | 9/2023 |
| WO | WO-2023177691 | A1 | 9/2023 |
| WO | WO-2023180450 | A1 | 9/2023 |
| WO | WO-2022260939 | A9 | 10/2023 |
| WO | WO-2023212273 | A1 | 11/2023 |

OTHER PUBLICATIONS

Accura Xtreme White, Xtreme Class, 3D Systems, Manufacturing the future, 2015, 1 page.

Chilean Office Action issued on Jan. 26, 2022, in counterpart Chilean Patent Application No. 01590-2020 (16 pages, in Spanish).

Chinese Office Action issued on Jun. 24, 2022 in counterpart Chinese Patent Application No. 201880080564.7 (9 pages, in Chinese).

Chinese Office Action issued on Nov. 26, 2021, in counterpart Chinese Patent Application No. 201880080564.7 (8 pages, in Chinese).

Columbian Office Action issued on Apr. 13, 2022, in counterpart Columbian Patent Application No. NC2020/0007231 (30 pages, in Spanish with English translation).

Dilution Table 3Dose Unit Dose Injector, Instructions for Use, www.tsklab.com, retrieved 2019, 1 page.

Gattex (teduglutide) for Injection, Instructions for Use, 2019, 2 pages.

Indian Office Action issued on May 18, 2022, in counterpart Indian Patent Application No. 202047023695 (7 pages, in English).

International Search Report and Written Opinion for Application No. PCT/US2018/065192, mailed on Jun. 4, 2019, 22 pages.

International Search Report and Written Opinion for Application No. PCT/US2020/36200, mailed on Oct. 26, 2020, 19 pages.

Japanese Notice of Allowance dated Oct. 25, 2021, in counterpart Japanese Patent Application No. 2020-026268 (4 pages, in Japanese with partial English translation).

Krader, Cheryl Guttman. "Pearls for Selecting a Syringe for Intravitreal Injection," Ophthamology Times, Jan. 2021, pp. 1 & 25, 52 pages.

Lucentis Dosage, Generic name: Ranibizumab 10mg in 1mL, Dosage form: injection, solution, Lucentis Dosage Guide—Drugs.com, [retrieved on May 28, 2020]. Retrieved from the Internet: (URL: https://www.drugs.com/dosage/ucentis.html), 7 pages.

Lucentis Ranibizumab Injection, Prefilled Syringe Administration Preparation, Genentech, 2018, 30 pages.

New, Novel Prefillable Microfilter Injection Device for Intraocular Therapeutics, Congruence Medical Solutions INC, Gautam Shetty, phD, 2018, 19 Pages.

Proven and innovative injection systems delivering your product's potential, Vetter—Packaging systems and technologies for pharmaceutical products, Retrieved from Internet: (https://www.vetter-pharma.com/en/clinical-manufacturing/packaging/systems), retrieved 2019, 7 pages.

(56) References Cited

OTHER PUBLICATIONS

Taiwanese Search Report dated Sep. 8, 2021, in counterpart Taiwanese Patent Application No. 109306859 (1 page, in English).
International Preliminary Report on Patentability issued on May 6, 2021, in counterpart International Patent Application No. PCT/US2020/036200 (12 pages, in English).
U.S. Appl. No. 62/467,065, filed Mar. 3, 2017.
Baudin F., et al., "Association of Acute Endophthalmitis With Intravitreal Injections of Corticosteroids or Anti-Vascular Growth Factor Agents in a Nationwide Study in France," JAMA Ophthalmology, 2018, vol. 136(12), pp. 1352-1358.
Dhoot D.S., "Rates of Suspected Endophthalmitis Following Intravitreal Injections in Clinical Practices in the United States," Ophthalmic Surgery, Lasers & Imaging Retina, 2021, vol. 52(6), 312-318.
Pancholy M., "Endophthalmitis Following Intravitreal Anti-Vascular Endothelial Growth Factor Therapy: Changes in Incidence and Outcomes over a 9-Year Period," Current Eye Research, 2021, vol. 46(9), pp. 1370-1377.
Reyes-Capo D.P., et al., "Trends in Endophthalmitis Associated With Intravitreal Injection of Anti-VEGF Agentsat a Tertiary Referral Center," Ophthalmic Surgery, Lasers Imaging Retina, 2021, vol. 52(6), pp. 319-326.
Storey P. P., et al., "The Impact of Prefilled Syringes on Endophthalmitis Following Intravitreal Injection of Ranibizumab," American Journal of Ophthalmology, 2019, vol. 199, pp. 200-208.
U.S. Department of Health and Human Services, Food and Drug Administration, Center for Drug Evaluation and Research (CDER), Center for Biologics Evaluation and Research (CBER), "Guidance for Industry Container Closure Systems for Packaging Human Drugs and Biologics", Chemistry, Manufacturing, and Controls Documentation, May 1999, 56 pages.
Office Action in Colombian Application No. NC2020/0007231, dated Apr. 13, 2023, 38 pages (in Spanish with English translation).
Office Action in Colombian Application No. NC2023/0001752, dated Apr. 18, 2023, 33 pages (in Spanish with English translation).
Office Action in Colombian Application No. NC/2023/0001925, dated Apr. 18, 2023, 17 pages (in Spanish with English translation).
Office Action in Colombian Application No. NC2020/0001926, dated Jun. 23, 2023, 11 pages (in Spanish with English translation).
Decision of Patent Grant in Korean Application No. 10-2020-7019695, dated Aug. 11, 2023, 4 pages (in Korean with English translation).
International Search Report in International Patent Application No. PCT/USUS2022/076090, dated Dec. 6, 2022, 3 pages.
Sassalos et al., "Prefilled syringes for intravitreal drug delivery", Clinical Ophthalmology, vol. 13, pp. 701-706, doi: 10.2147/OPTH.S169044, Apr. 23, 2019.
Schargus et al., "Comparison of Syringes With Intravitreal Anti-VEGF Drugs: Particle Burden and Protein Aggregates in Brolucizumab, Aflibercept and Bevacizumab", Translational Vision Science Technoloy, vol. 10, No. 9, p. 21, doi: 10.1167/tvst.10.9.21, Aug. 18, 2021.
Subhi et al., "Prefilled syringes for intravitreal injection reduce preparation time", Danish Medical Journal, PMID: 27034182, Apr. 1, 2016.
Parenky et al., "Container Closure and Delivery Considerations for Intravitreal Drug Administration", AAPS PharmSciTech. Vol. 22, No. 3, doi: 10.1208/s12249-021-01949-4, Mar. 11, 2021.
Colucciello , Michael, "Prefilled Syringe Delivery of Intravitreal Anti-VEGF Medications", 9th paragraph, XP002808066, retrieved from the Internet: URL:https://www.retinalphysician.com/issue s/2019/march-2019/prefilled- syringe-delive ry-of-intravitreal-anti-veretinalphysician.com, Mar. 1, 2019.
"Regeneron 2019 Annual Report", regenron.com, 2019, Slides 14 and 14, XP002808067, retrieved from the Internet: URL:https://investor.regeneron.com/static.files/d2933d3d-f409-47e4-a637-c5ca52cf3b87, Published 2019, Retrieved Nov. 23, 2022.
Philip et al., "The Impact of Prefilled Syringes on Endophthalmitis Following Intravitreal Injection of Ranibizumab", American Journal of Ophthalmology United States, vol. 199, First Paragraph, DOI: 10.1016/J.AJO.2018.11.023, Feb. 28, 2019.
Search Report in Eurasian Patent Application No. 202391326, dated Sep. 15, 2023, 6 pages (in Russian with English translation).
Regeneron Pharmaceuticals, Inc.; Instructions, Date of Publication Oct. 2022; www.regeneron.com/downloads/dupixent_ifu-100-spanish.pdf (3 pages).
Bayer AG Jeringa Precargada dated Nov. 26, 2012; https://nomenclator.org/med/eylea-40-mg-ml-solucion (4 pages).
Kocabora M.S., et al., "Intravitreal Silicone Oil Droplets Following Pegaptanib Injection," Acta Ophthalmologica, 88 (2):e44-e45, Mar. 2010.
Kunjukunju N., et al., "Bilateral Avastin Injections," ARVO Annual Meeting Abstract, Investigative Ophthalmology & Visual Science Apr. 2009, vol. 50, 1876, 02 pages.
"Assessing the Impact on Drug Dose Delivery of Passive Safety Devices," Copyright @ 2016 Frederick Furness Publishing Ltd., 4 pages.
"Special Feature—Injection Devices: Manufacturers Focus on 21st Century Technology While Still Tackling Traditional Challenges" (URL: https://drug-dev.com/special-feature-injection-devices-manufacturers-focus-on-21st-century-technology-while-still-tackling-traditional-challenges/); Contract Services, Drug Delivery, Featured Articles, Injection Devices, Sep. 2015, 24 pages.
Japanese Notice of Allowance issued in Japanese Patent Application No. 2023-084253 on Feb. 28, 2025 (3 pages; 3 pages English tranlsation).
Regeneron prefilled syringe, posted on market-scope.com, posting date Dec. 13, 2019, retrieved Apr. 4, 2025, online, URL: https://www.market-scope.com/pages/news/4010/regeneron-s-eylea-injection-prefilled--syringe-now-available(Year: 2019).

* cited by examiner

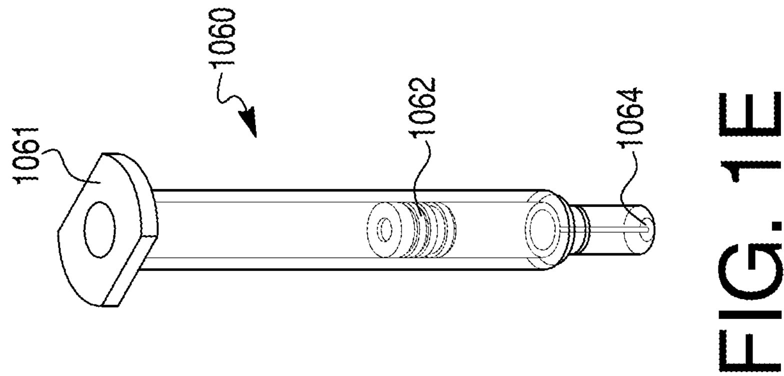
FIG. 1E
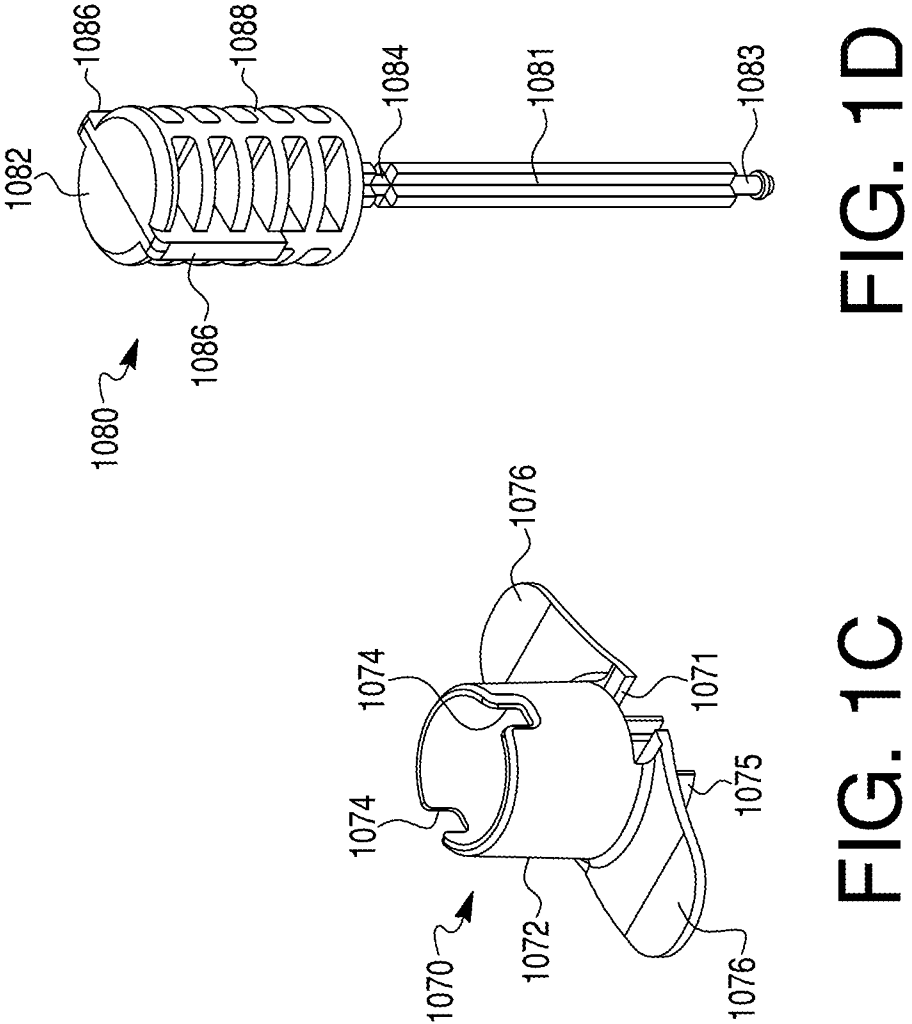
FIG. 1D
FIG. 1C 1097b
1093
1070
1073
1097a
1096
1076
1071

1096
1097b
1093
1070
1073
1097a
1076
1071

1097b
1093
1070
1096
1097a
1073
1076
1071

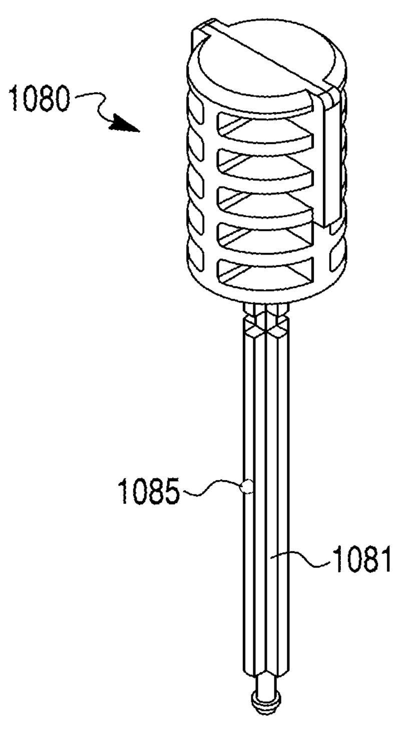
FIG. 1N
1070
1092
1073
FIG. 1O
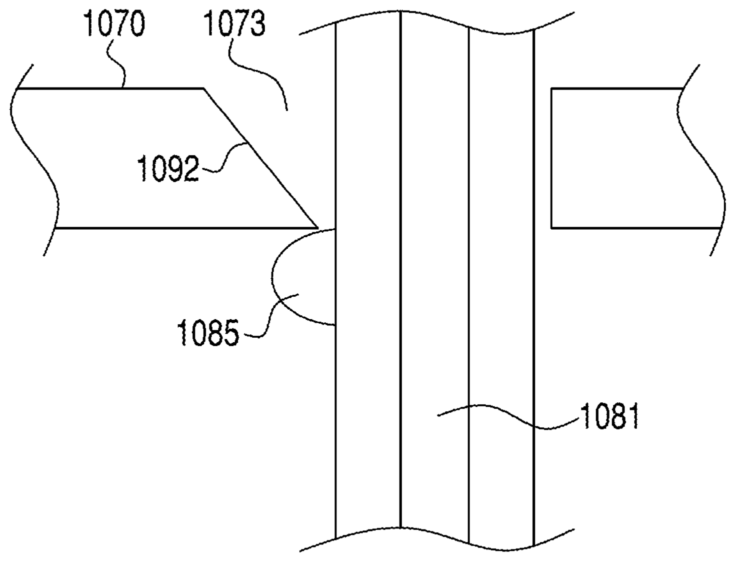
FIG. 1P 1050
1070C
1082
1072
1076
1075C
1077C
1060
1080
1071
1081
1062
1070B
1075B
1070A
1076A
1075A 1070
1073
1084
1072
1082

1070
1084
1073
1064
1060
1074
1082
1050

P
1082
1086
1072
1086
1062
1064
1050
1074

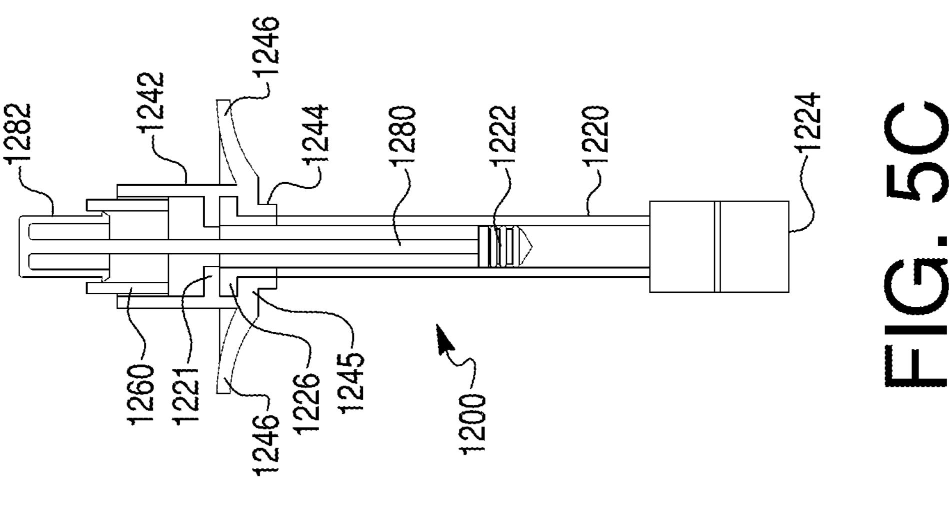
FIG. 5C
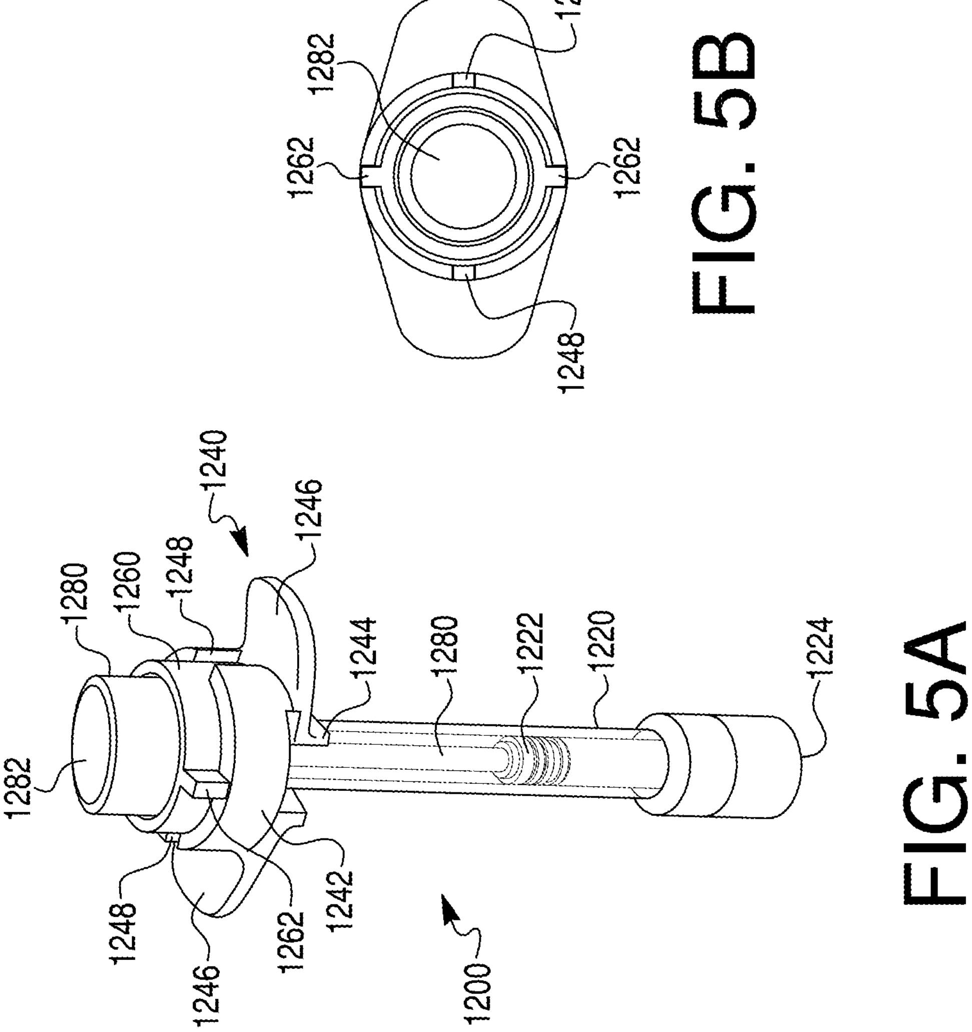
FIG. 5B
FIG. 5A

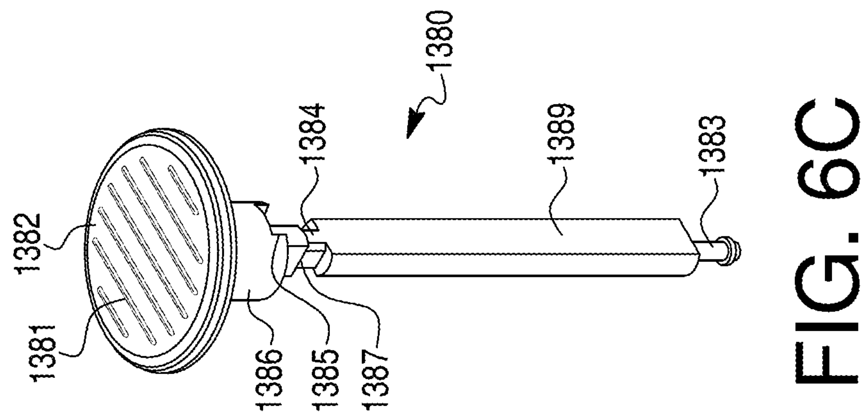
FIG. 6C
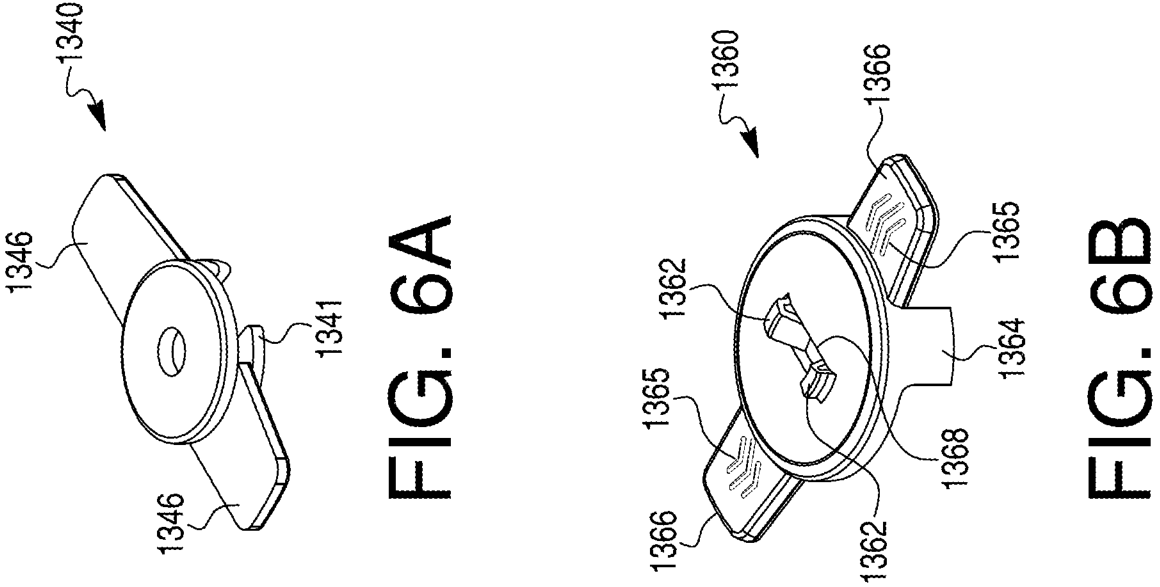
FIG. 6A
FIG. 6B

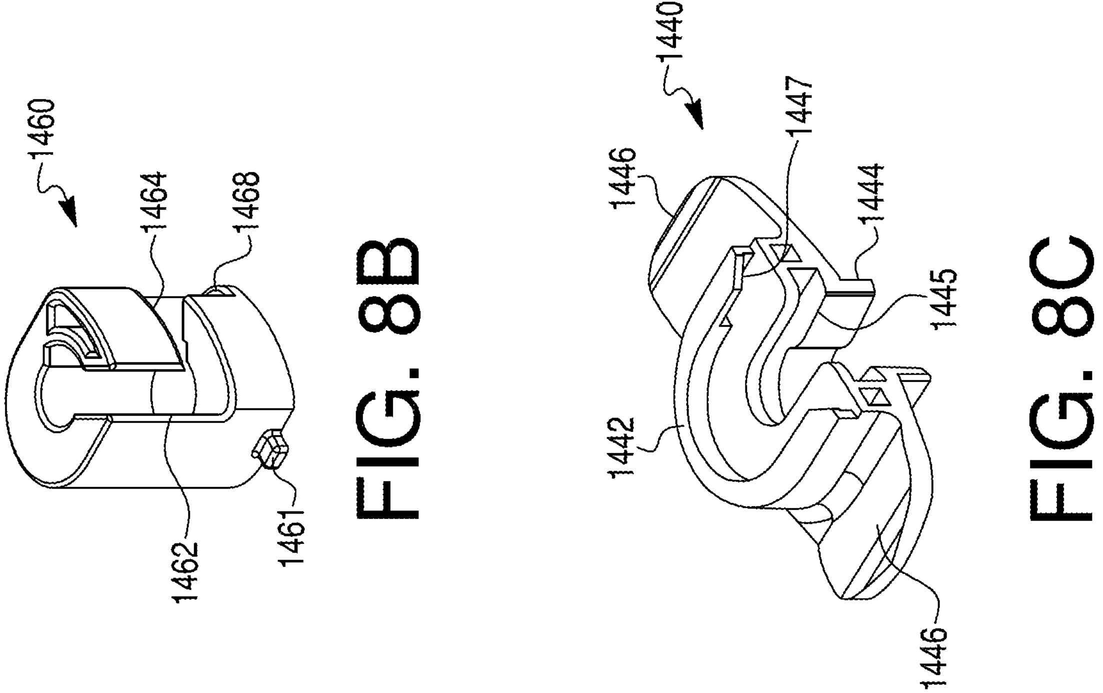
FIG. 8B
FIG. 8C
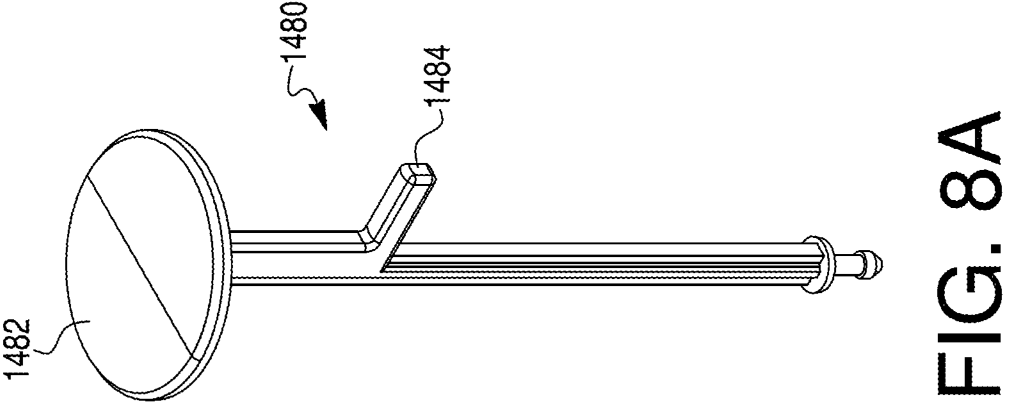
FIG. 8A 1500
1582
1586
1520
1522
1524
1542
1540
1584
1580
1588

1582
1588
1586
1584
1580
1520
1522
1524
1540
1500

1588
1582
1500
1520
1522
1524
1588
1542
1540

1586
1582
1500
1520
1522
1524
1588
1586
1542
1540

1850
1854
1856
1852

1820
1846
1844
1840
1842
1820
1846
1844
1842
1800

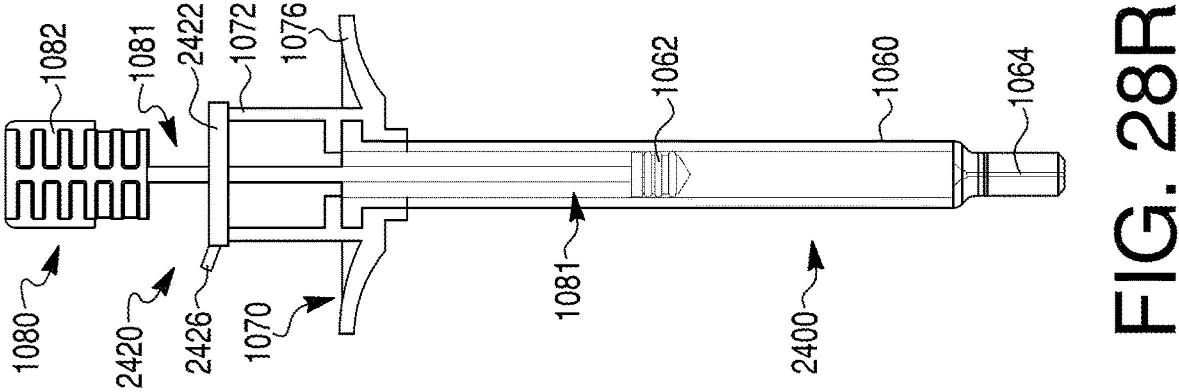
FIG. 28R
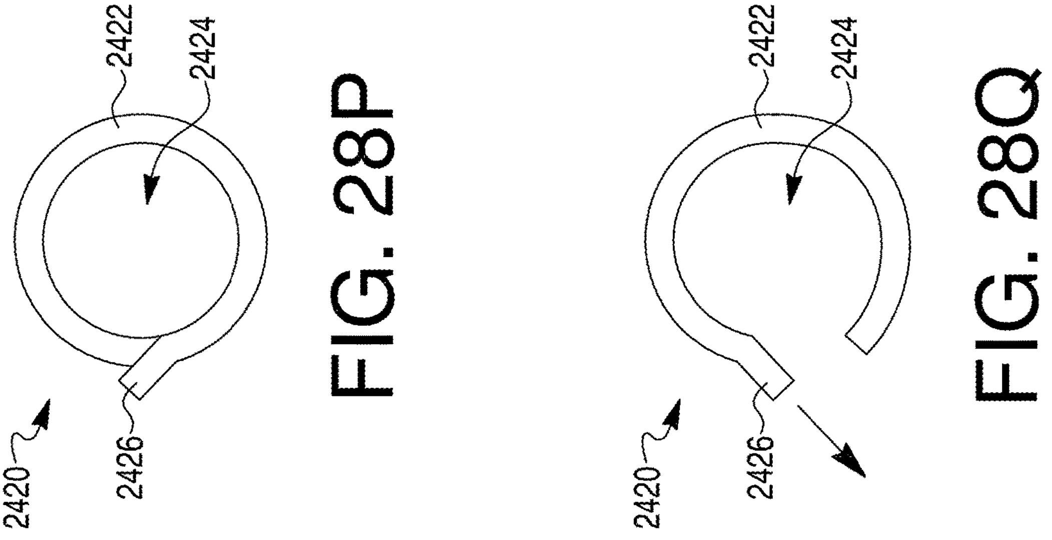
FIG. 28P
FIG. 28Q 1082
1072
1076
1060
1062
1064
1080
1070
1081
2400

2430
2434
1072
1076
1062
1060
1064
1080
1082
2432
1081
1070
1081
2400

2430
2434
1072
1076
1062
1060
1064
1080
1082
2432
1081
1070
1081
2400

2510
1072
1076
1060
1062
1064
2508
2504
2580
2502
1081
2500
1070

2510
2506
2502
1072
1076
1062
1060
1064
2508
2504
2505
2580
1081
2500
1070

2505
2504
2508
2506
2502
1072
1076
1062
1060
1064
2510
1088
2580
1070
1081
2500

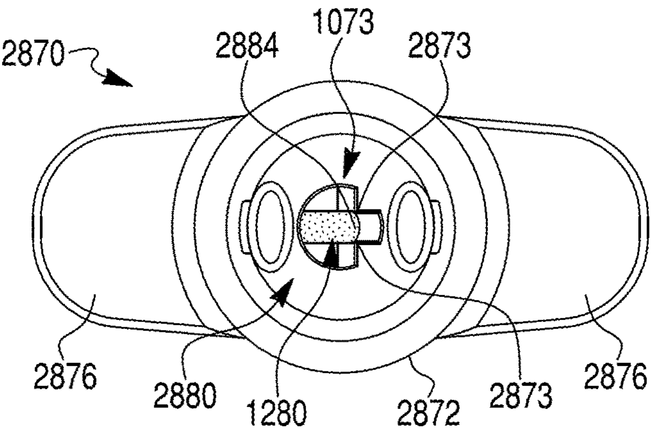
FIG. 40A
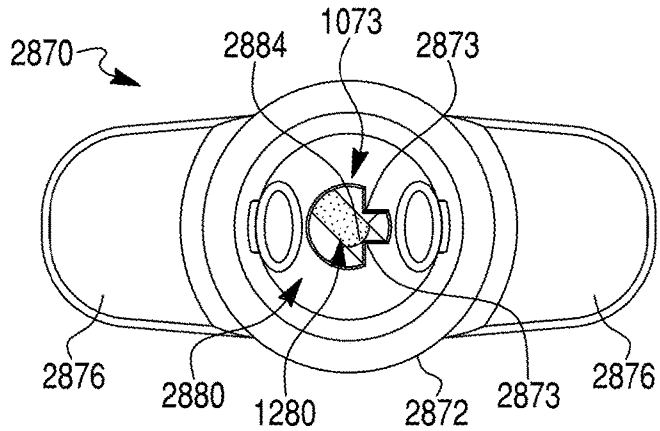
FIG. 40B
2870
1280
1073
2873
2876
2880
2884
2872
2873
2876
FIG. 40C

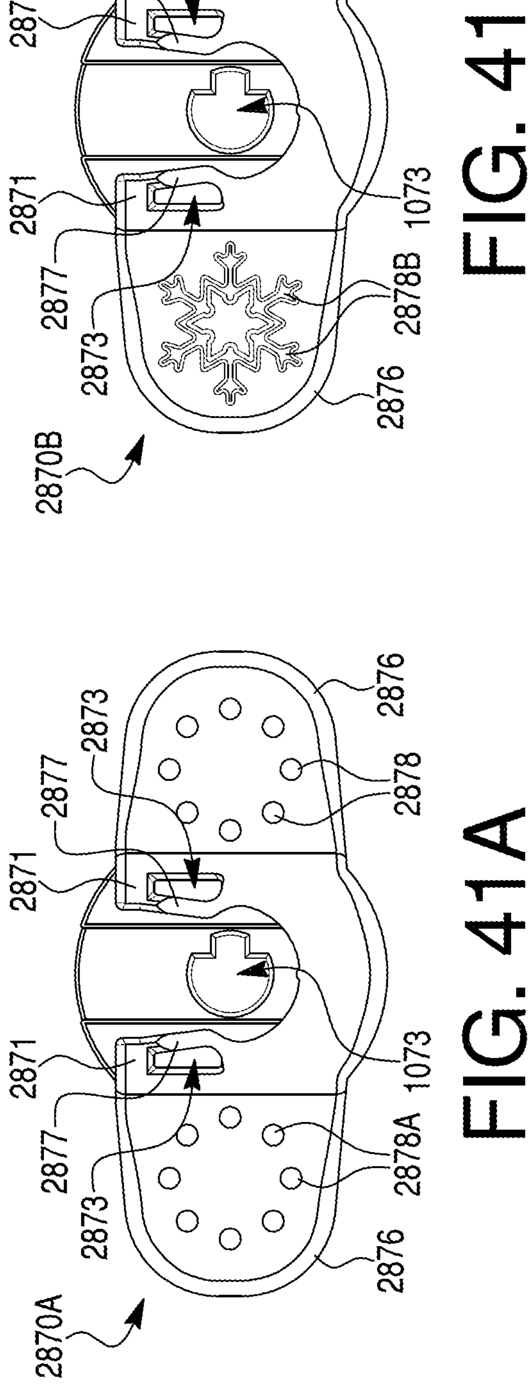
2870B
2871
2877
2873
2876
2878B
1073
FIG. 41B
2870A
2878
2878A
FIG. 41A
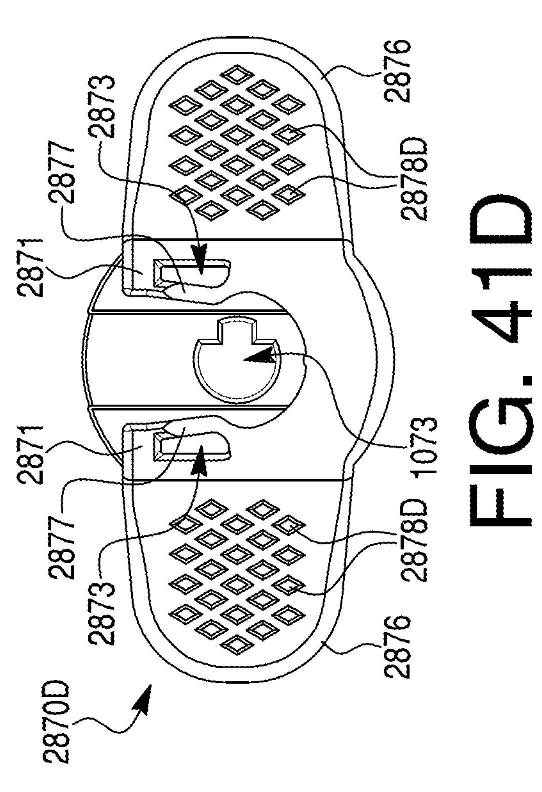
2870D
2871
2877
2873
2876
2878D
1073
FIG. 41D
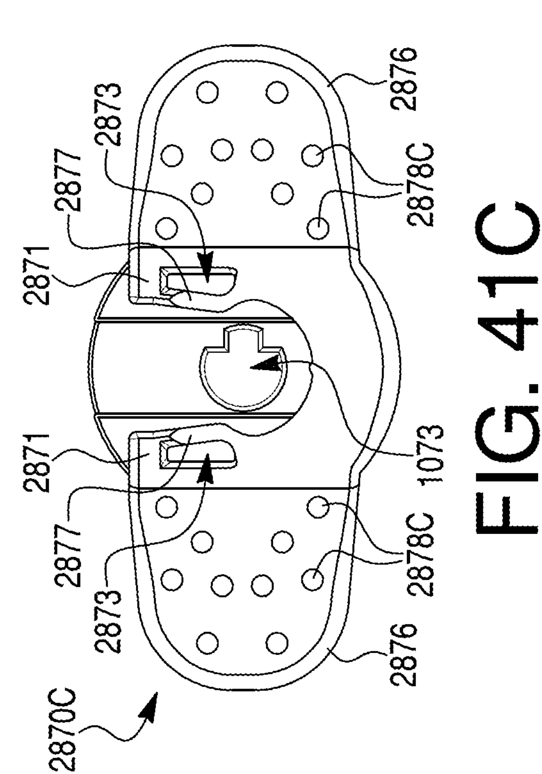
2870C
2871
2877
2873
2876
2878C
1073
FIG. 41C

DEVICES AND METHODS FOR PRECISION DOSE DELIVERY

CROSS-REFERENCE TO RELATED APPLICATIONS

This application is a continuation of U.S. patent application Ser. No. 17/354,850, filed on Jun. 22, 2021, which is a continuation application under 35 U.S.C. § 111(a) of pending International Application No. PCT/US2020/036200, filed Jun. 4, 2020, which claims priority to U.S. Provisional Application No. 62/857,678, filed on Jun. 5, 2019; and U.S. Provisional Application No. 62/860,481, filed on Jun. 12, 2019; each of which is incorporated by reference herein in their entireties. This application is also a continuation of U.S. patent application Ser. No. 17/457,526, filed on Dec. 3, 2021, which is a continuation application under 35 U.S.C. § 111(a) of International Application No. PCT/US2020/036200, each of which is incorporated by reference herein in their entireties.

FIELD OF DISCLOSURE

Aspects of the present disclosure relate to devices and methods for priming or otherwise configuring a dose delivery device, e.g., a syringe, to promote precision dose delivery. More specifically, embodiments of the present disclosure relate to devices and methods for loading, storing, transporting, and/or delivering precise doses of a drug substance or other fluid substance.

INTRODUCTION

Drug products including fluid drug substances may be deliverable to patients in a variety of ways, including via injection. In many cases, the precision and accuracy of a liquid drug product's volume is crucial. For example, medical professionals may have an interest in ensuring that an approved or prescribed volume of a drug substance is consistently delivered to each patient requiring the drug. Additionally, over- or under-dosing a patient with a drug substance, even slightly, may have an undesired (or even negative) clinical impact on the patient. Moreover, some drug products are prescribed at low volumes (e.g., under 100 μL). At low volumes, human error in preparing and delivering an accurate dose of a drug substance for injection may impact the drug's efficacy in a patient and the subsequent clinical effect on the patient.

Additional aspects of fluid drug delivery can complicate the goal of accurate dose delivery via injection. For example, for a correct dose of a drug substance to be dispensed from a device (e.g., a syringe), a corresponding accurate volume of the substance must be loaded into the device. Furthermore, handling, storage, packaging, and/or transportation of loaded devices must not result in inadvertent expulsion of drug substance from the devices. Additionally, prior to administration of a drug substance from a device, the device may need to be primed, e.g., to remove air bubbles and excess drug substance from within the device's needle and barrel. Incorrectly priming a device may result in expulsion of too much or too little drug substance from the device, which likewise may result in a decreased dose being delivered to a patient, or air bubbles being injected from the device into the patient.

The present disclosure also addresses needs unmet by prior publications WO2018/232408, published on Dec. 20, 2018; WO2018/224640, published on Dec. 13, 2018; and WO2018/224644, published on Dec. 13, 2018. Further, at least some embodiments of the present disclosure include features that are different than those features disclosed in publication WO2019/118588, published on Jun. 20, 2019. Some features include, for example, a plunger rod including one or more extensions extending distally from an actuation portion of the plunger rod and having hook or clip shaped parts for receipt with side openings of a flange piece. The plunger rod may include a neck having three or more sections, each having a different cross-sectional profile and/or shape relative to one another. Further features may include, for example, a flange piece including a collar having one or more internal grooves for receiving the hook or clip shaped parts of the one or more extensions, thereby allowing the extensions to flex radially-outward from a compressed configuration to an expanded configuration. The flange piece may include an opening configured to receive each of the three or more sections of the neck based on, for example, a rotational arrangement of the plunger rod relative to the flange piece.

A flange piece of the present disclosure may further include one or more movable ribs and/or one or more movable tabs for engaging a syringe body to couple the flange piece to the syringe body. For example, one or more movable ribs may be positioned proximal to a lip and lateral opening of the flange piece for receiving a top flange of the syringe body. The movable ribs may move, deflect, and/or deform in response to receiving the top flange through the lateral opening, and may be configured to apply a distally-directed force onto the top flange to secure the syringe body to the flange piece. By way of further example, the one or more movable tabs may be positioned distal to the lip and lateral opening. The movable tabs may move, deflect, and/or deform in response to the flange piece receiving the syringe body, and may be configured to apply a radially-directed force onto the syringe body to secure the syringe body to the flange piece. It should be appreciated that embodiments of the present disclosure include various other features shown and described herein that are different than those features disclosed in publication WO2019/118588.

SUMMARY

Disclosed herein are drug delivery devices. In one embodiment of the present disclosure, a drug delivery device includes a body, a plunger rod disposed partially inside the body, a protrusion extending from the plunger rod, and a blocking component on the body. When the protrusion is in a first position relative to the blocking component, the blocking component restricts distal movement of the plunger rod to a first stopping point, and when the protrusion is in a second position relative to the blocking component, the blocking component restricts distal movement of the plunger rod to a second stopping point.

In some aspects of the present disclosure, the drug delivery device further includes a stopper disposed in the body. Distal movement of the plunger rod distally moves the stopper, and a drug substance disposed in the body in between the stopper and a distal end of the body. Distal movement of the plunger rod to the first stopping point primes the drug delivery device, and distal movement of the plunger rod to the second stopping point dispenses a predetermined volume of the drug substance from a distal end of the device.

In some aspects of the present disclosure, moving the protrusion from the first position to the second position includes twisting the plunger rod relative to the blocking component. In some aspects of the present disclosure, the drug delivery device further includes a cavity in a proximal side of the blocking component, the cavity sized and configured to receive a portion of the protrusion. When the protrusion is in the second position relative to the blocking component, the protrusion is positioned proximally from the cavity, such that distal movement of the plunger rod moves the protrusion into the cavity.

In some aspects of the present disclosure, the cavity is a first cavity, and the drug delivery device further includes a second cavity in a proximal side of the blocking component, the second cavity sized and configured to receive a portion of the protrusion. The first and second cavity are located on opposite sides of a central longitudinal axis of the drug delivery device. In some aspects of the present disclosure, the blocking component includes a flange and is coupled to a proximal end portion of the body, and the plunger rod passes through an opening in the blocking component. In some aspects of the present disclosure, the drug delivery device further includes an actuation portion at a proximal end portion of the plunger rod, and the protrusion extends from the actuation portion.

In some aspects of the present disclosure, the actuation portion includes a generally cylindrical shape having a diameter greater than a width of the remainder of the plunger rod. The protrusion extends from a side of the generally cylindrical shape, and the actuation portion further includes a thumb pad on a proximal end of the actuation portion, and a ring on an exterior surface on the side of the generally cylindrical shape. In some aspects of the present disclosure, the drug delivery device further includes a proximal collar on the blocking component, and the actuation portion partially fits inside the proximal collar.

In some aspects of the present disclosure, the plunger rod further includes a pair of extensions protruding distally from the actuation portion and the blocking component includes a pair of openings. A portion of each extension is configured to be received by one of the pair of openings in the first stopping point. In some aspects of the present disclosure, the blocking component includes one or more indents formed along a bottom wall of the blocking component. A portion of each extension is configured to be received by the one or more indents upon distal movement of the plunger rod relative to the blocking component to allow distal movement of the plunger rod to the second stopping point.

In some aspects of the present disclosure, the blocking component includes a pair of internal grooves formed along a sidewall of the blocking component. A portion of each extension is configured to be received by at least one of the pair of internal grooves upon rotation of the plunger rod relative to the blocking component to expand the extensions radially-outward from a compressed state to a relaxed state. In some aspects of the present disclosure, the protrusion is a first protrusion, and the drug delivery device further includes a second protrusion extending from the plunger rod in a direction opposite to the first protrusion. In some aspects of the present disclosure, the blocking component is slidably coupled to the body and includes a pair of internal ribs that are configured to engage a top flange of the body when the body is slidably coupled to the blocking component. The pair of internal ribs are configured to apply a distally-directed force onto the top flange.

In some aspects of the present disclosure, the blocking component is slidably coupled to the body and includes a pair of movable tabs that are configured to engage a sleeve of the body when the body is slidably coupled to the blocking component. The pair of movable tabs are laterally deflectable upon receiving the sleeve in the blocking component and are configured to apply a radially-directed force onto the sleeve. In some aspects of the present disclosure, the blocking component further includes a pair of finger flanges. Each of the finger flanges includes a textured surface having a predefined pattern that increases a grip of the blocking component.

According to another embodiment of the present disclosure, a drug delivery device includes a body, a plunger rod having a distal end coupled to a stopper inside the body, and a proximal end including an actuation portion with a thumb pad, a plurality of protrusions extending from the actuation portion, and a blocking component disposed on the body, the blocking component including a proximal collar. When the protrusions and the blocking component are in a first configuration, the blocking component restricts distal movement of the plunger rod to a first stopping point, and when the protrusions and the blocking component are in a second configuration, the blocking component restricts distal movement of the plunger rod to a second stopping point. The proximal collar is configured to receive the protrusions upon distal movement of the plunger rod when the protrusions are in the second configuration.

In some aspects of the present disclosure, the protrusions and the blocking component are movable from the first configuration to the second configuration by rotation of the actuation portion about a longitudinal axis in relation to the blocking component. In some aspects of the present disclosure, a difference between the first stopping point and the second stopping point is equivalent to a distance that the stopper must travel to expel a predetermined volume of a drug product from a distal end of the body. In some aspects of the present disclosure, the plurality of protrusions includes two protrusions disposed symmetrically about the actuation portion. In some aspects of the present disclosure, the blocking component further includes a pair of finger flanges. In some aspects of the present disclosure, the drug delivery device is a pre-filled syringe.

In some aspects of the present disclosure, the drug delivery device is changeable: (a) from a pre-use state to a primed state, by longitudinally moving the plunger rod until the plunger rod reaches the first stopping point; (b) from the primed state to a delivery state by rotating the plunger rod in relation to the blocking component until the protrusions and the blocking component are in the second configuration; and (c) from a delivery state to a used state by longitudinally moving the plunger rod until the plunger reaches the second stopping point. In some aspects of the present disclosure, the plunger rod includes a neck disposed distally from the actuation portion, and the neck interfaces with an opening in the blocking component to prevent proximal movement of the plunger rod. In some aspects of the present disclosure, the neck further interfaces with the opening in the blocking component to prevent movement of the drug delivery device from the delivery state to the primed state.

In a further embodiment of the present disclosure, a drug delivery device includes a body, a plunger rod, including: a distal portion coupled to a stopper inside the body; a proximal end including a generally cylindrical actuation portion disposed outside of the body; and two protrusions extending from opposite sides of the actuation portion in a symmetrical configuration. The drug delivery device further includes a blocking component coupled to the body, the blocking component including a collar configured to accept a distal part of the actuation portion and two cavities in the collar having proximally-facing openings. Each cavity is configured to accept a distal portion of one of the two protrusions. The plunger rod is longitudinally movable and rotatable about a longitudinal axis relative to the blocking component. When the drug delivery device is in a pre-use state, the protrusions and the cavity openings are not longitudinally aligned, and when the drug delivery device is in a delivery state, the protrusions and the cavity openings are longitudinally aligned. In some aspects of the present disclosure, the blocking component further includes a finger flange, and the drug delivery device further comprises a ribbed surface on a side of the actuation portion.

In a further embodiment of the present disclosure, a method of dispensing a substance from a drug delivery device having a plunger rod and a body is disclosed. The method includes advancing the plunger rod by a predetermined distance into the body until advancement of the plunger rod is resisted by a stop, rotating the plunger rod about a longitudinal axis, and actuating the plunger rod to dispense a predetermined volume of the substance.

In some aspects of the present disclosure, advancing the plunger rod and actuating the plunger rod include pressing an actuation portion of the plunger rod. In some aspects of the present disclosure, the plunger rod includes a protrusion, the stop includes a blocking component coupled to the body, and the blocking component abuts against the protrusion to resist advancement of the plunger rod.

In some aspects of the present disclosure, rotating the plunger rod includes twisting an actuation portion of the plunger rod relative to a blocking component of the plunger rod, until a protrusion on the plunger rod becomes longitudinally aligned with a cavity in the blocking component. In some aspects of the present disclosure, actuating the plunger rod includes pressing the actuation portion of the plunger rod to advance the protrusion into the cavity.

In some aspects of the present disclosure, the method further includes advancing the protrusion into the cavity until the protrusion abuts a distal side of the cavity, and the predetermined volume of the substance is dispensed when the protrusion abuts the distal side of the cavity.

In a further embodiment of the present disclosure, a drug delivery device includes a body, a stopper disposed inside the body, and a sleeve having a proximal end and a distal end. The distal end being disposed inside the body, proximally from the stopper. The device includes a plunger rod disposed at least partially inside the sleeve. When the stopper is in a ready position, distal advancement of one of (a) only the sleeve, (b) only the plunger rod, or (c) both the sleeve and the plunger rod together, relative to the body advances the stopper to a primed position. When the stopper is in the primed position, distal advancement of another of (a) only the sleeve, (b) only the plunger rod, or (c) both the sleeve and the plunger rod together, relative to the body advances the stopper to a dose completion position.

In some aspects of the present disclosure, the drug delivery device further includes a removable blocking component disposed between a proximal portion of the sleeve and a proximal end of the body. The blocking component obstructing distal advancement of the sleeve relative to the body. Distal advancement of the sleeve relative to the body after removal of the blocking component advances the stopper to the primed position. The blocking component is a clip removably secured around at least a portion of the sleeve.

In some aspects of the present disclosure, the drug delivery device further includes a removable locking component that couples the plunger rod to the sleeve. Distal advancement of both the sleeve and the plunger rod together relative to the body advances the stopper to the primed position. Distal advancement of only the plunger rod relative to the body after removal of the locking component advances the stopper to the dose completion position. In the dose completion position, a proximal end of the plunger rod abuts against a distal end of the sleeve, such that the plunger rod is prevented from advancing distally any further relative to the body. The removable locking component includes one of a pin, a tab, or a bar.

In some aspects of the present disclosure, the drug delivery device further includes a protrusion disposed on the plunger rod and an inner protrusion disposed on an interior wall of the sleeve distally to the protrusion of the plunger rod. Distal advancement of only the plunger rod relative to the body advances the stopper to the primed position and causes the protrusion of the plunger rod to contact the inner protrusion of the sleeve. Distal advancement of both the plunger rod and the sleeve relative to the body, after the protrusion of the plunger rod has contacted the inner protrusion of the sleeve, advances the stopper to the dose completion position.

In some aspects of the present disclosure, a compressible protrusion on the plunger rod and an opening disposed on an interior wall of the sleeve, proximally from the protrusion on the plunger rod. Distal advancement of only the plunger rod relative to the body advances the stopper to the primed position. Proximal withdrawal of the plunger rod until the compressible protrusion of the plunger rod enters the opening of the sleeve couples the sleeve to the plunger rod. Distal advancement of both the plunger rod and sleeve coupled together relative to the body advances the stopper to the dose completion position. In some aspects of the present disclosure, when the sleeve is coupled to the plunger rod, a total length of the combined sleeve and plunger rod along a proximal-distal axis is greater than a length of the plunger rod alone.

In some aspects of the present disclosure, the sleeve includes a finger flange. In some aspects of the present disclosure, the drug delivery device further includes a stop disposed at a proximal end of the body. The stop sized to block distal advancement of the sleeve or the plunger rod once the stopper is in the completion position.

In further embodiments of the present disclosure, a drug delivery device includes a body and a plunger rod having a distal portion disposed inside the body and a proximal portion disposed outside a proximal end of the body. The proximal portion having a width greater than a width of the distal portion. The device further includes an obstruction that, in an obstructing position relative to the plunger rod, prevents distal advancement of the plunger rod from a primed position to a dose completion position. Displacement of the obstruction from the obstructing position permits distal advancement of the plunger rod to the dose completion position.

In some aspects of the present disclosure, the drug delivery device further includes a collar affixed to a proximal end portion of the body. The collar surrounding the proximal portion of the plunger rod. The drug delivery device further includes a collar projection extending radially inward from the collar. The proximal portion of the plunger rod includes a channel into which the collar projection protrudes, the channel including a circumferential path and an axial dose completion path. The obstruction comprises the collar projection, which, when disposed in the circumferential path of the channel, prevents distal advancement of the plunger rod to the dose completion position. Displacement of the obstruction from the obstructing position comprises twisting the plunger rod about a longitudinal axis to align the collar projection with the axial dose completion path.

In some aspects of the present disclosure, the channel further includes an axial priming path offset from the axial dose completion path, and connected to the axial dose completion path by the circumferential path. Distal movement of the plunger rod such that the collar projection travels on the axial priming path advances the plunger rod to the primed position. In some aspects of the present disclosure, the collar further comprises a finger flange.

In some aspects of the present disclosure, the proximal portion of the plunger rod includes a projection extending radially outward. The drug delivery device further includes a rotatable alignment component disposed in between the proximal portion of the plunger rod and the body. The alignment component including a channel, the channel sized and configured to accommodate the plunger rod projection. The obstruction comprises a wall of the channel that blocks a distal axial path of the plunger rod projection when the plunger rod is in the primed position. Displacement of the obstruction from the obstructing position comprises rotating the alignment component to remove the wall of the channel from the distal axial path of the plunger rod projection.

In some aspects of the present disclosure, the drug delivery device further includes a finger flange coupled to a proximal end portion of the body. The rotatable alignment component is disposed between the finger flange and the proximal portion of the plunger rod. In some aspects of the present disclosure, the drug delivery device further includes a flange piece disposed at the proximal end of the body. The obstruction includes a removable cap that, when in the obstructing position relative to the plunger rod, is disposed partially in between the proximal portion of the plunger rod and the flange piece. In some aspects of the present disclosure, removal of the cap allows the proximal portion of the plunger rod to advance to a dose completion position. In the dose completion position, the proximal portion of the plunger rod contacts the flange piece. In some aspects of the present disclosure, the removable cap covers the proximal portion of the plunger rod when in the obstructing position.

In some aspects of the present disclosure, drug delivery device further includes a collar disposed between the proximal end of the body and the proximal portion of the plunger rod. The collar defining an opening sized to accommodate the proximal portion of the plunger rod upon distal advancement of the plunger rod beyond a primed position. The obstruction comprises a tab protruding radially outward from the proximal portion of the plunger rod, the tab preventing the proximal portion of the plunger rod from fitting into the opening of the collar. A depth of the collar opening coincides with a distance the plunger rod must travel to advance distally to the dose completion position.

In some aspects of the present disclosure, displacement of the obstruction from the obstructing position comprises either removing the tab or compressing the tab into a side of the proximal portion of the plunger rod. In some aspects of the present disclosure, the tab is a first tab, and wherein the obstruction further comprises a second tab protruding radially outward from the proximal portion of the plunger rod in a direction opposite the protruding direction of the first tab. In some aspects of the present disclosure, the obstruction comprises a tab that, when in the obstructing position, is disposed between the body and the proximal portion of the plunger rod. The plunger rod includes a geometry disposed proximally from the tab, and the geometry cannot advance distally past the tab when the tab is in the obstructing position.

In some aspects of the present disclosure, displacement of the obstruction comprises removing the tab from the drug delivery device by pulling the tab. In some aspects of the present disclosure, the drug delivery device further includes a flange piece, wherein a portion of the tab is disposed inside a cavity of the flange piece. In some aspects of the present disclosure, displacement of the obstruction comprises removing the tab from the drug delivery device by breaking the tab.

In some aspects of the present disclosure, the obstruction includes a flange piece that, in the obstructing position, is disposed proximally from the proximal end of the body, between the proximal portion of the plunger rod and the body, and is spaced from the proximal end of the body by a removable blocking component. Displacement of the obstruction from the obstructing position includes removing the blocking component and shifting the flange piece distally towards the proximal end of the body.

In some aspects of the present disclosure, the plunger rod includes a projection extending radially outward. The obstruction includes a lever having an end that, in the obstructing position, is located distally from the projection and blocks distal movement of the projection and thereby distal movement of the plunger rod. Displacement of the obstruction from the obstructing position comprises actuating the lever to remove the end of the lever from its location distal from the projection. In some aspects of the present disclosure, distal advancement of the plunger rod beyond the dose completion position is prevented by contact between the proximal portion of the plunger rod and a portion of a flange piece coupled to the body.

In further embodiments of the present disclosure, a drug delivery device includes a body and a sleeve affixed to the body. The sleeve including a proximal end, a distal end, and an opening disposed in a circumferential wall of the sleeve. The drug delivery device further includes a plunger rod passing through the sleeve, the plunger rod including a distal end portion disposed inside the body, and a radially-extending protrusion. The plunger rod may be distally advanced into the body from a ready position to a primed position. In the primed position, the protrusion of the plunger rod is disposed inside the opening, and further distal advancement of the plunger rod is resisted by contact between the protrusion and a wall of the opening. Pressure may be exerted on the protrusion to overcome the resistance to further distal advancement of the plunger rod.

In some aspects of the present disclosure, the opening in the sleeve is a second opening, and the sleeve further includes a first opening disposed in the circumferential wall of the sleeve proximally from the second opening, and a third opening disposed in the circumferential wall of the sleeve distally from the second opening. In the ready position, the protrusion of the plunger rod is disposed in the first opening, and further distal advancement of the plunger rod is resisted by contact between the protrusion and a wall of the first opening. After further distal advancement of the plunger rod past the primed position, the protrusion of the plunger rod is disposed in the third opening, and further distal advancement of the plunger rod is prevented.

In some aspects of the present disclosure, the radially-extending protrusion is a first protrusion, and the plunger rod further includes a second radially-extending protrusion opposite the first protrusion. Squeezing the first and second protrusions towards one another while applying axial pressure in the distal direction on the plunger rod overcomes the resistance to further distal advancement of the plunger rod. In some aspects of the present disclosure, a proximal end of the sleeve includes a flared opening. Distally advancing the plunger rod from the ready position to the primed position includes advancing the protrusion into the flared opening and through the sleeve, whereby the protrusion is compressed between an interior of the sleeve and the plunger rod, until the protrusion extends into the opening disposed in the circumferential wall of the sleeve. In some aspects of the present disclosure, the protrusion includes a distally-tapering profile to aid in distal advancement of the plunger rod.

In further embodiments of the present disclosure, a drug delivery device includes a body, a plunger rod including a distal end portion disposed inside the body and a rotatable element, and a sleeve affixed to the body, the sleeve including a proximal opening into which the plunger rod may be advanced. Rotating the rotatable element causes distal advancement of the plunger rod to a primed position. Once the plunger rod is in the primed position, further rotation of the rotatable element is resisted.

In some aspects of the present disclosure, the rotatable element includes a cam lever. Once the plunger rod is in the primed position, the plunger rod may be depressed into the body to distally advance the plunger rod to a dose completion position. In some aspects of the present disclosure, the drug delivery device further includes a collar disposed at a proximal end of the body, an interior of the collar including a proximal threaded portion forming a proximal helical path. The rotatable element comprises a proximal portion of the plunger rod including a protrusion. The proximal portion of the plunger rod may be rotated about a longitudinal axis to cause the protrusion to travel distally along the proximal helical path. Once the protrusion reaches the end of the proximal threaded portion of the collar, the plunger rod is in the primed position.

In some aspects of the present disclosure, once the plunger rod is in the primed position, the plunger rod may be depressed axially into the body to distally advance the plunger rod to a dose completion position. In some aspects of the present disclosure, the interior of the collar further includes a distal threaded portion. Threads of the distal threaded portion form a distal helical path offset from, and opposite to, the proximal helical path. Alignment of the protrusion with the distal helical path places the plunger rod in the primed position. Rotation of the proximal portion of the plunger rod to cause the protrusion to travel distally along the distal helical path causes distal advancement of the plunger rod to a dose completion position.

In further embodiments of the present disclosure, a drug delivery device includes a body, a stopper disposed inside the body, and a first plunger rod having a first proximal end portion and a first distal end portion narrower than the first proximal end portion. The first distal end portion having a first length. The drug delivery device further includes a second plunger rod having a second proximal end portion and a second distal end portion narrower than the proximal end portion. The second distal end portion having a second length. The drug delivery device further includes a finger flange affixed to a proximal end portion of the body. The finger flange having a through hole aligned with a proximal opening of the body. The through hole sized to accommodate each of the first and second distal end portions without accommodating either of the first or second proximal end portions. Advancement of the first distal end portion through the through hole until the first proximal end portion abuts against the finger flange pushes the stopper distally to a primed position. Advancement of the second distal end portion through the through hole until the second proximal end portion abuts against the finger flange pushes the stopper distally to a dose completion position.

In further embodiments of the present disclosure, a method of assembling a drug delivery device includes coupling a body to a blocking component, wherein the blocking component is a flange piece, and coupling a plunger rod to the blocking component such that the plunger rod is disposed partially inside the body in a preassembled state and inhibited from proximal movement relative to the blocking component. In the preassembled state, the plunger rod is configured to move distally relative to the blocking component to a first stopping point with a protrusion of the plunger rod engaging the blocking component, thereby causing a priming dose of a medicament to be expelled from the body. When the protrusion is engaged to the blocking component, the blocking component is configured to restrict distal movement of the plunger rod to a first stopping point. The plunger rod is further configured to, while the plunger rod is at the first stopping point, rotate relative to the blocking component to disengage the protrusion from the blocking component, and move distally relative to the blocking component to a second stopping point with the protrusion engaging the blocking component, thereby causing a delivery dose of a medicament to be expelled from the body.

In some aspects of the present disclosure, the method further includes inserting a top flange of the body into an opening of the blocking component causing a tab of the blocking component to deflect radially-outward and a rib of the blocking component to deflect proximally. The tab applies a radially-inward directed force onto the body and the rib applies a distal force onto the top flange to secure the body to the blocking component. The method further includes inserting an extension of the plunger rod into a side opening of the blocking component to attach the plunger rod to the blocking component in the preassembled state. The plunger rod is configured to deflect the extension radially-inward in response to moving the plunger rod distally relative to the blocking component to the first stopping point, such that the extension is removed from the side opening. The extension is configured to move against an interior of the blocking component when the plunger rod rotates relative to the blocking component to align the protrusion with a slot of the blocking component. The extension flexes radially-outward within the blocking component when the protrusion is aligned with the slot. The extension is configured to extend into an indent along the interior of the blocking component when the plunger rod moves distally to the second stopping point.

BRIEF DESCRIPTION OF THE DRAWINGS

The accompanying drawings, which are incorporated into and constitute a part of this specification, illustrate various exemplary embodiments and, together with the description, serve to explain principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements in various embodiments, other than those specifically shown, are contemplated and are within the scope of the present disclosure.

There are many embodiments described and illustrated herein. The described devices and methods are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein.

FIGS. 5A-5C depict another exemplary delivery device according to additional embodiments of the present disclosure.

FIGS. 6A-6E depict a further exemplary delivery device according to additional embodiments of the present disclosure.

FIGS. 8A-8E depict a further exemplary delivery device according to embodiments of the present disclosure.

FIGS. 34-40C depict a further exemplary delivery device and method of using said delivery device, according to aspects of the present disclosure.

FIGS. 41A-41D depict exemplary flange pieces according to further embodiments of the present disclosure.

Figure 1B:
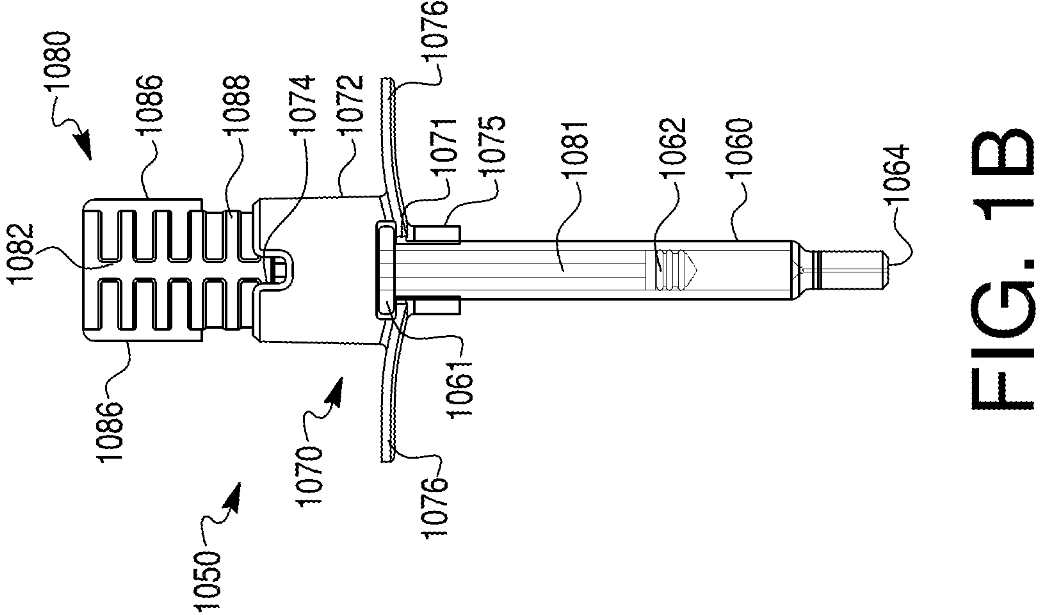
FIGS. 1A-1E depict an exemplary delivery device and components thereof, according to some embodiments of the present disclosure.

There are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

DETAILED DESCRIPTION

Embodiments of the present disclosure may be used in addition to and/or in combination with aspects of International Application No. PCT/US2018/065192, filed Dec. 12, 2018, which in incorporated by reference in its entirety herein.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Notably, an embodiment or implementation described herein as an "example" or "exemplary" is not to be construed as preferred or advantageous, for example, over other embodiments or implementations; rather, it is intended reflect or indicate the embodiment(s) is/are one "example," rather than "ideal." In addition, the terms "first," "second," and the like, herein do not denote any order, quantity, or importance, but rather are used to distinguish an element, a structure, a step or a process from another. Moreover, the terms "a" and "an" herein do not denote a limitation of quantity, but rather denote the presence of one or more of the referenced items. Additionally, the terms "about," "approximately," "substantially," and the like, when used in describing a numerical value, denote a variation of +/−10% of that value, unless specified otherwise.

Embodiments of the present disclosure may be used with any type of fluid-containing products, such as liquid drug substances, liquid placebos, or other liquids that may be dispensed in a dose form. As used herein, the term "drug substance" may refer to a formulated substance including an active ingredient or ingredients, such as, e.g., small or large molecules, such as pain medications, steroids, or biologics. As used herein, the term "biologic" may refer to a large molecule (e.g., having a size greater than 15 kDa, greater than 30 kDa, greater than 50 kDa, greater than 75 kDa, or greater than 100 kDa) created in a living system such as a cell. Biologics may include proteins (e.g., antibodies), nucleic acids, large sugars, etc. Unlike small molecules that may have well-defined chemical structures, biologics may have highly complex structures that cannot be easily quantified by laboratory methods. As used herein, the term "drug product" may refer to a volume of a drug substance apportioned into a primary packaging component for packaging, transportation, delivery, and/or administration to a patient.

The term "primary packaging component" refers to a packaging component for a drug product, such as a drug container, that is designed and manufactured to be in direct physical contact with the formulated drug substance. (See, for example, Guidance for Industry on Container Closure Systems for Packaging Human Drugs and Biologics, U.S. Department of Health and Human Services, Food and Drug Administration, Center for Drug Evaluation and Research, and Center for Biologics Evaluation and Research (May 1999), which is incorporated by reference herein.) Examples of primary packaging components include pre-fillable syringes, Luer syringes, cartridges, and vials made of glass, plastic, other polymers or co-polymers, and/or other materials.

As used herein, the terms "distal" and "distally" refer to a location (or portion of a device) relatively closer to, or in the direction of, a patient delivery site, and the terms "proximal" and "proximally" refer to a location (or portion of a device) relatively closer to, or in the direction of, a user end opposite a distal location/portion of a device.

As used herein, the term "body," when used in reference to a part of a device, may refer to a component of the device suitable for containing a volume of a drug substance. A body may include, e.g., a barrel (such as a syringe barrel), tube, cylinder, or other containing portion of a device. In some embodiments, a body may also include a distal end portion having a nozzle, needle, needle attachment site, and/or distal cap.

Embodiments of the present disclosure may be used with products typically having small dose volumes, such as, e.g., ophthalmic drug products. In some embodiments, devices of the present disclosure may be used with drug products including a large molecule, e.g., a molecular weight of 30 kDA or greater. In some embodiments, devices of the present disclosure may be used with drug products including a fragment of a large molecule. For example, in some embodiments, devices of the present disclosure may be used with drug products including an antigen-binding molecule. In some aspects, the antigen-binding molecule may be an antibody or antigen-binding fragment. In some embodiments, devices of the present disclosure may be suitable for use with drug products including ingredients such as, e.g., aflibercept, alirocumab, abicipar pegol, bevacizumab, brolucizumab, conbercept, dupilumab, evolocumab, tocilizumab, certolizumab, abatacept, rituximab, infliximab, ranibizumab, sarilumab, adalimumab, anakinra, trastuzumab, pegfilgrastim, interferon beta-la, insulin glargine [rDNA origin], epoetin alpha, darbepoetin, filigrastim, golimumab, etanercept, antigen-binding fragments of any of the above, or combinations of such binding domains, such as a bispecific antibody to VEGF or angiopoietin-2, among others.

In some embodiments, devices and aspects of the present disclosure can be used with any therapies for ophthalmic diseases, including for the treatment of patients with Diabetic Eye Disease, post-injection noninfectious Endophthalmitis, Neovascular (Wet) Age-related Macular Degeneration (AMD), Macular Edema following Retinal Vein Occlusion (RVO), Diabetic Macular Edema (DME), and Diabetic Retinopathy (DR). In particular, large molecule and small molecule antagonists of VEGF and/or ANG-2, such as aflibercept, ranibizumab, bevacizumab, conbercept, OPT-302, RTH258 (brolocizumab), abicipar pegol (a pegylated designed ankyrin repeating protein (DARPin)), RG7716, or fragments thereof and in any concentration. Intravitreal (IVT) administration of therapeutic agents may be an effective treatment for such eye disorders (e.g., macular degeneration, retinal vein occlusion, macular edema, retinopathy, etc.), however, IVT administration includes various challenges such as drug product development, administration procedure and adverse events. For example, providing accurate and precise delivery of small volumes (10-100 μL) requires precise design of container components. Accordingly, inaccuracies in a dosage delivery (e.g., over or under-dosing) may provide undesired adverse events or lack of efficacy resulting in unpredictable and variable clinical responses.

In some embodiments, devices and aspects of the present disclosure may provide accurate dose delivery while also providing a container closure system for maintaining the agent in a sterile, stable, and safe condition to increase an intended shelf-life and efficacy of the agent. IVT drug products are primarily presented in glass vials, however, pre-filled syringes offer a more convenient administration by reducing the number of steps required for dose preparation. Preassembling the agent in the devices of the present disclosure may minimize the steps necessary for preparing a dose for delivery to a patient. Product development studies may focus on primary container component characterization, material compatibility with the formulation, formulation stability, fill volume determination, extractable/leachable and terminal sterilization.

Additionally, careful selection of ancillary components such as disposable syringes and needles, and a detailed administration procedure that includes dosing instructions can ensure successful administration of the product. Despite significant efforts in improving the drug product and administration procedures, ocular safety concerns such as endophthalmitis, increased intraocular pressure and presence of silicone floaters have been reported. Devices and aspects of the present disclosure may provide detailed administration procedures (e.g., priming instructions, dosing instructions, etc.) to ensure successful administration of the agent to a patient to minimize such ocular safety concerns. In some embodiments, devices and aspects of the present disclosure can also be used for cosmetic applications or medical dermatology, such as treatment or diagnosis of allergic responses.

In some embodiments, devices and aspects of the present disclosure can be used to perform various eye injection procedures, such as, for example, intraocular treatments and surgeries involving an intravitreal injection of a drug product. Devices and aspects of the present disclosure may be used to dispense drug products of varying protein concentration and/or viscosity, including, for example, drug products having a viscosity ranging from about 1 centipoise to about 10 centipoise, from about 2 centipose to about 9 centipose, from about 3 centipose to about 8 centipose, from about 4 centipose to about 7 centipose, or from about 5 centipose to about 6 centipose. Drug products having still other viscosities also are contemplated. Providing a precise dose with a device of the present disclosure may be important given a possible variability in protein concentration or viscosity of a drug product being delivered to a patient. Devices and aspects of the present disclosure may be further used to dispense varying volumes and/or quantities of a drug product, such as, for example, volumes ranging from about 1 μL to about 200 μL, from about 10 μL to about 190 μL, from about 50 μL to about 150 μL, from about 75 μL to about 125 μL, from about 90 μL to about 110 μL, or about 100 μL. Devices of the present disclosure may be configured and operable to require application of a minimum force exceeding a threshold for performing one or more procedures, such as, for example, priming a device, delivering a dosage, and the like. By requiring application of the minimum force, devices of the present disclosure may promote control in administering a consistent dose of a drug product, and promote safety by minimizing inadvertent movement of the device's components, thereby potentially reducing pain, discomfort, and injury to a patient.

For some products in particular, e.g., ophthalmic or other drug products, dose accuracy may be particularly important. However, it is also contemplated that embodiments of the present disclosure may be applicable to any other liquid products or any other context for which precise methods for setting and administering a reliably accurate dose or delivery volume are beneficial.

In some embodiments, devices according to the present disclosure may be manufactured, packaged, filled, and/or otherwise prepared according to processes relevant to the products (e.g., drug products) of which they may be a part. For example, in some embodiments, devices according to the present disclosure may be sterilized, either before or after being filled and/or packaged. For example, in some embodiments, devices according to the present disclosure may be filled and packaged in, e.g., blister packaging, and/or may be terminally sterilized using any suitable method in the art. For example, devices according to the present disclosure may be terminally sterilized using a chemical sterilization method, such as a method including ethylene oxide or hydrogen peroxide (e.g., vaporized hydrogen peroxide). In some embodiments, devices according to the present disclosure may be terminally sterilized using methods described in, e.g., International Application No. PCT/US2018/021013, filed Mar. 6, 2018, which is incorporated by reference herein in its entirety.

Dose delivery devices available on the market, such as pre-filled syringes or syringes for use with vials, may not necessarily assist with accurately loading a desired volume of a substance, priming the devices, expelling an excessive volume of drug substance from the devices, and/or removing air bubbles from the devices. In dose delivery devices containing a small volume of a drug substance in particular (e.g., about 500 μL or less, about 300 μL or less, about 250 μL or less, about 200 μL or less, about 150 μL or less, about 100 μL or less, about 50 μL or less, or about 25 μL or less, such as between about 25 μL and about 50 μL, between about 50 μL and about 100 μL, between about 25 μL and about 100 μL, between about 50 μL and about 150 μL, between about 100 μL and about 250 μL, between about 100 μL and about 150 μL, between about 150 μL and about 250 μL, between about 200 μL and about 250 μL, between about 200 μL and about 500 μL, or between about 250 μL and about 500 μL), it may also be difficult to confirm the presence of the correct dose of a drug substance in the device with the naked eye. Currently in the dose delivery device market, and specifically in the syringe market, there is a need for mechanisms that allow a user to set precisely for delivery a small volume of a product in a syringe (e.g., a pre-filled or fillable/refillable syringe), prime the syringe, remove air bubbles from the syringe, and/or confirm or be assured that the dose volume in the syringe is correct. Embodiments of the present disclosure may assist manufacturers, drug product providers, medical professionals, and/or patients with accurately making, filling, or otherwise preparing a dose administration device, priming the device, removing bubbles from the device, confirming the dose, and/or administering a dose from the device to a patient. Moreover, embodiments of the present disclosure may assist in preventing or mitigating errors or variation in device manufacture or use, such as errors or variation in placement of dose lines on devices, variation in device geometry (e.g., variation in syringe neck geometry), variations in component manufacturing tolerance, and/or variation or errors in setting a dose line prior to delivery of a product.

In some instances, embodiments of the present disclosure may be of particular assistance to individuals who may have difficulty setting doses with precision and accuracy. For example, embodiments of the present disclosure may assist elderly individuals, young children, or persons with physical or mental disabilities in setting accurate doses.

Described herein are various embodiments of dose delivery devices, and in particular, for syringes. In some instances, embodiments or aspects of embodiments disclosed herein may be used in conjunction with existing syringe body parts to modify off-the-shelf products, which may reduce the development and manufacturing time for the dose delivery devices. In other instances, embodiments or aspects of embodiments disclosed herein may be included in devices during their manufacture. The syringes described herein may be pre-filled or may be fillable/refillable.

Embodiments of the present disclosure may include syringes having rotating parts, threaded parts, springs, gears, detents, channels, grooves, and the like, that may allow a user to precisely control the movement of priming and dosage delivery elements such as, e.g., plungers and/or stoppers. Such parts may be intended to reduce human error and/or increase accuracy.

In some embodiments, visualization devices, such as magnifiers, may be provided with, attached to, or otherwise disposed on, delivery devices, in order to help enhance visibility of dose measurement markers on the devices. It is contemplated that aspects of one embodiment (such as sleeves, channels, blocking components, protrusions, detents, threaded parts, grips, visual, tactile, or auditory indicators, etc.) may be combined with aspects of one or more other embodiments, to create various combinations and permutations of features in a single device.

In some embodiments, devices according to the present disclosure may be depicted as including one type of plunger rod and plunger, or as including a general schematic representation of a plunger rod and plunger. For example, some devices according to the present disclosure may be depicted or described as including, e.g., a plunger rod having a ball-tipped end, which engages with a stopper such that the plunger rod and the stopper may be attached together. It is contemplated that multiple and/or different configurations of plunger rods and stoppers may be appropriate for each of the embodiments disclosed herein. For example, in some cases, the aforementioned ball-tipped plunger rod may be used with embodiments disclosed herein. In some embodiments, a plunger rod may not be affixed to a stopper, and instead may be disposed near, next to, or flush against a stopper such that pressure from the plunger rod towards the stopper may push the stopper, but withdrawal, twisting, or other movement of the plunger rod may not cause the stopper to likewise be withdrawn, twisted, or otherwise moved. As another example, in some embodiments, a plunger rod may be affixed to a stopper by threads, a clip, or an adhesive, or may be of a single piece with a stopper (e.g., may have been manufactured in a single mold with a stopper).

In some embodiments, devices according to the present disclosure may include various cosmetic features relevant to intended users of the devices. For example, devices according to the present disclosure may be manufactured and sold for use with pediatric, elderly, or differently-abled patients. In such cases, devices according to the present disclosure may include child-friendly coloring, cartoon images, or other cosmetic features to appeal to children, or high-contrast coloring, textured surfaces, or other features to enhance ease of identification and/or use. In some cases, devices according to the present disclosure may include lettering, labeling, or other features designed to be easily recognized by the intended users. For example, lettering on a pediatric device or a device for use by a disabled or differently-abled person or an elderly person may have larger, more accessible labeling so that it may be more easily recognized and read by the user(s) of the device. In some embodiments, lettering or labeling may be raised, molded, or embossed.

Referring now to FIGS. 1A-1E, views of a delivery device 1050 and component parts are depicted. Device 1050 includes a body 1060, and a blocking component in the form of a flange piece 1070 with a proximal collar 1072 surrounding an opening 1073 (shown in, e.g., FIGS. 4B-4E), through which a plunger rod 1080 may pass into body 1060. Plunger rod 1080 includes an actuation portion 1082 which may be actuated (e.g., pushed or twisted) to rotate plunger rod 1080, or to move plunger rod 1080 longitudinally into body 1060. Actuation portion 1082 may be sized and configured to fit (e.g., nest or otherwise fit) inside proximal collar 1072.

Device 1050 may be, for example, an injection device, such as a syringe, for dispensing a predetermined volume of a formulated drug substance. In some embodiments, device 1050 may be a pre-filled syringe. For example, a user may receive an assembled and packaged device 1050 ready for use, with a volume of formulated drug substance already disposed between a stopper 1062 in body 1060 and an expulsion end 1064 of body 1060. In some embodiments, an air bubble (not shown) may also be disposed between stopper 1062 and expulsion end 1064. In further embodiments, device 1050 may be a fillable syringe.

Body 1060 may be any suitable body configured for holding and expelling a predetermined volume of a formulated drug substance. In some embodiments, body 1060 may have, e.g., a hollow cylindrical portion. Body 1060 may be configured to hold any suitable volume of a formulated drug substance for delivering to, e.g., a patient, and (together with other components of device 1050) to expel a predetermined amount of the held volume through, e.g., expulsion end 1064 in a priming step and/or delivery step. In some embodiments, body 1060 may be configured to hold and (together with other components of device 1050) expel a relatively small volume of formulated drug substance (e.g., less than about 100 μl, such as less than about 80 μl, less than about 60 μl, less than about 40 μl, less than about 20 μl, less than about 10 μl, about 95 μl, about 90 μl, about 85 μl, about 80 μl, about 75 μl, about 70 μl, about 65 μl, about 60 μl, about 55 μl, about 50 μl, about 45 μl, about 40 μl, about 35 μl, about 30 μl, about 25 μl, about 20 μl, about 15 μl, about 10 μl, or about 5 μl). Device 1050, together with its other components, may be further configured to minimize a residual volume of the formulated drug substance remaining in body 1060 after delivering the predetermined small volume to the patient. In some embodiments, body 1060 may be pre-filled (e.g., prior to completed assembly, packaging, sterilization and/or shipment of device 1050 to users). In some embodiments, stopper 1062 may be configured to hold a predetermined volume of a formulated drug substance inside a cavity of body 1060.

Flange piece 1070 may be of any suitable size and/or shape to serve as a blocking component in delivery device 1050, to close, partially close, cover, or partially cover an end of body 1060 opposite expulsion end 1064, and/or to support and hold plunger rod 1080 in place inside body 1060. In some embodiments, flange piece 1070 may include a distal collar 1075 configured to engage with body 1060 and hold flange piece 1070 in place in relation to body 1060. For example, distal collar 1075 may include a lip 1071 that may slide under or otherwise in relation to a body flange 1061, to hold flange piece 1070 in place (e.g., to slidably couple flange piece 1070 to body 1060). In alternative embodiments, lip 1071 of distal collar 1075 may be made of a flexible or semi-flexible material, so that it may snap in place over body flange 1061. In further embodiments, distal collar 1075 or another portion of flange piece 1070 may be adhered to, molded to, or otherwise affixed to, body 1060, or may engage with body 1060 via a friction fit.

Flange piece 1070 may be or include a blocking component; i.e., part or all of flange piece 1070 may be sized and configured to control movement of plunger rod 1080 by blocking movement of plunger rod 1080 when plunger rod 1080 is in certain configurations relative to flange piece 1070. For example, flange piece 1070 may be configured to control rotational and longitudinal movement of plunger rod 1080, e.g., via opening 1073 (see, e.g., FIGS. 4B-4E) that complements the size and shape of parts of plunger rod 1080 (e.g., neck 1084 and actuation portion 1082, and/or other portions of plunger rod 1080 as shown in FIGS. 4K-4O). As described in further detail herein, flange piece 1070 may be formed of various materials having a minimum strength and/or rigidity which may provide further control of a rotational or longitudinal movement of plunger rod 1080. For example, flange piece 1070 may be configured to resist proximal movement (or "pull back") of plunger rod 1080 (e.g., to inhibit disassembly of device 1050 by retracting plunger rod 1080) up to a predetermined force based at least in part on a material composition of flange piece 1070. It should be appreciated that flange piece 1070 may be configured such that applying a force exceeding the predetermined force may cause one or more of flange piece 1070 and plunger rod 1080 to break, thereby rendering device 1050 inoperable.

By way of further example, flange piece 1070 may be configured to resist rotational movement of plunger rod 1080 (e.g., to inhibit inadvertent rotation) up to a predetermined force based at least in part on a material composition of flange piece 1070. Additionally and/or alternatively, flange piece 1070 may be configured to resist distal movement of plunger rod 1080 to control a rate of dosage delivery (e.g., to inhibit inadvertent delivery) based at least in part on a material composition of flange piece 1070. Various other components of device 1050 other than flange piece 1070 may include a material composition providing a frictional interference to inhibit disassembly of device 1050, inadvertent rotation of plunger rod 1080, and/or inadvertent dosage delivery.

Figure 1A:
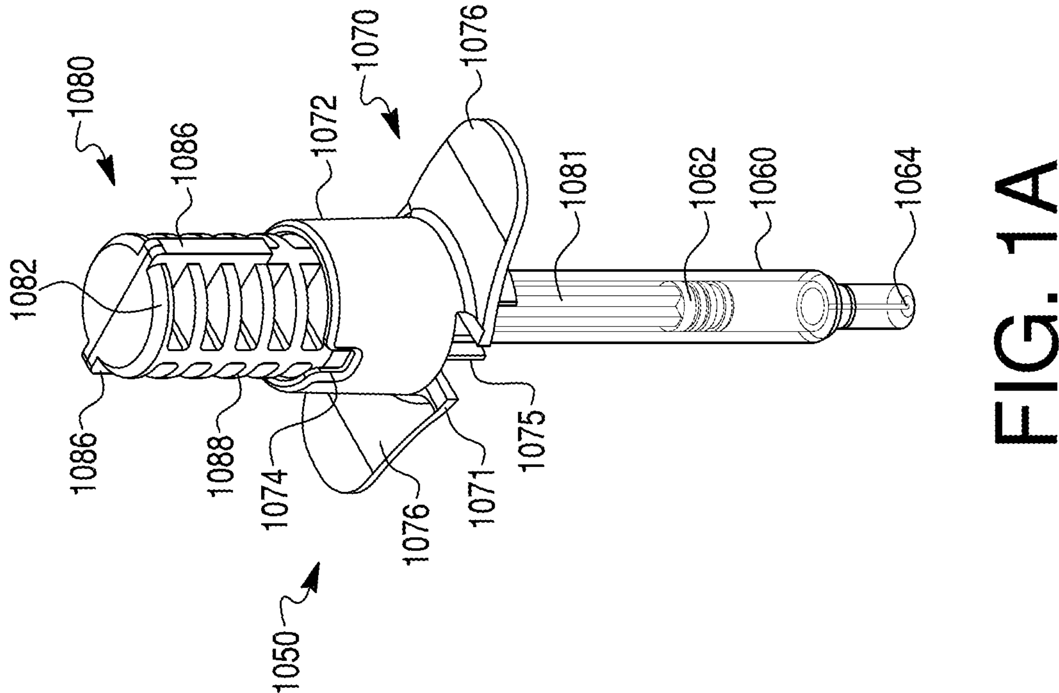

Proximal collar 1072 of flange piece 1070 may be sized and configured to accept part of actuation portion 1082 of plunger rod 1080, while blocking protrusions 1086 of plunger rod 1080 from moving distally past a predetermined point until plunger rod 1080 is rotated to a particular position. As shown in FIGS. 1A and 1B, collar 1072 may be cylindrical; in alternate embodiments, collar 1072 may have any suitable size or shape compatible with actuation portion 1082. Collar 1072 may also include cavities, e.g., slots 1074 into which protrusions 1086 of plunger rod 1080 may be received. Slots 1074 may have proximally-facing openings and may have a depth dimension parallel to a longitudinal axis of device 1050. A number and configuration of slots 1074 may correspond to a number and configuration of protrusions 1086 on plunger rod 1080. In some embodiments, slots 1074 may be disposed about a perimeter of collar 1072 in a radially symmetrical configuration. In further embodiments, collar 1072 may include only one slot 1074. The depth of slots 1074 may correspond to a distance plunger rod 1080 must move in order to push stopper 1062 towards expulsion end 1064, and dispense a predetermined volume of formulated drug substance from body 1060 through expulsion end 1064. Advantageously, the predetermined volume of formulated drug substance that is to be dispensed from body 1060 may be controlled during manufacturing, by, e.g., selecting a particular depth of slots 1074. In some embodiments, device 1050 may be configured such that normal variations in manufacturing of other parts of device 1050 (e.g., body 1060 or plunger rod 1080) may not cause variations in the volume of formulated drug substance that is to be dispensed from body 1060. As such, the predetermined volume may be controlled by simply varying manufacture of flange piece 1070.

In some embodiments, flange piece 1070 may include one or more flanges 1076, which may be sized and configured to aid a user in holding device 1050 and/or expelling a formulated drug substance from device 1050. In some embodiments, as depicted in FIGS. 1A-1E, flange piece 1070 may include two flanges 1076 opposite to one another and extending perpendicularly from a longitudinal dimension of device 1050. In some embodiments, flange piece 1070 may include other arrangements of a flange or flanges, such as four flanges, or one circumferential flange extending radially outward from a central longitudinal axis of device 1050. In some embodiments, flange piece 1070 may extend radially outward from a central longitudinal axis of device 1050 farther than a circumference of body 1060. In such embodiments, flange piece 1070 may support device 1050 if device 1050 is placed on a surface, may prevent device 1050 from rolling on a flat surface, and/or may allow device 1050 to be picked up more easily. In still further embodiments, blocking component aspects of flange piece 1070 (e.g., collar 1072) may be separate from flange piece 1070, such that delivery device 1050 includes a separate flange piece and blocking component.

Plunger rod 1080 in general may be rotatable about a central longitudinal axis (e.g., in one direction or in both directions). In some embodiments, rotation of plunger rod 1080 may be accomplished by grasping and/or twisting actuation portion 1082 relative to flange piece 1070 and/or body 1060. In some embodiments, protrusions 1086 may assist a user in grasping and/or twisting actuation portion 1082 relative to flange piece 1070 and/or body 1060, by providing additional surface area that a user may grasp and/or push against to twist actuation portion 1082. In some embodiments, only a part or parts of plunger rod 1080 (e.g., actuation portion 1082 and/or a neck 1084) may be rotatable relative to flange piece 1070 and/or body 1060. In some embodiments, plunger rod 1080 may be configured to rotate relative to flange piece 1070 in response to applying a predetermined twisting force onto actuation portion 1082. A material composition of flange piece 1070 may be determinative of the predetermined twisting force required to rotate plunger rod 1080 relative to flange piece 1070. For example, flange piece 1070 may be formed of various materials having a predetermined rigidity that may generate frictional resistance against plunger rod 1080 to control rotational movement of plunger rod 1080 up to the predetermined force (e.g., to inhibit inadvertent rotation/accidental twisting of plunger rod 1080). Further, a material composition of flange piece 1070 may provide a frictional tolerance to control a distal translation of plunger rod 1080 up to a predetermined force (e.g., to inhibit inadvertent dosage delivery by device 1050).

A stem 1081 of plunger rod 1080 may have any thickness and cross-sectional shape suitable for fitting into body 1060, while maintaining sturdiness. For example, in some embodiments, stem 1081 may have as great a thickness, along at least one dimension, as can fit and slide into body 1060. Advantageously, such a thickness may help in preventing unwanted wobbling of plunger rod 1080 relative to the other components of device 1050. In further embodiments, stem 1081 may have a smaller thickness while still maintaining sturdiness (e.g., not bending, breaking, or warping during assembly and/or use of device 1050). In some embodiments, portions of stem 1081 may be configured to allow for plunger rod 1080 to rotate relative to flange piece 1070, whereas other portions of stem 1081 may not (see, e.g., FIGS. 4K-4S).

Plunger rod 1080 may also include a distal tip 1083 (see, e.g., FIG. 1D) sized and configured to push, attach to, or otherwise interface with stopper 1062. Tip 1083 may have any size or shape suitable to achieve this purpose. In some embodiments, for example, tip 1083 may be sized and configured to clip to stopper 1062 via an opening in stopper 1062. In further embodiments, tip 1083 may have a ball-shape configured to fit into an opening in stopper 1062. In yet further embodiments, tip 1083 may present a flat surface parallel to a proximal surface of stopper 1062, and may be configured to push stopper 1062 distally without attaching to stopper 1062. In further embodiments, tip 1083 may have any shaped surface suitable for pushing stopper 1062 distally.

In some embodiments, neck 1084 of plunger rod 1080 and opening 1073 of flange piece 1070 may have complementary geometries that restrict the extent and direction that plunger rod 1080 (or a part thereof) may rotate, depending on the specific longitudinal and/or rotational position of plunger rod 1080 relative to flange piece 1070. In some embodiments, actuation portion 1082 of plunger rod 1080 and collar 1072 may also include complementary geometries that control the extent and direction that plunger rod 1080 may move relative to flange piece 1070. For example, rotation and/or longitudinal movement of plunger rod 1080 may be restricted based on priming, preparing, and/or drug delivery steps of a method of using device 1050 (see, e.g., the method described with respect to FIGS. 4A-4F and the additional/alternative method described with respect to FIGS. 4G-4H and 4I-4J), and the corresponding position of plunger rod 1080 with respect to each step in such methods. For example, plunger rod 1080 may be restricted from being moved out of flange piece 1070 in a proximal direction (e.g., falling out or being pulled out) once device 1050 is assembled. Moreover, plunger rod 1080 may be restricted from rotation about a longitudinal axis before device 1050 is in a "primed" state, and/or after device 1050 is in a "delivery" state. Additionally, longitudinal movement of plunger rod 1080 in the proximal direction (e.g., to "back out" plunger rod 1080), may be restricted after device 1050 is in a "primed" and/or "delivery" state by complementary geometries of neck 1084 of plunger rod 1080 and opening 1073 of flange piece 1070 and/or of actuation portion 1082 of plunger rod 1080 and collar 1072 of flange piece 1070. Advantageously, this may prevent unwanted plunger rod back out in cases where plunger rod 1080 is not held inside body 1060 by, e.g., being affixed to stopper 1062. For example, in some embodiments, plunger rod 1080 may be configured to simply contact or rest against stopper 1062, such that proximal movement of plunger rod 1080 does not move stopper 1062 proximally. In such cases, proximal movement of plunger rod 1080 may be prevented by interaction between complementary geometries of plunger rod 1080 and flange piece 1070. Moreover, interaction between actuation portion 1082 of plunger rod 1080 and collar 1072 of flange piece 1070 may restrict longitudinal movement of plunger rod 1080 in a distal direction. As an example, plunger rod 1080 may be restricted from moving distally after the "primed" state but before the "delivery" state.

Upon being moved to the "delivery" state, protrusions 1086 on actuation portion 1082 may be longitudinally aligned with slots 1074 of collar 1072, allowing for distal movement of plunger rod 1080 to dispense a desired volume of a drug substance from body 1060. As such, plunger rod 1080 may include a number and configuration of protrusions 1086 such that each protrusion 1086 may move distally into a slot 1074 when plunger rod 1080 is in a particular position (e.g., a "delivery" state). In some embodiments, one, two, three, or more protrusions 1086 may extend from actuation portion 1082, corresponding to one, two, three, or more slots 1074, respectively. For example, as depicted, two protrusions 1086 may extend from the sides of actuation portion 1082 in a radially symmetrical configuration (corresponding to two slots 1074 in collar 1072). In some embodiments, radial symmetry of multiple protrusions 1086 (and slots 1074) may advantageously allow for protrusions 1086 to fit into slots 1074 in multiple configurations (e.g., depending on whether actuation portion 1082 is twisted in one direction or another). In such embodiments, actuation portion 1082 may be twisted in either direction based on, e.g., user preference, right-handedness or left-handedness, or other factors. In some embodiments, plunger rod 1080 may not be pulled proximally or backed out of body 1060 (e.g., towards actuation portion 1082) after plunger rod 1080 is in a "primed" state and/or after a desired volume of formulated drug substance has been delivered from device 1050 by depression of plunger rod 1080 into body 1060 (e.g., due to a geometry of neck 1084 and/or opening 1073).

In some embodiments, device 1050 may be configured for ease of use, and may include one or more features that aid a user by providing tactile or visual feedback. For example, one, two, or more components of device 1050 may have contrasting colors or textures. In some embodiments, for example, flange piece 1070 may have a different coloring than plunger rod 1080. As a further example, a single component of device 1050 may have two or more colors or textures. In some embodiments, for example, actuation portion 1082 may include a first color on a distal part of actuation portion 1082, that becomes covered by collar 1072 when device 1050 is primed, and a second color on a second portion of actuation portion 1082, that moves adjacent to collar 1072 when device 1050 is primed, to help indicate to a user that device 1050 has been properly primed. As a further example, in some embodiments, flange piece 1070 may have a different tactile feel than plunger rod 1080 and/or body 1060. For example, flange piece 1070 may be relatively rougher or smoother than plunger rod 1080 and/or body 1060. As yet another example, one or more components of device 1050 may have textures that aid in holding, gripping, identifying, or using device 1050. For example, flange piece 1070 may have a slightly rough or raised texture to aid a user in gripping flanges 1076, and/or to prevent a user's fingers from slipping off of the flanges 1076 during use. In some embodiments, some or all of flange piece 1070 may have a smooth-feeling surface. As another example, actuation portion 1082 of plunger rod 1080 may include a rough or raised texture to aid in gripping and rotating plunger rod 1080. For example, as depicted in FIGS. 1A-1I, 3A-3C, 3E, and 4A-4I, actuation portion 1082 may include circumferential ribbing on its side(s). Actuation portion 1082 may have any suitable number of ribs on its side(s) to provide texture. In further embodiments, actuation portion 1082 may have no ribbing on its side(s).

In some embodiments, device 1050 or one or more of its components may include colors, labels or markers, which may indicate contents or a status of device 1050, and/or which may direct or provide instructions to a user of device 1050. Examples include one or more labels to indicate a priming position versus a dosage delivery position of the plunger rod, one or more labels to indicate directions in which to rotate or otherwise move plunger rod 1080, and/or one or more labels to indicate an amount of formulated drug substance included in device 1050 (e.g., linear markings on body 1060). Labels may be, e.g., adhered or printed on components of device 1050, or may be embossed on, or molded as a part of, components of device 1050. In some embodiments, one or more textured labels (e.g., embossed or molded on device 1050) may also serve as a textured, rough, or raised surface to aid a user in gripping or using device 1050. One or more exemplary labels may include words, numerals, indicators, and/or symbols (e.g., lines, padlocks, arrows, diagrams, etc.).

In some embodiments, device 1050 may be configured to make one or more sounds during its use. For example, device 1050 may make a "clicking" noise upon completion of a priming step, or upon rotation of the plunger rod to a position suitable for dispensing a predetermined volume of a formulated drug substance. A "clicking" noise may be produced by, e.g., friction between two or more components (e.g., plunger rod 1080 and flange piece 1070), or a portion of one component contacting another portion (e.g., neck 1084 of plunger rod 1080 contacting opening 1073 of flange piece 1070). In some embodiments, device 1050 may include one or more detents or protrusions on adjacent surfaces of, e.g., plunger rod 1080 and flange piece 1070, which may produce a clicking sound when contacting one another (e.g., wings 1089 on neck 1084 contacting detents 1078 surrounding opening 1073, as shown in FIGS. 4T-4X). Such sounds may serve as auditory feedback to indicate that a user has reached a particular step in the use of device 1050.

In some embodiments, device 1050 may include additional features or components to control movement of plunger rod 1080 relative to body 1060. For example, as shown in FIG. 1F, flange piece 1070 may include an opening 1079 through which a pin 1077 may be disposed. Pin 1077 may be sized and configured to interface with actuation portion 1082 of plunger rod 1080 (e.g., to slide into an opening (not shown) in actuation portion 1082), such that when pin 1077 is inserted so as to engage actuation portion 1082, plunger rod 1080 may not be moved proximally or distally relative to body 1060 and flange piece 1070. In some embodiments, pin 1077 may also prevent rotational movement of plunger rod 1080 relative to flange piece 1070. Pin 1077 may be inserted upon filling and assembly of a device (e.g., device 1050 shown in FIGS. 1A and 1B), to prevent unwanted movement of plunger rod 1080 prior to its use. In some embodiments, pin 1077 may remain inserted during packaging, transportation, and delivery of device 1050. Before use of device 1050, pin 1077 may be removed or otherwise positioned so that it does not engage actuation portion 1082.

Figure 1H:
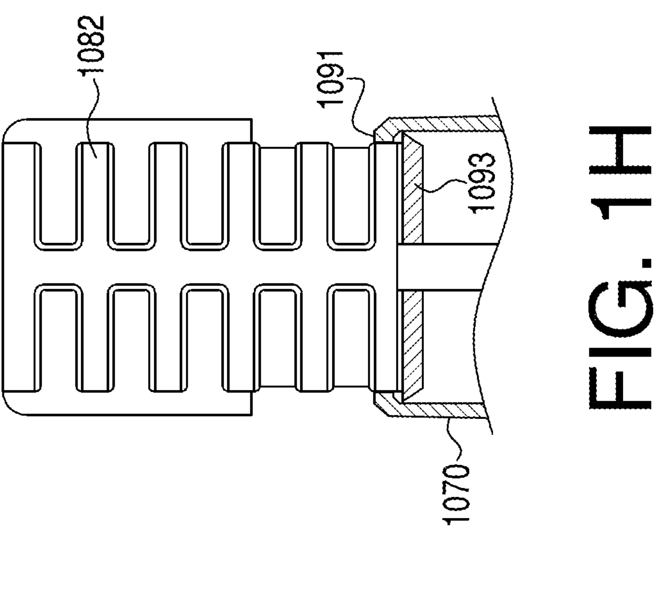
FIGS. 1F-2T depict additional aspects and embodiments of the exemplary delivery device of FIGS. 1A-1E.
Figure 1G:
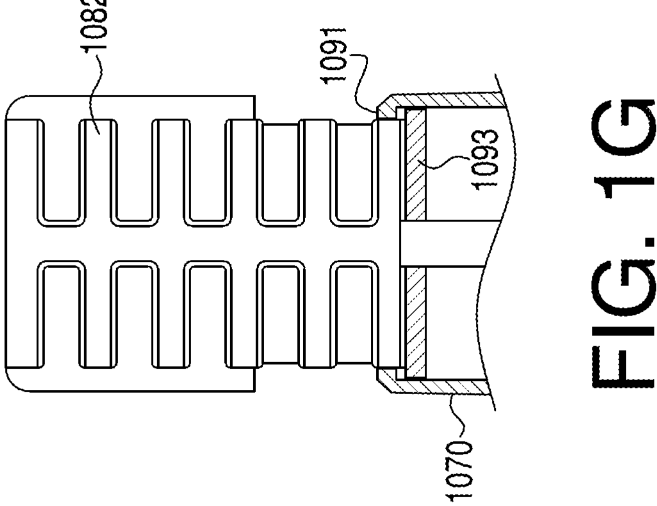
Figure 1F:
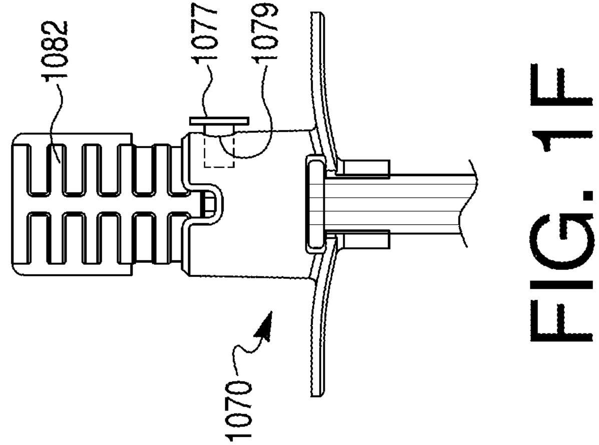

As shown in FIGS. 1G and 1H, in some embodiments, a protrusion 1093 may be disposed at a distal portion of actuation portion 1082, which may be located inside flange piece 1070 upon assembly of device 1050. An inward lip 1091 of flange piece 1070 may overhang protrusion 1093, such that actuation portion 1082 may not be pulled proximally out of flange piece 1070. In some embodiments, either protrusion 1093, lip 1091, or both may be disposed circumferentially about actuation portion 1082, such that lip 1091 blocks protrusion 1093 regardless of a rotational position of actuation portion 1082 relative to flange piece 1070. Protrusion 1093 and lip 1091 may have squared-off cross-sectional profiles, as shown in FIG. 1G, angled cross-sectional profiles, as shown in FIG. 1H, or any other suitable cross-sectional profiles. In some embodiments, a cross-sectional profile of protrusion 1093, lip 1091, or both may be selected to improve ease of manufacturing (e.g., machining or molding the shape of protrusion 1093 or lip 1091), or may be selected to improve assembly (e.g., insertion of plunger rod 1080 into and partially through flange piece 1070).

Figure 1J:
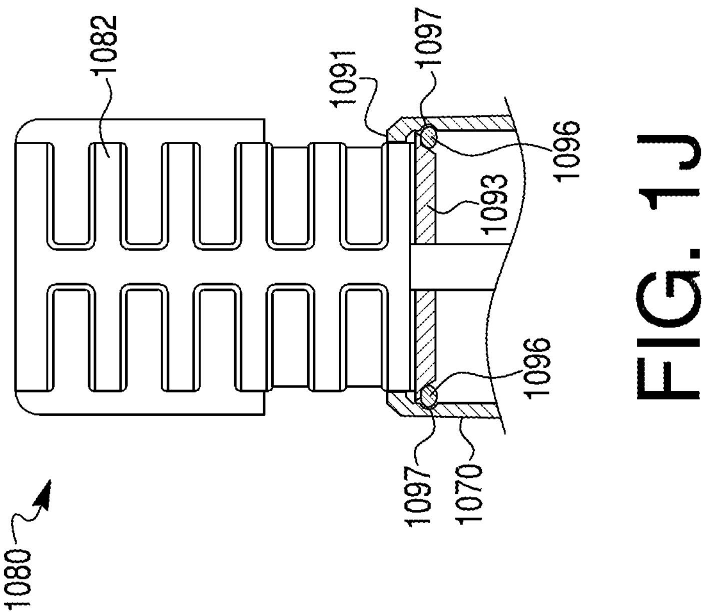
Figure 1I:
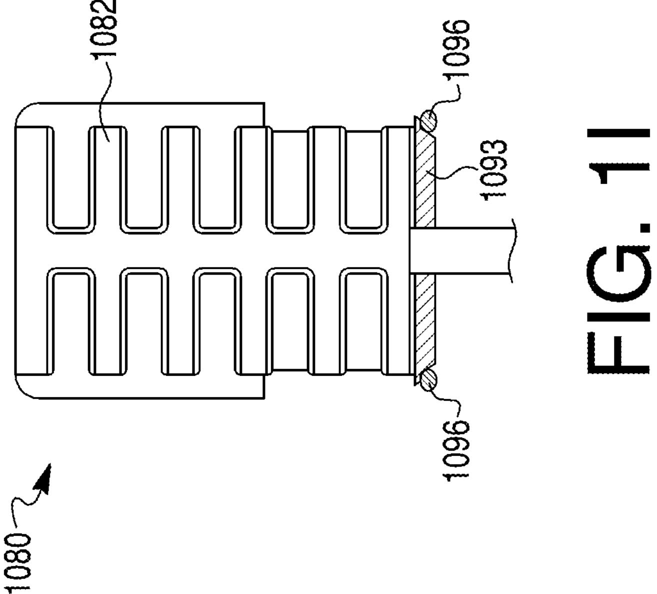

As shown in FIG. 1I, in some embodiments, actuation portion 1082 may include one or more projections 1096 extending radially outward from an exterior perimeter of protrusion 1093. For example, protrusion 1093 may include a pair of projections 1096 disposed about protrusion 1093 at opposite locations relative to one another. Projections 1096 may include various suitable sizes, shapes, and/or cross-sectional profiles. In some embodiments, projections 1096 may have a circular shape with a rounded exterior profile to facilitate movement of protrusion 1093 within flange piece 1070.

In the present example, projections 1096 may be positioned along a side of protrusion 1093 that longitudinally aligned with a corresponding side of actuation portion 1082 including protrusions 1086. In other examples, projections 1096 may be positioned along a side of protrusion 1093 that is offset (e.g., not in longitudinal alignment) with the side of actuation portion 1093 including protrusions 1086. Projections 1096 may be formed of various flexible materials, including, for example, a polymer such as plastic, rubber, etc. It should be appreciated that plunger rod 1080 may include additional and/or fewer projections 1096 on protrusion 1093, or other portions of actuation portion 1082, than those shown and described herein without departing from a scope of this disclosure.

FIG. 1J depicts a distal end portion of flange piece 1070 including one or more recesses 1097 along an interior surface. Recesses 1097 may be sized and shaped to receive projections 1096 when protrusion 1093 is received within flange piece 1070 and positioned adjacent and/or in contact with lip 1091. It should be appreciated that lip 1091 may be configured to require application of a hydrodynamic force onto plunger rod 1080 to receive projections 1096 and protrusion 1093 distally of lip 1091 and into flange piece 1070, thereby priming device 1050 and inhibiting retraction (e.g., proximal movement) of plunger rod 1080 relative to flange piece 1070. It should be appreciated that by inhibiting removal of plunger rod 1080 after an initial assembly into flange piece 1070, device 1050 may be configured to prevent reuse of device 1050 after an initial use, and/or to prevent inadvertent air intake forming bubbles within device 1050. In the present example, flange piece 1070 may include a plurality of recesses 1097 disposed about the distal end portion in an annular array relative to one another. The plurality of recesses 1097 may be spaced apart from one another about a circumference of flange piece 1070. In some embodiments, flange piece 1070 may include recesses 1097 having varying sizes and/or shapes relative to one another.

As described in further detail below, a subset of the plurality of recesses 1097 may be sized and shaped to receive and allow passage of projections 1096 therethrough upon movement of protrusion 1093 relative to flange piece 1070. A second subset of the plurality of recesses 1097 may be sized and shaped to receive and inhibit passage of projections 1096 therethrough such that protrusion 1093 is restricted from further movement relative to flange piece 1070, as explained in further detail below.

Figures 1K, 1L, 1M:
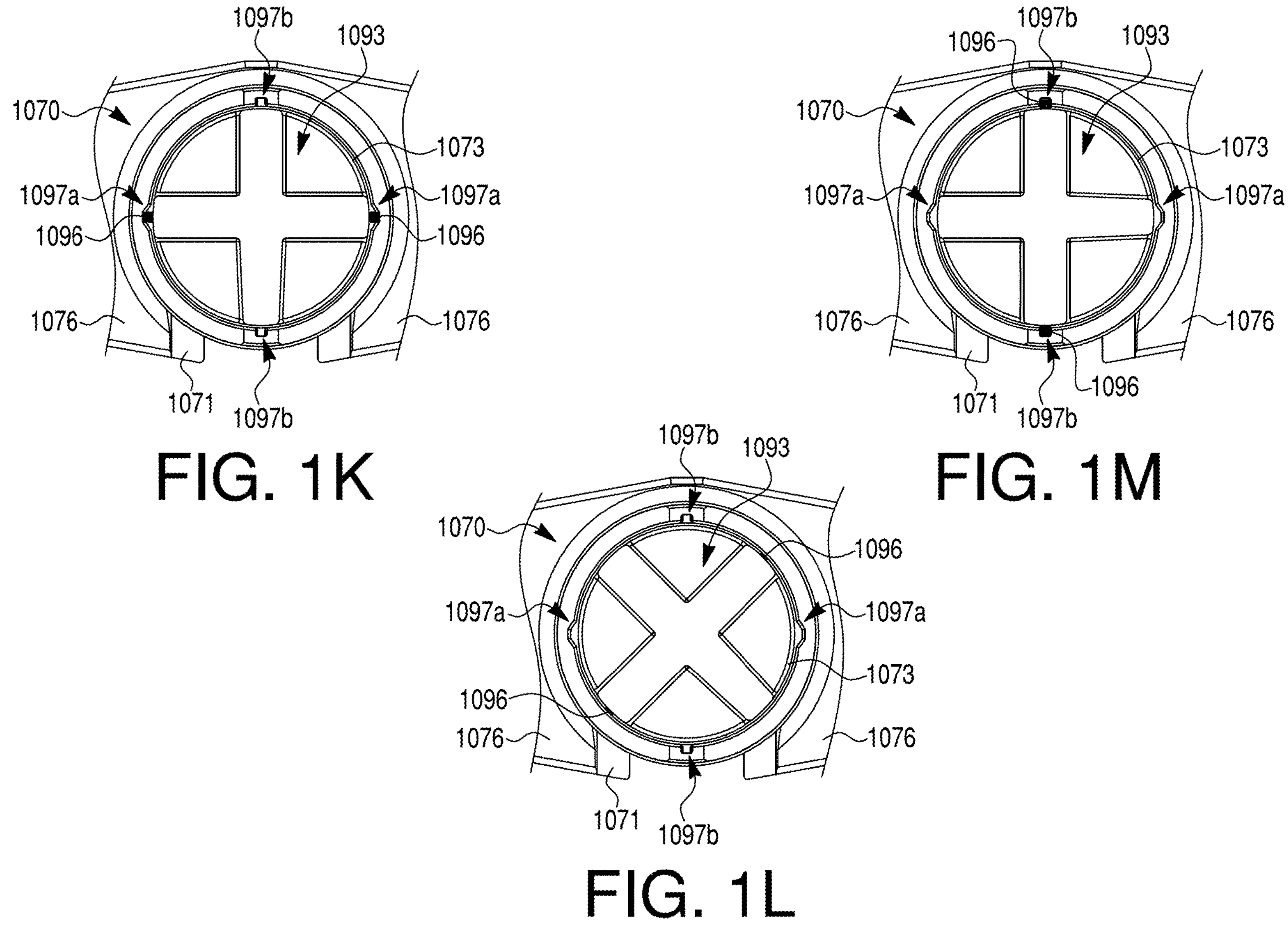

For example, as shown in FIG. 1K, flange piece 1070 includes a pair of widened recesses 1097*a* positioned about opening 1073 (with plunger rod 1080 received therethrough) at opposite locations relative to one another (e.g., spaced about 180 degrees apart from one another). Flange piece 1070 further includes a pair of narrowed recesses 1097*b* positioned about opening 1073 at opposite locations relative to one another (e.g., about 180 degrees from one another). A recess 1097*a* may be positioned about 90 degrees apart from an adjacent recess 1097*b*, along the circumference of flange piece 1070. Widened recesses 1097*a* may include a center wall transverse (e.g., perpendicular) to a longitudinal length of flanges 1076 and sidewalls that are angled relative to the center wall. Narrowed recesses 1097*b* may include a center wall parallel to the longitudinal length of flanges 1076 and sidewalls that are perpendicular to the center wall. It should be appreciated that widened recesses 1097*a* may form a larger opening for receiving projections 1096 relative to narrowed recesses 1097*b*. It should further be understood that sidewalls of recesses 1097*a*, 1097*b* may have a height that is parallel to a longitudinal length of device 1050.

In a first configuration seen in FIG. 1K, plunger rod 1080 is received through flange piece 1070 and protrusion 1093 is oriented relative to opening 1073 such that projections 1096 are received within widened recesses 1097*a*. The angled sidewalls of widened recesses 1097*a* may provide clearance to facilitate movement of projections 1096 out of widened recesses 1097*a* in response to a rotation of plunger rod 1080 relative to flange piece 1070. In this instance, projections 1096 may move along the angled sidewalls of widened recesses 1097*a* as protrusion 1093 rotates relative to opening 1073.

As seen in FIG. 1L, projections 1096 may abut against the interior surface of flange piece 1070 defining opening 1073 as protrusion 1093 rotates. Projections 1096 may generate a frictional interference against flange piece 1070 while moving between adjacent recesses 1097. FIG. 1M shows protrusion 1093 positioned relative to opening 1073 with projections 1096 aligned with and received in narrowed recesses 1097*b*. In this instance, plunger rod 1080 may be configured to generate an audible and/or tactile feedback in response to narrowed recesses 1097*b* receiving projections 1096. For example, a "click" or "snap" noise may be generated in response to a release of pressure applied to projections 1096 by the interior surface of flange piece 1070 when projections 1096 are received in narrowed recesses 1097*b*. Additionally and/or alternatively, an audible feedback may be produced in response to projections 1096 expanding and striking one or more walls defining narrowed recesses 1097*b* when received therein.

It should be appreciated that a frictional interference between projections 1096 and flange piece 1070 may be removed upon receipt of projections 1096 within narrowed recesses 1097*b*. The sidewalls of narrowed recesses 1097*b* may provide a physical restriction that inhibits further movement of projections 1096. In this instance, plunger rod 1080 may be fixed relative to flange piece 1070 such that protrusion 1093 is inhibited from further rotation relative to opening 1073 when projections 1096 are received within narrowed recesses 1097*b*.

As shown in FIGS. 1N-1P, in some embodiments, plunger rod 1080 may additionally or alternatively include a protrusion 1085 on stem 1081, which may be configured to interact with opening 1073 of flange piece 1070, such that protrusion 1085 may only move distally through opening 1073. A side 1092 of opening 1073 may be angled to allow for distal passage of protrusion 1085, and to block proximal passage of protrusion 1085, as stem 1081 moves through opening 1073. Protrusion 1085 and/or side 1092 may have any suitable shape or configuration to achieve this purpose. In some embodiments, a shape or configuration of protrusion 1085 and/or side 1092 may be selected to improve ease of manufacturing (e.g., machining or molding the shape of protrusion 1085 and/or flange piece 1070).

Figure 1R:
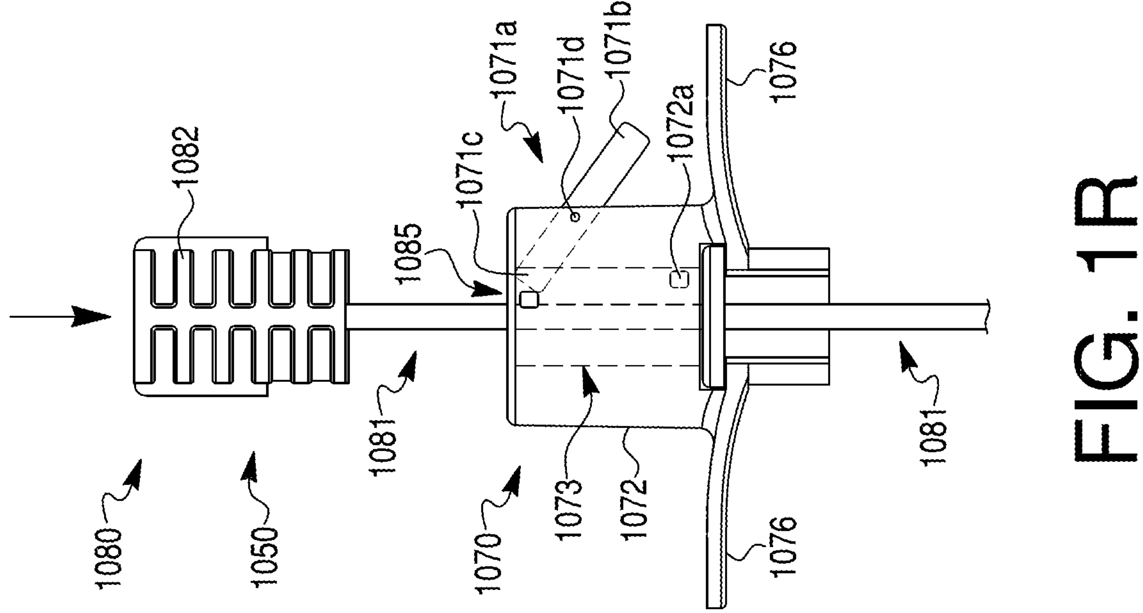
Figure 1Q:
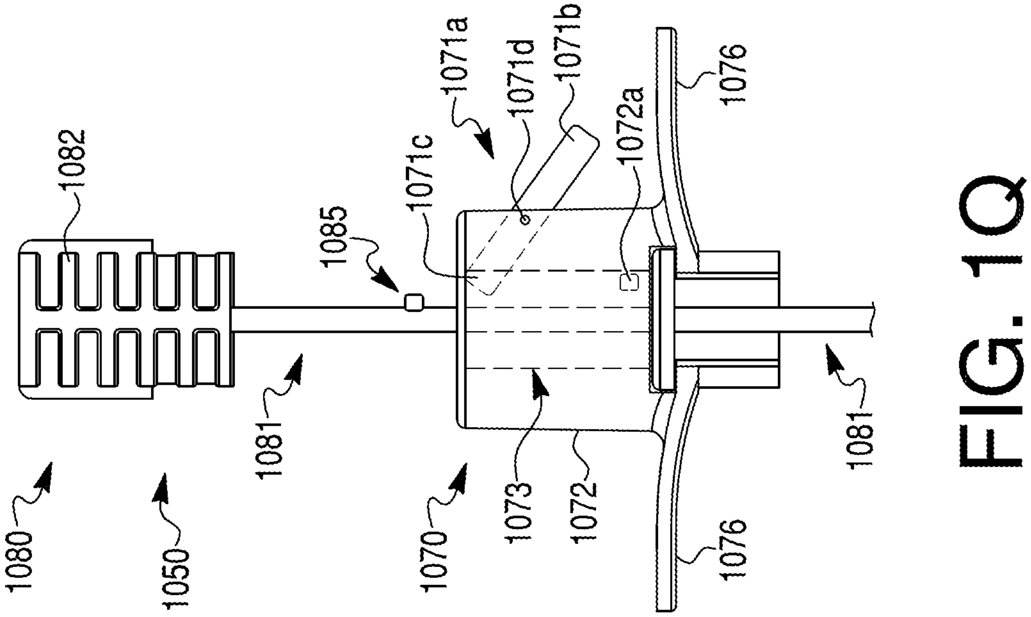

In other embodiments, flange piece 1070 may include a movable lever 1071*a* as seen in FIGS. 1Q-1T. Movable lever 1071*a* may include a first end 1071*b* extending outwardly from collar 1072 and a second end 1071*c* disposed within collar 1072. Movable lever 1071*a* may be movable (e.g., pivotable) about a rotation pin 1071*d*. Second end 1071*c* may be positioned within opening 1073 such that movable lever 1071*a* is configured to interact with protrusion 1085 upon receipt of plunger rod 1080 in flange piece 1070. Referring initially to FIG. 1Q, plunger rod 1080 may be configured to prime device 1050 by translating stem 1081 distally through flange piece 1070 until encountering movable lever 1071*a*.

As seen in FIG. 1R, second end 1071*c* may abut against protrusion 1085 when movable lever 1071*a* is in an obstructing position. Second end 1071*c* may be configured to inhibit translation of plunger rod 1080 relative to flange piece 1070 when plunger rod 1080 is in a primed position. It should be appreciated that a distance between second end 1071*c* and protrusion 1085 may define a priming distance for moving plunger rod 1080 to prime device 1050. Movable lever 1071*a* may be configured to move (e.g., pivot) relative to collar 1072 and about rotation pin 1071*d* to displace second end 1071*c* from the obstruction position. The pivoting axis, along which rotation pin 1071*d* extends, may be substantially perpendicular to the longitudinal axis along which plunger rod 1080 extends.

Figure 1T:
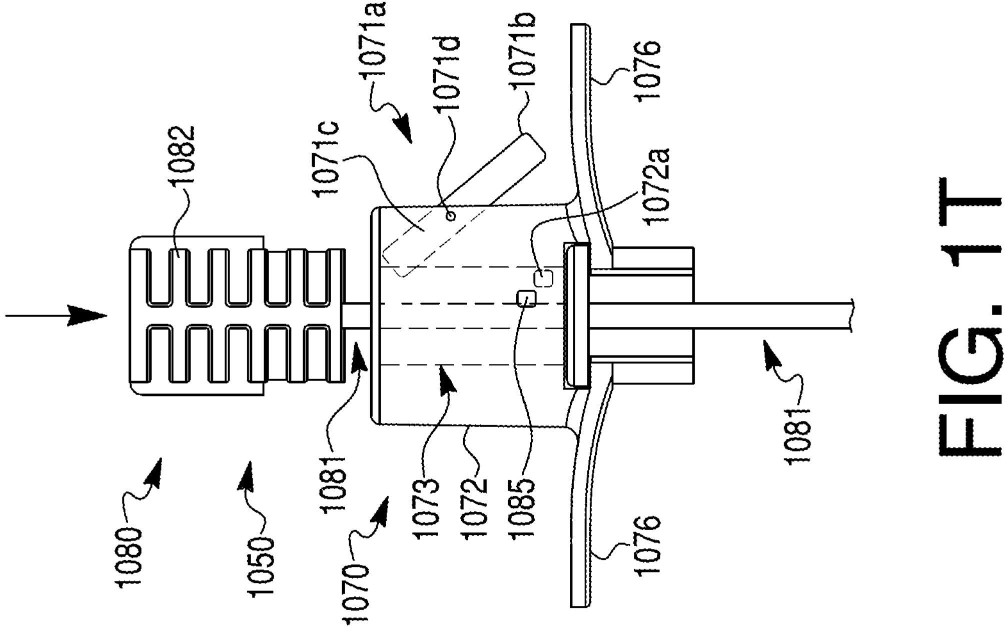
Figure 1S:
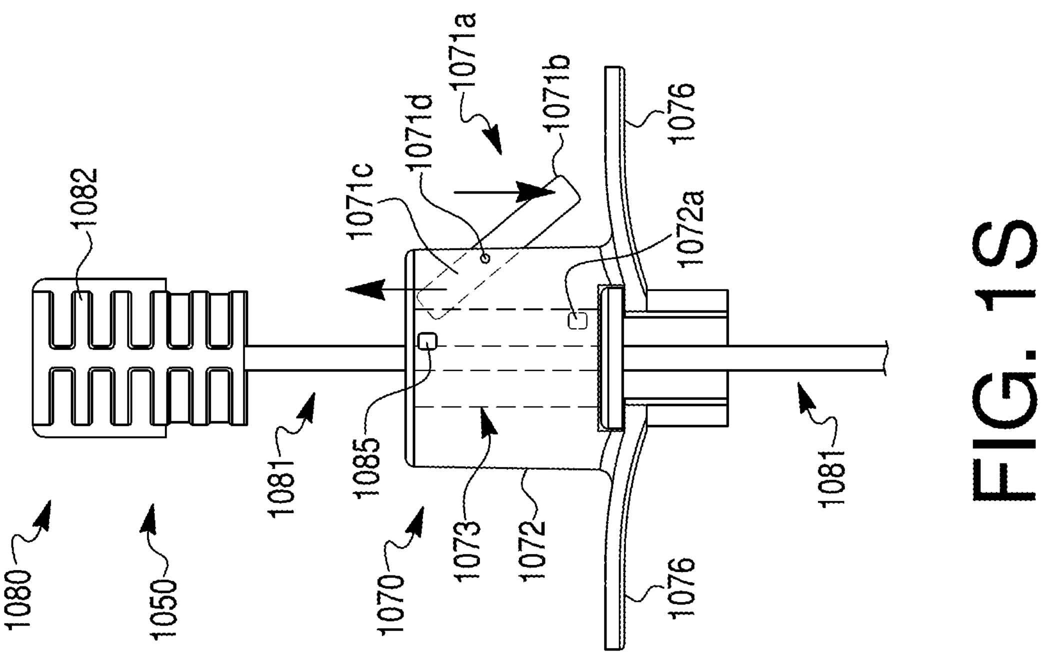

For example, as seen in FIG. 1S, movable lever 1071*a* may be actuated in response to moving first end 1071*b* distally toward flange 1076 and about rotation pin 1071*d*. In some embodiments, first end 1071*b* may be actuated in response to receiving a distally-directed force applied thereto by, for example, a user of device 1050. Second end 1071*c* may be moved in a proximal direction away from flange 1076 and relative to rotation pin 1071*d* in response to first end 1071*b* moving distally, thereby causing second end 1071*c* to disengage protrusion 1085.

Accordingly, as shown in FIG. 1T, movable lever 1071*a* may allow plunger rod 1080 to translate relative to flange piece 1070 until protrusion 1085 encounters an abutment 1072*a* positioned at a distal end of opening 1073. Abutment 1072*a* may cause plunger rod 1080 to settle into a dose completion position of plunger rod 1080 when protrusion 1085 is engaged thereto. It should be appreciated that a distance between second end 1071*c* and abutment 1072*a* may define a dosage delivery distance for moving plunger rod 1080 to dispense a controlled volume of substance from device 1050.

Figure 1V:
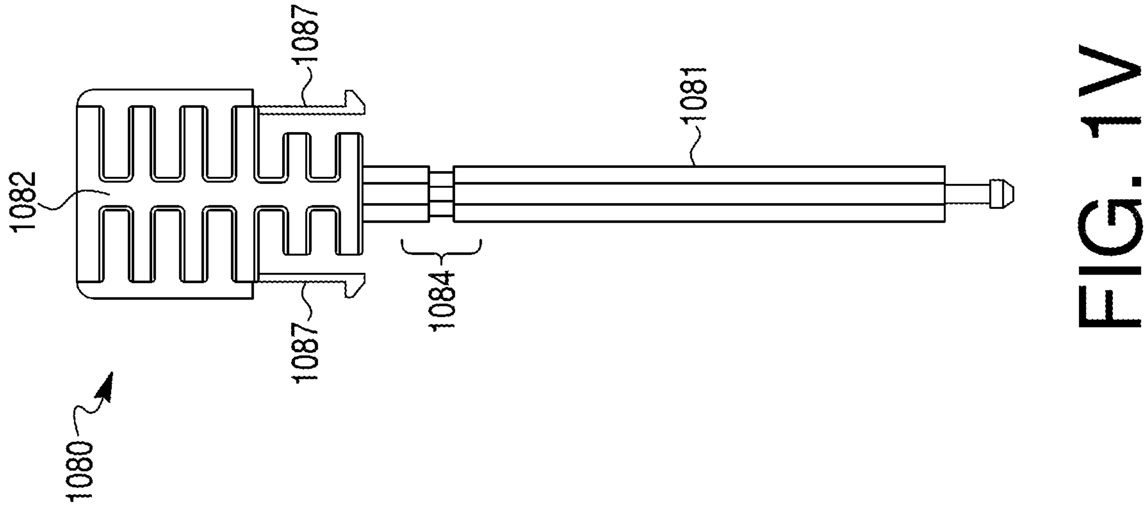
Figure 1U:
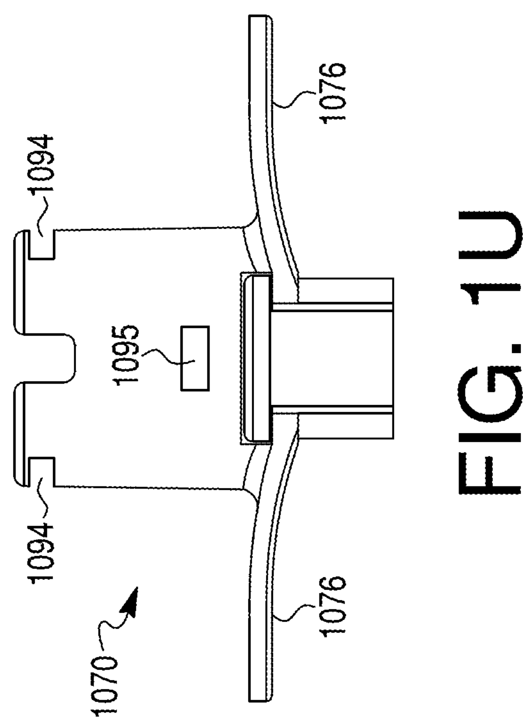

As shown in FIGS. 1U and 1V, in some embodiments, actuation portion 1082 of plunger rod 1080 may additionally or alternatively include one or more extensions 1087 configured to interface with side openings 1094, 1095 in collar 1072 of flange piece 1070. Extensions 1087 may extend distally from actuation portion 1082, and may have an angled or rounded distal portion sized and configured to be pushed inward toward a central axis of plunger rod 1080 when actuation portion 1082 is pushed distally into collar 1072. The angled or rounded distal portion of each extension 1087 may include a hook or clip shaped part 1087*a*. Extensions 1087 may additionally be made of a flexible material, allowing them to be pushed inward into collar 1072 and spring back outwards when no longer being restricted by a side of collar 1072. Side openings 1094, 1095 in collar 1072 may be sized and configured to receive hook or clip shaped part 1087*a* of an extension 1087, such that once an extension 1087 reaches a side opening 1094 or 1095, a hook or clip shaped part 1087*a* may spring outward into the side opening 1094 or 1095 and thereafter prevent proximal movement of plunger rod 1080. A number of extensions 1087 may coincide with a number of each of side openings 1094 and side openings 1095, such that each extension 1087 may be received in a corresponding side opening 1094 or 1095 simultaneously as plunger rod 1080 moves distally relative to flange piece 1070.

Specifically, first side openings 1094 may be configured to receive hook or clip shaped parts 1087*a* of extensions 1087 upon assembly of device 1050, to prevent proximal movement of plunger rod 1080 once plunger rod 1080 is inserted to a ready-to-use position. As hook or clip shaped part 1087*a* of each extension 1087 is received in first side openings 1094, it may make a "clicking" sound as it interfaces with collar 1072, thereby providing auditory and/or tactile feedback, indicating that the device is in a ready-to-use position. In some embodiments, first side openings 1094 may each extend around a partial circumference of collar 1072, such that the hook or clip shaped parts 1087*a* of extensions 1087 may be received in side openings 1094 in a range of rotational positions of plunger rod 1080 relative to flange piece 1070. Second side openings 1095 may be configured to receive hook or clip shaped parts 1087*a* of extensions 1087 once device 1050 is in a "delivery" configuration (e.g., after priming and additional rotation of actuation portion 1082 to align protrusions 1086 with slots 1074). In the embodiment depicted in FIGS. 1U and 1V, extensions 1087 are longitudinally aligned with protrusions 1086, and, as depicted in FIGS. 3C-3F, side openings 1095 are likewise longitudinally aligned with slots 1074, to allow for distal movement of actuation portion 1082 further into collar 1072 when device is in the "delivery" configuration. It should be appreciated that device may be transitioned to the "delivery" configuration in response to applying a distally-directed force onto actuation portion 1082, to overcome an engagement of side openings 1094 with extensions 1087, and a rotative force to overcome a frictional force between an interior of collar 1072 and extensions 1087. However, in other embodiments, it is contemplated that extensions 1087 and side openings 1094, 1095 may be in any suitable complementary configuration to assist in controlling proximal movement of plunger rod 1080.

Figure 1W:
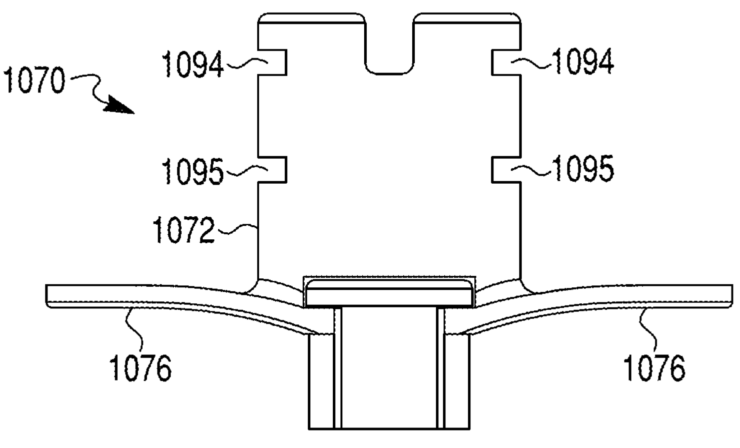

In other embodiments, as shown in FIG. 1W, side openings 1094 may be positioned along collar 1072 in longitudinal alignment with side openings 1095. Device 1050 may be primed upon receiving hook or clip shaped parts 1087*a* of extensions 1087, initially positioned proximally of side openings 1094, within side openings 1094. In some instances, a feedback (e.g., tactile, auditory, etc.) may be generated in response to extensions 1087 being received within side openings 1094. It should be understood that a proximal end of collar 1072 may resist distal advancement of plunger rod 1080 relative to flange piece 1070 in response to hook or clip shaped parts 1087*a* being engaged to collar 1072 at side openings 1094. Applying a distally-directed force onto plunger rod 1080 may cause extensions 1087 to be released from side openings 1094 and translated distally through collar 1072 until received within side openings 1095.

It should be appreciated that the distally-directed force required to deflect extensions 1087 inwardly and to release hook or clip shaped parts 1087*a* from side openings 1094 may correspond to a minimum priming and hydrodynamic force. Accordingly, plunger rod 1080 may be maintained in a constant radial orientation during a priming step and delivery step of device 1050. In other embodiments, additional and/or fewer side openings may be included along a circumferential wall of collar 1072 in longitudinal alignment and/or offset (e.g., not longitudinally aligned) with side openings 1094, 1095.

Figure 1X:
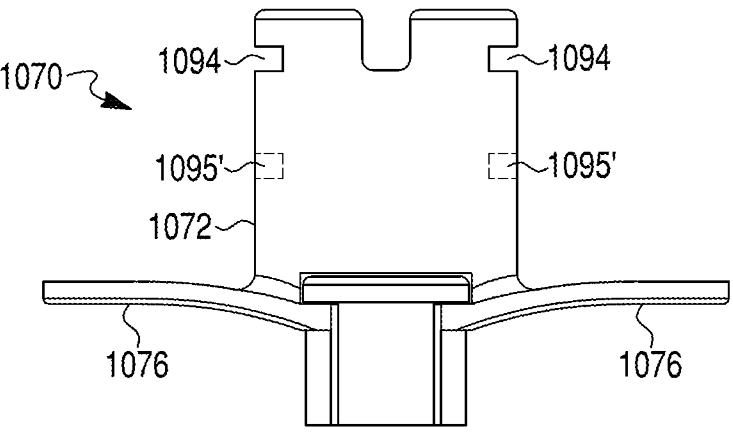

As seen in FIG. 1X, flange piece 1070 may alternatively include one or more inner projections 1095' in lieu of side openings 1095 shown and described above. In this instance, plunger rod 1080 may be preassembled into flange piece 1070 with extensions 1087 (FIG. 1V) squeezed into collar 1072 and positioned relatively proximal to side openings 1094. Device 1050 may be primed by pushing plunger rod 1080 distally through flange piece 1070 until extensions 1087 are received within side openings 1094. In some instances, a feedback (e.g., tactile, auditory, etc.) may be generated in response to extensions 1087 being received within side openings 1095. In further embodiments, side openings 1094 may be flared and/or extensions 1087 may have a distally-tapering profile to facilitate further distal advancement of plunger rod 1080 from a primed position to a dose completion position.

Further translation of plunger rod 1080 relative to flange piece 1070 may cause extensions 1087 to bend radially-inward toward one another, thereby allowing plunger rod 1080 to translate distally to deliver a dose from device 1050. Plunger rod 1080 may continue to translate distally relative to collar 1072 until hook or clip shaped parts 1087*a* (FIG. 1V) encounter inner projections 1095'. Inner projections 1095' may be configured to contact extensions 1087 and fix plunger rod 1080 to the dose completion position, and/or prevent further distal movement of plunger rod 1080 relative to flange piece 1070. Accordingly, further movement (e.g., proximal and/or distal) of plunger rod 1080 relative to flange piece 1070 may be inhibited by inner projections 1095' engaging hook or clip shaped parts 1087*a* within collar 1072. Inner projections 1095' may include complimentary hooks or clip-shaped parts that are sized and/or shaped to interact with hook or clip shaped parts 1087*a* or extensions 1087. It should be appreciated that a distance between side openings 1094 and inner projections 1095' may define a dosage delivery distance to dispense a controlled volume of substance from device 1050.

Figures 2A, 2B:
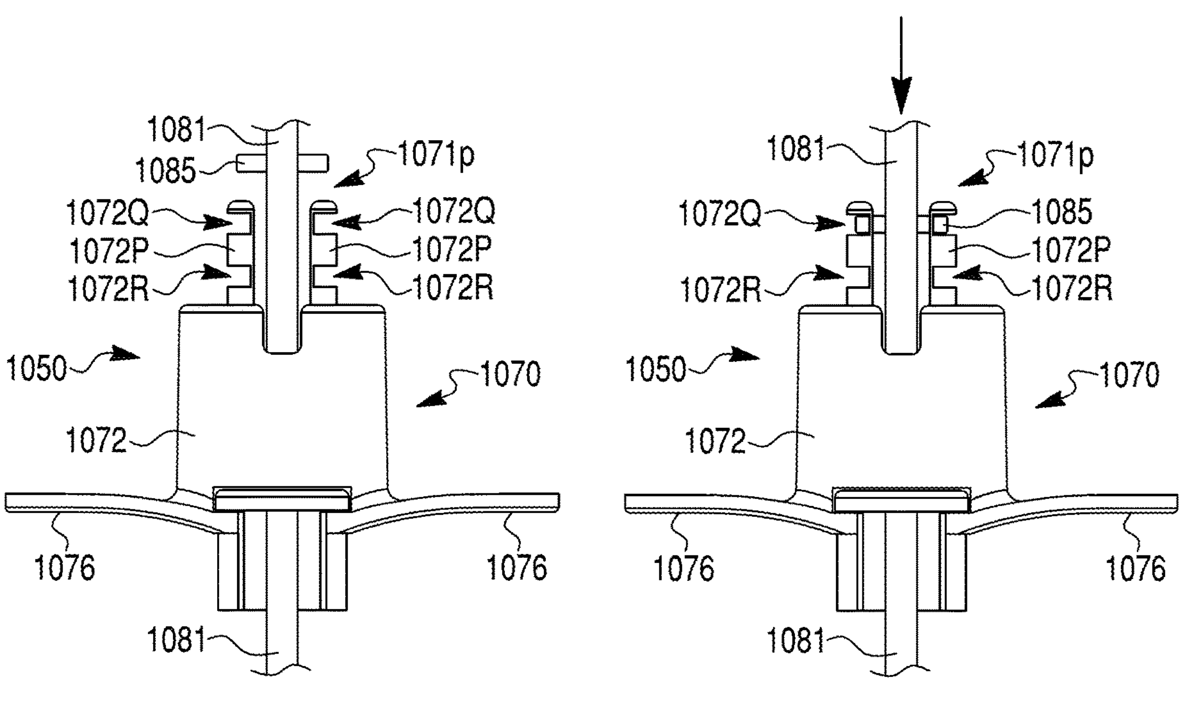
Figure 2C:
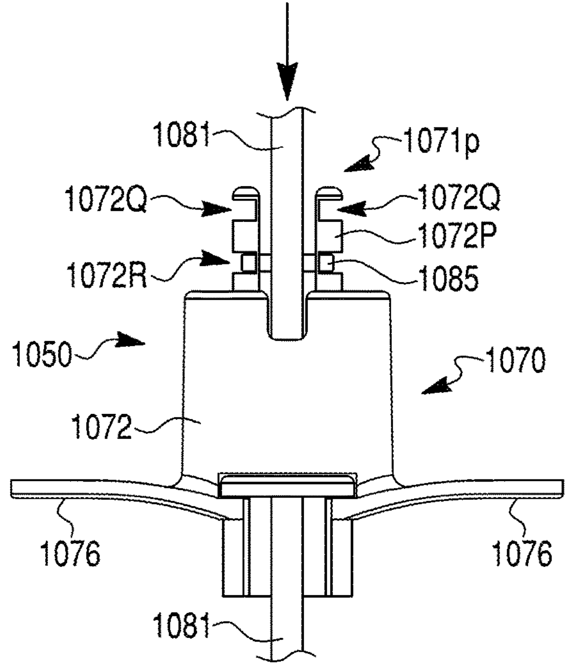

In other embodiments, as shown in FIGS. 2A-2C, flange piece 1070 may include a fixed sleeve 1072P extending proximally from collar 1072. Fixed sleeve 1072P may have a circular cross-section defining an inner channel with an opening at each terminal end of the fixed sleeve 1072P. The inner channel of fixed sleeve 1072P may extend through a longitudinal length of fixed sleeve 1072P and may be longitudinally aligned with opening 1073 (FIG. 10) such that a respective longitudinal axis of the inner channel and opening 1073 are coaxial with one another. Fixed sleeve 1072P may be sized, shaped, and configured to receive stem 1081. In some embodiments, fixed sleeve 1072P may be integral with collar 1072, while in other embodiments fixed sleeve 1072P may be a separate component assembled onto flange piece 1070.

Fixed sleeve 1072P may include a plurality of openings that are sized and shaped to receive protrusion 1085. For example, fixed sleeve 1072P may include a pair of proximal openings 1072Q and a pair of distal openings 1072R longitudinally spaced apart from one another by an offset distance. Further, the pair of proximal openings 1072Q are located at the same longitudinal position as one another, and the pair of distal openings 1072R are located at the same longitudinal position as one another. As described in further detail below, the longitudinal offset between proximal openings 1072Q and distal openings 1072R may define a dosage delivery distance for moving plunger rod 1080 to dispense a controlled volume of substance from device 1050. Alternatively, the longitudinal offset between openings 1072Q, 1072R may define a priming distance of device 1050 such that protrusion 1085 may be initially received within proximal openings 1072Q during an assembly of device 1050 to inhibit proximal retraction of plunger rod 1080. In this instance, a dosage delivery distance may correspond to a longitudinal offset between a distal end of actuation portion 1082 and a bottom surface of collar 1072 when protrusion 1085 is received within distal opening 1072R. Although not shown, it should be appreciated that an additional set of openings may be included on fixed sleeve 1072P (e.g., proximal of proximal openings 1072Q, distal of proximal openings 1072Q, and/or distal of distal openings 1072R) to further define a priming distance and/or dosage delivery distance.

A proximal end of fixed sleeve 1072P may include an angled interface 1071P defining a proximal opening of fixed sleeve 1072P. Angled interface 1071P may be tapered radially-inward toward the inner channel of fixed sleeve 1072P and configured to guide stem 1081 and protrusion 1085 into the inner channel. In the present example, protrusion 1085 may extend radially outward from stem 1081 in opposing lateral directions and may be compressible and/or formed of a flexible/deformable material, such that protrusion 1085 is configured to retract or deform radially inward into and/or toward stem 1081 in response to a force being applied thereto. In other embodiments, protrusion 1085 may be configured to at least partially deform fixed sleeve 1072P to facilitate movement of protrusion 1085 toward and/or between openings 1072Q, 1072R. In this instance, fixed sleeve 1072P may be formed of a flexible material operable to flex radially-outward when applying a distally-directed force onto stem 1081, thereby causing protrusion 1085 to apply a radial force onto fixed sleeve 1072P.

Still referring to FIG. 2A, fixed sleeve 1072P may be configured to receive plunger rod 1080 through the inner channel and allow stem 1081 to pass through collar 1072 to prime device 1050. Protrusion 1085 may be received within fixed sleeve 1072P in response to encountering angled surface 1071P and compressing radially inward relative to stem 1081 until plunger rod 1080 is moved distally enough so that protrusion 1085 is received by proximal openings 1072Q. As shown in FIG. 2B, protrusion 1085 may be configured to expand radially outward (decompress) when longitudinally aligned with proximal openings 1072Q to lock stem 1081 relative to flange piece 1070. In this instance, device 1050 may be in a primed position such that further translation of stem 1081 distally relative to fixed sleeve 1072P and flange piece 1070 may deliver a dose from device 1050. Alternatively, device 1050 may be preassembled with protrusion 1085 received in proximal openings 1072Q such that translation of stem 1081 distally relative to fixed sleeve 1072P may prime device 1050 until protrusion 1085 is received within distal openings 1072R.

As seen in FIG. 2C, while protrusion 1085 is positioned within proximal openings 1072Q applying a distally-directed force onto stem 1081 may cause fixed sleeve 1072P to compress (or deform) protrusion 1085 radially inward, thereby allowing stem 1081 to translate distally relative to fixed sleeve 1072P. Alternatively, protrusion 1085 may be manually compressed (or deformed) by applying a radially inward-directed force through proximal openings 1072Q. Protrusion 1085 may move distally through an inner channel of fixed sleeve 1072P and may be received by distal openings 1072R. As stem 1081 translates distally relative to collar 1072, device 1050 may transition from the primed position to a dose completion position when protrusions 1085 are received within distal openings 1072R, thus delivering the dose.

It should be appreciated that a volume of the dose delivered by device 1050 may be controlled based on the longitudinal offset distance between proximal openings 1072Q and distal openings 1072R. In some embodiments, fixed sleeve 1072P may include additional openings for receiving protrusion 1085 after priming and delivering a dose to inhibit proximal retraction of stem 1081 (e.g., pull back of plunger rod 1080) relative to flange piece 1070. For example, protrusion 1085 may be received within proximal openings 1072Q during an assembly of device 1050 at a manufacturing stage such that distal openings 1072R may define a priming position and a third set of openings (not shown) distal to distal opening 1072R may define a dosage delivery position. Alternatively, a bottom, interior surface of flange piece 1070 distal to distal opening 1072R may define the dosage delivery position of plunger rod 1080.

In some embodiments, as seen in FIGS. 2D-2G, flange piece 1070 may include a movable sleeve 1072S extending distally and proximally from collar 1072. Movable sleeve 1072S may have a circular cross-section defining an inner channel with an opening at each terminal end of movable sleeve 1072S. The inner channel of movable sleeve 1072S may extend through a longitudinal length of movable sleeve 1072S. Movable sleeve 1072S may be sized, shaped, and configured to be received through opening 1073, and the inner channel of movable sleeve 1072S may be sized to receive stem 1081. Movable sleeve 1072S may be fixed relative to collar 1072 when in an preassembled configuration and may be movable relative to collar 1072 upon engagement with plunger rod 1080.

Movable sleeve 1072S may include a plurality of openings that are sized and shaped to receive protrusion 1085. For example, movable sleeve 1072S may include a proximal opening 1072U at a proximal end of movable sleeve 1072S and a distal opening 1072T at a distal end of movable sleeve 1072S. A proximal end of movable sleeve 1072S may further include an angled interface 1071S defining a proximal opening of movable sleeve 1072S. Angled interface 1071S may be tapered radially-inward toward the inner channel of movable sleeve 1072S and configured to guide stem 1081 and protrusion 1085 into the inner channel of movable sleeve 1072S. In some embodiments, protrusion 1085 may extend radially outward from stem 1081 in opposite directions and may be compressible such that protrusion 1085 is configured to compress into and/or toward stem 1081 in response to a force being applied thereto.

Figure 2E:
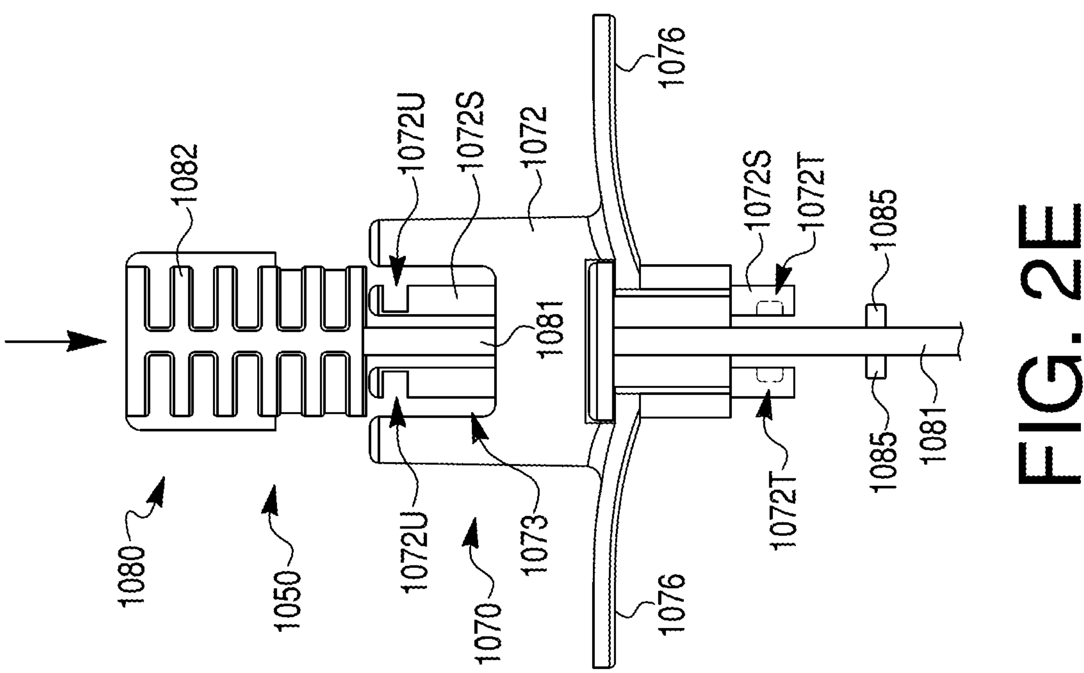
Figure 2D:
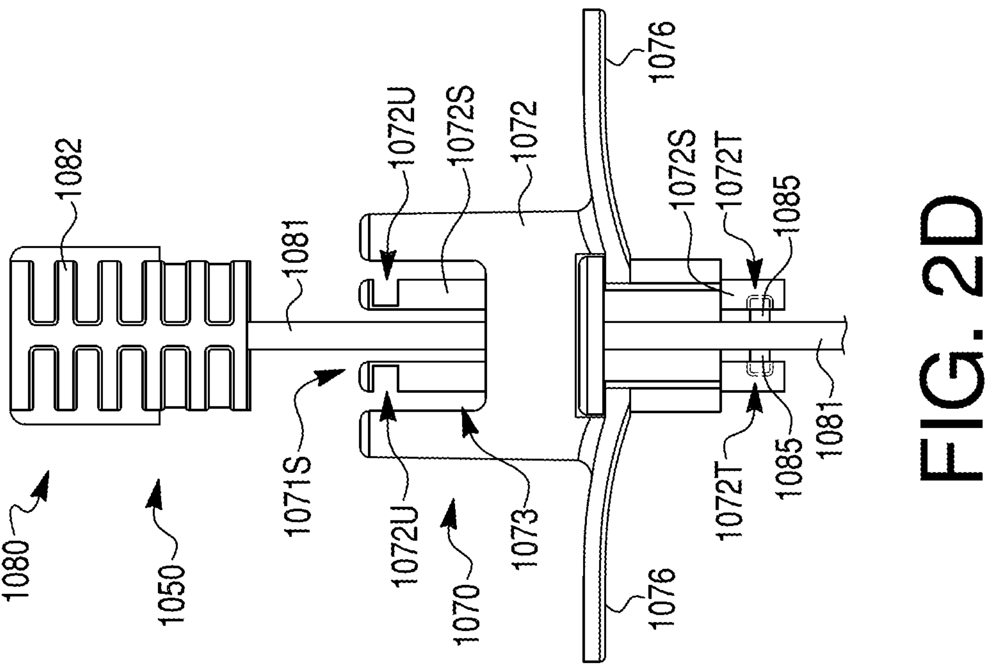

Still referring to FIG. 2D, the proximal end of movable sleeve 1072S may be positioned adjacent to a proximal end of collar 1072 and a distal end of movable sleeve 1072S may be positioned adjacent to a distal end of collar 1072 when in the preassembled position. Plunger rod 1080 may be received through the inner channel of movable sleeve 1072S with stem 1081 extending through collar 1072. Protrusion 1085 may be received within distal opening 1072T such that plunger rod 1080 may be fixed to movable sleeve 1072S. Protrusion 1085 may be configured to exit distal opening 1072T and expand laterally outward in response to plunger rod 1080 translating relative to movable sleeve 1072S.

For example, as shown in FIG. 2E, applying a distally-directed force onto actuation portion 1082 may cause protrusion 1085 to compress radially inward, thereby allowing stem 1081 to translate distally relative to movable sleeve 1072S. In this instance, protrusion 1085 may exit distal opening 1072T and expand upon translating distally from a distal end of movable sleeve 1072S. Device 1050 may transition from a preassembled state to a primed state, in response to stem 1081 translating distally relative to collar 1072, until actuation portion 1082 abuts against a proximal end of movable sleeve 1072S. In this instance, device 1050 may be in a primed state and further translation of stem 1081 relative to collar 1072 may be inhibited by the presence of movable sleeve 1072S.

Figure 2F:
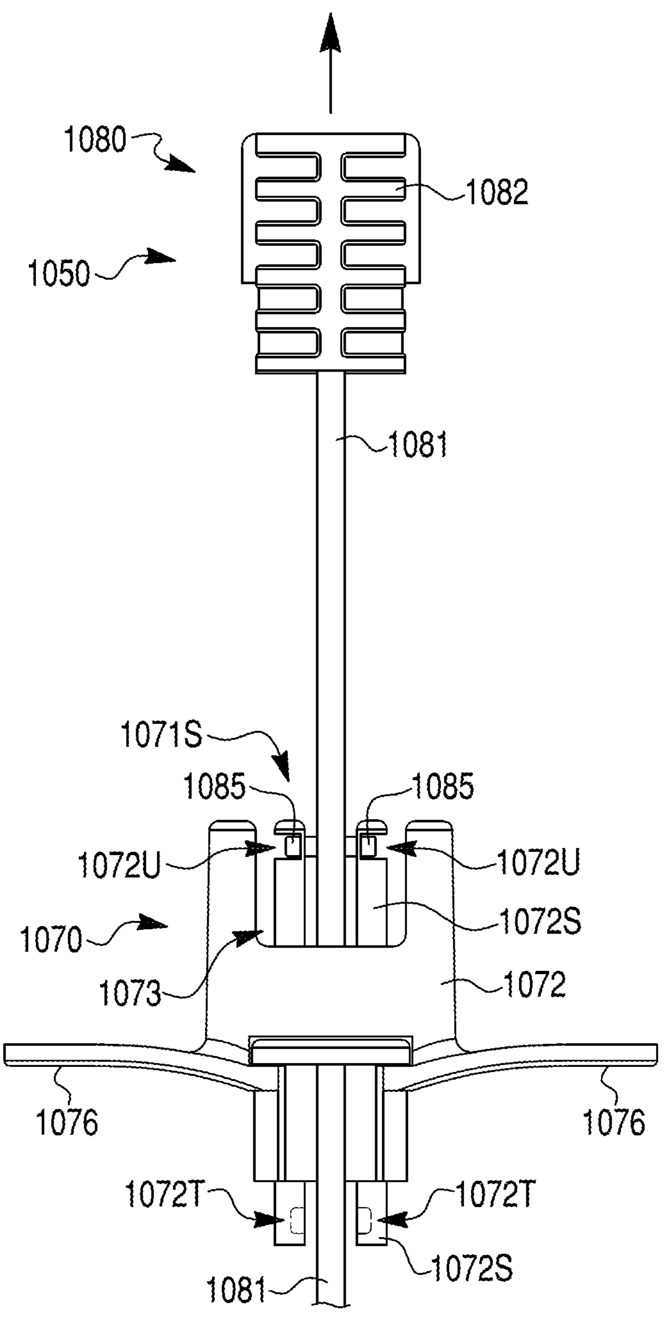

Referring now to FIG. 2F, plunger rod 1080 may couple to movable sleeve 1072S in response to proximal translation of stem 1081 relative to collar 1072 until protrusion 1085 engages proximal opening 1072U. It should be understood that protrusion 1085 may be in a compressed state when translating through an inner channel of movable sleeve 1072S and may expand into proximal opening 1072U upon longitudinal alignment therewith. With protrusion 1085 engaged to proximal opening 1072U, a distal translation of plunger rod 1080 relative to flange piece 1070 may provide a simultaneous movement of movable sleeve 1072S relative to collar 1072. It should be appreciated that a collective length of movable sleeve 1072S and plunger rod 1080 may be greater than a longitudinal length of plunger rod 1080 alone.

Figure 2G:
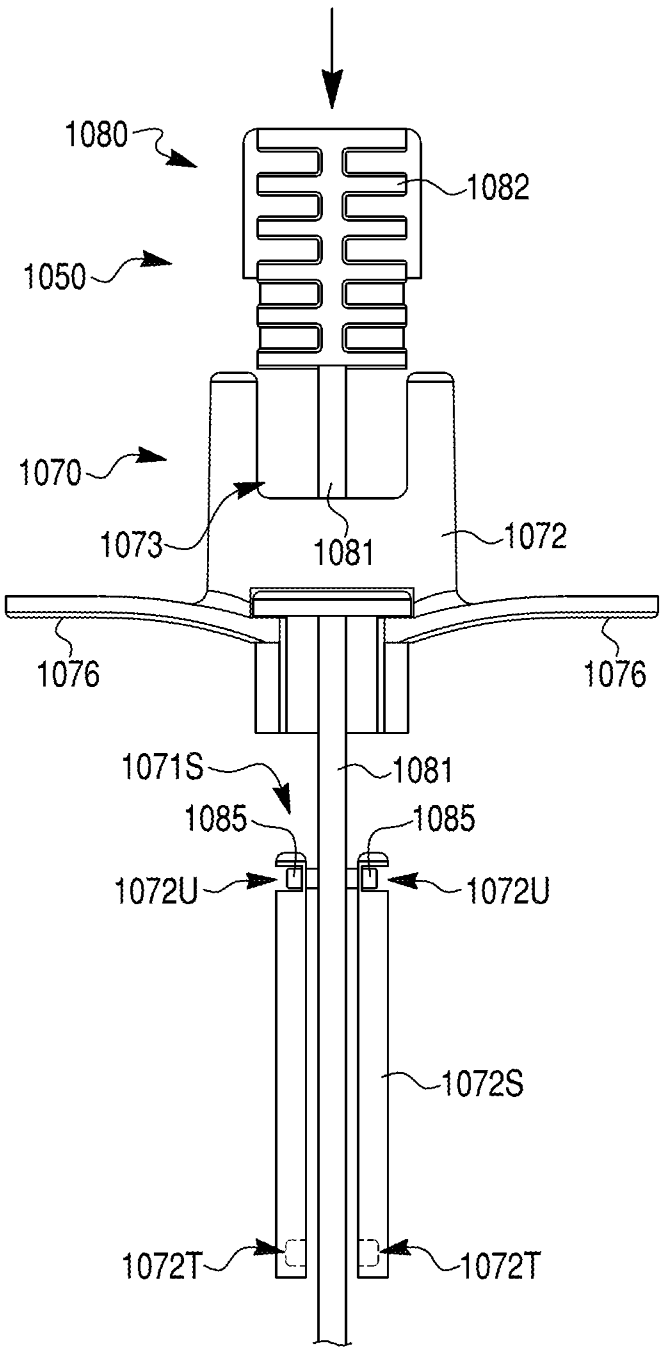

As seen in FIG. 2G, plunger rod 1080 may be configured to move movable sleeve 1072S through a channel of flange piece 1070 by a predetermined distance until actuation portion 1082 encounters a proximal end of collar 1072. Plunger rod 1080 may be configured to deliver a dose from device 1050 in response to translating movable sleeve 1072S distally relative to collar 1072. It should be appreciated that the dosage delivered by device 1050 may be controlled based on the predetermined distance between actuation portion 1082 and collar 1072 when protrusion 1085 is received within proximal opening 1072U. In some embodiments, flange piece 1070 may be configured to inhibit proximal movement of movable sleeve 1072S relative to collar 1072 when protrusion 1085 is received within proximal opening 1072U. Although not shown, flange piece 1070 may include one or more blocking components operable to restrict proximal retraction of movable sleeve 1072S from opening 1073.

In other embodiments, as seen in FIGS. 2H-2M, plunger rod 1080 may include at least one protrusion 1085W positioned on actuation portion 1082. In the example, protrusion 1085W may be positioned at or adjacent a distal end of actuation portion 1082 such that protrusion 1085W may be received within flange piece 1070 in response to translation of plunger rod 1080 into collar 1072.

Figure 2I:
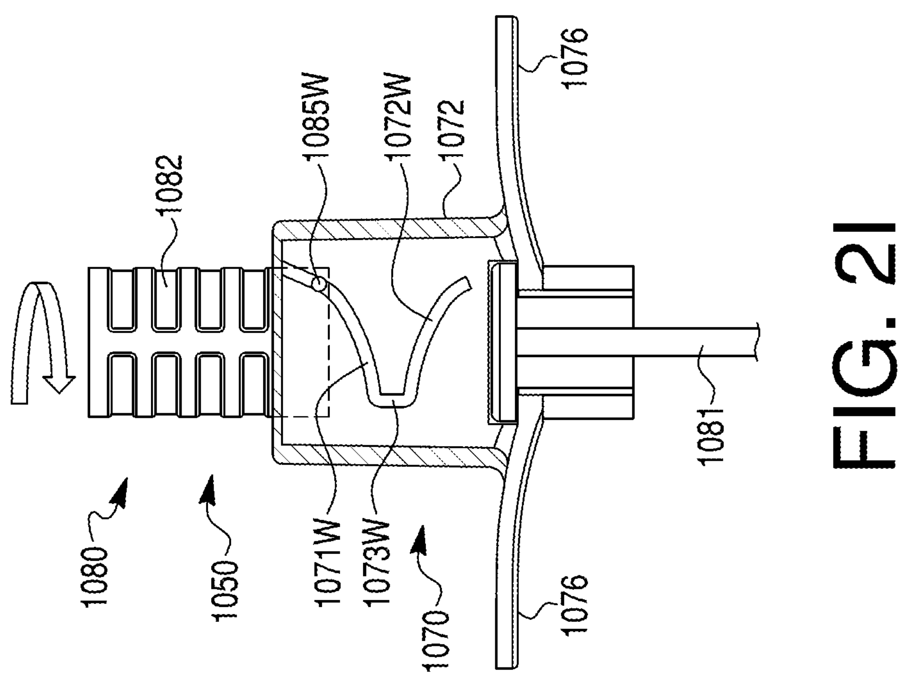
Figure 2H:
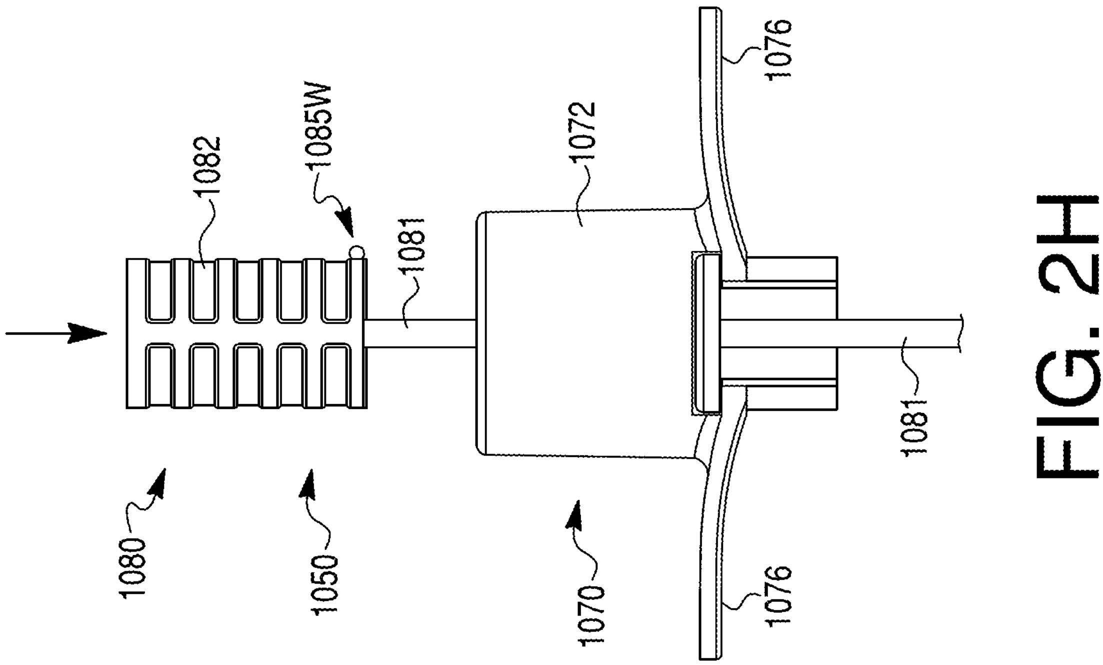
Figure 2K:
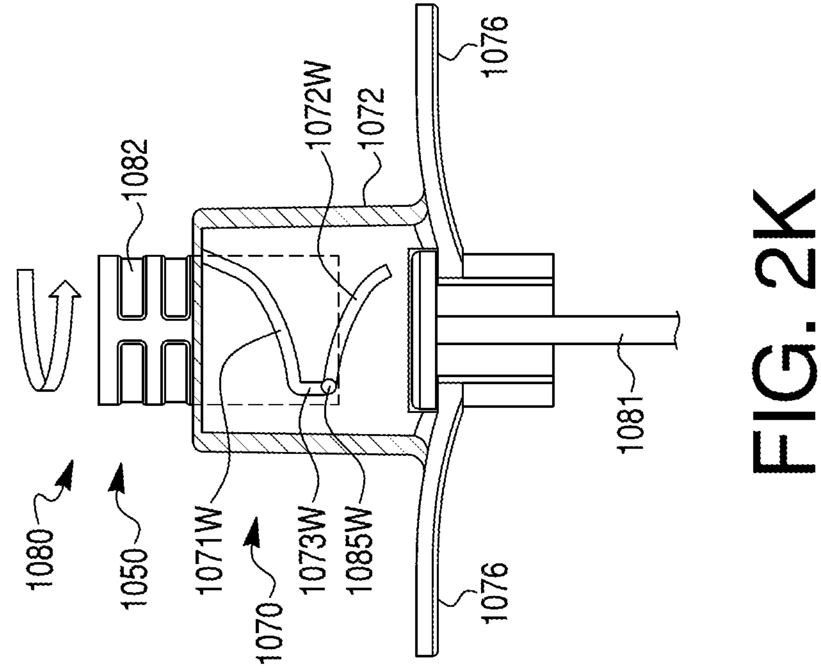

As seen in FIG. 2K, flange piece 1070 may include one or more channels formed along an inner surface of collar 1072. In particular, collar 1072 may include a first (proximal) helical channel 1071W formed along an interior of collar 1072 and having a first curvature, and a second (distal) helical channel 1072W formed along the interior of collar 1072 and having a different and/or opposite curvature than the first helical channel 1071W. For example, when viewed from the proximal end of actuation portion 1082, first helical channel 1071W may be concave, while second helical channel 1072W may be convex when viewed from the same vantage point. Or, first helical channel 1071W may be convex when viewed from the proximal end of actuation portion 1082, while second helical channel 1072W is concave from the same vantage point. Further, second helical channel 1072W may be longitudinally spaced apart from first helical channel 1071W. First helical channel 1071W may be connected with second helical channel 1072W by an intermediate, third channel 1073W extending therebetween.

Third channel 1073W may extend along or substantially parallel to a longitudinal axis of collar 1072. It should be understood that a size, shape, and/or orientations of the one or more channels on collar 1072 are merely exemplary such that other suitable configurations may be included without departing from a scope of this disclosure. As described in detail below, the plurality of channels 1072 are configured to receive protrusion 1085W. In some embodiments, first helical channel 1071W and second helical channel 1072W may be threaded and configured to mesh with a corresponding component of plunger rod 1080 (e.g., protrusion 1085W). Opposite rotational movement may be required for protrusion 1085W to traverse through first helical channel 1071W and second helical channel 1072W. For example, a first rotational movement of actuation portion (e.g., clockwise) may cause protrusion 1085W to traverse first helical channel 1071W, while an opposing rotational movement (e.g., counterclockwise) may cause protrusion 1085W to traverse through second helical channel 1072W.

Referring to FIG. 2H, with plunger rod 1080 in a ready position, protrusion 1085W may be received within collar 1072 in response to a distal translation of actuation portion 1082 toward flange piece 1070. As seen in FIG. 2I, protrusion 1085W may be received within first helical channel 1071W and moved therethrough in response to a rotation of plunger rod 1080 (e.g., in a first direction) relative to flange piece 1070. It should be appreciated that plunger rod 1080 may be configured to translate axially in a distal direction relative to flange piece 1070 as plunger rod 1080 rotates within collar 1072, due to the curvature of first helical channel 1071W. For example, plunger rod 1080 may translate a first distance defined by a configuration of first helical channel 1071W until reaching a terminal end of first helical channel 1071W. The first distance may correspond to a priming step of device 1050 such that device 1050 may be at least partially primed upon protrusion 1085W moving through first helical channel 1071W.

Figure 2J:
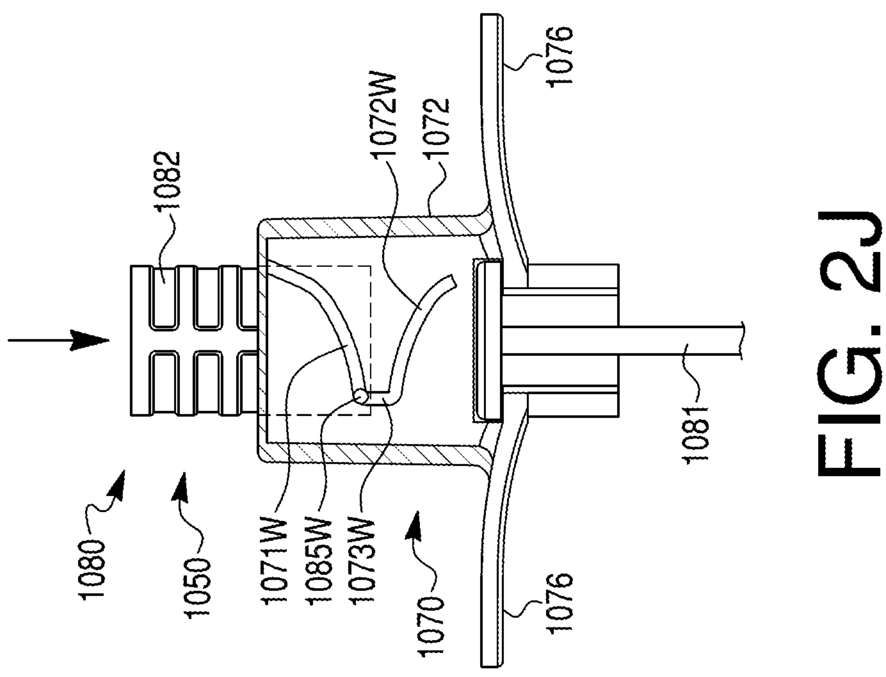

Referring now to FIG. 2J, protrusion 1085W may be positioned at a terminal end of first helical channel 1071W and a proximal (e.g., top) end of third channel 1073W. In some embodiments, plunger rod 1080 may experience a tactile feedback formed by the terminal end of first helical channel 1071W. Plunger rod 1080 may be translated distally through third channel 1073W to complete a priming step of device 1050, as shown in FIG. 2K. It should be understood that first helical channel 1071W and third channel 1073W may collectively define a priming distance of device 1050 such that plunger rod 1080 is in a primed position when protrusion 1085W translates through third channel 1073W.

With protrusion 1085W received within second helical channel 1072W, plunger rod 1080 may be rotated in the second direction (opposite of the first direction) to translate plunger rod 1080 distally by a second distance that is defined by a configuration of second helical channel 1072W. The second distance may be less than, greater than, and/or substantially equal to the longitudinal dimension of second helical channel 1072W, depending on the particular application and need. Plunger rod 1080 may be rotated in the second direction and translated by the second distance until reaching a terminal end of second helical channel 1072W to deliver a dose from device 1050. It should be understood that the second distance may correspond to a dosage delivery step of device 1050 such that device 1050 may deliver the dose upon protrusion 1085W moving through second helical channel 1072W and arriving at a dose completion position.

In other embodiments, as seen in FIGS. 2L-2O, plunger rod 1080 may include a protrusion, a knob, and/or a thread 1085X positioned on actuation portion 1082. In the example, thread 1085X may be positioned about a circumference of actuation portion 1082 and along a distal end such that thread 1085X may be received within flange piece 1070 in response to translation of plunger rod 1080 into collar 1072.

Flange piece 1070 may further include a threaded portion 1072X disposed within opening 1073 and forming a helical path that is configured to receive thread 1085X. In the example, threaded portion 1072X may be positioned along a proximal portion of opening 1073 such that a distal portion of opening 1073 may include a non-threaded portion 1071X. As described in further detail herein, threaded portion 1072X may define a longitudinal distance corresponding to a priming step of device 1050 and non-threaded portion 1071X may define a distance corresponding to a dosage delivery step of device 1050.

Figure 2M:
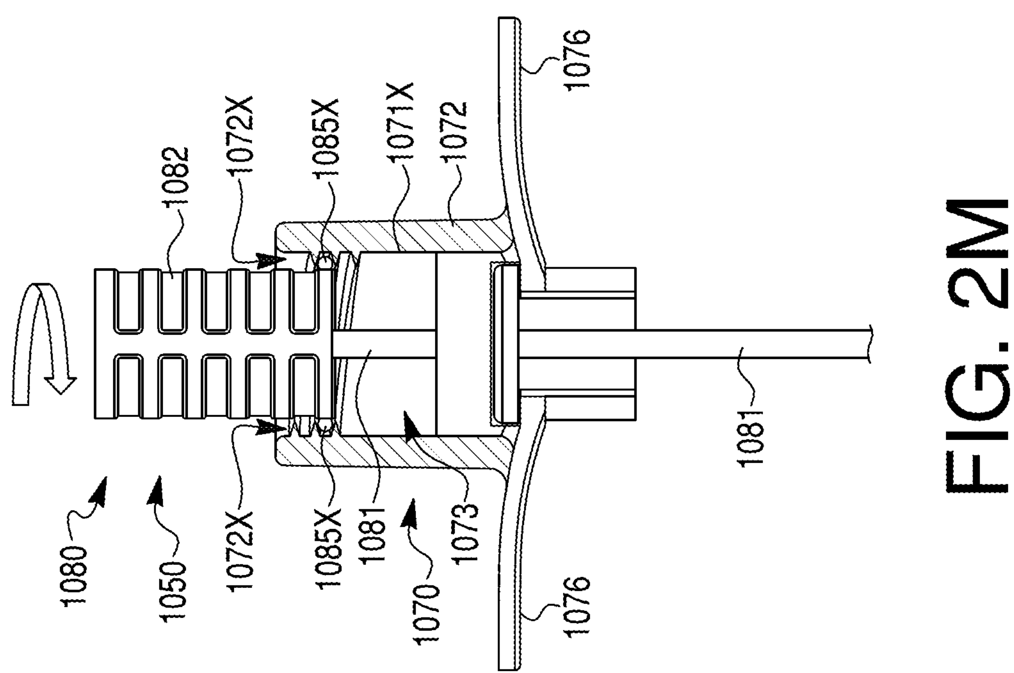
Figure 2L:
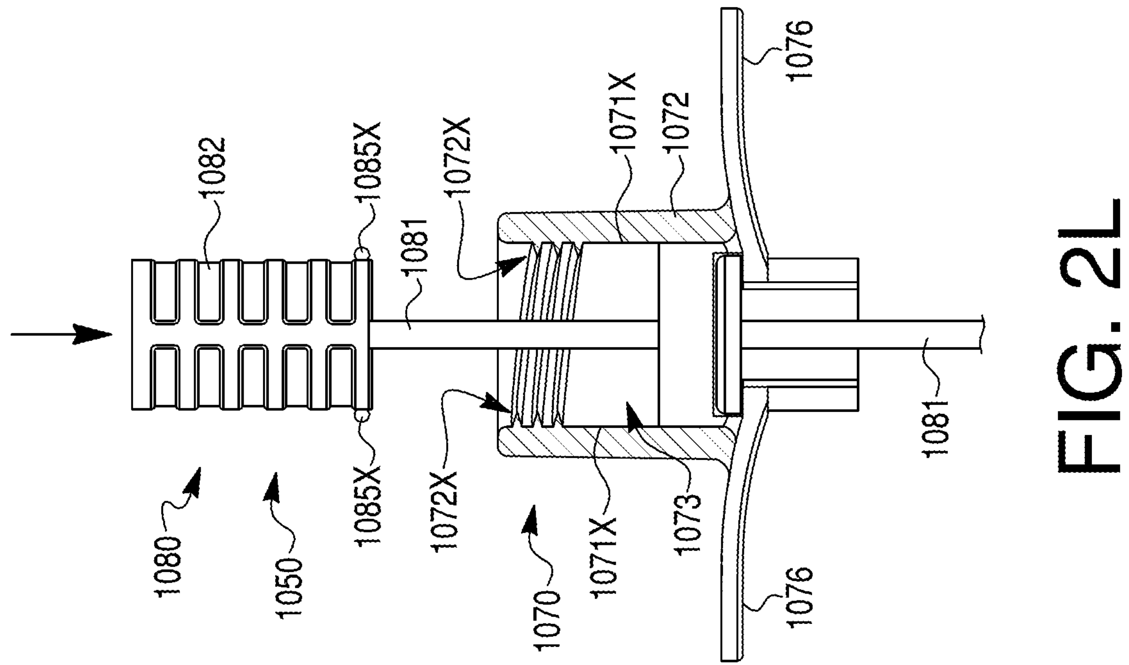

For example, as seen in FIG. 2L, actuation portion 1082 may be translated distally toward flange piece 1070 until thread 1085X encounters a distal end of collar 1072. Rotation of plunger rod 1080 in a first direction (e.g., clockwise or counter clockwise) may cause thread 1085X to engage threaded portion 1072X. As shown in FIG. 2M, rotation of plunger rod 1080 may provide axial/longitudinal translation of actuation portion 1082 into collar 1072 as thread 1085X moves through the helical path of threaded portion 1072X. It should be appreciated that rotation and translation of thread 1085X through threaded portion 1072X may transition device 1050 from a ready position (FIG. 2L) to a primed position (FIG. 2N). With thread 1085X disengaged from threaded portion 1072X and positioned along non-threaded portion 1071X, device 1050 may be in the primed position. In some instances, a feedback (e.g., tactile, auditory, etc.) may be generated in response to thread 1085W exiting threaded portion 1072X and/or entering non-threaded portion 1071X.

Figure 2O:
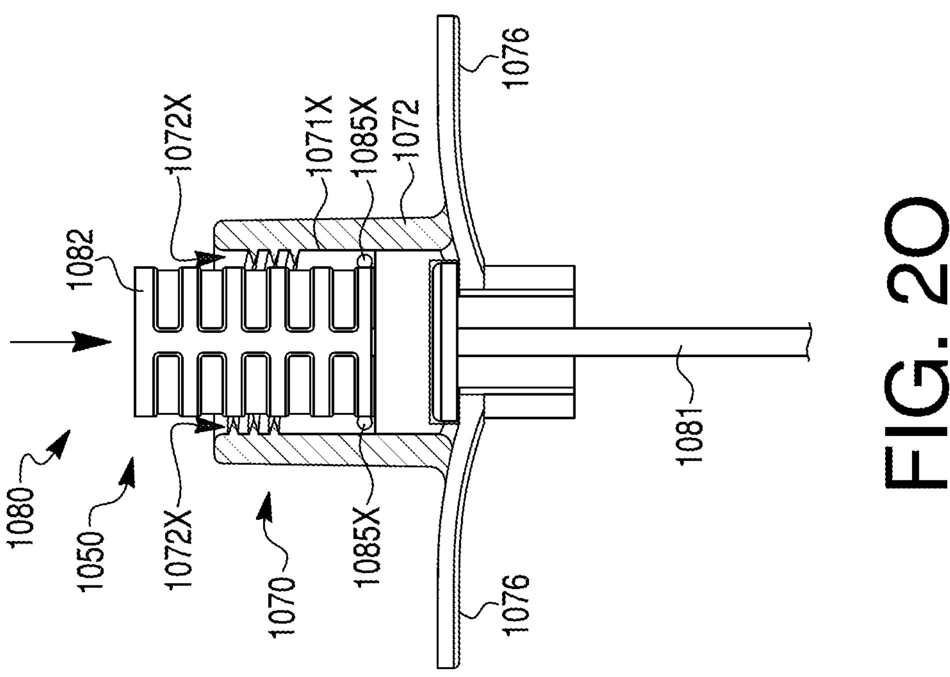
Figure 2N:
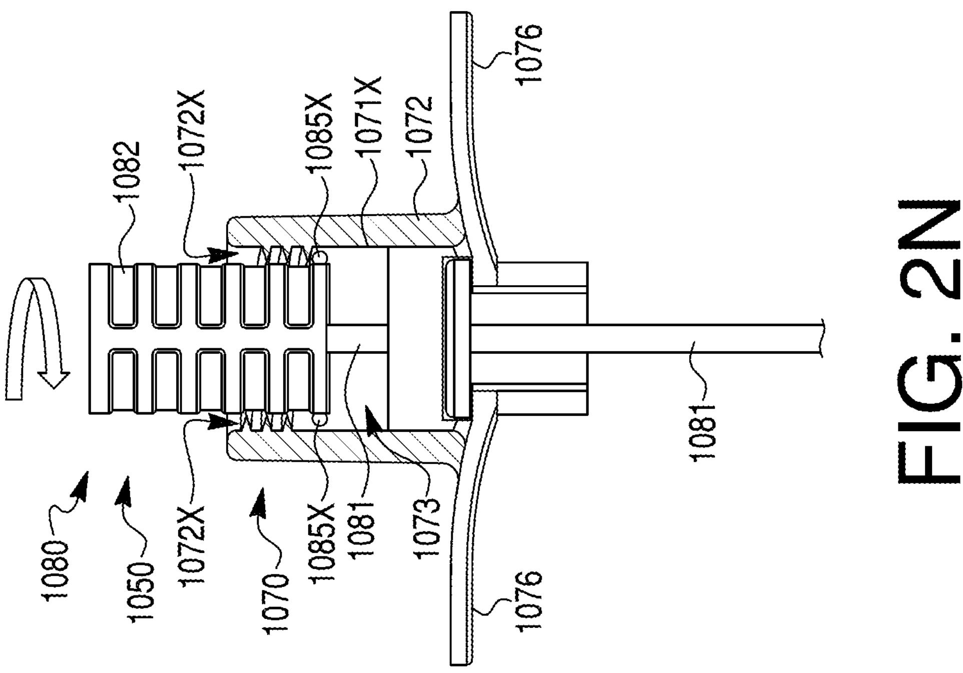

In this instance, as shown in FIG. 2O, actuation portion 1082 may be translated distally relative to flange piece 1070 to deliver a dose from device 1050 by application of a distally-directed force against actuation portion 1082. Thread 1085X may move through the distal portion of opening 1073 when thread 1085X is positioned within non-threaded portion 1071X. A longitudinal length of non-threaded portion 1071X defined between a distal end of thread portion 1072X and a distal end of opening 1073 may control a dosage delivery of device 1050. Device 1050 may complete delivery of a dose when actuation portion 1082 engages a proximally-facing and distal surface of collar 1072 and plunger rod 1080 arrives at the dose completion position.

FIGS. 2P-2T illustrate further embodiments of a flange piece that may be configured and operable similar to flange piece 1070 shown and described above except for the differences explicitly noted herein. It should be understood that like reference numerals are used to identify like components and the flange pieces described below may be readily incorporated with one or more components of device 1050 shown and described above.

Figures 2P, 2Q, 2R:
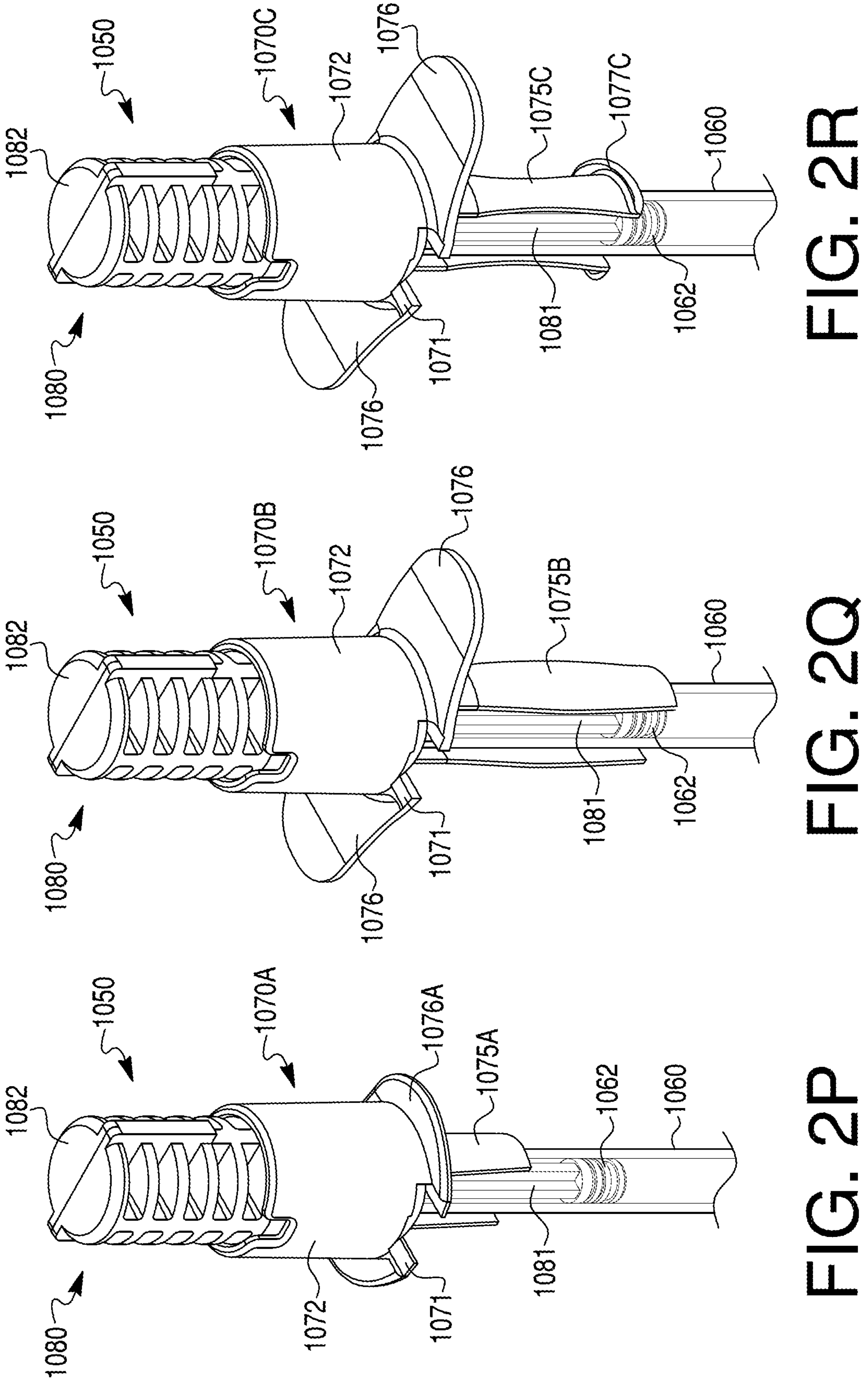
Figure 24A:
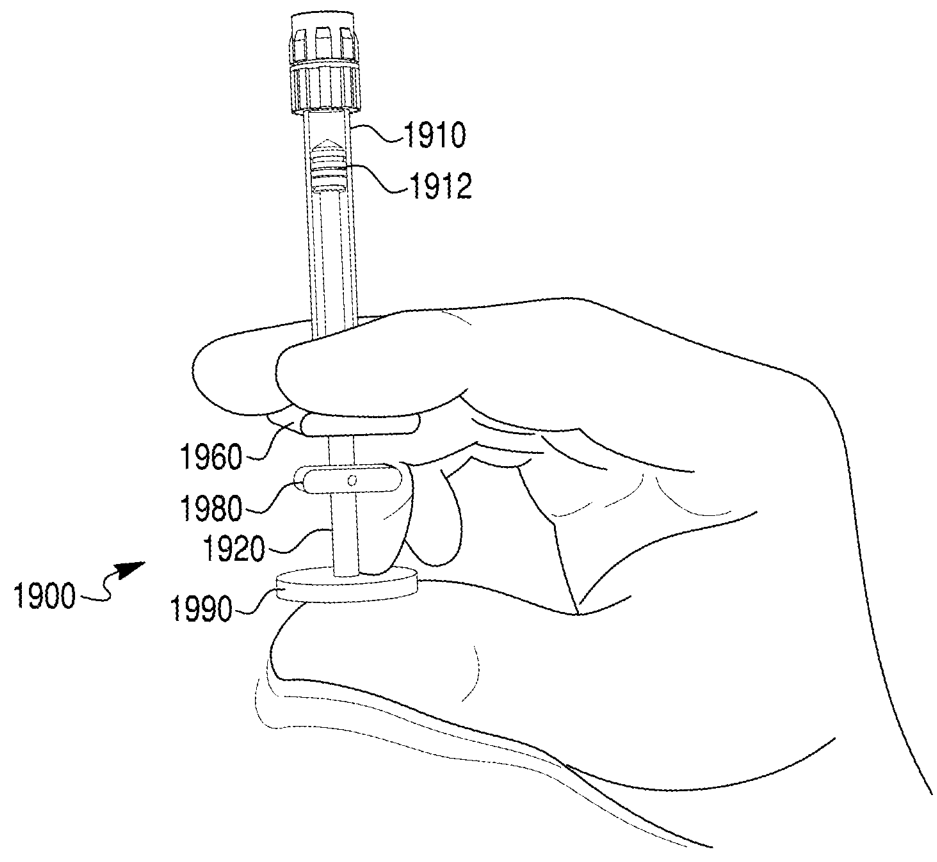
FIGS. 24A-24E depict a further exemplary delivery device and method of using said delivery device, according to aspects of the present disclosure.

For example, referring initially to FIG. 2P, a flange piece 1070A may include one or more flanges 1076A that may be sized and configured to aid a user in holding device 1050 and/or expelling a formulated drug substance from device 1050. Flanges 1076A may be further sized and/or shaped to allow a user to hold device 1050 with a plurality of hand/grip positions, arrangements, and/or orientations. By way of illustrative example, flanges 1076A may be sized and/or shaped such that flange piece 1070A may be held similar to a writing instrument (e.g., pencil, pen, etc.) without requiring use of flanges 1076A, or sized in accordance with the example shown in FIG. 24A such that flanges 1076A may abut against one or more fingers of a user. Flange piece 1070A may include a pair of flanges 1076A extending radially outwardly from collar 1072 in opposite radial directions relative to one another. Flanges 1076A may extend transversely from collar 1072 (e.g., flanges 1076A may include an angled surface that is sloped radially-inward in a distal direction) and configured to inhibit a user's fingers from slipping off of flange piece 1070A during use of device 1050.

Flanges 1076A may be coupled to one another to form a semi-circular profile with a minimal radius relative to collar 1072. Accordingly, flanges 1076A may form a slim profile to facilitate visualization of a target treatment site at a distal end of device 1050 (not shown) when using device 1050 from a perspective proximal of finger flange 1070A. It should be understood that flange piece 1070A may include various other quantities and/or arrangements of flanges 1070A than those shown and described herein without departing from a scope of this disclosure. In other embodiments, flanges 1076 may include various other suitable sizes and/or shapes.

Flange piece 1070A may further include a distal collar 1075A extending distally from collar 1072 and configured to engage body 1060 to hold flange piece 1070A in a fixed position relative to body 1060. Distal collar 1075A may be adhered to, molded, or otherwise affixed to body 1060, or may engage body 1060 via a friction fit. In the example, distal collar 1075A includes a longitudinal length that is generally less than a longitudinal length of collar 1072. In some embodiments, distal collar 1075A may be sized sufficiently small enough to facilitate adequate exposure of body 1060 for user grasp and/or manipulation during use of device 1050. Additionally, distal collar 1075A may include a material composition that is similar to and/or different from collar 1072. For example, distal collar 1075A may be formed of a flexible material such that distal collar 1075A may be configured to flex radially-outward when receiving body 1060 into flange piece 1070A and flex radially-inward once body 1060 is fully received to facilitate a snap-fit connection (without breaking distal collar 1075A). It should be appreciated that, in other embodiments, flange piece 1070A may omit distal collar 1075A entirely.

In other embodiments, as seen in FIG. 2Q, a flange piece 1070B may include a distal collar 10756 that is substantially longer than distal collars 1075, 1075A shown and described above. For example, distal collar 1075B may be enlarged with a longitudinal length that is greater than a longitudinal length of collar 1072. In the example, distal collar 1075A may be sized sufficiently large enough to encompass a substantial length of body 1060. In this instance, an exterior surface of distal collar 10756 may provide an interface for a user to grasp and/or manipulate during use of device 1050. Additionally, distal collar 1075B may include an expanded diameter that exceeds a diameter of body 1060 to provide an enhanced surface area for grasping flange piece 10706. Stated differently, distal collar 10756 may have a widened size and/or shape to facilitate ease in gripping and/or manipulating device 1050. In the present example, distal collar 1075B may have a barrel-shape with a convex outer surface when viewed from an exterior of device flange piece 10706.

Alternatively, as seen in FIG. 2R, a flange piece 1070C may include a distal collar 1075C that is substantially similar to distal collar 1075B and includes a longitudinal length that is greater than a longitudinal length of collar 1072. In the example, an exterior surface of distal collar 1075C may be configured to provide an interface for a user to grasp and/or manipulate during use of device 1050. Distal collar 1075C may include a slim profile with a diameter that is greater than a diameter of body 1060 such that distal collar 1075C does not substantially increase a profile of body 1060. Stated differently, distal collar 1075C may have a narrowed size relative to distal collar 1075B. In some embodiments, distal collar 1075C may include a terminal lip 1077C that extends radially outward at a distal end. Terminal lip 1077C may be sized, shaped, and configured to enhance gripping and/or manipulation of distal collar 1075C. In the present example, distal collar 1075C may have a flared-shape with a concave outer surface when viewed from an exterior of device flange piece 1070C.

Figure 2T:
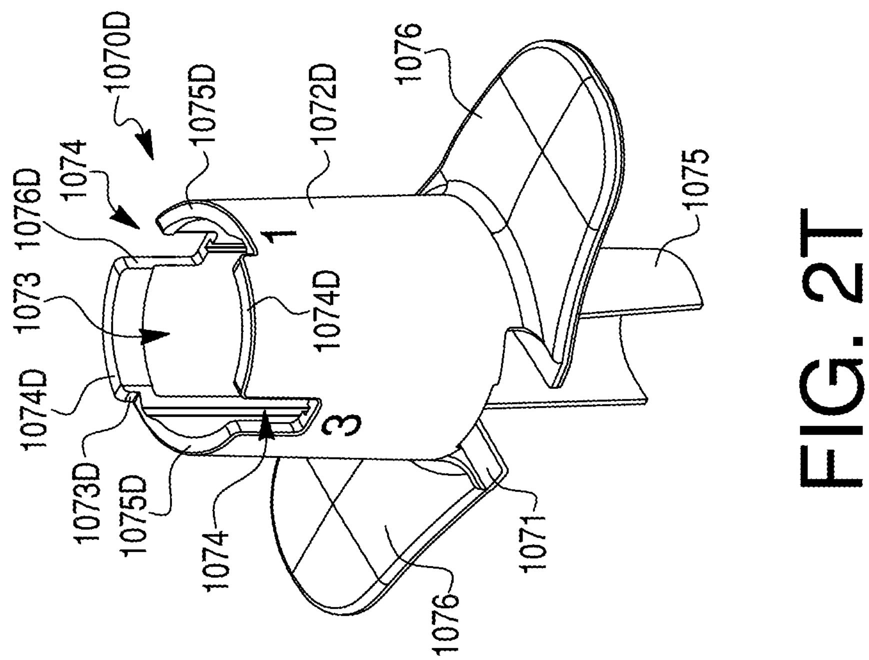
Figure 2S:
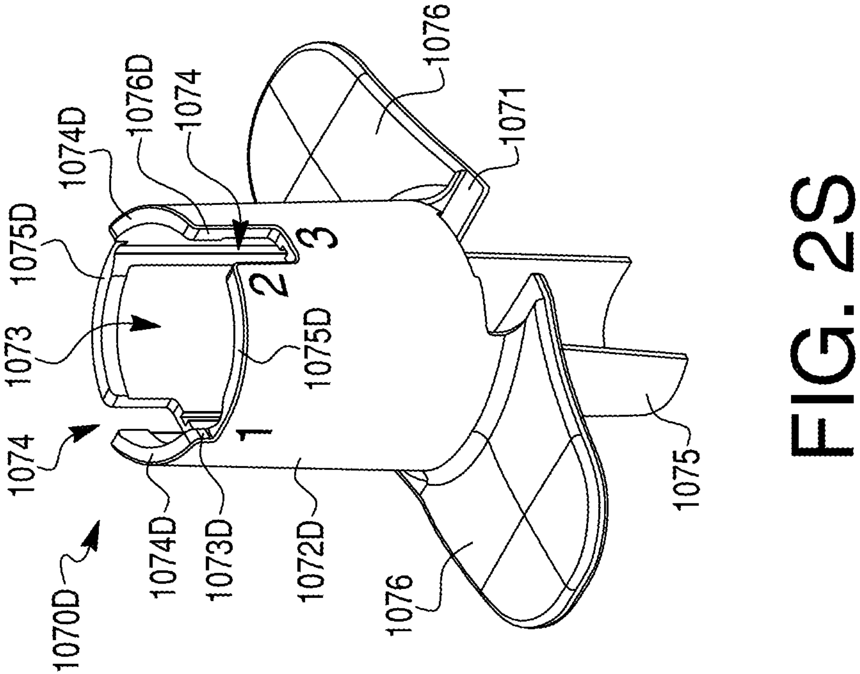

In other embodiments shown in FIGS. 2S-2T, a flange piece 1070D may include a collar 1072D having a proximal lip 1074D. Proximal lip 1074D may define an irregular surface configured to interface with plunger rod 1080 when actuation portion 1082 is received by collar 1072D. For example, proximal lip 1074D may include a pair of recessed surfaces 1075D positioned along opposing sides from one another along proximal lip 1074D. In other words, recessed surfaces 1075D may be separated from one another by surfaces and/or portions of proximal lip 1074D that are not recessed. In the example, recessed surfaces 1075D may be positioned adjacent to slots 1074 and may define a pathway for moving plunger rod 1080 relative to collar 1072D for priming and delivering a dose from device 1050. In some embodiments, recessed surfaces 1075D may include a spiral configuration (e.g., have a distally-directed slope) such that recessed surfaces 1075D may be tapered in a distal direction between a first ledge 1073D and a second ledge 1076D.

In some embodiments, flange piece 1070D may include visualization mechanisms, such as, for example, one or more labels or markings disposed on collar 1072D to provide instructions to a user of device 1050. For example, the one or more labels (e.g., numbering) may indicate directions in which to rotate or otherwise move plunger rod 1080 relative to flange piece 1070D to prime and deliver a dosage from device 1050. By way of example, the one or more labels may include markings that indicate a start position (e.g., "1"), a priming position (e.g., "2"), and a dosage delivery position (e.g., "3") of protrusions 1086 relative to proximal lip 1074D. The one or more labels may be adhered, printed, embossed, and/or molded onto collar 1072D.

As described in greater detail herein, flange piece 1070D may be configured to allow movement of plunger rod 1080 in a single direction when priming and delivering a dosage from device 1050. In exemplary use, plunger rod 1080 (not shown) may initially be received through flange piece 1070D and actuation portion 1082 may be positioned against collar 1072D with protrusions 1086 positioned along a first end of recessed surfaces 1075D at marking "1" and opposite of slot 1074. Protrusions 1086 may only be rotated in a single direction along recessed surface 1075D, toward marking "2," due to first ledge 1073D inhibiting protrusions 1086 from moving in an opposite direction away from marking "2".

When protrusions 1086 are received along recessed surfaces 1075D at marking "2," second ledge 1076D may further prevent protrusions 1086 from moving past slots 1074 and passing by marking "3". It should be appreciated that a configuration of proximal lip 1074D is exemplary such that flange piece 1070D may include various other sizes, shapes, and/or configurations of proximal lip 1074D and/or recessed surfaces 1075D than those shown and described herein to facilitate movement of plunger rod 1080 during use of device 1050.

In other embodiments, the components of device 1050 may include one or more color indicators in lieu of and/or in addition to the markings described above to provide instructions to a user of device 1050. For example, device 1050 may include colors, symbols (e.g., arrows), and the like indicating a direction in which to rotate or otherwise move plunger rod 1080 relative to flange piece 1070D to prime and deliver a dosage. In one embodiment, an exterior surface of plunger rod 1080 may be provided with different colors along various portions of actuation portion 1082 to indicate a respective start position (e.g., green), priming position (e.g., yellow), and dosage delivery position (e.g., red) of plunger rod 1080 relative to collar 1072D. The one or more color indicators may be printed or molded onto plunger rod 1080. In other embodiments, the various portions of plunger rod 1080 may include different textures in lieu of and/or in addition to the color indicators described above to provide instructions to a user of device 1050.

Components of device 1050 may be made of any suitable material, and each component may be made from the same or different materials as other components. It should be appreciated that, in some embodiments, one or more components of device 1050 (e.g., flange piece 1070, proximal collar 1072, plunger rod 1080, actuation portion 1082, and more) may be formed of a flexible material having sufficient flexibility to prevent breakage during flexing. In some embodiments, the one or more components of device 1050 may be rigid and have enough strength to maintain shape and provide support. In other embodiments, one or more components of device 1050 (or at least a portion of a component) may having a varying rigidity along a longitudinal length or lateral width such that the component may have a variable flexibility. In still further embodiments, the one or more components of device 1050 may have sufficient flexibility to prevent breakage during flexing while also having sufficient rigidity and strength to maintain shape and provide support. In some embodiments, such features may further provide a user feedback (e.g., tactile, audible, visual, etc.) when flexing and/or interacting with other components of device 1050. For example, each of body 1060, flange piece 1070, and plunger rod 1080 may be made of a material including a polymer, such as a plastic. In some embodiments, one or more of body 1060, flange piece 1070, and plunger rod 1080 may include multiple different materials (e.g., glass, rubber, and/or plastic). In some embodiments, for example, the cylindrical portion of body 1060 may be made of glass, Plexiglas, or any other suitable polymer (e.g., cyclic olefin polymer or cyclic olefin copolymer) or other material, and stopper 1062 may be made of, e.g., plastic, rubber, or other polymer or copolymer. By way of further example, flange piece 1070 may include a polypropylene homopolymer, an ABS (Acrylonitrile, Butadiene, and Styrene) polymer, ABS polycarbonate blend, and other suitable materials. In some embodiments, plunger rod 1080 may include an ABS polycarbonate blend. Such materials may provide greater tolerances for manufacturing (e.g., injection molding) flange piece 1070 and/or plunger rod 1080, or facilitate an increased reproducibility of said components of device 1050. As described in greater detail above, in some embodiments, one or more components of device 1050 may be formed of a flexible and/or deformable material composition providing greater tolerances for flexing or deforming said components (e.g., without breaking) when priming or delivering a dose from device 1050.

In some embodiments, a portion of body 1060 configured to contain a formulated drug substance may be made of a transparent or translucent material. In some embodiments, flange piece 1070 and plunger rod 1080 may be made of the same, similar, or different materials, such as similar or different plastics (e.g., each having a similar or different hardness). In some embodiments, parts of device 1050 may include elastic materials. For example, parts of device 1050 may include rubber or plastic configured to allow a user to better grip device 1050, or to create an airtight or otherwise sealing fit between two components of device 1050 (e.g., between body 1060 and stopper 1062). In some embodiments, some or all of plunger rod 1080 (e.g., actuation portion 1082 and/or extensions 1087, or alternately the entirety of plunger rod 1080) may be made of a material having some flexibility, e.g., to allow for bending of extensions 1087. One or more of the materials listed above (e.g., plastic, rubber, polymers, or copolymers) may have such characteristics. In some embodiments, some or all of device 1050 may be suitable for sterilization, e.g., heat or chemical sterilization.

Figures 3A, 3B:
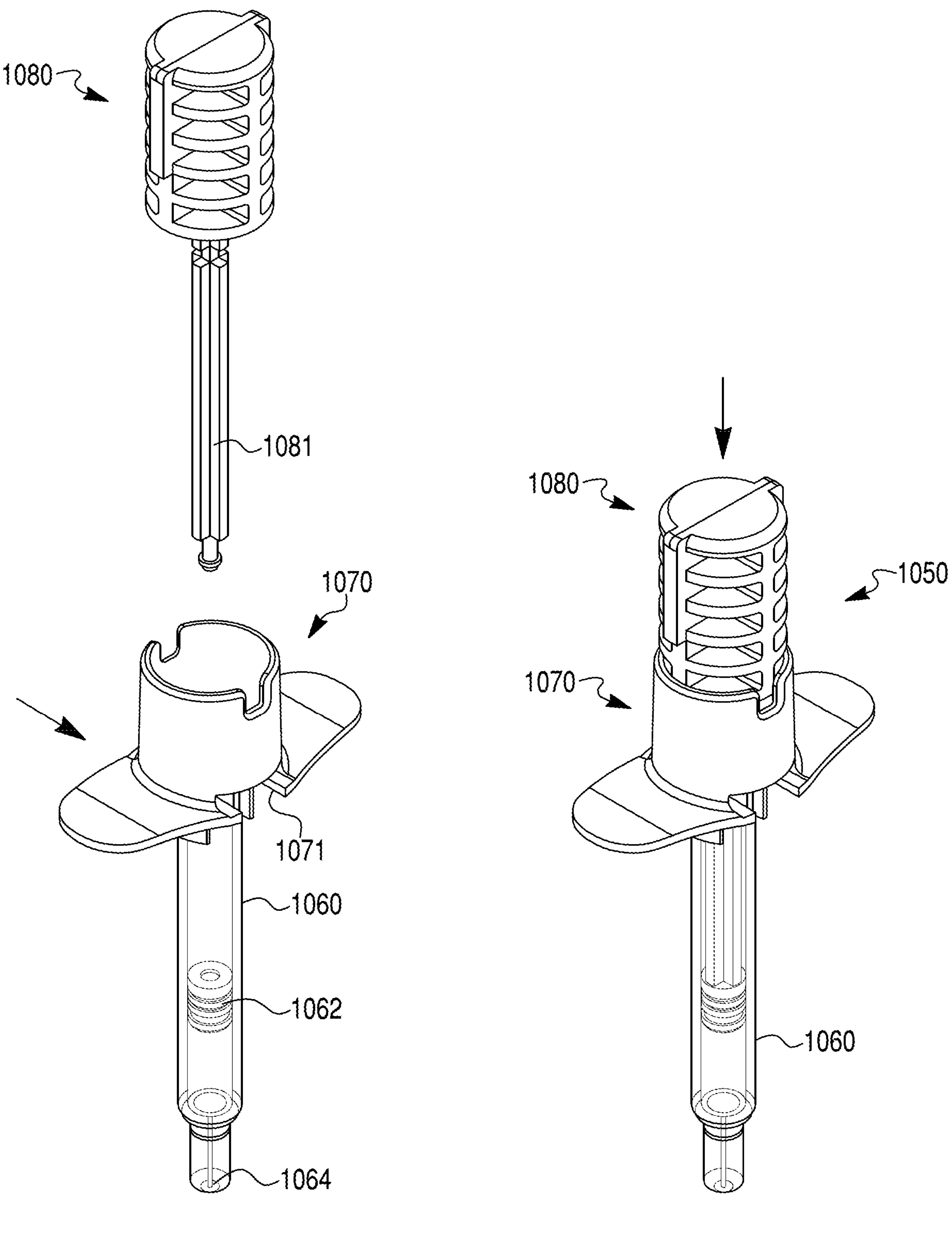
FIGS. 3A and 3B depict an exemplary method of assembling the delivery device depicted in FIGS. 1A-1E, according to aspects of the present disclosure.
Figure 3C:
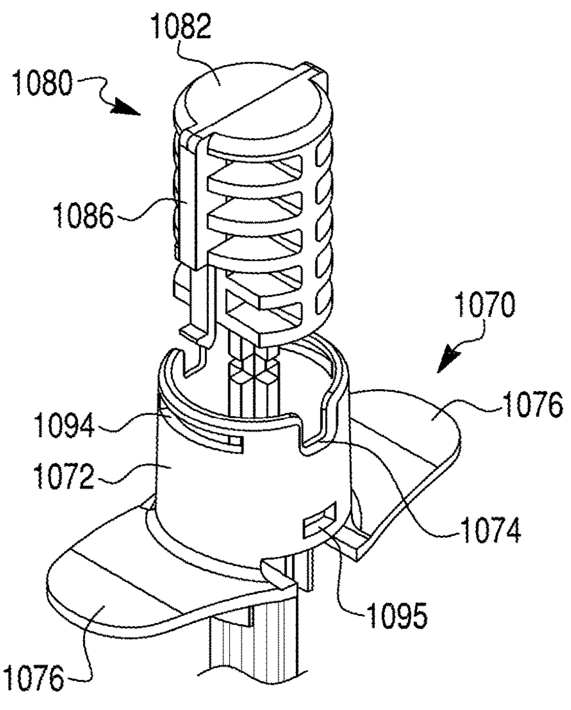
FIGS. 3C-3F depict an exemplary method of assembling an embodiment of the delivery device depicted in FIGS. 1A-1E, according to aspects of the present disclosure.
Figure 3E:
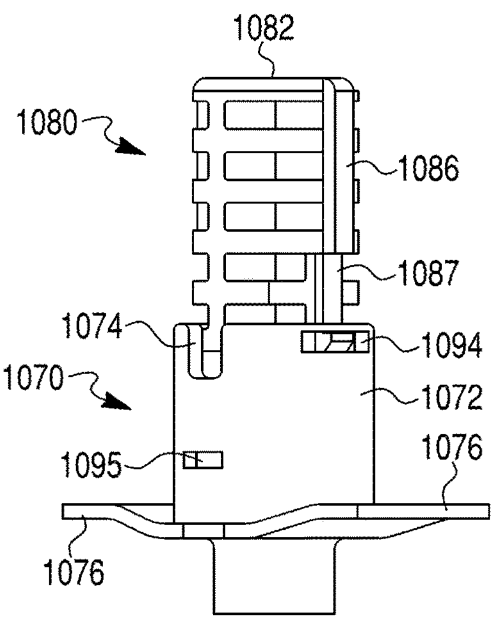
Figure 3D:
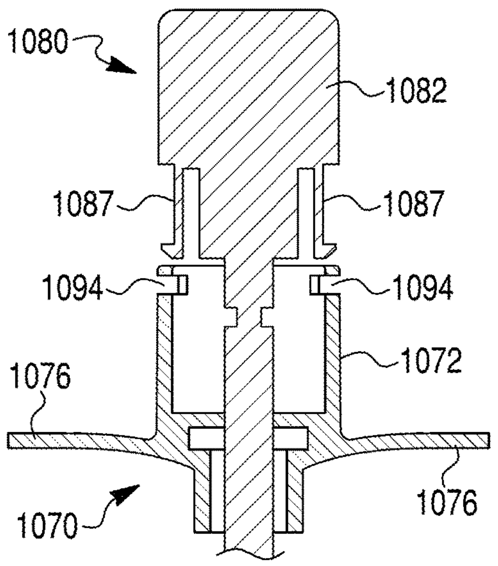
Figure 3F:
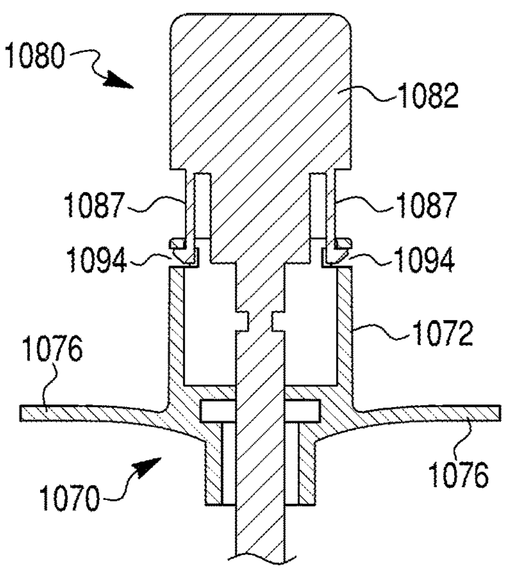

FIGS. 3A and 3B depict an exemplary method of assembling the delivery device depicted in FIGS. 1A-1E. Flange piece 1070 may be assembled to body 1060, as shown in FIG. 3A. The assembly of flange piece 1070 to body 1080 may include sliding, snapping, adhering, or otherwise affixing the two components together. As depicted in FIG. 3A, flange piece 1070 may be slid onto body 1060, e.g., such that lip 1071 of flange piece 1070 engages with body flange 1061. Plunger rod 1080 may be inserted through the assembled flange piece 1070 and body 1060, such that a distal end of plunger rod 1080 contacts stopper 1062. The assembled device 1050 may then be in a configuration suitable for packaging, sterilization, and/or use.

FIGS. 3C-3F depict an exemplary method of assembling device 1050 in which actuation portion 1082 includes extensions 1087 and collar 1072 includes side openings 1094. In such an embodiment, plunger rod 1080 may be inserted through flange piece 1070 until the hook or clip portions of extensions 1087 are received within side openings 1094, at which point the assembled device 1050 may be in a configuration suitable for packaging, sterilization, and/or use. It should be appreciated that side openings 1094 may be configured to inhibit a proximal retraction of plunger rod 1080 relative to flange piece 1070 once the hook or clip portions of extensions 1087 are received therein. Side openings 1094 may function as a first lock when device 1050 is placed into an initial assembly state to prevent disassembly of device 1050.

As described in further detail herein (see FIGS. 4G-4J), side openings 1095 may be configured to inhibit a proximal retraction of plunger rod 1080 once the hook or clip portions of extensions 1087 are received therein. Side openings 1095 may function as a second lock when device 1050 is placed in a dosage delivery state to prevent extracting patient fluid after completion of drug/medicament delivery. It should be appreciated that side openings 1094, 1095 may generate a feedback indicating a relative position of plunger rod 1080 to flange piece 1070, such as, for example, an audible feedback, a tactile feedback, and the like. In some embodiments, device 1050 may include additional and/or fewer side openings 1094, 1095 than those shown and described herein to increase and/or decrease a quantity of locks on device 1050.

In some embodiments, assembling device 1050 may include pre-filling body 1060 before combining it with flange piece 1070 and stopper 1080; for example, a predetermined amount of drug substance may be disposed in body 1060 between stopper 1062 and needle end 1064. In some embodiments, an alternate order of assembly of the components of device 1050 may be employed, depending on contemplated variations in the structures of components of device 1050. For example, in an embodiment (not shown) in which flange piece 1070 is configured to be assembled to body 1060 using a snap-fit interface, plunger rod 1080 may be first inserted through flange piece 1070, and the combined flange piece 1070 and plunger rod 1080 may be assembled to body 1060, e.g., such that flange piece 1070 snaps over a proximal body flange 1061 of body 1060 and plunger rod 1080 is inserted into body 1060.

Figures 4A, 4B, 4C:
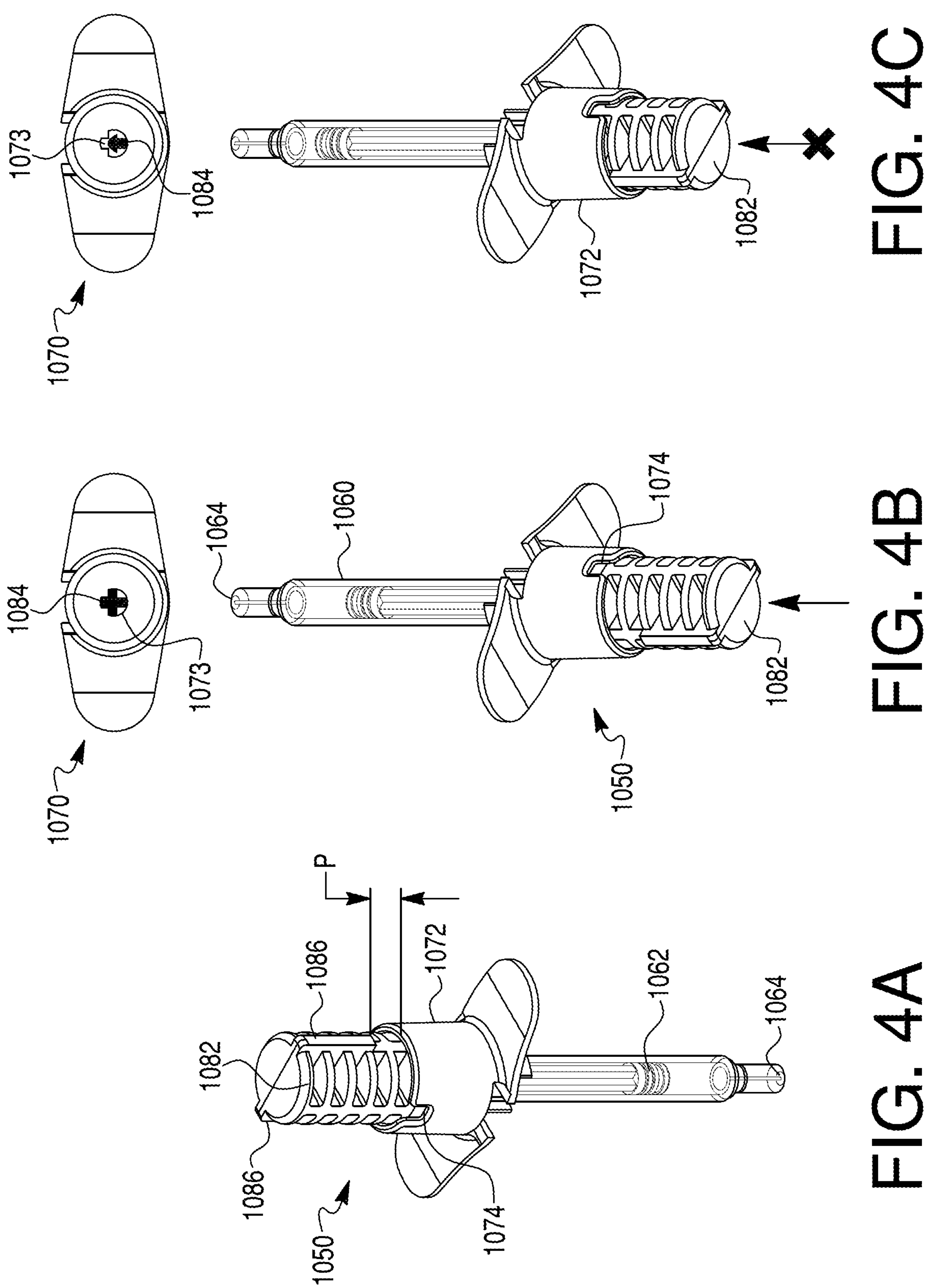
FIGS. 4A-4F depict an exemplary method of using the delivery device depicted in FIGS. 1A-1E, according to aspects of the present disclosure.

FIGS. 4A-4F depict an exemplary method of using device 1050, according to aspects of the present disclosure. In a pre-use configuration depicted in FIG. 4A, device 1050 may hold a volume of a drug substance in between stopper 1062 and expulsion end 1064. A priming distance p may exist between protrusions 1086 and a proximal end of proximal collar 1072, and protrusions 1086 may be non-aligned with slots 1074. In a priming step depicted in FIG. 4B, plunger rod 1080 may be moved longitudinally further into body 1060. For example, a user may press actuation portion 1082 partially into proximal collar 1072 of flange piece 1070. In some embodiments, device 1050 may be held in an inverted position during this step, to ensure that air trapped in body 1060 may be expelled via expulsion end 1064, as stopper 1062 is pushed distally by plunger rod 1080. In the pre-use configuration of FIG. 4A and during the priming step shown in FIG. 4B, plunger rod 1080 may be prevented from rotating about the longitudinal axis of the syringe, due to the geometries of opening 1073 in flange piece 1070, and neck 1084 of plunger rod 1080 (as shown in the top cross-sectional view in FIG. 4B). As shown in FIG. 4C, the priming step may be stopped when protrusions 1086 of plunger rod 1080 abut a proximal end of proximal collar 1072. When the priming step is completed, neck 1084 of plunger rod 1080 may be positioned longitudinally with respect to opening 1073 of flange piece 1070, such that it may now be rotatable with respect to flange piece 1070. For example, when the priming step is completed, a narrower portion of neck 1084 may be disposed inside opening 1073 than when device was in a pre-use configuration.

Figure 4F:
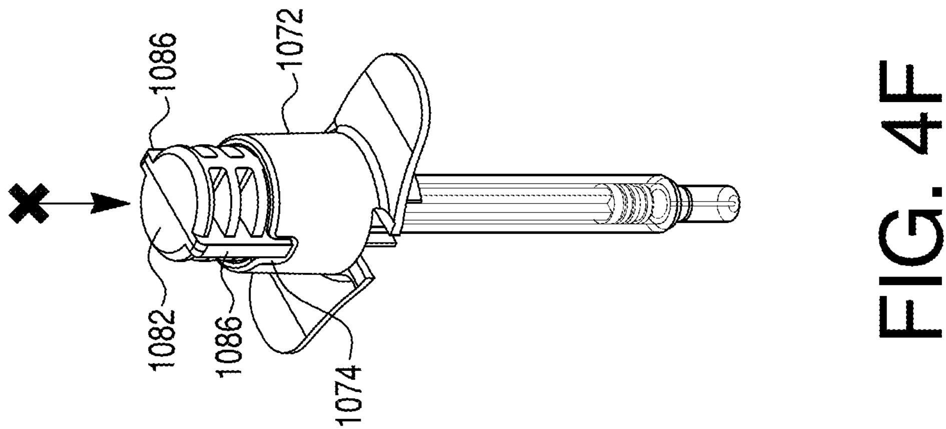
Figure 4E:
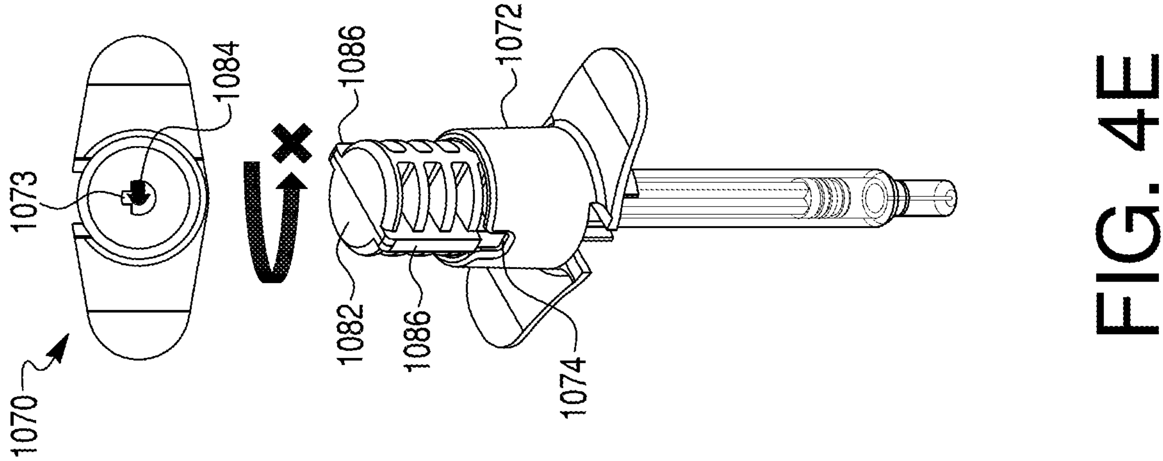
Figure 4D:
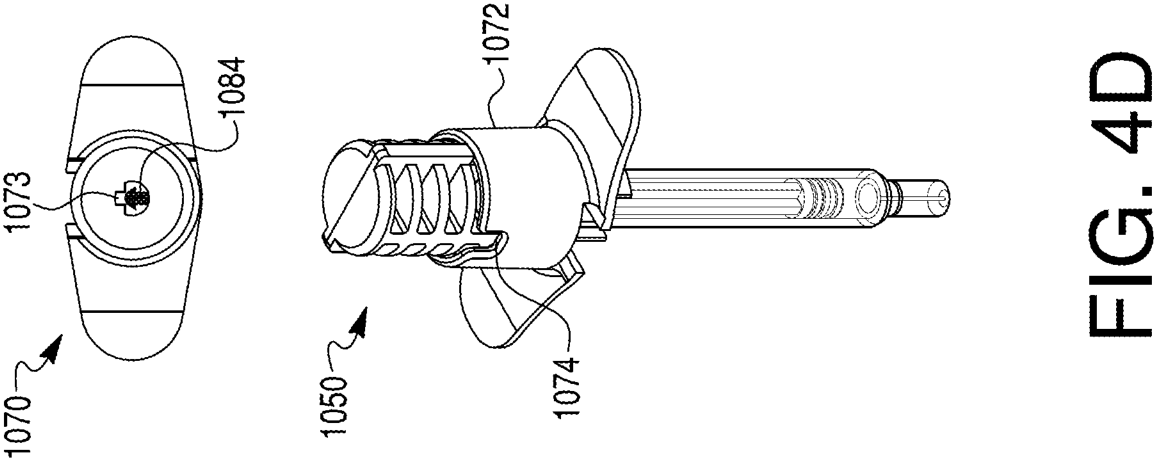

As depicted in FIG. 4D, device 1050 may be in a primed configuration. In a dispensing preparation step depicted in FIG. 4E, plunger rod 1080 may be rotated about a longitudinal axis to align protrusions 1086 with slots 1074. To do so, a user may grasp and twist actuation portion 1082. In some embodiments, as has been described elsewhere, it may be possible to twist actuation portion 1082 in either direction to align protrusions 1086 and slots 1074. In other embodiments, actuation portion 1082 may be rotatable only in one direction. In some embodiments, once protrusions 1086 are aligned with slots 1074, further rotation of plunger rod 1080 relative to flange piece 1070 may be stopped by, e.g., contact between the geometries of neck 1084 and opening 1073. Thus, aligning protrusions 1086 and slots 1075 may lock device 1050 in a ready-to-dispense configuration. In some embodiments, rotation of actuation portion 1082 may align protrusions 1086 with slots 1074, and may allow plunger rod 1080 to remain longitudinally stationary relative to flange piece 1070 (e.g., no proximal or distal movement of plunger rod 1080 is caused by rotation of actuation portion 1082). As depicted in FIG. 4F, in a dispensing step, plunger rod 1080 may be moved longitudinally further into body 1060. For example, a user may press actuation portion 1082 distally into proximal collar 1072 of flange piece 1070, such that protrusions 1086 slide into slots 1074. Once protrusion 1086 abut distal ends of slots 1074, further distal movement of plunger rod 1080 is stopped. The dispensing step may ensure that a predetermined volume of a drug substance inside body 1060 is dispensed from device 1050. In some embodiments, when protrusions 1086 abut distal ends of slots 1074, stopper 1062 does not "bottom out" or abut an interior of expulsion end 1064 in body 1060. Advantageously, by ensuring that a predetermined volume of a drug substance inside body 1060 is dispensed from device 1050 before stopper 1062 can bottom out, any variations in the manufacture of expulsion end 1064 (e.g., altering the exact size or shape of expulsion end 1064) are less likely to affect the predetermined volume of drug substance that is delivered from device 1050. Indeed, in some embodiments, the predetermined volume of drug substance that is delivered from device 1050 may not be affected by typical variations in manufacturing of any component of device 1050, particularly in any component except for flange piece 1070. Advantageously, this may allow for the existence of different or larger tolerances in manufacturing variation in several components of device 1050 (e.g., variations in formation of a glass body 1060 or other glass components), without affecting the predetermined volume of drug substance to be delivered from device 1050.

Figure 4G:
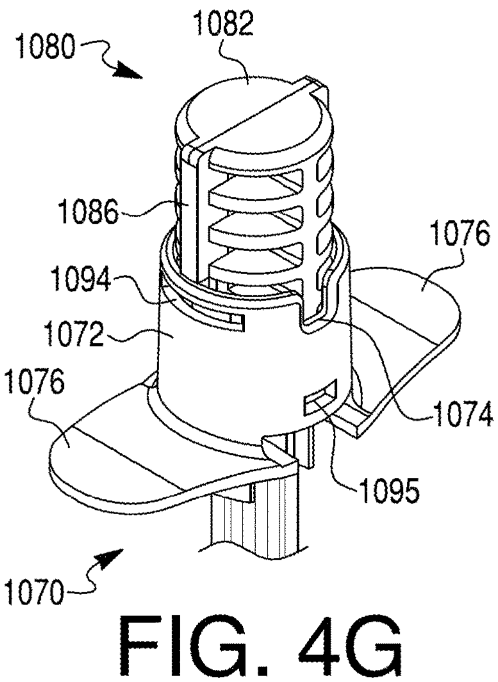
FIGS. 4G-4J depict an exemplary method of using an embodiment of the delivery device depicted in FIGS. 1A-1E, according to aspects of the present disclosure.
Figure 4I:
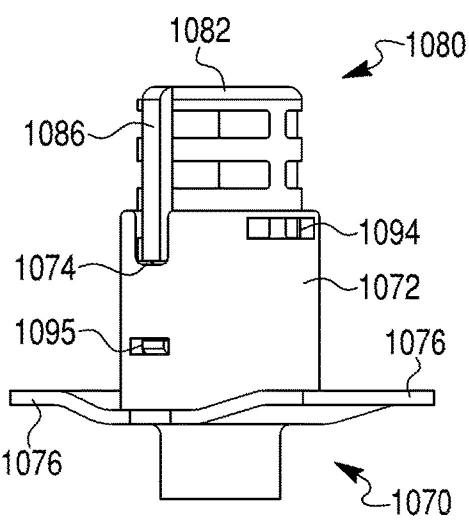
Figure 4H:
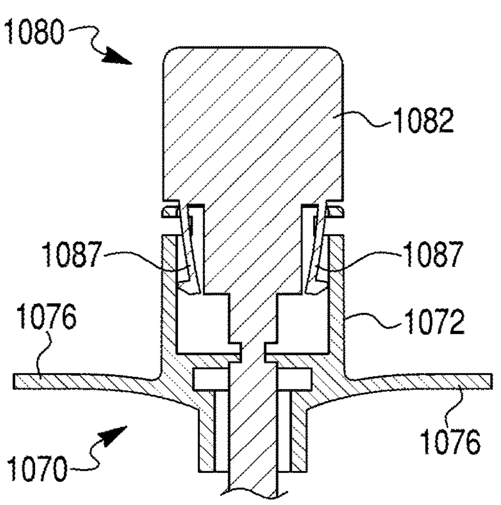
Figure 4J:
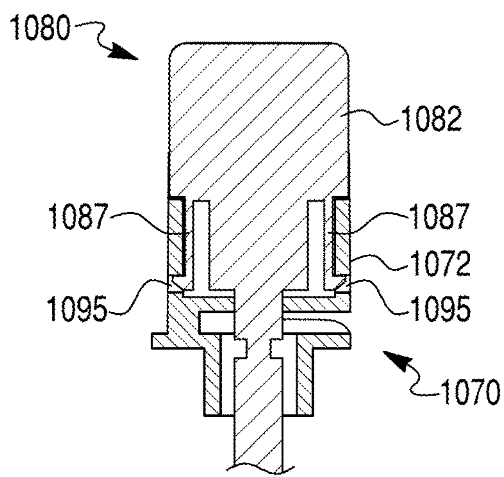

In some embodiments, after one or more steps in the use of device 1050, a user may be prevented from re-doing a step, and/or from reversing one or more steps. For example, geometries of, e.g., plunger rod neck 1084 and opening 1073 may prevent a user from pulling plunger rod 1080 proximally (e.g., out of) body 1060, from rotating plunger rod 1080 preemptively (e.g., before the priming step shown in FIG. 4C), and/or from over-rotating plunger rod 1080 during a dispensing preparation step (e.g., shown in FIG. 4E). In particular, FIGS. 4G-4J depict steps in the use of an embodiment of device 1050 having extensions 1087 on actuation portion 1082 and corresponding side openings 1094, 1095 in collar 1072 of flange piece 1070. FIGS. 4G and 4H depicts device 1050 as actuation portion 1082 is being pushed distally into collar 1072. Due to their angled distal portions, extensions 1087 are pushed inward into collar 1072. Once plunger rod 1080 has been rotated to a "delivery" position and actuation portion 1082 is further pushed distally into collar 1072 to deliver a predetermined volume of drug substance from device 1050, extensions 1087 may be received into side openings 1095 (shown in FIGS. 41 and 4J), thereafter restricting proximal movement of plunger rod 1080. Advantageously, restricting proximal movement of plunger rod 1080 may prevent inadvertent withdrawal of material into device 1050 from, e.g., a site into which a drug substance is delivered. In some embodiments, device 1050 may include either side openings 1094, or side openings 1095. In other embodiments, as shown in FIGS. 4G-4J, device 1050 may include both side openings 1094 and side openings 1095.

Figure 4K:
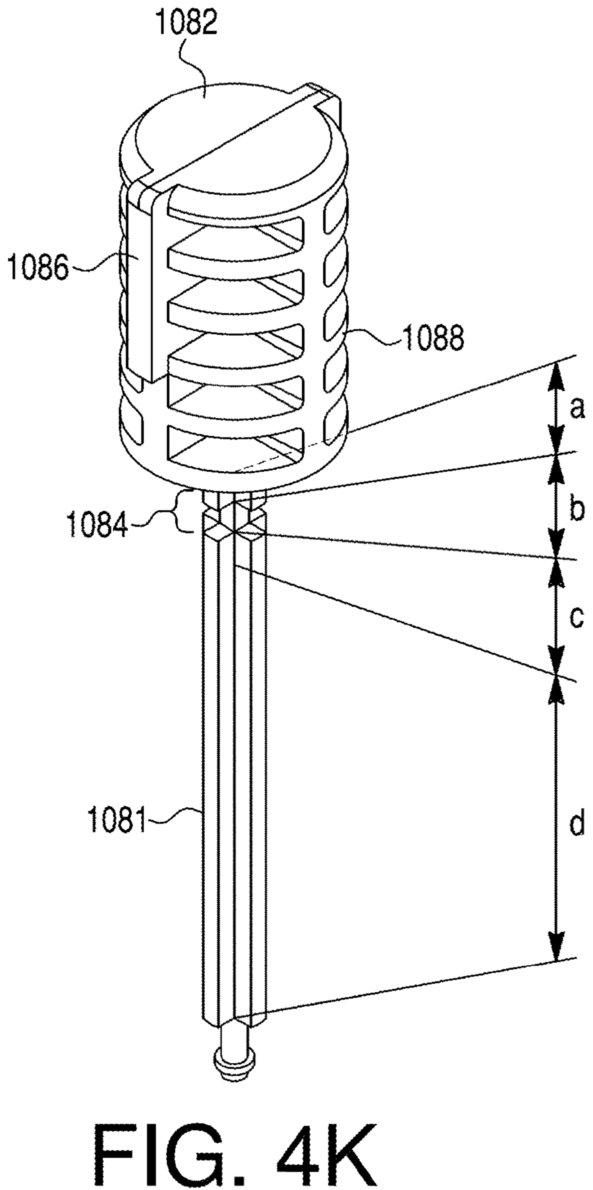
FIGS. 4K-4S depict exemplary aspects of plunger rods for use in embodiments of the delivery device depicted in FIGS. 1A-1E.
Figure 4L:
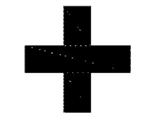
Figure 4M:
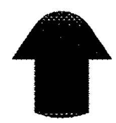
Figure 4N:
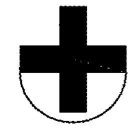
Figures 4O, 4P, 4Q, 4R, 4S:
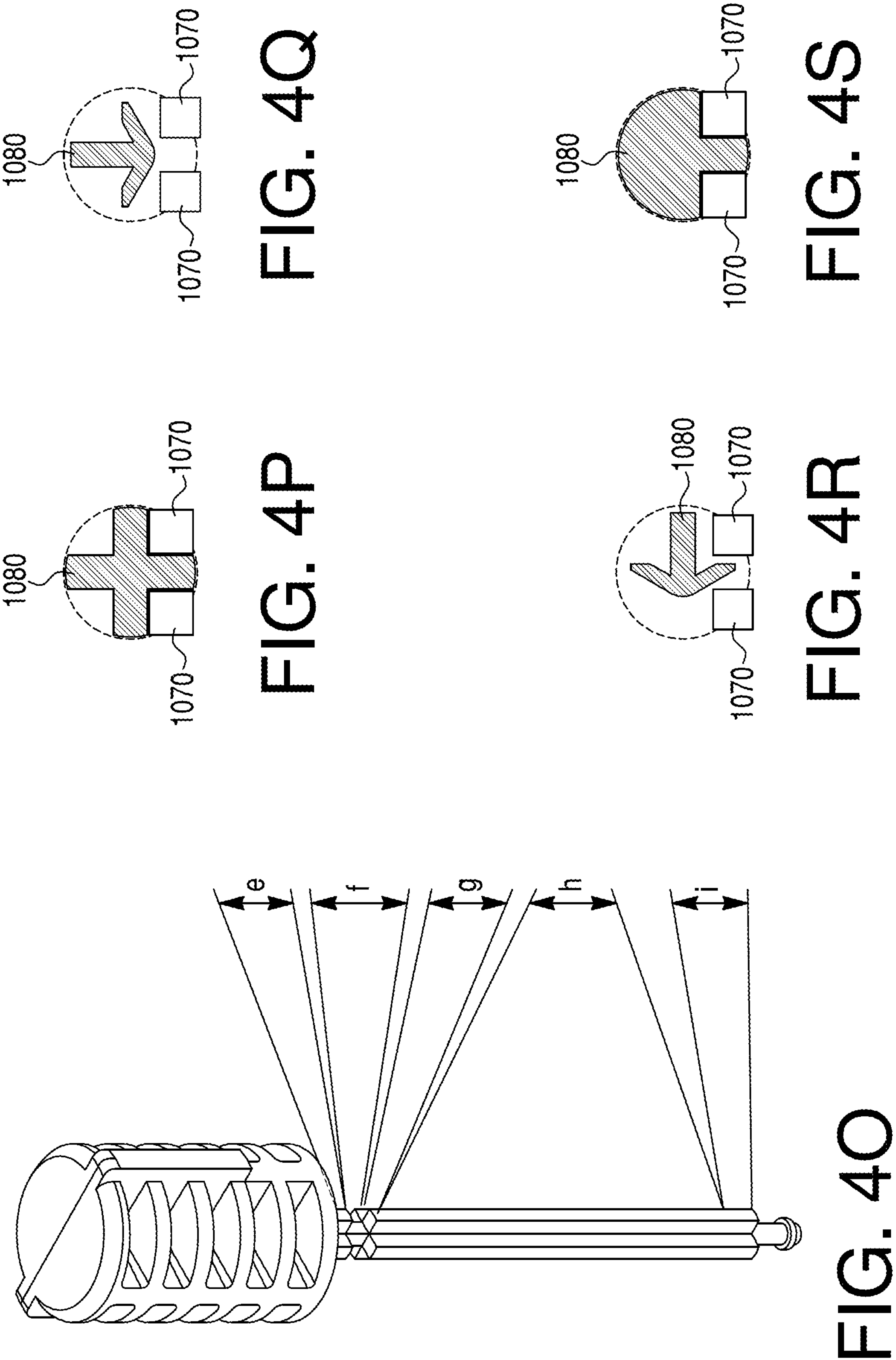

FIGS. 4K and 4O depicts in further detail exemplary aspects of a geometry of neck 1084, which may help to control movement of plunger rod 1080. For example, a proximal-most portion a of neck 1084 and stem 1081 (indicated by section d in FIG. 4K) may both have a first cross-sectional shape, as shown in FIG. 4L. This shape may allow for corresponding portions of plunger rod 1080 to move proximally/distally through an opening (e.g., opening 1073) of a blocking component (e.g., flange piece 1070), but may prevent rotation of plunger rod 1080 about a longitudinal axis. A narrow portion b of neck 1084 may have a smaller cross-sectional shape, as shown in FIG. 4M. This shape, when disposed in an opening (e.g., opening 1073) of a blocking component (e.g., flange piece 1070) may allow for unidirectional or bidirectional rotation of plunger rod 1080 about a longitudinal axis. It should be appreciated that the respective portion of neck 1084 allowing for transitional rotation of plunger rod 1080 (e.g., at narrow portion b) may have a geometry with the smallest cross-sectional shape to allow greater space for such movement, relative to the cross-sectional shapes of other portions of plunger rod 1080. A third portion c of neck 1084 may have a larger cross-sectional shape, as shown in FIG. 4N, which may correspond directly with the size and shape of an opening (e.g., opening 1073) of a blocking component (e.g., flange piece 1070). As such, proximal or distal movement of this portion of neck 1084 through opening 1073 may only be possible when plunger rod 1080 is in a specific rotational orientation relative to flange piece 1070. Moreover, plunger rod 1080 will not be rotatable while portion c of neck 1084 is disposed within opening 1073. This may ensure that, e.g., plunger rod 1080 is in a desirable position relative to flange piece 1070 (e.g., priming is complete and portion c is no longer disposed within opening 1073) before plunger rod 1080 may be rotated. Together, the various cross-sectional shapes of neck 1084 and the size and shape of opening 1073 may combine to create a specific sequence of movements of plunger rod 1080 needed to prime and deliver a drug substance from device 1050. In the example, a distal portion of opening 1073 may have the greatest cross-sectional profile relative to an intermediate and/or proximal portion of opening 1073 to accommodate the varying geometries of plunger rod 1080 therethrough (e.g., neck 1084, stem 1081, etc.).

In a further embodiment depicted in FIG. 4O, a proximal-most portion e of neck 1084 and a majority portion h of stem 1081 may both have a first cross-sectional shape, as shown in FIG. 4P. This shape may allow for corresponding portions of plunger rod 1080 to move proximally/distally through an opening (e.g., opening 1073) of a blocking component (e.g., flange piece 1070), but may prevent rotation of plunger rod 1080 about a longitudinal axis. A narrow portion f of neck 1084 may have a smaller winged (or arrow-shaped) cross-sectional shape, as shown in FIG. 4Q (in a pre-rotation configuration relative to flange piece 1070) and FIG. 4R (in a post-rotation configuration relative to flange piece 1070). This "winged" shape, when disposed in an opening (e.g., opening 1073) of a blocking component (e.g., flange piece 1070) may allow for unidirectional or bidirectional rotation of plunger rod 1080 about a longitudinal axis, and may restrict or resist "backwards" rotation of plunger rod 1080 in the opposite direction after rotation has been completed (as described further with respect to FIGS. 4T-4X). Portions g and/of plunger rod 1080 may have a larger cross-sectional shape, as shown in FIG. 4S, which may correspond directly with the size and shape of an opening (e.g., opening 1073) of a blocking component (e.g., flange piece 1070). As such, proximal or distal movement of these portions of plunger rod 1080 through opening 1073 may only be possible when plunger rod 1080 is in a specific rotational orientation relative to flange piece 1070. Moreover, plunger rod 1080 will not be rotatable while portions g or l of plunger rod 1080 are disposed within opening 1073. This may ensure that, e.g., plunger rod 1080 is in a desirable position relative to flange piece 1070 at certain steps during assembly and use of device 1050, allowing for precise assembly and use of device 1050. Additionally, the "larger" cross sectional area of portions g and l may assist in preventing plunger rod "back-out", as they will not be able to move proximally through opening 1073 unless in a particular rotational position relative to flange piece 1070. For example, after rotation of plunger rod 1080 from a "primed" position to a "delivery" position, portion g of plunger rod 1080 may not be able to move through opening 1073, thus preventing plunger rod "back-out" at that stage of use of device 1050. Together, the various cross-sectional shapes of plunger rod 1080 and the size and shape of opening 1073 may combine to create a specific sequence of movements of plunger rod 1080 needed to assemble, prime, and deliver a drug substance from device 1050.

Figure 4T:
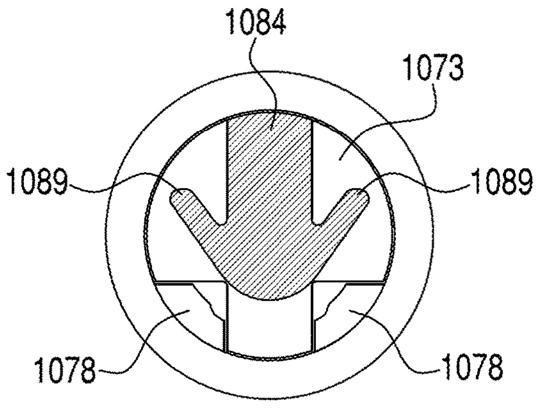
FIGS. 4T-4X depict views of an exemplary neck portion of a plunger rod and opening of a flange piece in embodiments of the delivery device depicted in FIGS. 1A-1E.
Figure 4U:
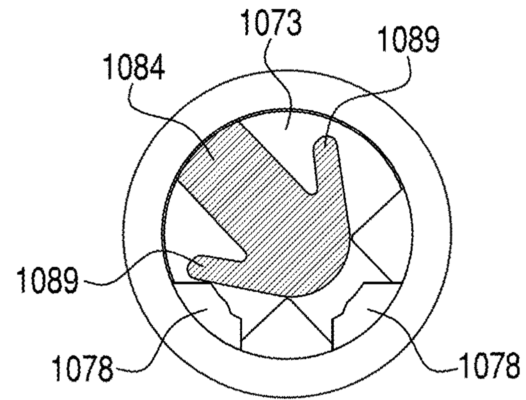
Figure 4V:
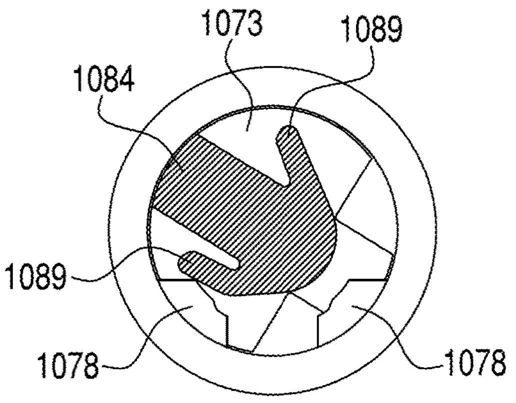
Figure 4W:
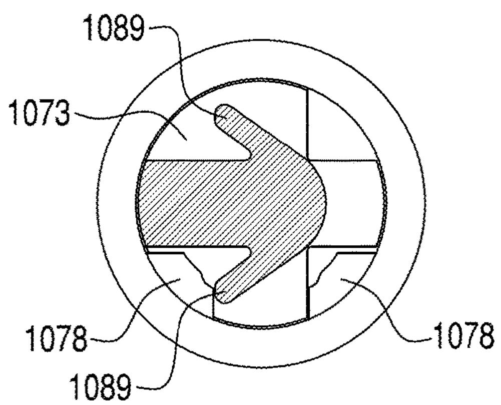
Figure 4X:
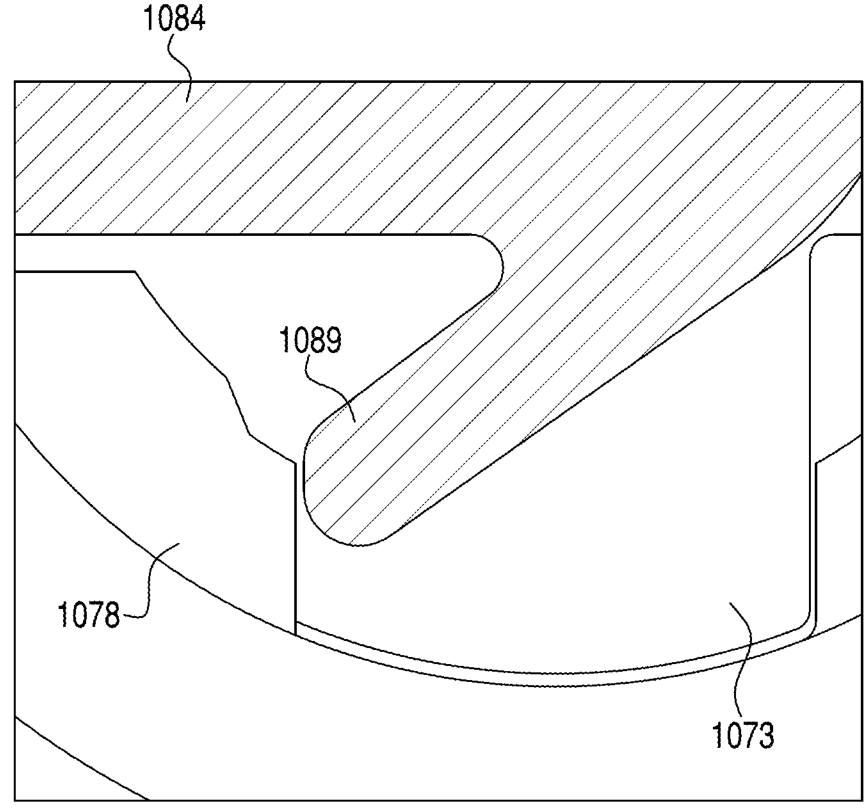

FIGS. 4T-4X depict in further detail specific interactions between a wing-shaped part of neck 1084 and opening 1073 in flange piece 1070. Flange piece 1070 may include detents 1078 either adjacent to or within opening 1073, which may interface with wings 1089 on neck 1084. FIG. 4T depicts a cross-sectional view of neck 1084 inside opening 1073 in a pre-rotation configuration (e.g., after device 1050 has been primed but before plunger rod 1080 has been rotated to a "delivery" configuration relative to flange piece 1070). FIG. 4U depicts that, as plunger rod 1080 is rotated about a longitudinal axis, one of wings 1089 may contact one of detents 1078 (depending on the direction of rotation). As rotation continues, one of detents 1078 may cause one of wings 1089 to be compressed towards the remainder of neck 1084. When rotation is complete, the one of wings 1089 has passed the one of detents 1078 and has expanded. This expansion of a wing 1089 past detent 1078 may cause an auditory "click" feedback and/or a tactile feedback to indicate that rotation is complete, and may thereafter prevent "backwards" rotation of plunger rod 1080 relative to flange piece 1070. Wings 1089 and detents 1078 may be configured to interact in a similar fashion regardless of whether plunger rod 1080 is rotated in a clockwise or counterclockwise direction, thereby allowing for bidirectional rotation of plunger rod 1080 to move plunger rod 1080 from a "primed" position to a "delivery" position. As shown in further detail in FIG. 4X, each wing 1089 may have a rounded shape to allow for ease of rotation in one direction, and the expansion of a wing 1089 past a detent 1078 may place the wing 1089 in a position relative to detent 1078 that greatly resists or otherwise prohibits rotation in the opposite direction. Detent 1078 may have any suitable contour configured to assist unidirectional movement of a wing 1089 past detent 1078.

Advantageously, the various configurations of plunger rod 1080 described herein may allow for modeling, molding, and/or manufacturing one piece (e.g., plunger rod 1080) or two pieces (e.g., plunger rod 1080 and flange piece 1070) in order to achieve several goals—e.g., control desired plunger rod movement and assembly, reduce user error, prevent plunger rod back-out, and minimize a number of disparate parts needing to be manufactured and handled in order to assemble device 1050.

Figures 4Y, 4Z:
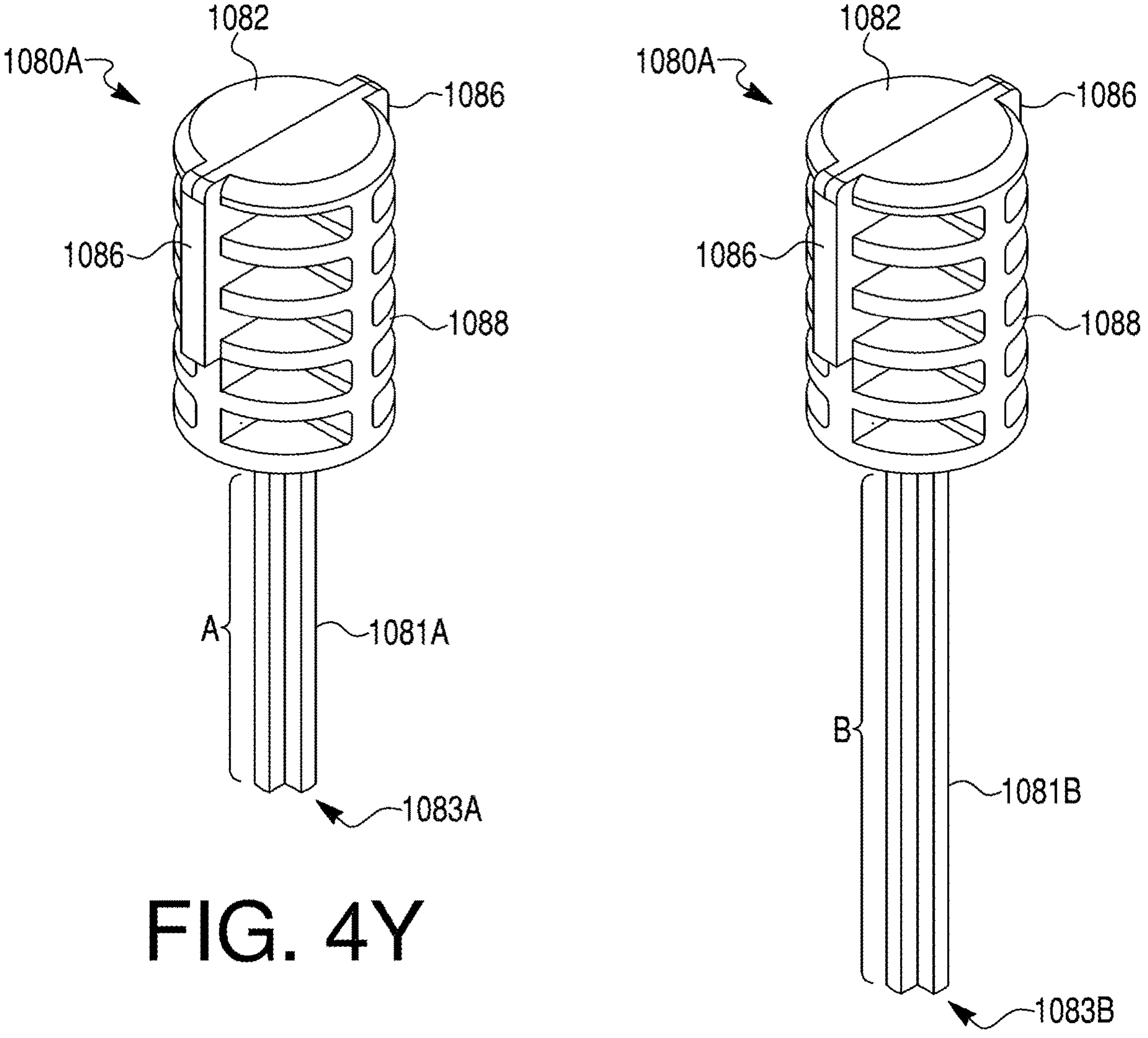
FIGS. 4Y-4Z depict exemplary aspects of plunger rods for use in embodiments of the delivery device depicted in FIGS. 1A-1E.
Figure 6E:
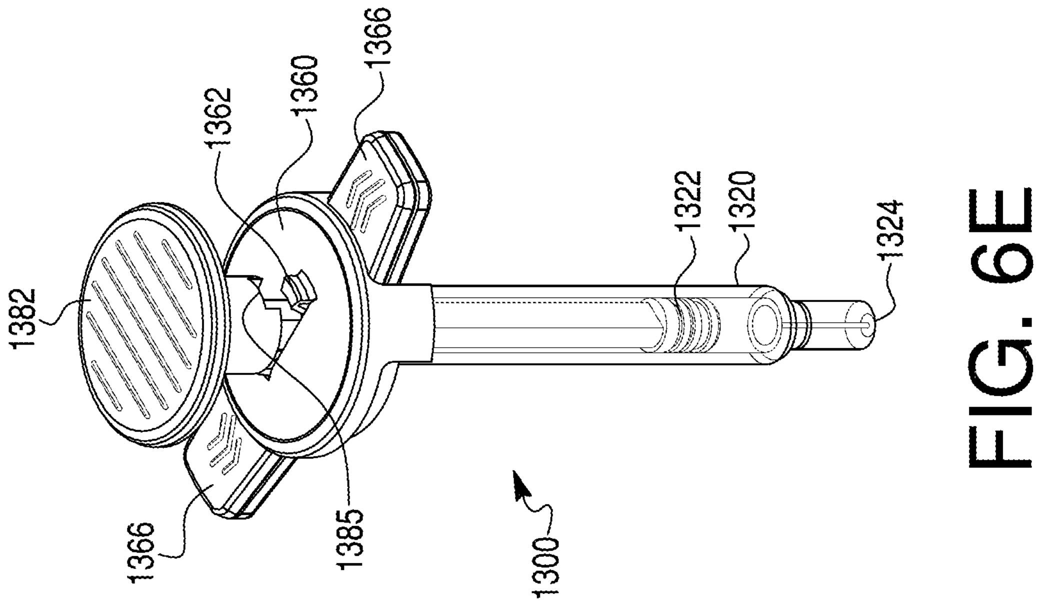
Figure 6D:
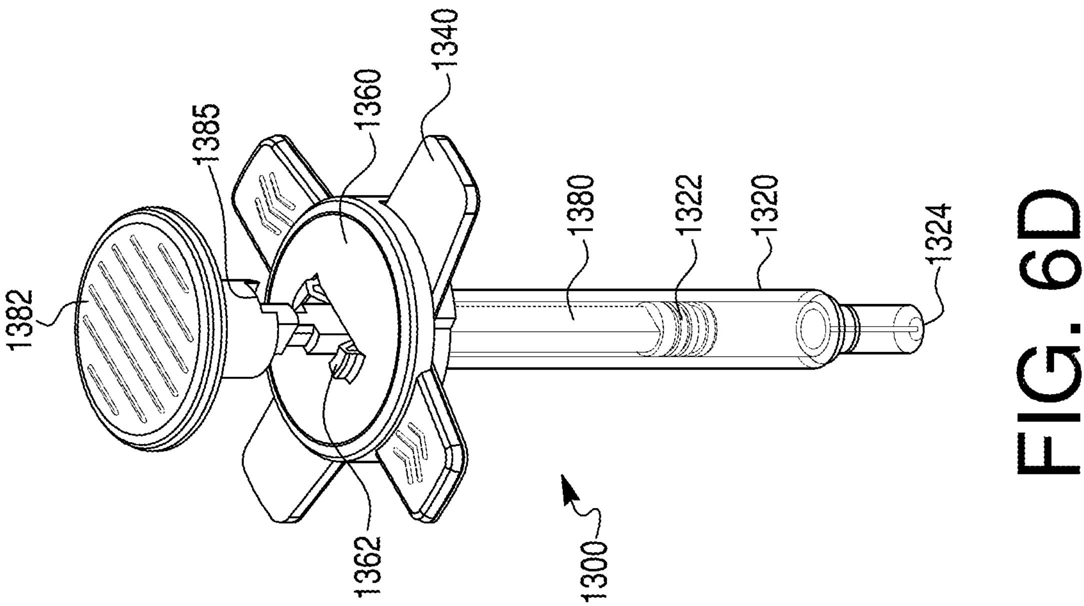

In some embodiments, as seen in FIGS. 4Y-4Z, device 1050 may include a pair of plunger rods in one kit, interchangeable with a single actuation portion 1082, or coupled to separate actuation portions 1082. For example, referring initially to FIG. 4Y, device 1050 may include a first plunger rod 1080A that is substantially similar to plunger rod 1080 shown and described above except for the differences explicitly noted herein. First plunger rod 1080A may include a stem 1081A having a longitudinal length A defined between a distal end of actuation portion 1082 and a tip 1083A. As described in detail below, longitudinal length A may define a priming distance for moving plunger rod 1080A relative to flange piece 1070 for priming device 1050. Tip 1083A may have a flat and/or planar interface that may be configured to inhibit engagement of stopper 1062 when first plunger rod 1080A is received within body 1060.

Referring now to FIG. 4Z, device 1050 may further include a second plunger rod 1080B that is substantially similar to plunger rod 1080. Second plunger rod 1080B may include a stem 1081B extending distally from actuation portion 1082 and having a longitudinal length B defined between a distal end of actuation portion 1082 and a tip 1083B. Tip 1083B is substantially similar to tip 1083A described above. Longitudinal length B of stem 1083B is relatively greater than longitudinal length A of stem 1081A and may define a dosage delivery distance for moving plunger rod 1080A relative to flange piece 1070 to deliver a dose from device 1050.

First plunger rod 1080A may be configured to prime device 1050 in response to translating stem 1081A through collar 1072 and into body 1060 (see FIGS. 1A-1B). In this instance, tip 1083A may contact and push stopper 1062 distally by the priming distance. It should be understood that the priming distance of device 1050 may be controlled based on a size of longitudinal length A of first plunger rod 1080A. Upon priming device 1050, first plunger rod 1080A may be removed from body 1060 and flange piece 1070 without retracting stopper 1062 due to a flattened-interface of tip 1083A. Accordingly, stopper 1062 may remain at a fixed position relative to body 1060 upon retraction of first plunger rod 1080A.

Second plunger rod 1080B may be configured to deliver a dose from device 1050 in response to translating stem 1081B through collar 1072 and into body 1060 (see FIGS. 1A-1B), after the priming step described above using stem 1081A. In this instance, tip 1083B may contact and push stopper 1062 distally by the dosage delivery distance. It should be understood that the dosage delivery distance of device 1050 may be controlled based on a size of longitudinal length B of second plunger rod 1080B. The dosage delivery distance may be substantially equal to the difference in length between stem 1081B and stem 1081A.

FIGS. 5A-5C depict another exemplary delivery device 1200 according to additional embodiments of the present disclosure. Device 1200 includes a body 1220, and a flange piece 1240 with a proximal collar 1242, in which an inner collar 1260 may be disposed. Together, proximal collar 1242 and inner collar 1260 may form a blocking component for device 1200. A plunger rod 1280 may pass through inner collar 1260 and flange piece 1240, into body 1060. Plunger rod 1280 may share a longitudinal axis with a central axis of proximal collar 1242 and inner collar 1260, and may have an actuation portion 1282 sized and configured to fit (e.g., nest or otherwise fit) inside inner collar 1260.

Device 1200 may be, for example, an injection device, such as a syringe, for dispensing a predetermined volume of a formulated drug substance. Generally, device 1200 may share size, capacity, material, preparation, assembly, manufacturing, operation, or use characteristics with device 1050, or with other delivery devices disclosed herein. As with device 1050, device 1200 may be configured for ease of use and may include one or more features that aid a user by providing tactile, auditory, or visual feedback (e.g., using any of the features described elsewhere herein).

Body 1220 may have any or all of the same characteristics as, e.g., body 1060 of device 1050, or as any syringe body known in the art. For example, in some embodiments, body 1220 may be pre-fillable or pre-filled (e.g., fillable or filled with a drug substance prior to completed assembly, packaging, sterilization and/or shipment of device 1200 to users). In some embodiments, a stopper 1222 may be configured to be inserted into body 1220 and may be configured to hold a predetermined volume of a formulated drug substance inside body 1200, between stopper 1222 and an expulsion end 1224.

Flange piece 1240 may be of any suitable size and/or shape to close, partially close, cover, or partially cover an end of body 1220 opposite expulsion end 1224, and/or to support and hold plunger rod 1280 in place inside body 1220. In some embodiments, flange piece 1240 may share some characteristics with flange piece 1070 of device 1050. For example, flange piece 1240 may include a distal collar 1244 configured to engage with body 1220 and hold flange piece 1240 in place in relation to body 1220. For example, distal collar 1244 may include a lip 1245 that may slide over a body flange 1226, to hold flange piece 1240 in place. In alternative embodiments, lip 1245 of distal collar 1244 may be made of a flexible or semi-flexible material, so that it may snap in place over body flange 1226. In further embodiments, distal collar 1244 or another portion of flange piece 1240 may be adhered to, molded to, or otherwise affixed to, body 1220, or may engage with body 1220 via a friction fit.

In some embodiments, flange piece 1240 may include one or more flanges 1246, which may be sized and configured to aid a user in holding device 1200 and/or expelling a formulated drug substance from device 1200. In some embodiments, as depicted in FIGS. 1A-1E, flange piece 1240 may include two flanges 1246 opposite to one another and extending perpendicularly from a longitudinal dimension of device 1200. In some embodiments, flange piece 1240 may include other arrangements of a flange or flanges, such as four flanges, or one circumferential flange extending radially outward from a central longitudinal axis of device 1200. In some embodiments, flange piece 1240 may extend radially outward from a central longitudinal axis of device 1200 farther than a circumference of body 1220. In such embodiments, flange piece 1240 may support device 1200 if device 1200 is placed on a surface, may prevent device 1200 from rolling on a flat surface, and/or may allow device 1200 to be picked up more easily.

In some embodiments, flange piece 1240 and inner collar 1260 may be sized and configured to serve as a blocking component in device 1200, e.g., by limiting and/or directing rotational and longitudinal movement of plunger rod 1280. Proximal collar 1242 of flange piece 1240 may be sized and configured to accept part of inner collar 1260, while blocking protrusions 1262 from moving distally until inner collar 1260 is rotated to a particular position. In turn, inner collar 1260 may be sized and configured to receive part or all of an actuation portion 1282 of plunger rod 1280. As shown in FIGS. 5A-5C, proximal collar 1242, inner collar 1260, and actuation portion 1282 may all have generally cylindrical shapes; in alternate embodiments, each of proximal collar 1242, inner collar 1260, and actuation portion 1282 may have any suitable size or shape that allows for actuation portion 1282 to fit (e.g., nest) within inner collar 1260, and inner collar 1260 to fit within proximal collar 1242.

Plunger rod 1280 and inner collar 1260 may be in general rotatable about a shared central longitudinal axis (e.g., in one direction or in both directions). Moreover, both plunger rod 1280 and inner collar 1260 may be movable along the central longitudinal axis, e.g., in a distal direction to prime device 1200 and/or deliver a volume of drug substance from distal end 1224 of body 1220. Actuation portion 1282 of plunger rod 1280 may include a distal geometry which, when actuation portion 1282 is moved distally into inner collar 1260, interfaces with inner collar 1260 to prevent proximal movement (e.g., back-out) of plunger rod 1280 from inner collar 1260. For example, actuation portion 1282 may include a wedge-shaped distal portion that, when it passes a distal portion of inner collar 1260, expands distally from inner collar 1260 so that actuation portion 1282 can no longer move freely in relation to inner collar 1260.

Flange piece 1240 may include cavities, such as slots 1248, into which protrusions 1262 of inner collar 1260 may slide when inner collar 1260 is rotated to a particular position. As with slots 1074 of device 1050, slots 1248 may have a depth dimension parallel to a longitudinal axis of device 1200, and the depth of slots 1248 may correspond to a distance plunger rod 1280 must move distally in order to push stopper 1222 towards expulsion end 1224, and dispense a predetermined volume of formulated drug substance from body 1220 through expulsion end 1224.

In some embodiments, device 1200 may have additional features. For example, in some embodiments, a neck of plunger rod 1280 may have a geometry complementary to an opening of flange piece 1240 that restricts the extent and direction that plunger rod 1280 may rotate or move longitudinally, similar to neck 1084 and opening 1073 of device 1050. For example, rotation and/or longitudinal movement of plunger rod 1280 may be restricted based on priming, preparing, and/or drug delivery steps during use of device 1200. As another example, plunger rod 1280 may be prevented from being pulled or backed out of body 1220 at any point during preparation or use of device 1200.

In a contemplated method of use of device 1200, device 1200 may be filled with a predetermined volume of drug substance. The predetermined volume of drug substance may be greater than a volume of drug substance suitable for delivery to a patient. In some embodiments, device 1200 (e.g., body 1220) may contain both a predetermined volume of drug substance and an air bubble (not shown) that should be removed prior to delivery of the drug substance to a patient. In some embodiments, device 1200 may be a pre-filled syringe. In order to prime device 1200 (e.g., removing an air bubble if any and ensuring that a suitable volume of the drug substance will be delivered to a patient), a user may push actuation portion 1282 of plunger rod 1280 into inner collar 1260. A geometry of actuation portion 1282 may interact with inner collar 1260 (e.g., a distal wedge or clip of actuation portion 1282 may expand on a distal side of inner collar 1260) to secure actuation portion 1282 in and/or to inner collar 1260 and to prevent back-out of plunger rod 1280. At this point, device 1200 may be in a "primed" state. Subsequently, inner collar 1260 may be rotated about a longitudinal axis, until protrusions 1262 become longitudinally aligned with slots 1248. At this point, device 1200 may be in a "delivery" state. To deliver a predetermined volume of drug substance from device 1200, inner collar 1260, together with actuation portion 1282 and plunger rod 1280, may then be moved distally until protrusions 1262 abut a distal end of slots 1248. The distance traveled by plunger rod 1280 in this step may push stopper 1222 distally by a distance required to dispense the predetermined volume of drug substance from expulsion end 1224 of device 1200.

Referring now to FIGS. 6A-6E, views of a delivery device 1300 and component parts are depicted. Delivery device 1300 includes a blocking component comprising a distal flange piece 1340 and a proximal flange piece 1360, a plunger rod 1380, and a body 1320. Distal flange piece 1340 and proximal flange piece 1360 each include flanges (1346 and 1366, respectively). The flanges 1366 of proximal flange piece 1360 optionally may include a texture 1365. Distal flange piece 1340 includes a channel 1341 which may allow for distal flange piece 1340 and body 1320 to be slidably assembled. Proximal flange piece 1360 includes a clip 1364 which may allow for proximal flange piece 1360 and distal flange piece 1340 to be movably affixed to one another, such that they may still be rotatable relative to one another about a longitudinal axis of delivery device 1300 (see, e.g., FIGS. 6D and 6E). Proximal flange piece 1360 includes clips 1362 bordering a central opening 1368 through which plunger rod 1380 may pass. Plunger rod 1380 includes an actuation portion 1382, which optionally may include a texture 1381. Plunger rod 1380 further includes a distal neck shape 1384, a proximal neck shape 1387, and a proximal stop 1386 having a cavity 1385, all of which are configured to interface with distal flange piece 1340 and proximal flange piece 1360 in a plurality of configurations to allow for controlled priming and delivery of a predetermined volume of a drug substance using delivery device 1300. Plunger rod 1380 further includes a distal tip 1383 at a distal end of a stem 1389, where tip 1383 is configured to interface with stopper 1322. Tip 1383 may have any suitable size, shape, and mode of attaching to, affixing to, or pushing stopper 1322 as has been described with respect to, e.g., tip 1083 of plunger rod 1080. As with stem 1081, stem 1389 may have any size and configuration suitable to fit inside body 1320. In some embodiments, step 1389 may be sized and configured to provide sufficient size (e.g., thickness), stability and/or rigidity to reduce a likelihood of undesirable bending, wobbling, or breaking.

Body 1320 (depicted in FIGS. 6D and 6E) may have any or all of the same characteristics as, e.g., body 1060 of device 1050, or as any syringe body known in the art. For example, in some embodiments, body 1320 may be prefillable or pre-filled. A stopper 1322 may be configured to be inserted into body 1320 and may be configured to hold a predetermined volume of a formulated drug substance inside body 1320, between stopper 1322 and an expulsion end 1324.

Delivery device 1300 may be, for example, an injection device, such as a syringe, for dispensing a predetermined volume of a formulated drug substance. Generally, delivery device 1300 may share size, capacity, material, preparation, assembly, or manufacturing characteristics with device 1050, device 1200, or with other delivery devices disclosed herein. As with devices 1050 and 1200, delivery device 1300 may be configured for ease of use and may include one or more features that aid a user by providing tactile, auditory, or visual feedback (e.g., textures 1365, 1381, other textures, labels, colors, or tactile or auditory feedback, or using any of the other features described elsewhere herein). As with devices 1050 and 1200, such features are optional, and one or more such features may be combined to improve ease of use.

Proximal flange piece 1360 and distal flange piece 1340 may be of any suitable size and/or shape to serve as a blocking component in delivery device 1300, to close, partially close, cover, or partially cover an end of body 1320 opposite expulsion end 1324, and/or to support and hold plunger rod 1380 in place inside body 1320. In some embodiments, proximal flange piece 1360 and distal flange piece 1340 may each include one or more flanges, which may be sized and configured to aid a user in holding device 1300 and/or expelling a formulated drug substance from expulsion end 1324. In some embodiments, as depicted in FIGS. 6A-6E, flange pieces 1360, 1340 may each include two flanges 1366, 1346 respectively, where each pair of flanges is opposite to one another and extending perpendicularly from a longitudinal dimension of device 1300. In general, other arrangements of a flange or flanges, such as one flange on each of flange pieces 1360, 1340, are possible. Each of flange pieces 1340, 1360 may extend radially outward from a central longitudinal axis of device 1300 farther than a circumference of body 1320, to, e.g., support device 1300 if device 1300 is placed on a surface, prevent device 1300 from rolling on a flat surface, and/or allow device 1300 to be picked up more easily.

Flange pieces 1360 and 1340 may, in combination, form a central opening having a changeable size and/or shape depending on a relative position of proximal flange piece 1360 and distal flange piece 1340. For example, in the configuration depicted in FIG. 6D, proximal flange piece 1360 and distal flange piece 1340 may combine to form an opening sized and configured to allow for distal passage of distal neck portion 1384 of plunger rod 1380, but to block passage of proximal neck portion 1387. In the second configuration depicted in FIG. 6E (e.g., where flanges 1346 and 1366 are in alignment), the central opening formed by flange pieces 1360 and 1340 may be sized and configured to allow for distal passage of proximal neck portion 1387. Proximal stop 1386 may be of a size and shape that is too large to pass through the central opening formed by flange pieces 1360 and 1340 in any combination. In some embodiments, distal flange 1340 may be assembled with body 1320 and plunger rod 1380 such that distal flange 1340 is not movable relative to body 1320 and not rotatable relative to plunger rod 1380. Proximal flange 1360 may, in contrast, be assembled to distal flange 1340 (and body 1320) such that it is rotatable about a longitudinal axis in relation to distal flange 1340, body 1320, and plunger rod 1380, which may pass through central opening 1368. Specifically, proximal flange 1360 may be rotatable relative to distal flange 1340 from a first configuration in which flanges 1346, 1366 are offset from one another (see FIG. 6D), to a second configuration in which flanges 1346, 1366 overlay one another (see FIG. 6E). One of ordinary skill in the art will understand that in alternate embodiments, distal flange 1340 may be rotatable in relation to other parts of device 1300, while proximal flange 1360 may not be rotatable. In yet further embodiments, both proximal flange 1360 and distal flange 1340 may be assembled with body 1320 and plunger rod 1380 such that they are both rotatable relative to other components of device 1300.

Clips 1362 of proximal flange piece 1360 may overhang and be biased towards opening 1368. In a pre-use configuration (depicted in FIG. 6D), clips 1362 may be compressed by plunger rod 1380. They may be positioned on proximal flange piece 1360 such that, upon distal movement of plunger rod 1380 such that distal neck portion 1384 passes through opening 1368, they expand inward to abut the sides of distal neck portion 1384. Once clips 1362 expand in this manner, they may block proximal movement of plunger rod 1380, e.g., to prevent plunger rod back-out (see, e.g., FIG. 7C). A cavity 1385 may be positioned on proximal stop 1386 for each clip 1362, such that when plunger rod 1380 is moved distally into body 1320 to a fullest desired extent, each clip 1362 may fit into a cavity 1385.

Figures 7A, 7B, 7C:
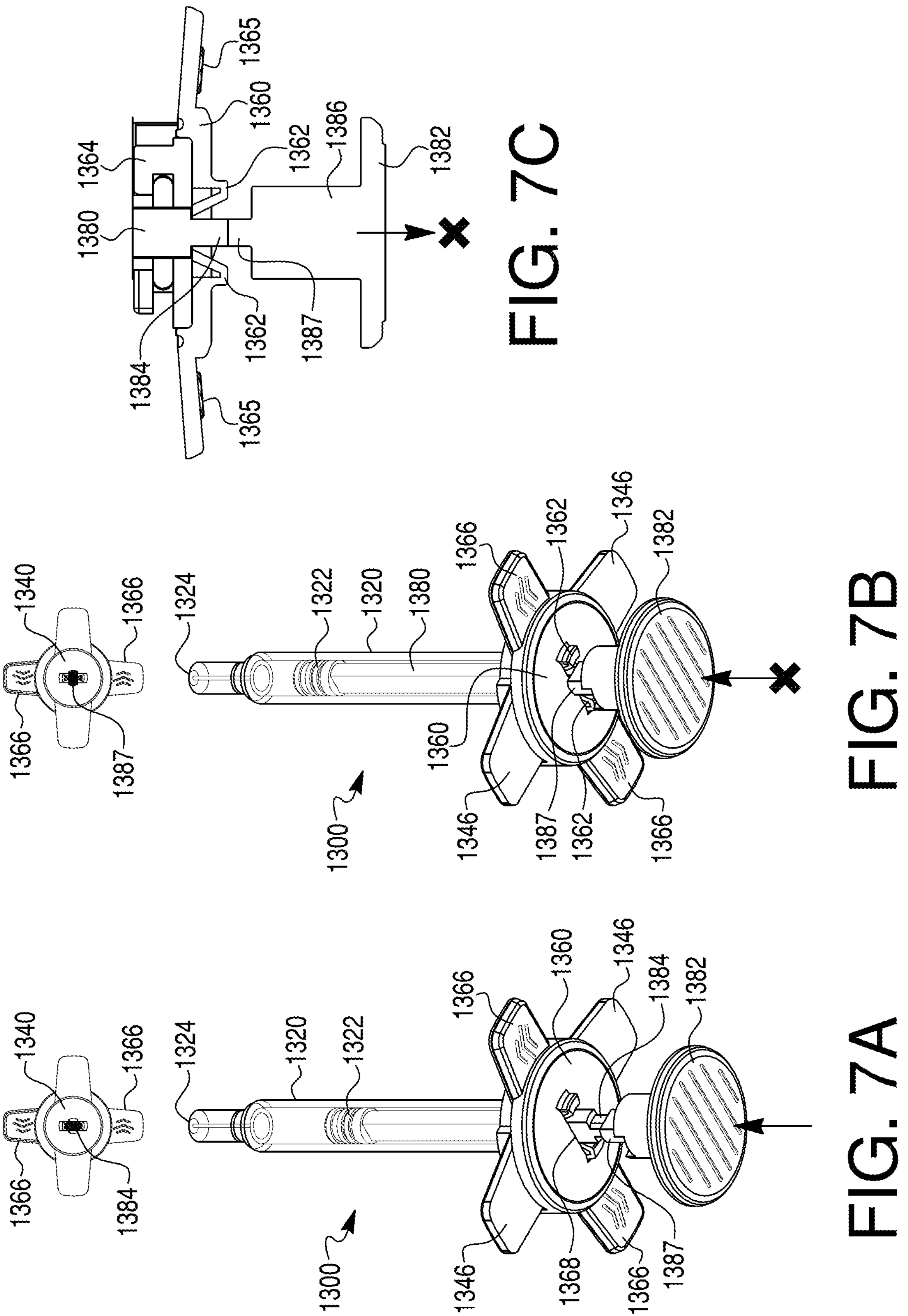
FIGS. 7A-7F depict an exemplary method of using the delivery device depicted in FIGS. 6A-6E, according to aspects of the present disclosure.

FIGS. 7A-7F depict an exemplary method of using device 1300, according to aspects of the present disclosure. In a pre-use configuration depicted in FIG. 7A, device 1300 may hold a volume of a drug substance in between stopper 1322 and expulsion end 1324. Flange pieces 1340 and 1360 may be in a pre-use configuration, in which flanges 1346, 1366 are offset from one another. Plunger rod 1380, which may abut or be assembled to stopper 1322, may be partially inserted into body 1320 through flange pieces 1340, 1360. Proximal flange piece 1360 may be prevented from rotating about the longitudinal axis of the syringe, due to the geometries of plunger rod 1380 and flange piece 1360. In a priming step depicted in FIG. 7B, plunger rod 1380 may be moved longitudinally further into body 1320, until distal movement is blocked by the abutment of proximal neck portion 1385 against a surface of proximal flange piece 1360. For example, a user may press actuation portion 1382 towards proximal flange piece 1360. In some embodiments, device 1300 may be held in an inverted position during this step, to ensure that air trapped in body 1320 may be expelled via expulsion end 1324, as stopper 1322 is pushed distally by plunger rod 1380. In the "primed" configuration, distal neck portion 1384 may be disposed in opening 1368 of proximal flange piece 1360. Moreover, as depicted in FIG. 7C, once the priming step is stopped, clips 1362 may be released from their compressed configuration such that they may expand inwards and abut a side of distal neck portion 1384. As distal neck portion 1384 may be comparatively narrower than the part of plunger rod 1380 previously disposed in opening 1368, the expansion of clips 1362 may prevent proximal movement (e.g., back-out) of plunger rod 1380.

Figures 7D, 7E, 7F:
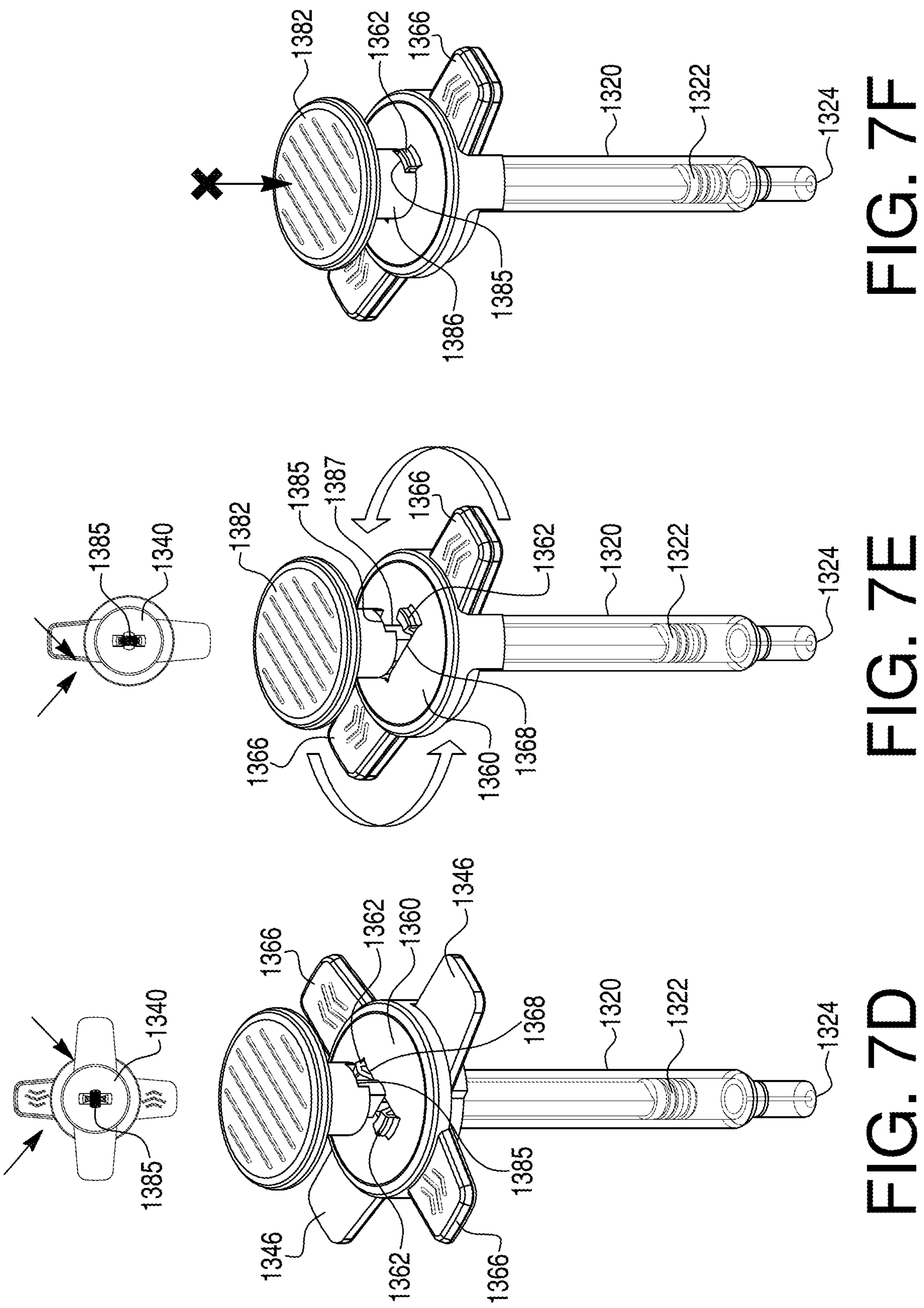

As depicted in FIG. 7D, device 1300 may be in a primed configuration. In a dispensing preparation step depicted in FIG. 7E, proximal flange piece 1360 may be rotated about a longitudinal axis to align flanges 1366 and flanges 1346, and to change (e.g., enlarge) a shape of the central opening formed by the combined openings of proximal flange piece 1360 and distal flange piece 1340. To do so, a user may grasp and twist proximal flange piece 1360. In some embodiments, it may be possible to twist proximal flange piece in either direction to align flanges 1366 and flanges 1346. In other embodiments, proximal flange piece 1360 may be rotatable only in one direction. In some embodiments, once flanges 1366 and flanges 1346 are aligned (as shown in, e.g., FIG. 7E), further rotation of plunger rod 1080 relative to flange piece 1070 may be stopped by, e.g., clip 1362 abutting against flange 1346. Thus, device 1300 may be locked in a ready-to-dispense configuration. As depicted in FIG. 7F, in a dispensing step, plunger rod 1380 may be moved longitudinally further into body 1320. For example, a user may press actuation portion 1382 distally, until each of clips 1362 enter a cavity 1385 in a proximal stop 1386, and/or until proximal stop 1386 abuts a proximal surface of proximal flange piece 1360. The dispensing step may ensure that a predetermined volume of a drug substance inside body 1320 is dispensed from device 1300.

In some embodiments, after each successive step in the use of device 1300, a user may be prevented from re-doing a step, and/or from reversing one or more steps. For example, geometries of, e.g., plunger rod 1380 and the combined openings of proximal flange piece 1360 and distal flange piece 1340 may prevent a user from pulling plunger rod 1380 proximally (e.g., out of) body 1320, from rotating plunger rod 1380, from rotating proximal flange piece 1360 preemptively (e.g., before completion of the priming step shown in FIGS. 7B and 7C), and/or from over-rotating flange piece 1360 during a dispensing preparation step (e.g., shown in FIG. 7E).

FIGS. 8A-8G depict a further exemplary delivery device 1400 and component parts Delivery device 1400 includes a plunger rod 1480, a blocking component 1460, a flange piece 1440, and a body 1420. Plunger rod 1480 includes an actuation portion 1482 and a protrusion 1484. Blocking component 1460 may be a rotatable alignment component that is configured to partially or fully surround plunger rod 1480, and includes three connected channels 1462, 1464, 1468 sized and configured to allow for passage of protrusion 1484. Flange piece 1440 includes a proximal collar 1442 having a channel 1447 into which tabs 1461 of blocking component 1460 may slidably fit, a distal collar 1444 including a channel 1445 into which a flange 1421 of body 1420 may fit (e.g., may be slidably assembled), and flanges 1446.

Body 1420 (depicted in FIGS. 8D and 8E) may have any or all of the same characteristics as, e.g., body 1060 of device 1050, or as any syringe body known in the art. For example, in some embodiments, body 1420 may be pre-fillable or pre-filled. A stopper 1422 may be configured to be inserted into body 1420 and may be configured to hold a predetermined volume of a formulated drug substance inside body 1420, between stopper 1422 and an expulsion end 1424.

Delivery device 1400 may be, for example, an injection device, such as a syringe, for dispensing a predetermined volume of a formulated drug substance. Generally, delivery device 1400 may share size, capacity, material, preparation, assembly, or manufacturing characteristics with device 1050, device 1200, device 1300, or with other delivery devices disclosed herein. As with other devices disclosed herein, delivery device 1400 may be configured for ease of use and may include one or more features that aid a user by providing tactile, auditory, or visual feedback, using any of the features described elsewhere herein.

Blocking component 1460 may be of any suitable size and/or shape to assist in controlling proximal and distal movement of plunger 1480 in device 1400.

Flange piece 1440 may be of any suitable size and shape to close, partially close, cover, or partially cover an end of body 1420 opposite expulsion end 1424, and/or to support and hold blocking component 1460 and plunger rod 1480 in relation to body 1420. For example, proximal collar 1442 and channel 1447 may be sized and configured to hold blocking component 1460, and distal collar 1444 and channel 1445 may be sized and configured to hold a flange 1421 of body 1420, such that blocking component 1460 is held stationary in relation to body 1420. Further, blocking component 1460 may be sized and configured to plunger rod 1480 inside body 1420, and to limit movement of plunger rod 1480 with respect to body 1420. Flange piece 1440 may include one or more flanges 1446, which may be sized and configured to aid a user in holding device 1400 and/or expelling a formulated drug substance from expulsion end 1424. In some embodiments, as depicted in FIGS. 8A-8E, flange piece 1440 may include two flanges 1446, opposite to one another. In general, other arrangements of a flange or flanges, such as one flange or three flanges, are possible. Flange piece 1440 may extend radially outward from a central longitudinal axis of device 1400 farther than a circumference of body 1420, to, e.g., support device 1400 if device 1400 is placed on a surface, prevent device 1400 from rolling on a flat surface, and/or allow device 1400 to be picked up more easily.

Channels 1462, 1464, 1468 in blocking component 1460 together form a path through which protrusion 1484 may travel, to allow for controlled movement of plunger rod 1480. A first channel 1462 may allow for sufficient distal movement of plunger rod 1480 to prime device 1400. A second channel 1464 may allow for movement of the plunger rod between a "primed" state and a "delivery" state. Channel 1464 may have a path requiring rotation of plunger rod 1480 about a longitudinal axis of device 1400 (as opposed to distal movement of plunger rod 1480), such that the likelihood of plunger rod 1480 being accidentally or unintentionally moved to a "delivery" state may be reduced. Channel 1464 may provide a path of any suitable length (corresponding to any suitable angle of rotation of plunger rod 1480) to ensure adequate separation between the "primed" state and the "delivery" state. A third channel 1468 may allow for sufficient distal movement of plunger rod 1480 to dispense a predetermined volume of drug substance from device 1400.

Figure 8E:
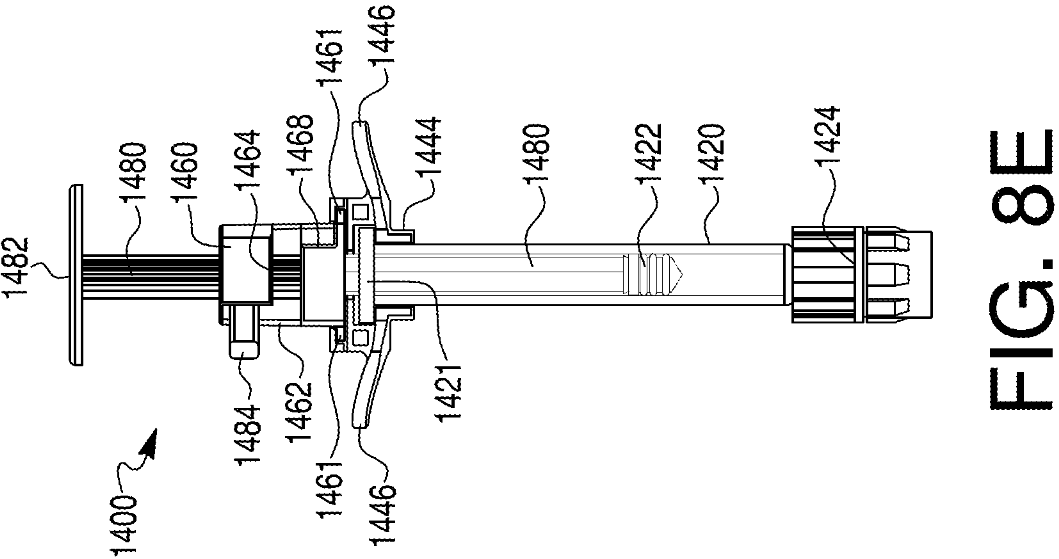
Figure 8D:
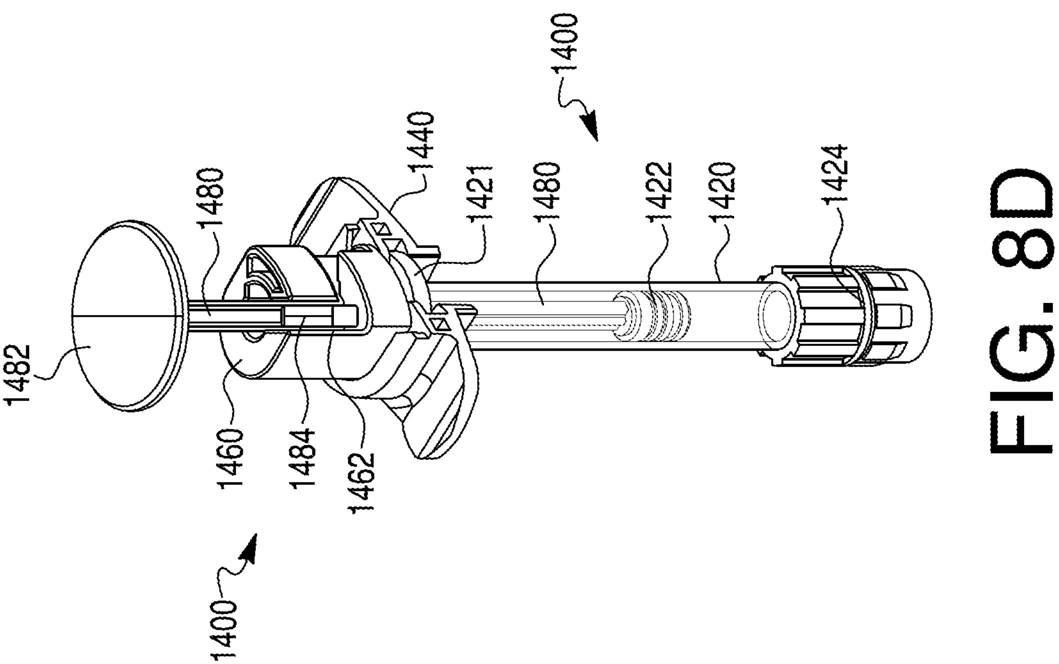
Figure 8F:
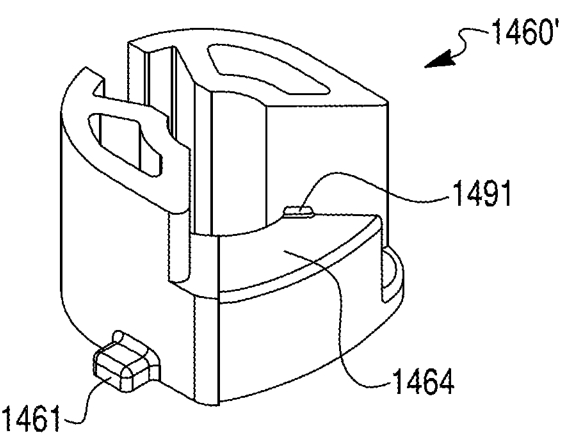
FIGS. 8F and 8G depict a blocking component of the delivery device depicted in FIGS. 8A-8E according to embodiments of the present disclosure.
Figure 8G:
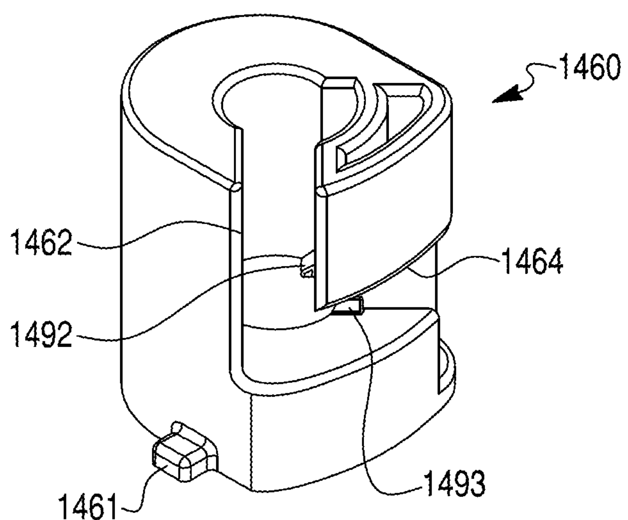

One or more of each channel 1462, 1464, 1468 may include one or more detents, as shown in FIGS. 8F and 8G. For example, a cross sectional view of blocking component 1460 in FIG. 8F shows an interior of channel 1464 having a small detent 1491 disposed on one side. FIG. 8G depicts two larger detents 1492, 1493 in channels 1462, 1464, respectively. Each detent may provide resistance to the movement of protrusion 1484 through channels 1462, 1464, and/or 1468 to provide auditory feedback and/or to prevent unintended movement of protrusion 1484. In some embodiments, detents 1491, 1492, 1493 may be angled on one side, to allow for passage of protrusions 1484 in one direction, but not in the other direction. Detents such as those shown in FIGS. 8F and 8G may be suitable for inclusion in any device disclosed herein, as well as in device 1400.

FIGS. 9A-9E depict an exemplary method of using device 1400, according to aspects of the present disclosure. In a pre-use configuration depicted in FIG. 9A, device 1400 may hold a volume of a drug substance in between stopper 1422 and expulsion end 1424. Plunger rod 1480 may be partially inserted into body 1420 such that protrusion 1484 of plunger rod 1480 is disposed in a proximal end portion of channel 1462. In a priming step depicted in FIG. 9B, plunger rod 1480 may be moved longitudinally further into body 1420, until distal movement is blocked by the abutment of protrusion 1484 against a distal end of channel 1462. For example, a user may press actuation portion 1482 distally through blocking component 1460. In some embodiments, device 1400 may be held in an inverted position during this step, to ensure that air trapped in body 1420 may be expelled, as stopper 1422 is pushed distally by plunger rod 1480. In the "primed" configuration, depicted in FIG. 9C, protrusion 1484 of plunger rod 1480 may be disposed at a first end of channel 1464.

Figure 9B:
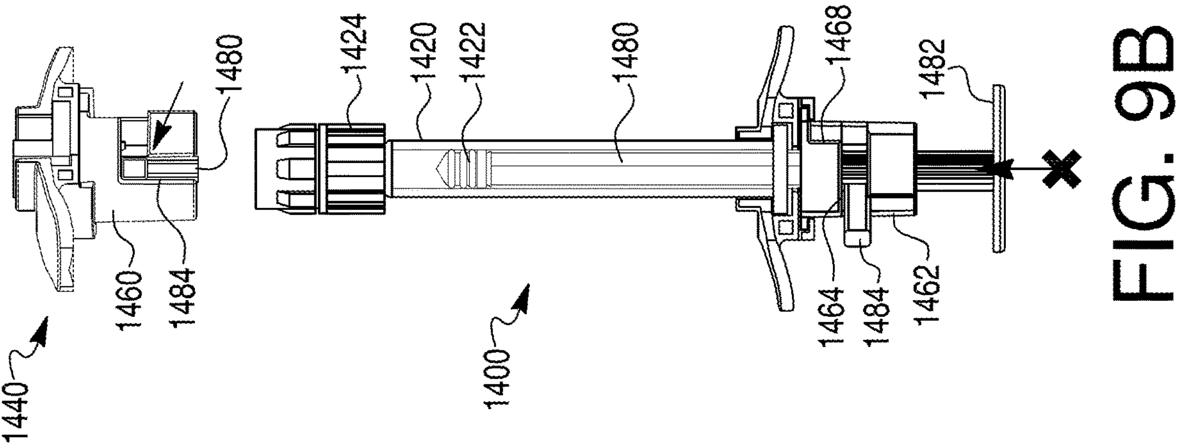
FIGS. 9A-9E depict an exemplary method of using the delivery device depicted in FIGS. 8A-8E, according to aspects of the present disclosure.
Figure 9A:
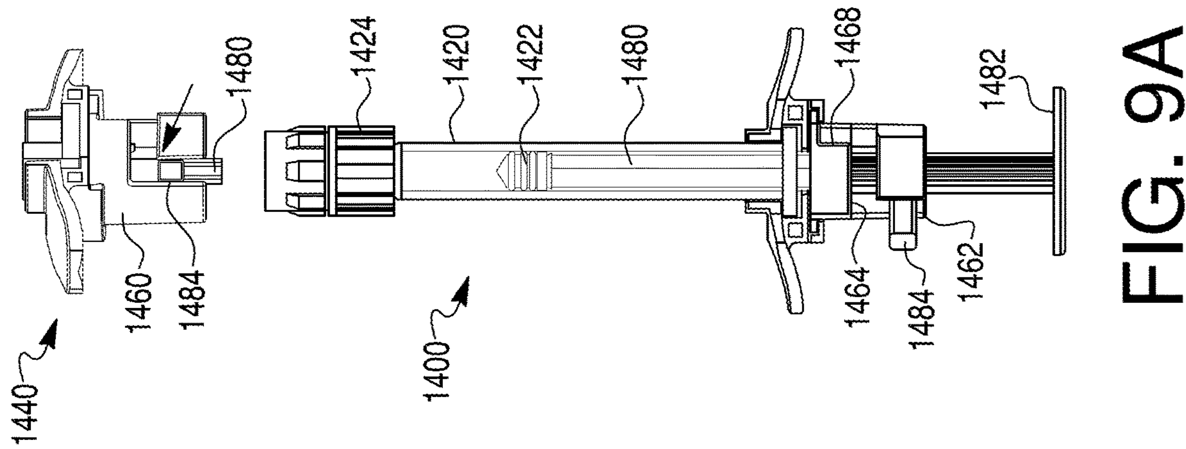
Figure 9E:
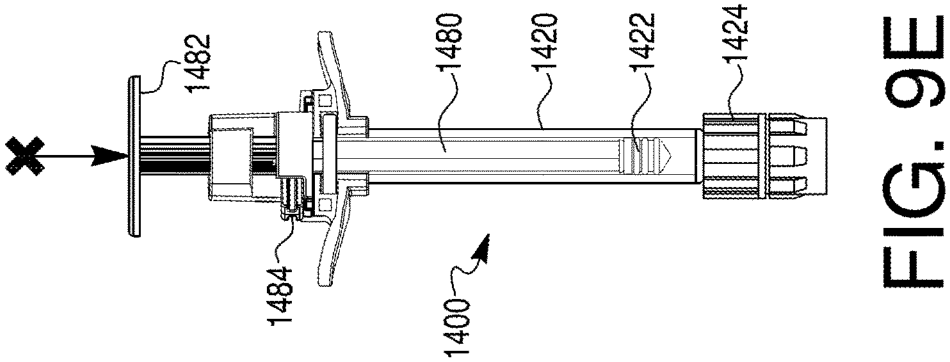
Figure 9D:
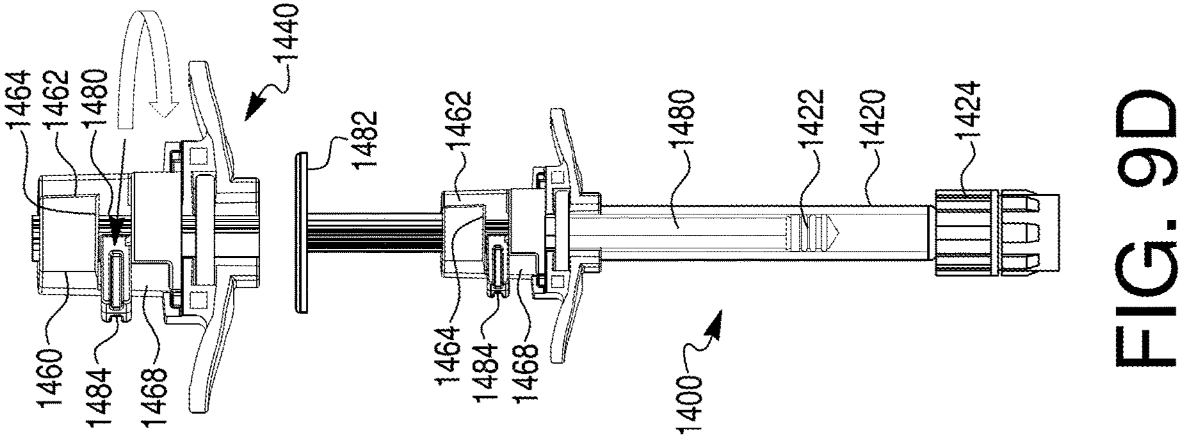
Figure 9C:
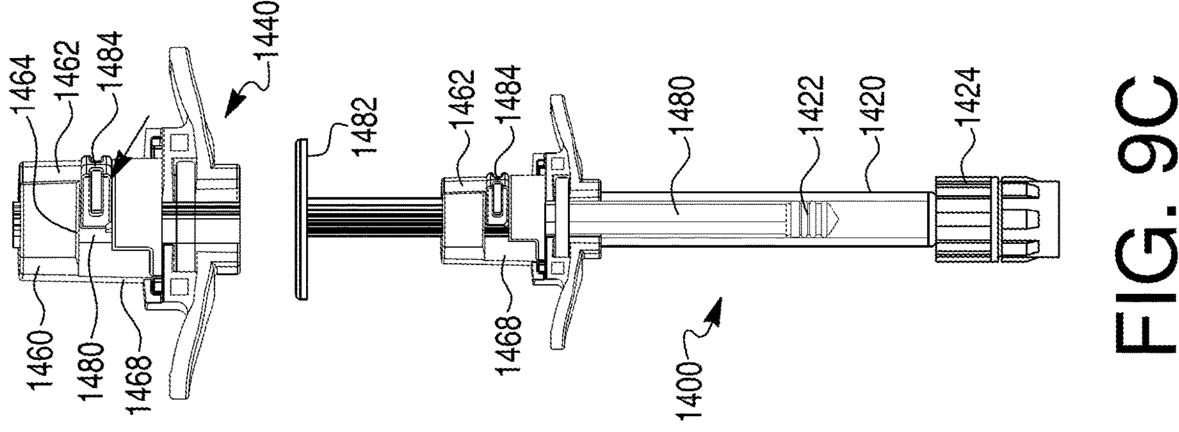

In a dispensing preparation step depicted in FIG. 9D, plunger rod 1480 may be rotated about a longitudinal axis such that protrusion 1484 is moved from a first end of channel 1464 to a second end of channel 1464. For example, a user may grasp and twist actuation portion 1482 of plunger rod 1480. Device 1400 may then be in a ready-to-dispense configuration, wherein protrusion 1484 is disposed at a proximal end of channel 1468. As depicted in FIG. 9E, in a dispensing step, plunger rod 1480 may be moved longitudinally further into body 1420. For example, a user may press actuation portion 1482 distally, until protrusion 1484 abuts a distal end of channel 1468. The dispensing step may ensure that a predetermined volume of a drug substance inside body 1420 is dispensed from device 1400.

In some embodiments, after each successive step in the use of device 1050, a user may be prevented from re-doing a step, and/or from reversing one or more steps. For example, geometries of, e.g., plunger rod 1480, protrusion 1484, and/or channels 1462, 1464, 1468 may prevent a user from pulling plunger rod 1480 proximally (e.g., out of) body 1420.

Figure 10A:
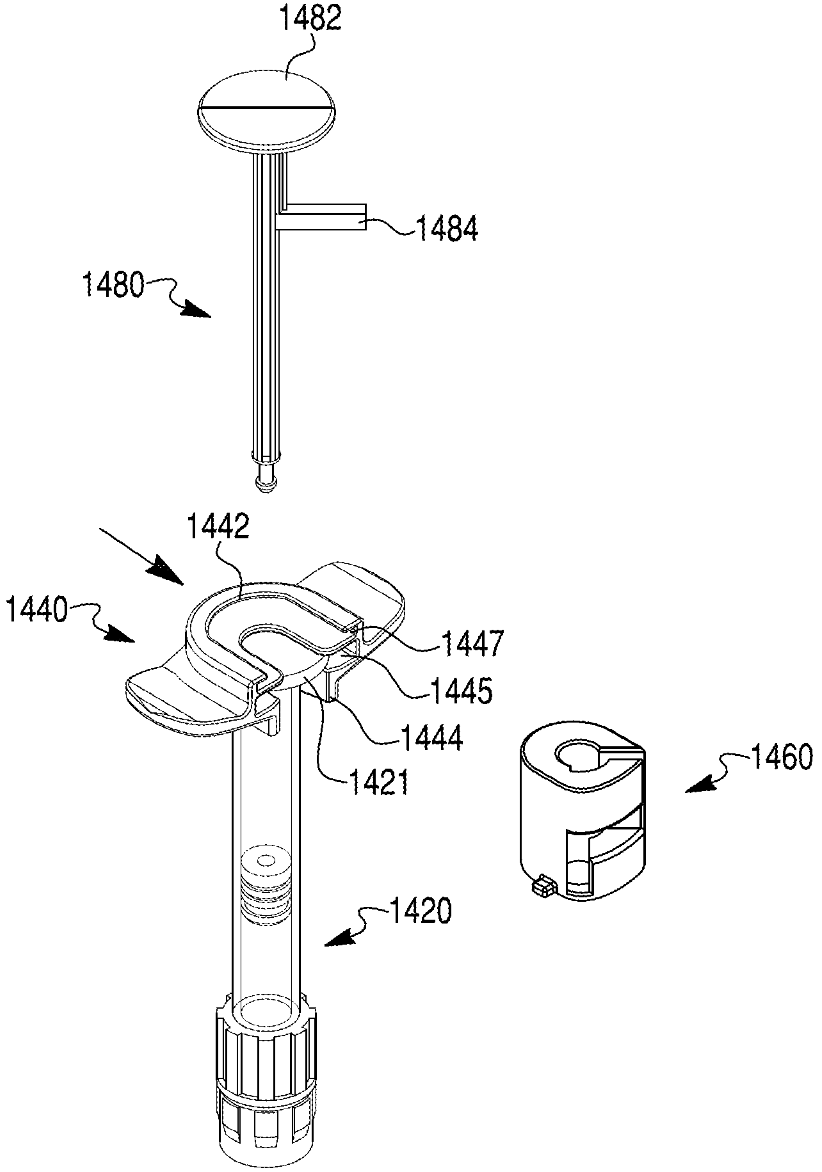
FIGS. 10A-10C depict an exemplary method of assembling the delivery device depicted in FIGS. 8A-8E, according to aspects of the present disclosure.
Figure 10B:
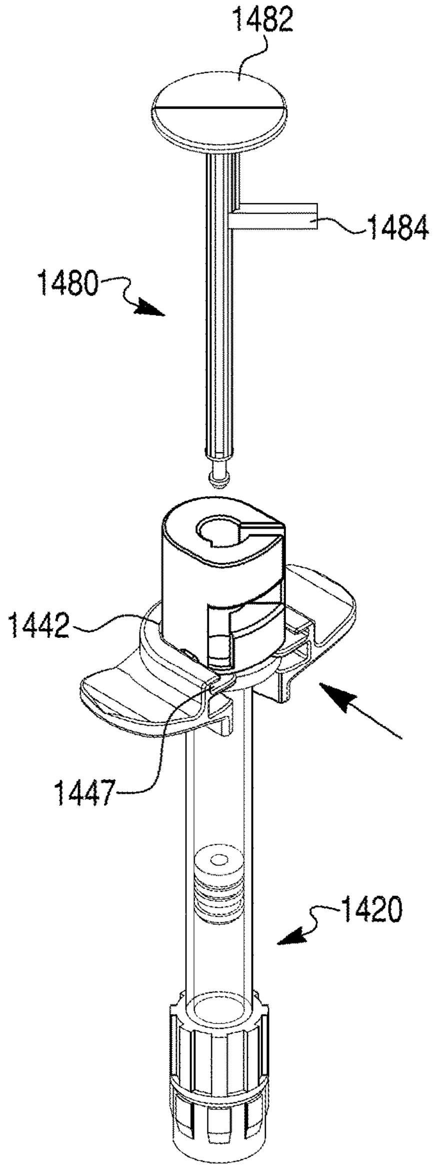
Figure 10C:
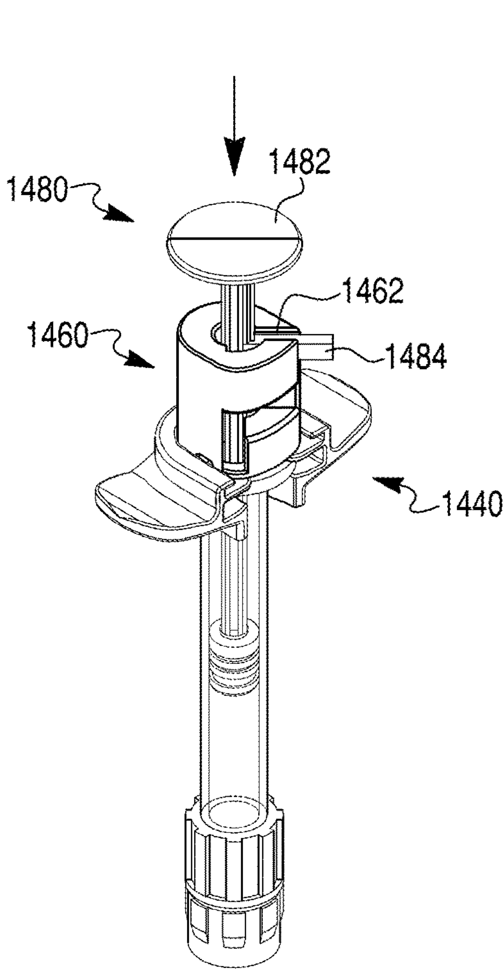

FIGS. 10A-10C depict an exemplary method of assembly of device 1400. As depicted in FIG. 10A, flange piece 1440 may be slidably assembled to body 1420 such that flange 1421 fits into channel 1445 and collar 1444 partially surrounds body 1420. As depicted in FIG. 10B, blocking component 1460 may be slidably assembled to flange piece 1440, such that tabs 1461 rest within channels 1447 and blocking component 1460 abuts proximal collar 1442. As depicted in FIG. 100, plunger rod 1480 may then be inserted into the combined blocking component 1460, flange piece 1440, and body 1420, such that protrusion 1484 is disposed within channel 1462 of body 1460.

Figure 10E:
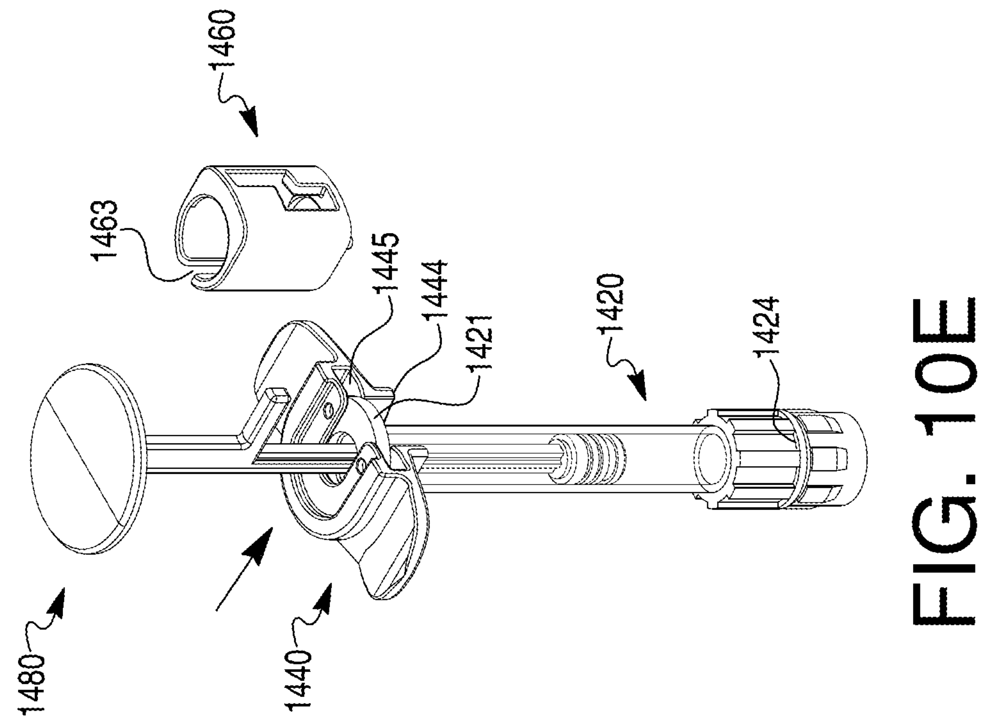
FIGS. 10D-10G depict another exemplary method of assembling a variation of the delivery device depicted in FIGS. 8A-8E, according to aspects of the present disclosure.
Figure 10D:
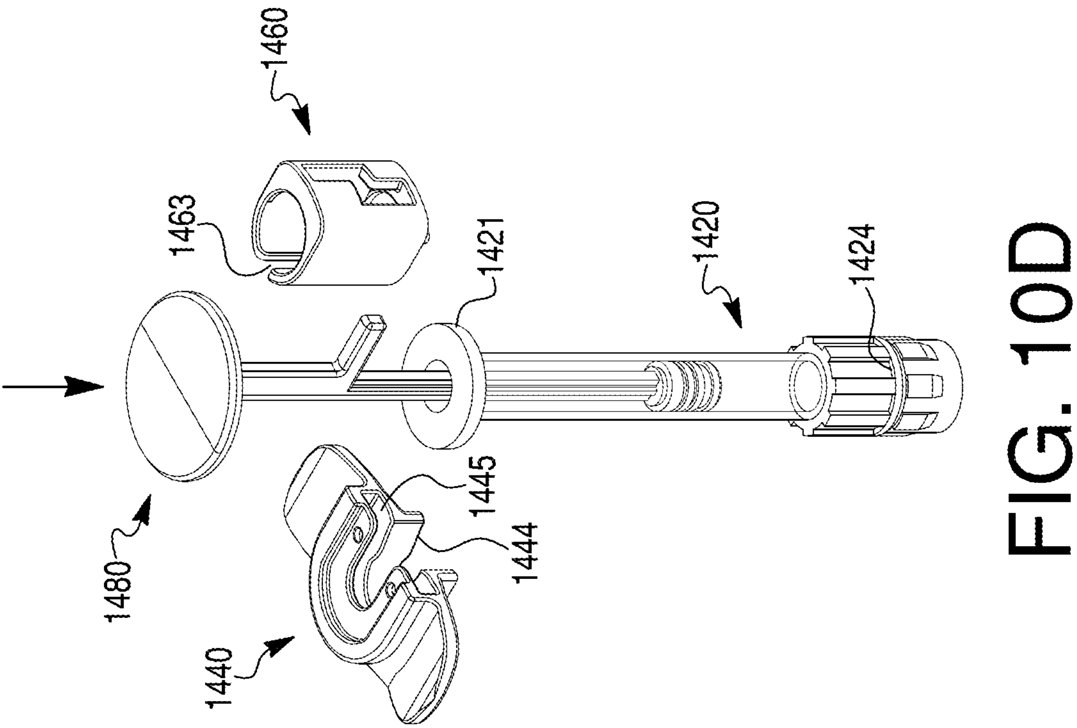
Figure 10G:
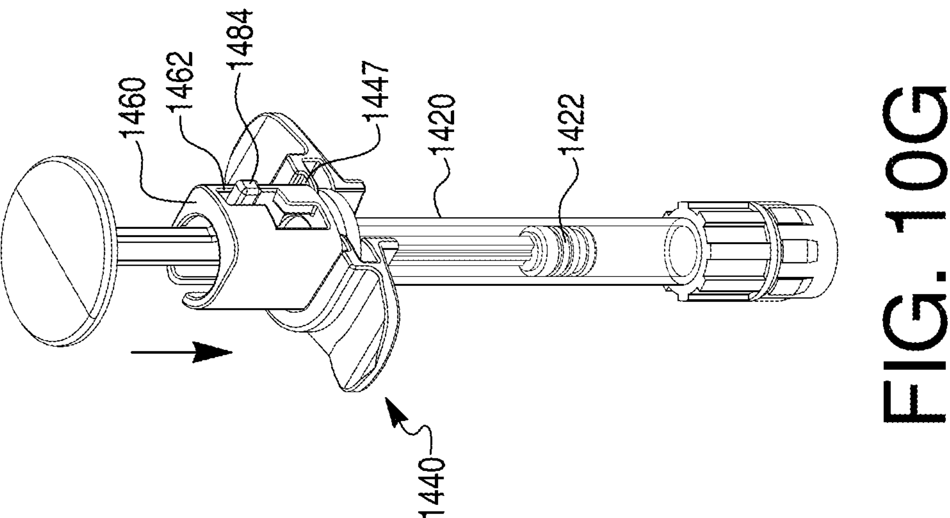
Figure 10F:
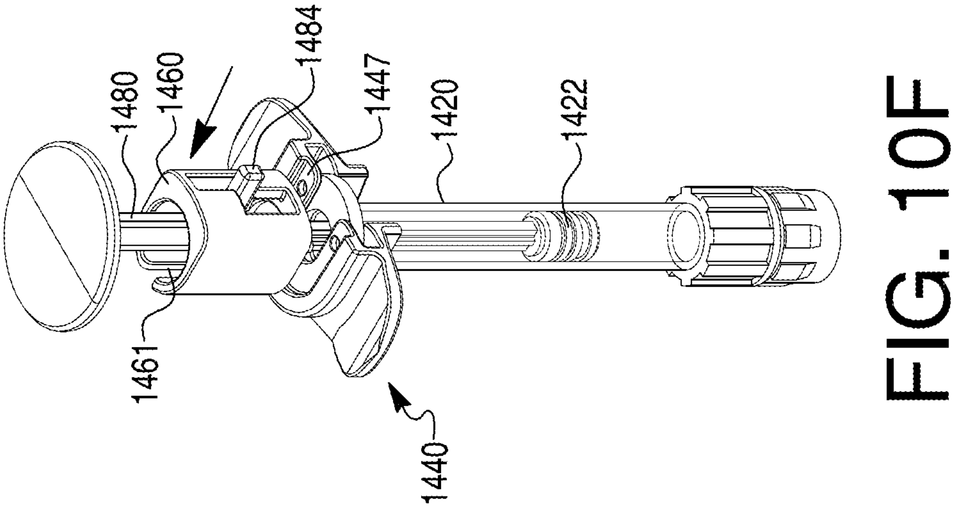
Figure 11C:
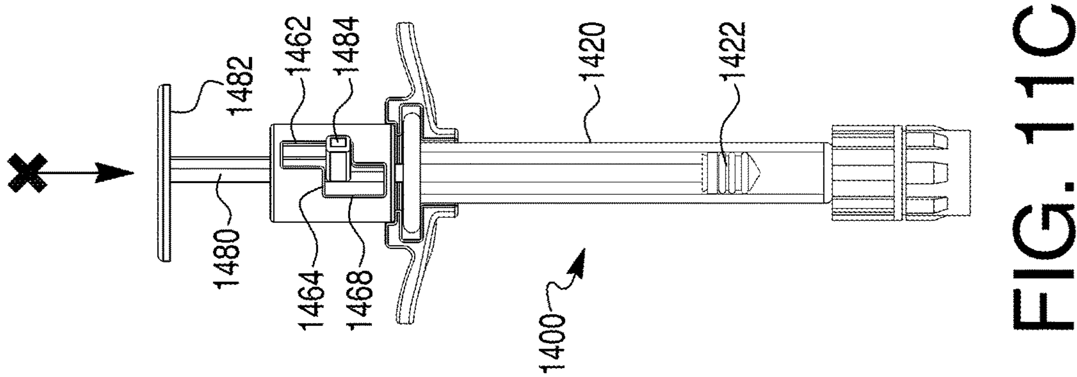
FIGS. 11A-11E depict an exemplary method of using the delivery device depicted in FIGS. 10D-10G according to aspects of the present disclosure.
Figure 11B:
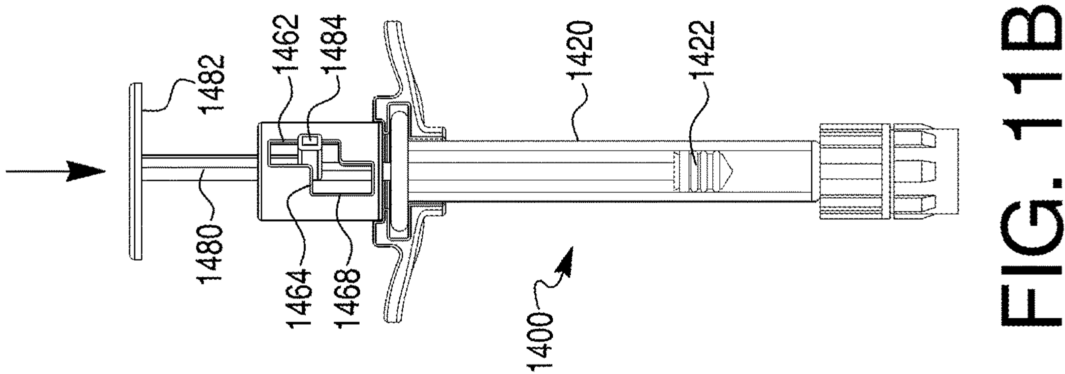
Figure 11A:
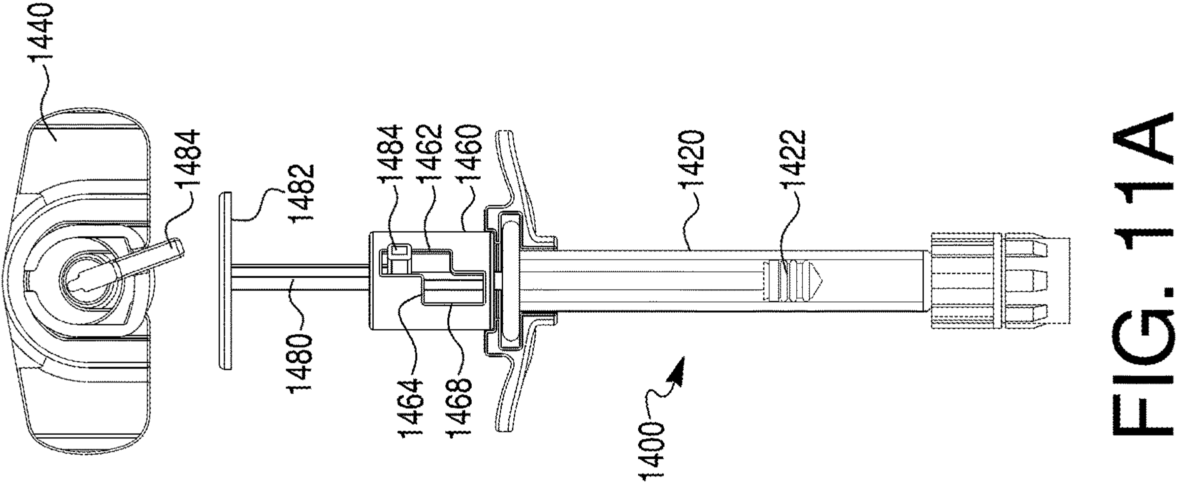
Figure 11E:
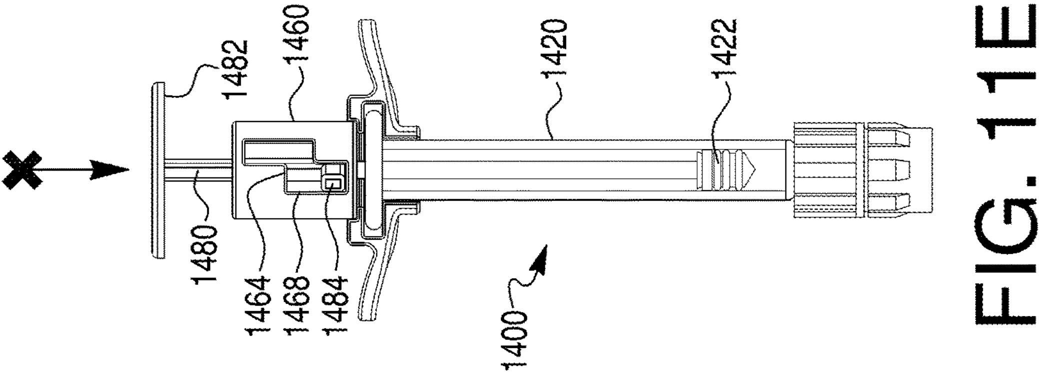
Figure 11D:
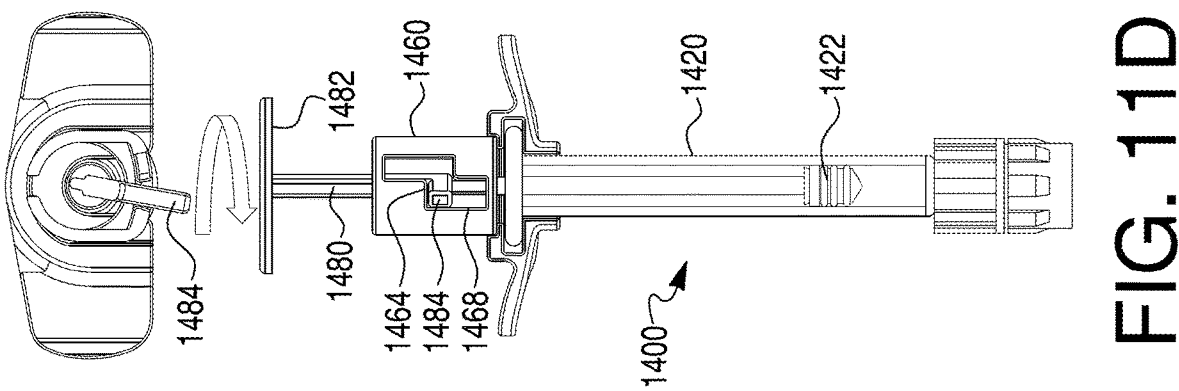
Figure 12A:
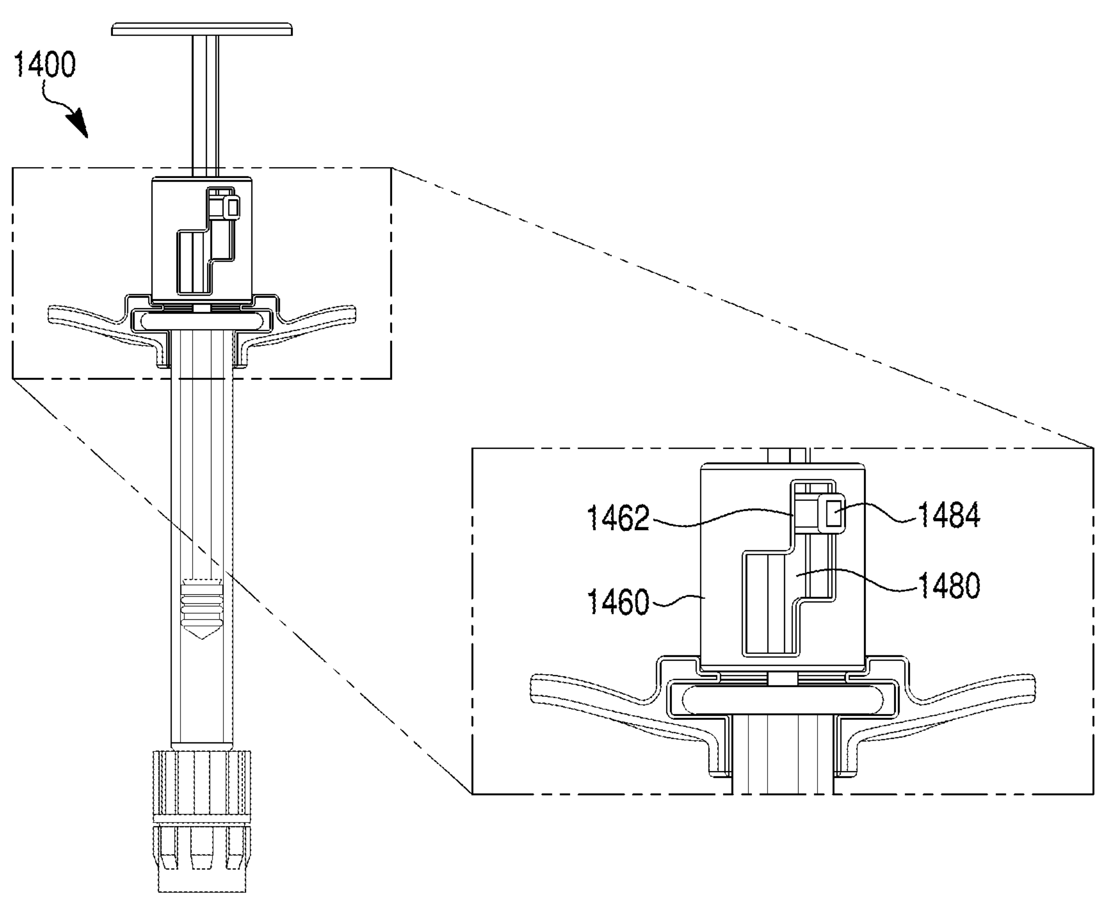
FIGS. 12A-12D depict a close-up view of aspects of the exemplary method depicted in FIGS. 11A-11E.
Figure 12B:
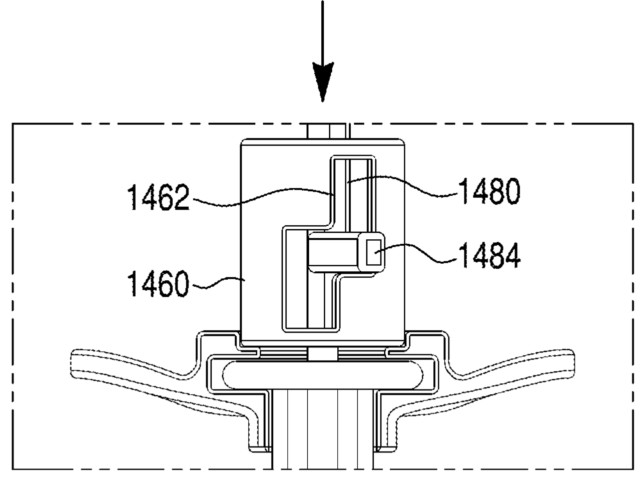
Figure 12C:
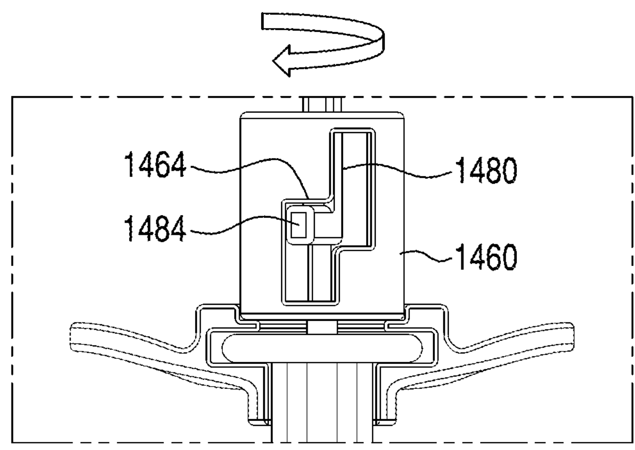
Figure 12D:
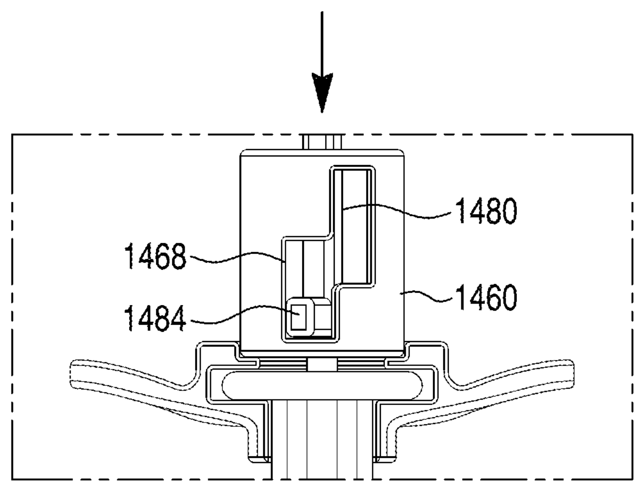

FIGS. 10D-10G, 11A-11E, and 12A-12D depict a variation on a configuration and method of use of device 1400, and to avoid redundancy will not be described in great detail. FIGS. 10D-10G depict an alternate method of assembly of device 1400, where blocking component 1460 includes an opening 1463 through which plunger rod 1480 may fit. In this embodiment, the channels within blocking component 1460 (e.g., channels 1462, 1468) may be closed on a proximal and distal end, to prevent back-out or over-insertion of plunger rod 1480 relative to body 1420. As depicted in FIG. 10E, plunger rod 1480 may be partially inserted into body 1420, and flange piece 1440 may be slidably assembled to body 1420 such that flange 1421 fits into channel 1445 and collar 1444 partially surrounds body 1420. As depicted in FIG. 10F, blocking component 1460 may be assembled to plunger rod 1480, such that protrusion 1484 is disposed within one of the channels in blocking component 1460. As depicted in FIG. 10G, blocking component 1460 may then be assembled to flange piece 1440 such that it is disposed in channel 1447. Blocking component may be affixed to flange piece 1440 in any suitable manner (e.g., using clips, adhesive, a friction fit, a dovetail connection, etc.). FIGS. 12A-12D depict a close-up view of protrusion 1484 moving through the channels of blocking component 1460, per the method of use shown in FIGS. 11A-11E.

Figure 13B:
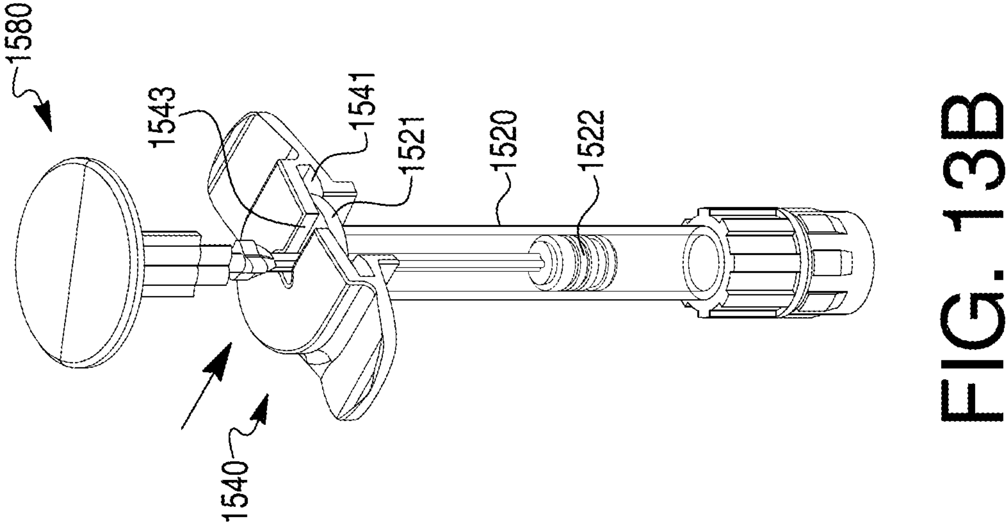
FIGS. 13A and 13B depict a further exemplary delivery device and method of assembling said delivery device, according to additional embodiments of the present disclosure.
Figure 13A:
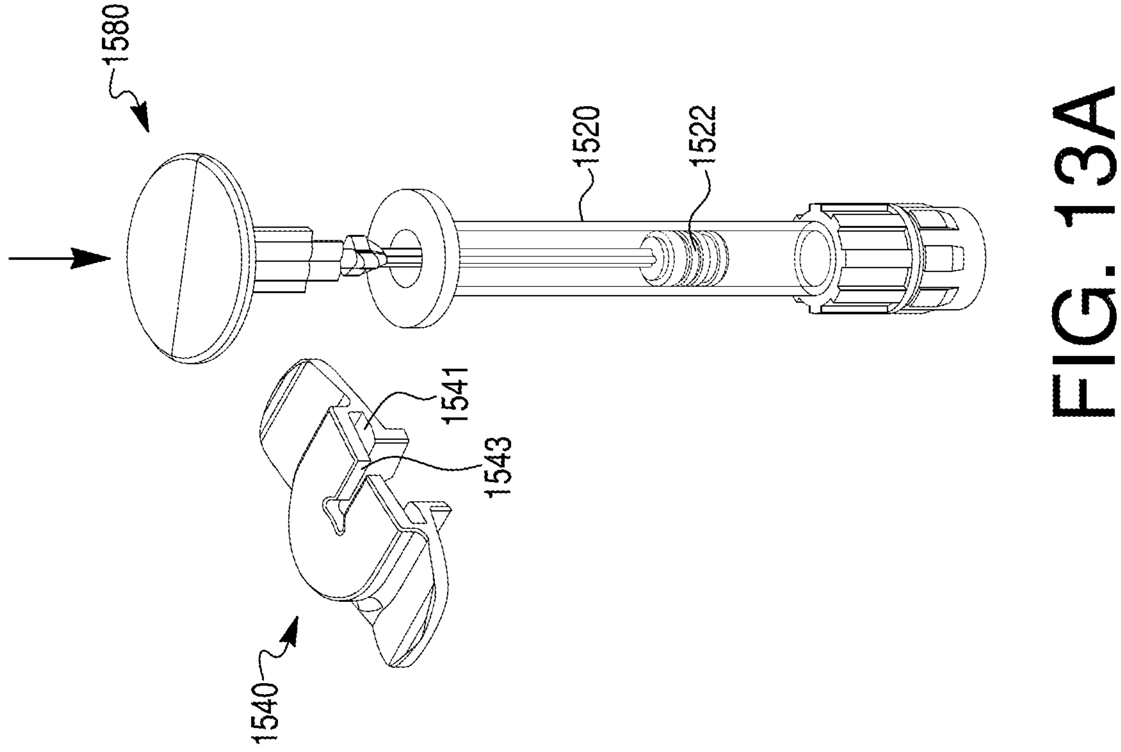

FIGS. 13A and 13B depict a further exemplary delivery device 1500, and a method of assembling said delivery device, according to additional embodiments of the present disclosure. Device 1500 includes a plunger rod 1580, a blocking component in the form of flange piece 1540, and a body 1520. To assemble device 1500, plunger rod may be inserted into body 1520 (e.g., as shown in FIG. 13A), such that it abuts or attaches to a stopper 1522 in body 1520, and flange piece 1540 may be slidably assembled to 1521, e.g., by sliding a channel 1541 on to a flange 1521 of body 1520 (e.g., as shown in FIG. 13B). An opening 1543 may allow for flange piece 1540 to be assembled to body 1520 around plunger rod 1580. It is contemplated that, depending on the size, shape, and structure of each component of device 1500, alternate methods of assembly are possible.

Delivery device 1500 may be, for example, an injection device, such as a syringe, for dispensing a predetermined volume of a formulated drug substance. Generally, delivery device 1500 may share size, capacity, material, preparation, assembly, or manufacturing characteristics with device 1050, device 1200, device 1300, or with other delivery devices disclosed herein. As with other devices disclosed herein, delivery device 1500 may be configured for ease of use and may include one or more features that aid a user by providing tactile, auditory, or visual feedback, using any of the features described elsewhere herein.

Figures 14A, 14B, 14C:
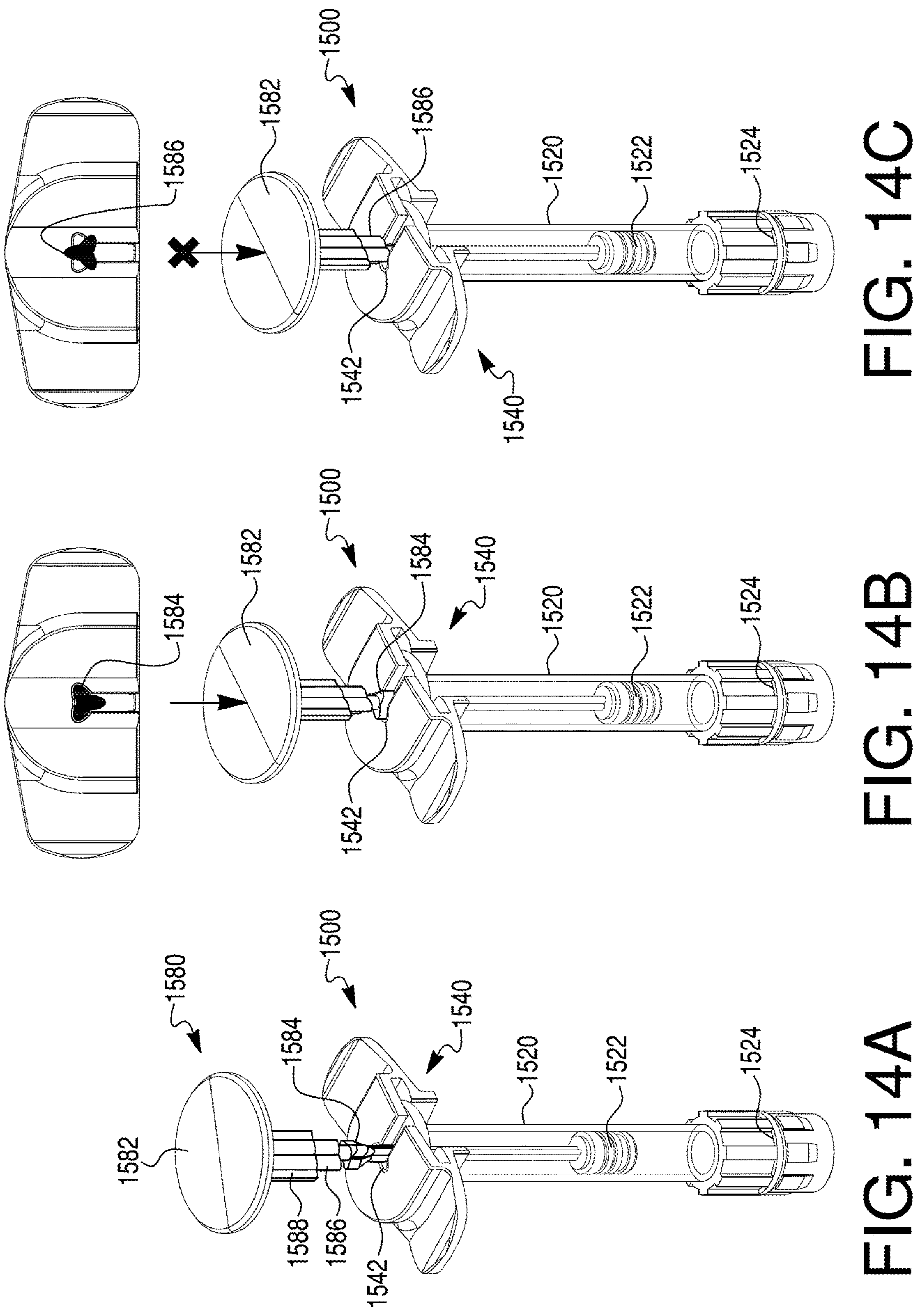
FIG. 14A-14F depict a method of using the delivery device depicted in FIGS. 12A and 12B.

FIG. 14A-14F depict a further view of device 1500 and a method of using device 1500. As shown in FIG. 14A, plunger rod 1580 may include an actuation portion 1582, a proximal stop 1588, a proximal neck portion 1586, and a distal neck portion 1584. Body 1520 may have any or all of the same characteristics as, e.g., body 1060 of device 1050, or as any syringe body known in the art. For example, in some embodiments, body 1520 may be pre-fillable or pre-filled. Stopper 1522 may be configured to be inserted into body 1520 and may be configured to hold a predetermined volume of a formulated drug substance inside body 1520, between stopper 1522 and an expulsion end 1524.

Flange piece 1540 may be of any suitable size and shape to partially close, cover, or partially cover an end of body 1520 opposite expulsion end 1524, and/or to support and hold plunger rod 1580 in body 1520. An opening 1542 may have a size and shape configured to allow passage of plunger rod 1580 in two different configurations. Distal neck portion 1584 and proximal neck portion 1586 may have similar shapes, but may be rotationally offset from one another (e.g., such that once distal neck portion 1584 passes through opening 1542, plunger rod 1580 must be rotated about a longitudinal axis to allow proximal neck portion 1587 to pass. Distal neck portion 1584 may include, e.g., a tapered distal side, which may assist in orienting plunger rod 1580 such that distal neck portion 1584 may pass through opening 1542. This may increase the ease of, e.g., a priming step.

FIG. 14A depicts a pre-use configuration of device 1500. In such a configuration, device 1500 may hold a volume of a drug substance in between stopper 1522 and expulsion end 1524. Plunger rod 1580 may be partially inserted into body 1520 such that distal neck portion 1584 is positioned proximally from flange piece 1540. In a priming step depicted in FIG. 14B, plunger rod 1580 may be moved longitudinally further into body 1520, until distal movement is blocked by the abutment of proximal neck portion 1586 against opening 1542 (as shown in FIG. 14C). For example, a user may press actuation portion 1582 until distal neck portion passes through opening 1542. In some embodiments, device 1500 may be held in an inverted position during this step, to ensure that air trapped in body 1520 may be expelled, as stopper 1522 is pushed distally by plunger rod 1580. In the “primed” state, depicted in FIG. 14D, proximal neck portion 1586 may be disposed against a surface of flange piece 1540.

Figures 14D, 14E, 14F:
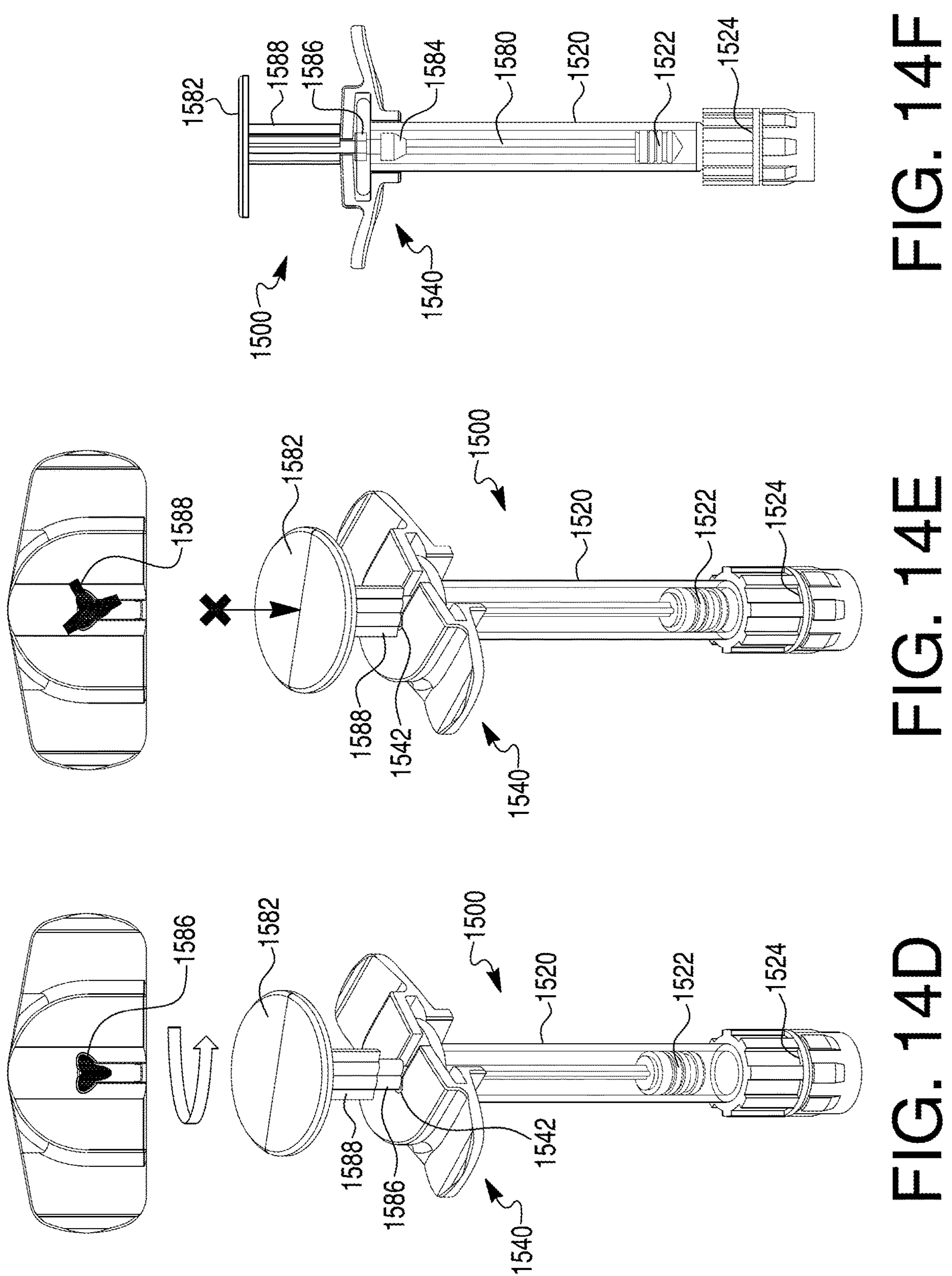

In a dispensing preparation step depicted in FIG. 14D, plunger rod 1580 may be rotated about a longitudinal axis such that the shape of proximal neck portion 1586 aligns with opening 1542. For example, a user may grasp and twist actuation portion 1582 of plunger rod 1580. Device 1500 may then be in a ready-to-dispense configuration. As depicted in FIG. 14E, in a dispensing step, plunger rod 1580 may be moved longitudinally further into body 1520. For example, a user may press actuation portion 1582 distally, until proximal stop 1588 abuts a surface of flange piece 1540. The dispensing step may ensure that a predetermined volume of a drug substance inside body 1520 is dispensed from device 1500.

In some embodiments, after each successive step in the use of device 1500, a user may be prevented from re-doing a step, and/or from reversing one or more steps. For example, geometries of, e.g., plunger rod 1580, distal neck portion 1584, proximal neck portion 1586, and opening 1542 may interface with one another to prevent a user from pulling plunger rod 1580 proximally (e.g., out of) body 1520.

Figure 16B:
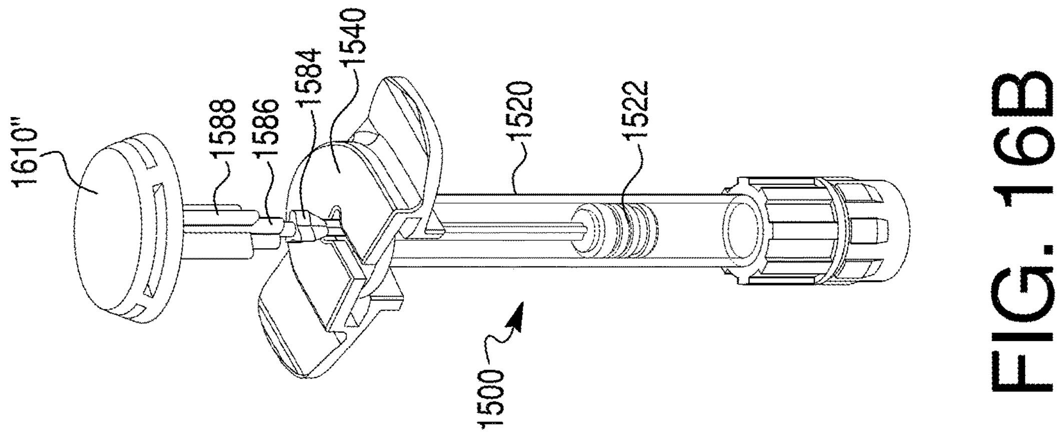
FIGS. 15A-15B, and 16A-16B depict exemplary plunger rod dials according to further embodiments of the present disclosure.
Figure 15B:
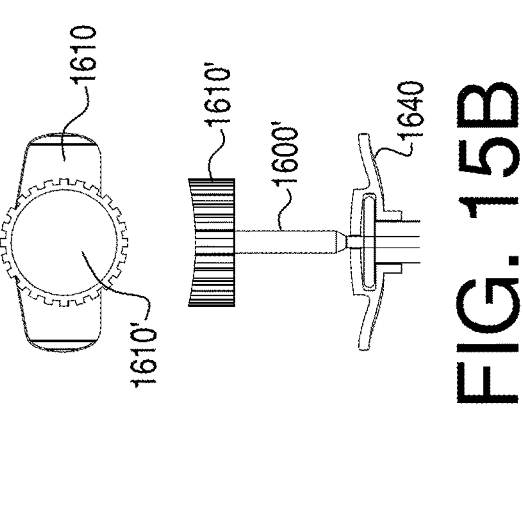
Figure 16A:
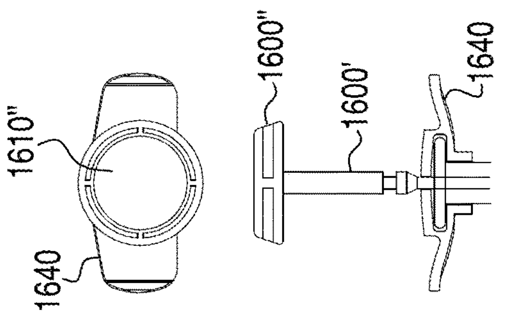
Figure 15A:
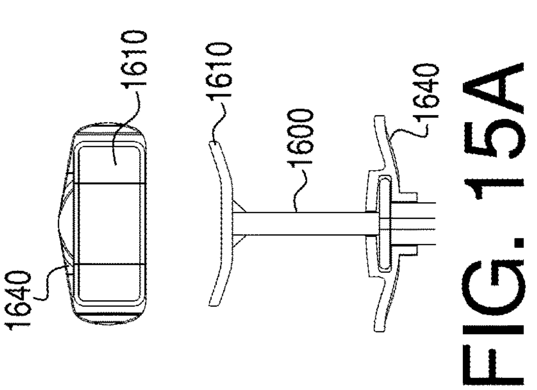

Additional variations on blocking components, dosage control components, and the like will now be described. FIGS. 15A-230 depict exemplary plunger rod dials according to further embodiments of the present disclosure. For example, FIG. 15A depicts a plunger rod 1600 having an actuation portion 1610. Actuation portion 1610 may have a shape generally corresponding to a flange piece 1640. Plunger rod 1600 may be rotatable with respect to flange piece 1640 and/or a body of the device. A device may be in a configuration suitable for delivery of a desired amount of a drug substance when, e.g., a shape of plunger rod 1610 is generally aligned with shape of 1640 (as shown in, e.g., the top view of FIG. 15A). As another example, FIG. 15B depicts an actuation portion 1610' with a ridged side, to allow for ease of rotation of plunger rod 1600' with respect to flange piece 1640 and/or a remainder of the syringe. FIG. 16A depicts an actuation portion 1610" with a ribbed side, again to allow for ease of rotation of plunger rod 1600. FIG. 16B depicts an exemplary combination of actuation portion 1610" with device 1500. One of ordinary skill in the art will understand that any of the actuation portions or other features described herein may be combined with devices described herein.

Figure 18B:
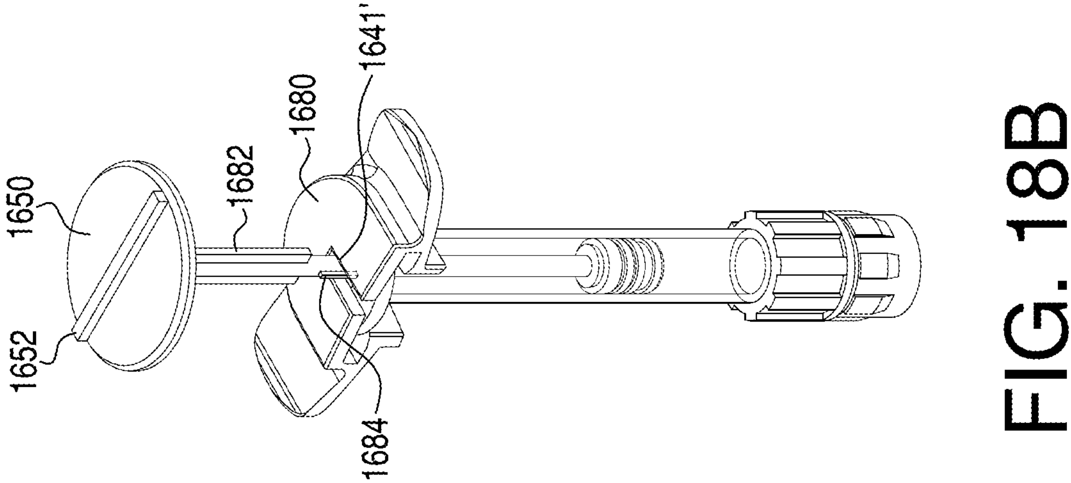
FIGS. 18A and 18B depict a further exemplary plunger rod and dial according to additional embodiments of the present disclosure.
Figure 18A:
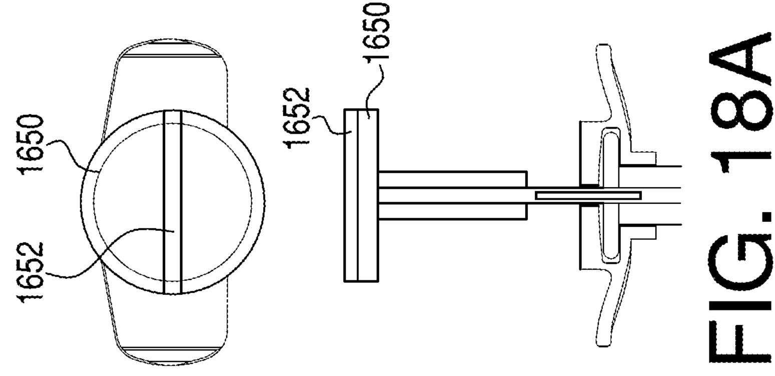
Figure 17:
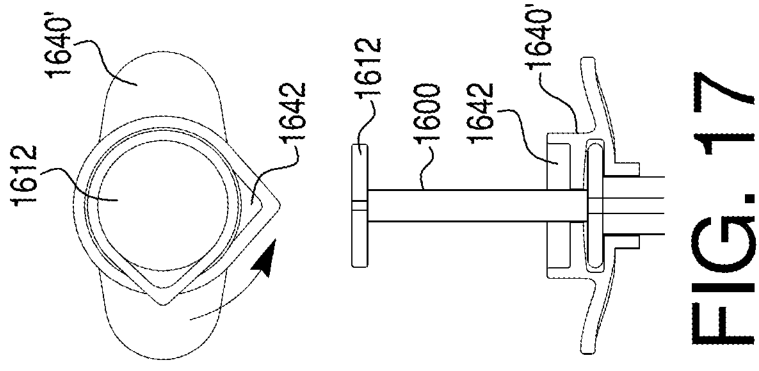
FIG. 17 depicts an exemplary plunger rod and dial according to further embodiments of the present disclosure.

FIG. 17 depicts an exemplary plunger rod and dial according to further embodiments of the present disclosure. An actuation portion 1612 may be sized and configured to fit into a collar 1642 of a flange piece 1640' in only a particular configuration. A depth of collar 1642 may correspond to, e.g., a distance that plunger rod 1600 must travel to dispense a predetermined volume of a drug substance from a drug delivery device. In one embodiment, actuation portion 1612 may be moved distally until it abuts collar 1642, and then may be rotated until its shape corresponds with the shape of collar 1642 so that it may be pushed into collar 1642 in a dispensing step. FIGS. 18A and 18B depict a further exemplary plunger rod and dial, which combine exemplary features that allow for precision dose delivery. The plunger rod may include, e.g., protrusions 1684 and 1682, which may each fit through an opening 1641' in a flange piece 1680 in a particular configuration. Each of protrusions 1682 and 1684 may correspond to a distance required to deliver a desired volume of a drug substance from a device and/or prime the device. Actuation portion 1650 may include a raised portion 1652, which may aid a user in twisting the plunger rod in relation to flange piece 1680.

Figure 19A:
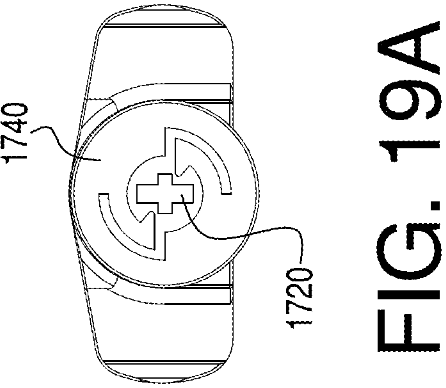
FIGS. 19A and 19B depict an exemplary rotation lock mechanism according to additional embodiments of the present disclosure.
Figure 19B:
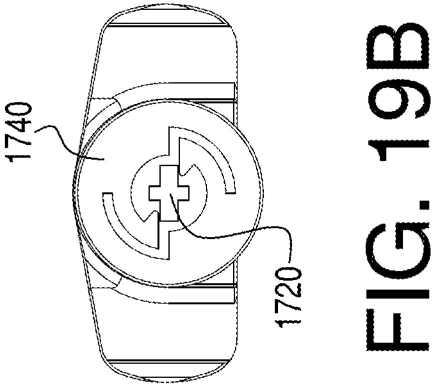

FIGS. 19A and 19B depict a top view of a flange piece 1740 and a plunger rod 1720. Flange piece 1740 and plunger rod 1720 may have a cross-sectional shape allowing for limited rotation of plunger rod 1720 relative to flange piece 1740 in a single direction. For example, flange piece 1740 may have inner protrusions that may interact with an irregular cross-sectional shape of plunger rod 1720 to resist a first portion of plunger rod 1720 as it rotates past the inner protrusions, and to stop a second portion of plunger rod 1720 when it abuts the inner protrusions.

Figure 20:
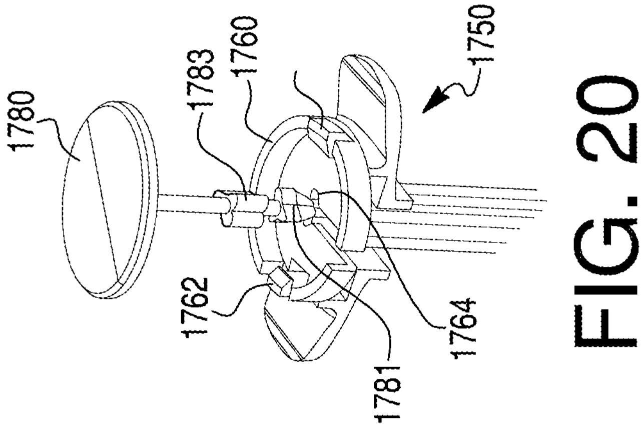
FIG. 20 depicts an exemplary plunger rod snap feature according to additional embodiments of the present disclosure.

FIG. 20 depicts an exemplary flange piece 1750 with a well 1760 having clips 1762. A plunger rod actuation portion 1780 may be pushed distally into well 1760 until clips 1762 overlay actuation portion 1780, to hold actuation portion 1780 in place and, e.g., prevent back-out of the plunger rod. The plunger rod includes a distal protrusion 1781 and a proximal protrusion 1783, each of which is sized to fit through an opening 1764 when the plunger rod is rotated to a particular position. Distal protrusion 1781 includes a tapered distal side, which may assist in orienting the plunger rod into the position required to advance the plunger rod distally such that distal protrusion 1781 passes through opening 1764. This may increase the ease of, e.g., a priming step. In some embodiments, a height of well 1760 and/or actuation portion 1780 may correspond to a height that a plunger rod must travel to dispense a predetermined volume of a drug substance. Thus, a device may be primed when actuation portion 1780 abuts a proximal side of well 1760, and may deliver a predetermined volume of a drug substance as actuation portion 1780 travels distally into well 1760.

Figure 21:
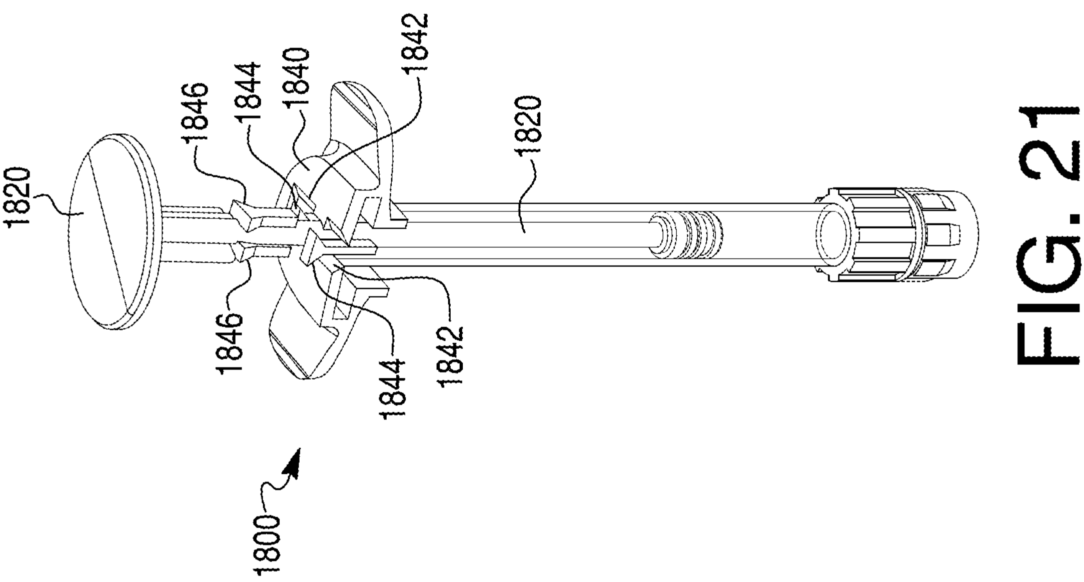
FIG. 21 depicts an exemplary plunger rod with a bump feature according to additional embodiments of the present disclosure.

FIG. 21 depicts an exemplary device 1800 with a plunger rod 1820 and a complementary flange piece 1840. Plunger rod 1820 may include, e.g., protrusions 1844, 1846 having an angled or wedge shape, corresponding to a shape of one or more openings 1842 in flange piece 1840. The wedge or angled shapes of protrusions 1844, 1846 and openings 1842 may suffice to resist distal movement of plunger rod 1820 when a protrusion 1844 or 1846 abuts a side of opening 1842, but may be able to move past one another given enough force. The resistance provided by the abutment of protrusions 1844, 1846 against the sides of openings 1842 may suffice to indicate to a user that a particular step in the use of device 1800 is completed. A user may then apply enough force to move plunger rod 1820 past the resistance and continue to a next step (e.g., from a completed priming step to a delivery-ready step).

Figure 22:
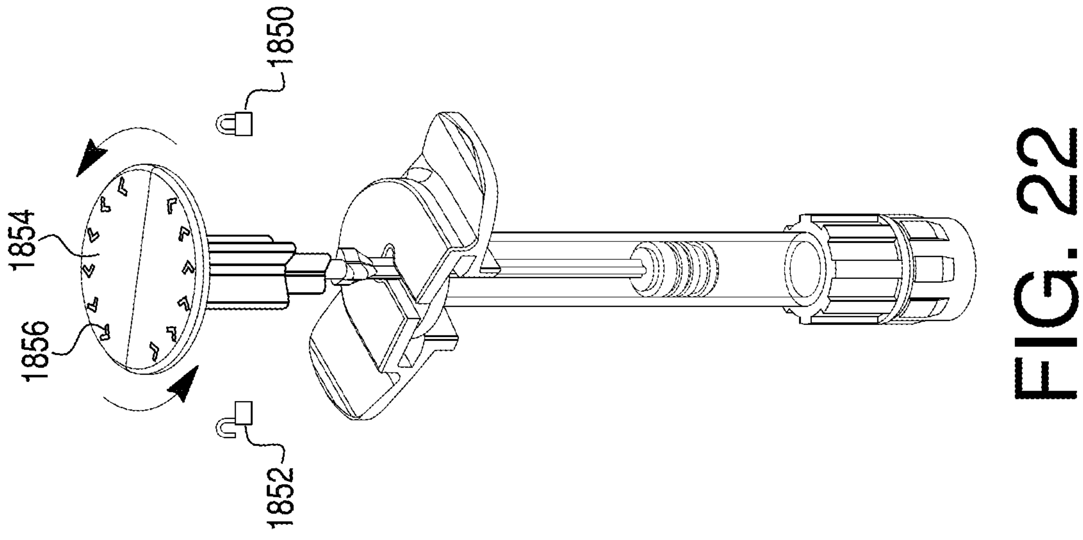
FIG. 22 depicts exemplary visual feedback features according to some embodiments of the present disclosure.

As has been described elsewhere, any of the devices disclosed herein may be combined with labels, auditory feedback, and/or tactical feedback in the form of symbols (e.g., in FIG. 22 depicted as lock and unlock symbols 1850, 1852, chevrons 1856 on actuation portion 1854). Rotation of a plunger rod also may be accompanied by a "clicking" sound.

Figure 23C:
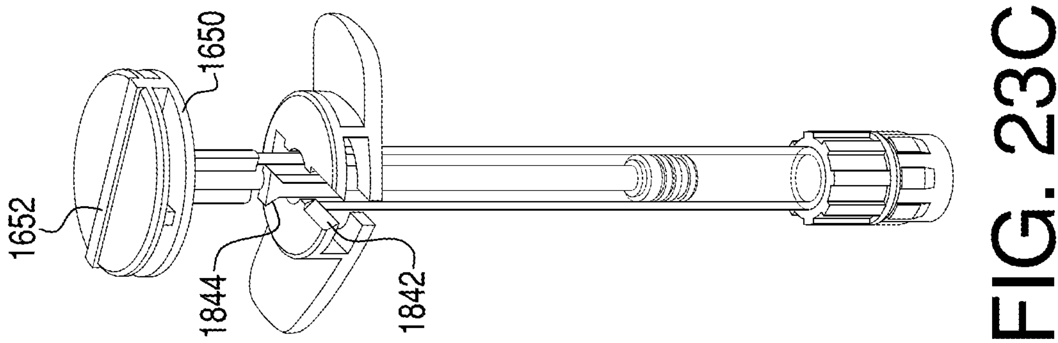
FIGS. 23A-23C depict a further exemplary delivery device according to aspects of the present disclosure.
Figure 23B:
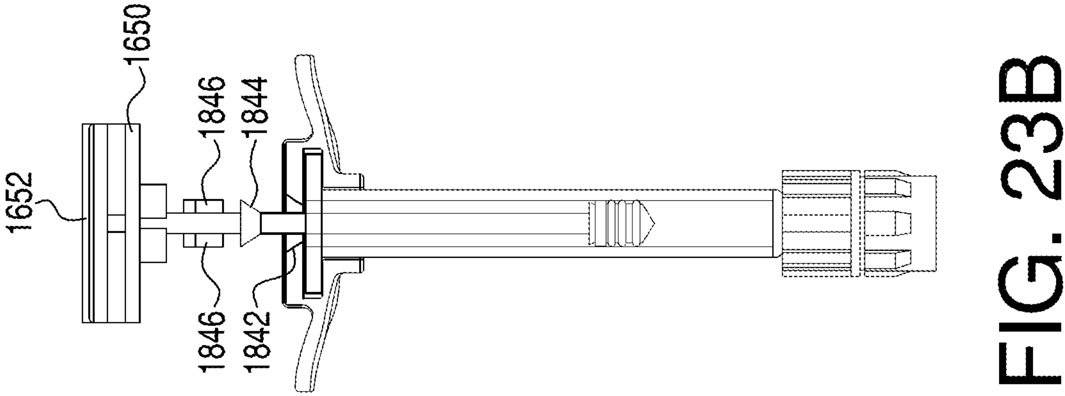
Figure 23A:
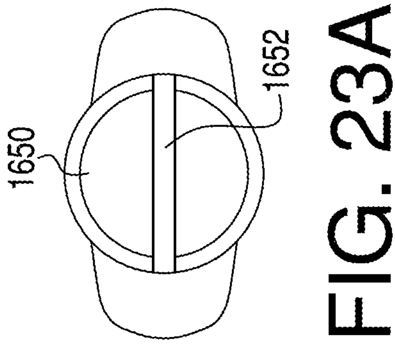

FIGS. 23A-23C depict a further exemplary combination of components in a delivery device. For example, a plunger rod actuation portion 1650 may include, e.g., ribbed sides and a raised portion 1652, to assist in twisting the actuation portion. A device with these characteristics may include, e.g., openings 1842 and corresponding angled protrusions 1844, 1846 (described with respect to FIG. 21).

Figures 24B, 24C, 24D, 24E:
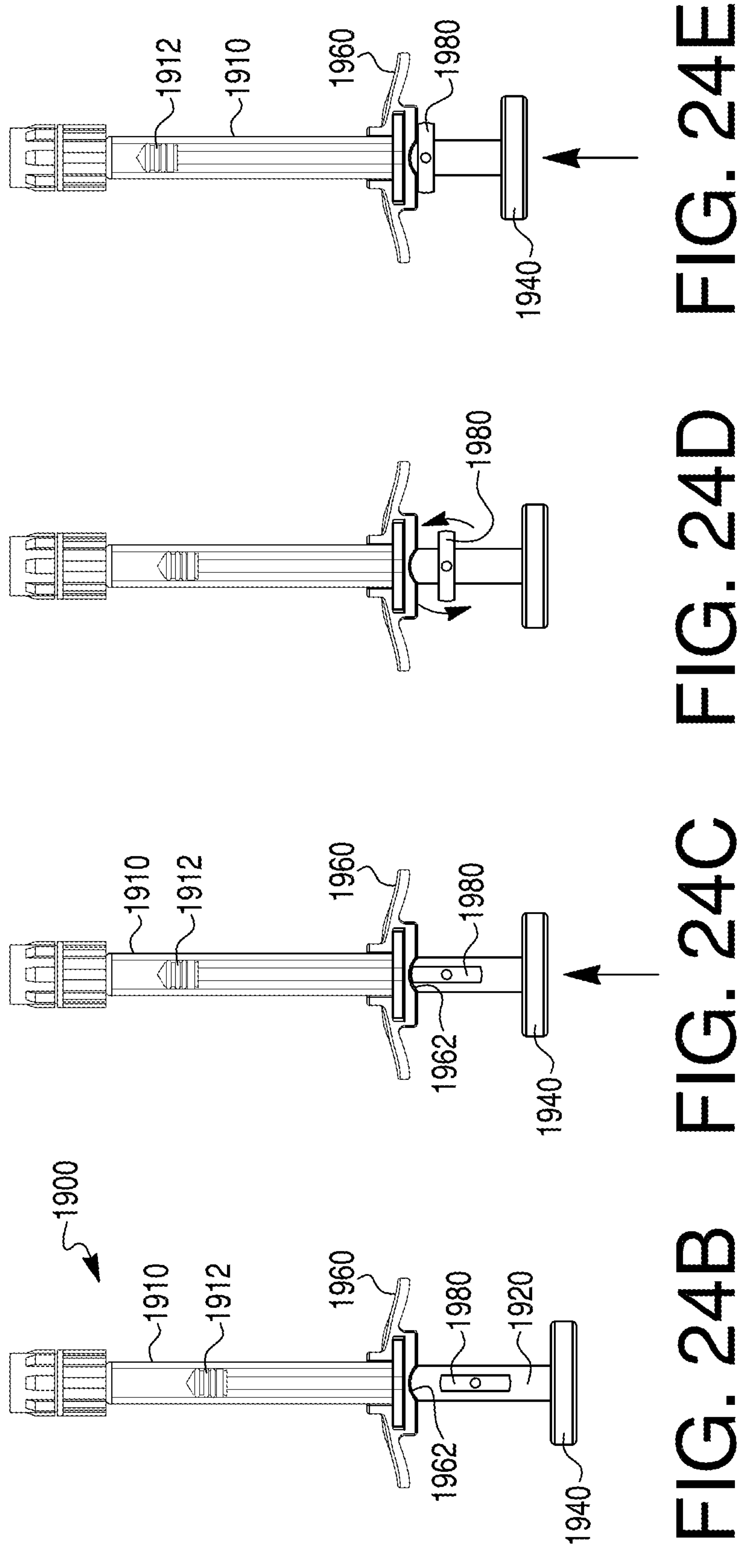

FIGS. 24A-24E depict a further exemplary delivery device 1900 and a method of using device 1900. Device 1900 may include an actuation portion 1940 and a blocking component 1980 depicted on a plunger rod 1920. Plunger rod 1240 may abut a stopper 1912 in a body 1910. Blocking component 1980 may be rotatable relative to plunger rod 1920. In a pre-use configuration depicted in FIG. 24B, blocking component 1980 may be in a first position with respect to plunger rod 1920 and flange piece 1960. In a priming step depicted in FIG. 24C, plunger rod 1920 may be moved longitudinally further into body 1910, until distal movement is blocked by the abutment of blocking component 1980 against a recess 1962 in flange piece 1960. For example, a user may press actuation portion 1940 distally towards flange piece 1960. In a dispensing preparation step depicted in FIG. 24D, blocking component 1980 may be rotated such that a shorter dimension of blocking component 1980 faces flange piece 1960. Recess 1962 may be curved to allow for ease of rotation of blocking component 1980. A distance between blocking component 1980 and flange piece 1960 after blocking component 1980 is rotated may correspond to a distance that plunger rod 1920 may move to dispense a predetermined volume of a drug substance from device 1900. As depicted in FIG. 24E, in a dispensing step, plunger rod 1920 may be moved longitudinally further into body 1910, until the rotated blocking component 1980 abuts flange piece 1960 in a second position. For example, a user may press actuation portion 1940 distally, until protrusion blocking component abuts flange piece 1960. The dispensing step may ensure that a predetermined volume of a drug substance inside body 1910 is dispensed from device 1900.

Figure 25B:
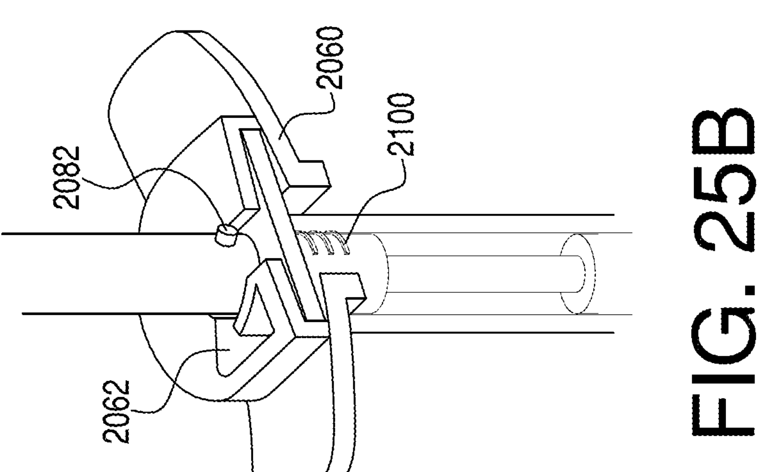
FIGS. 25A-25E depict a further exemplary delivery device and method of using said delivery device, according to aspects of the present disclosure.
Figure 25A:
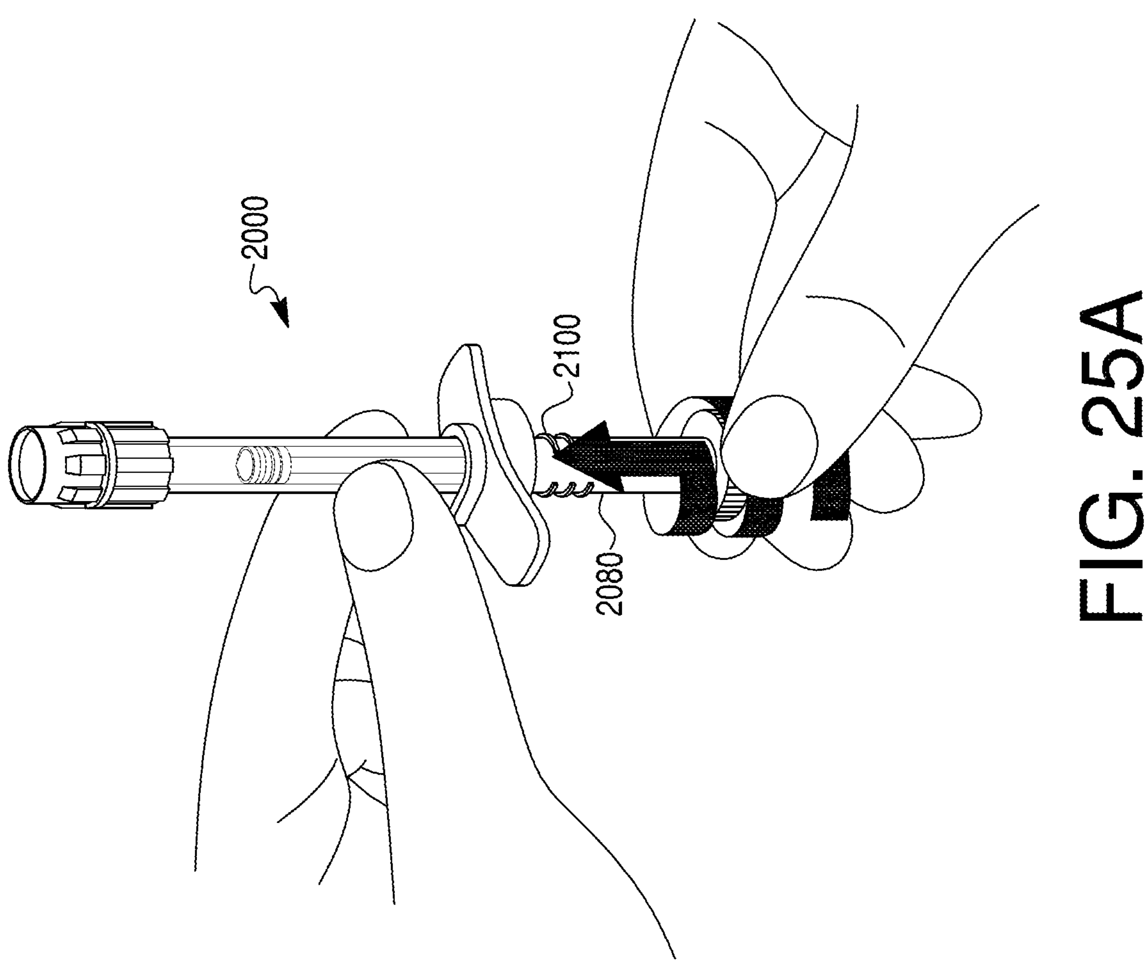
Figure 25E:
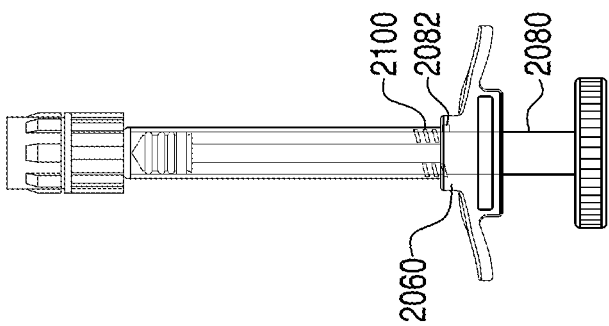
Figure 25D:
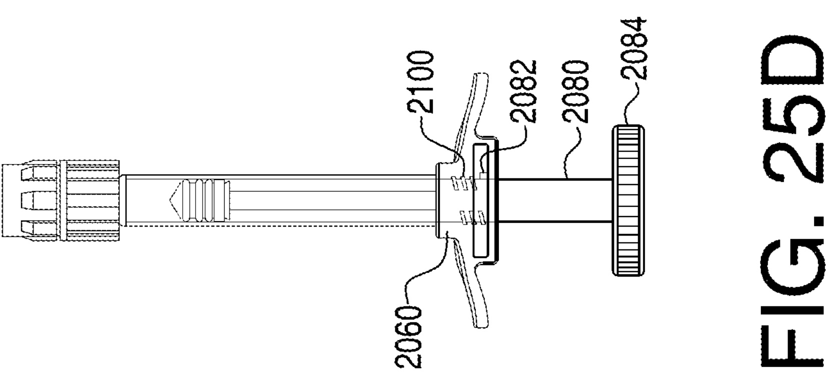
Figure 25C:
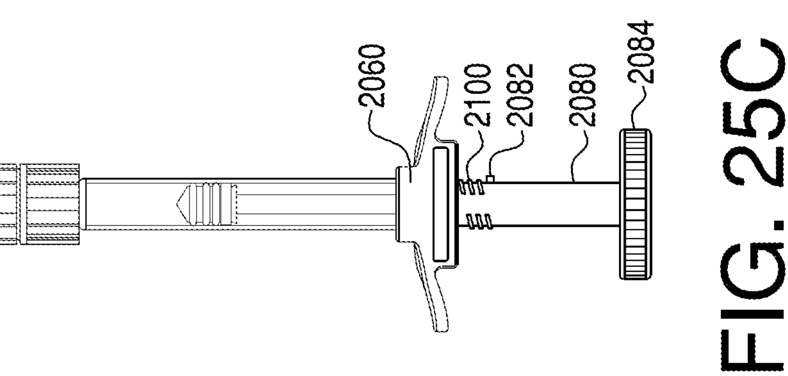

FIGS. 25A-25E depict a further exemplary delivery device 2000, and a method of using delivery device 2000. A plunger rod 2080 of device 2000 may include threads 2100, corresponding to inner threads (not pictured) in a flange piece 2062. As depicted in FIG. 25A, plunger rod 2080 may be rotatable relative to other portions of device 2000. Plunger rod 2080 may also include a protrusion 2082 located proximally from threads 2100 (see, e.g., FIG. 25B), which may correspond to an opening 2062 in a flange piece 2062, such that plunger rod 2080 must be in a particular configuration and position to allow protrusion 2082 to pass into and/or through flange piece 2060. In a pre-use configuration depicted in FIG. 25C, threads 2100 and protrusion 2082 may be positioned proximally to flange piece 2060. In a priming step, plunger rod 2080 may be rotated with respect to the inner threads of flange piece 2060 until threads 2100 pass through flange piece 2060 and/or protrusion 2082 prevents further rotation or distal movement of plunger rod 2080. In a dispensing preparation step, protrusion 2082 may be moved towards opening 2062. In a dispensing step, protrusion 2082 may be moved through opening 2062 to further advance plunger rod 2080, and to dispense a predetermined volume of a drug substance inside the body of device 2000.

Figure 26B:
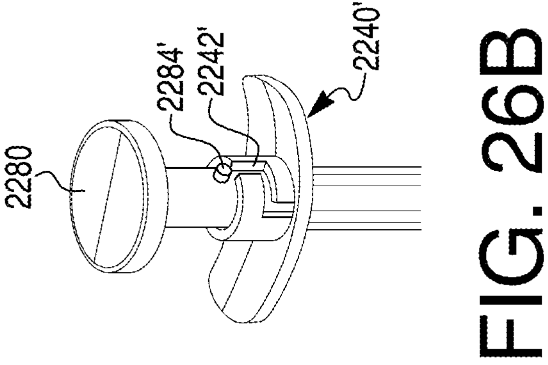
FIGS. 26A-26G depict further exemplary delivery devices and a method of using one such delivery device, according to aspects of the present disclosure.
Figure 26A:
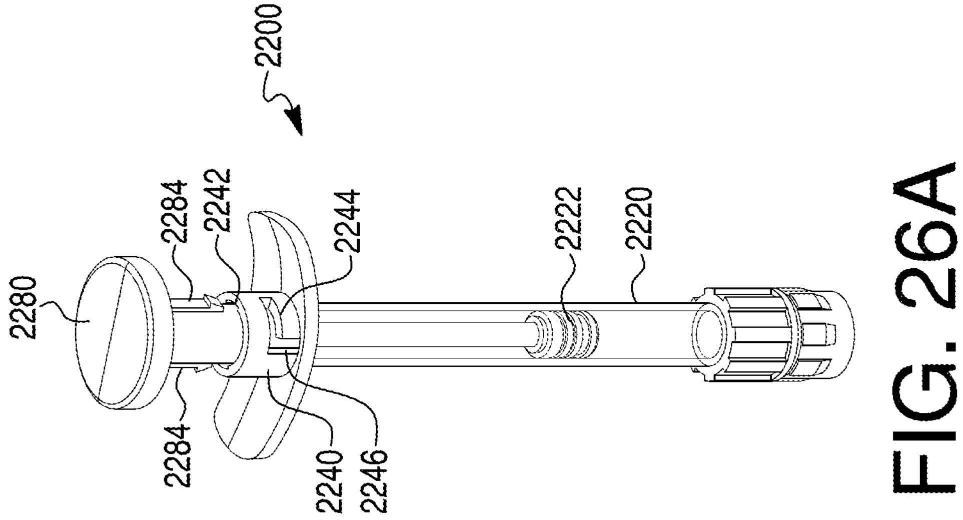
Figure 26E:
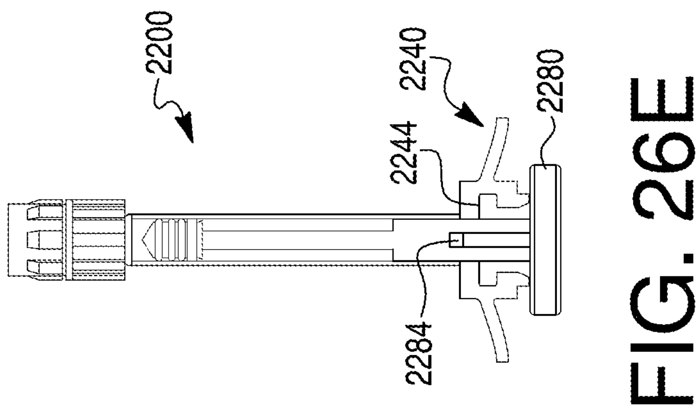
Figure 26D:
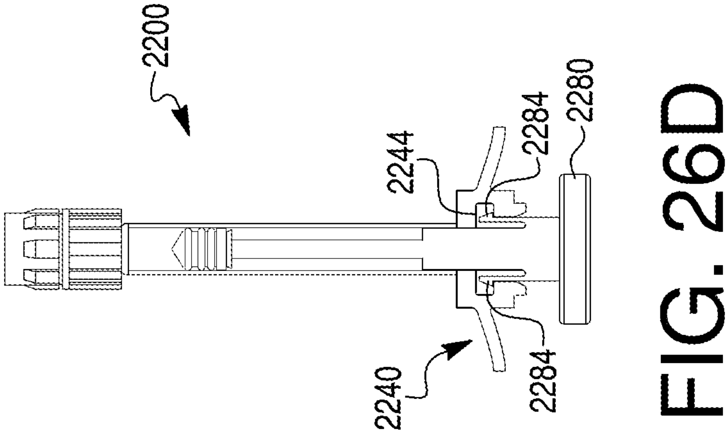
Figure 26C:
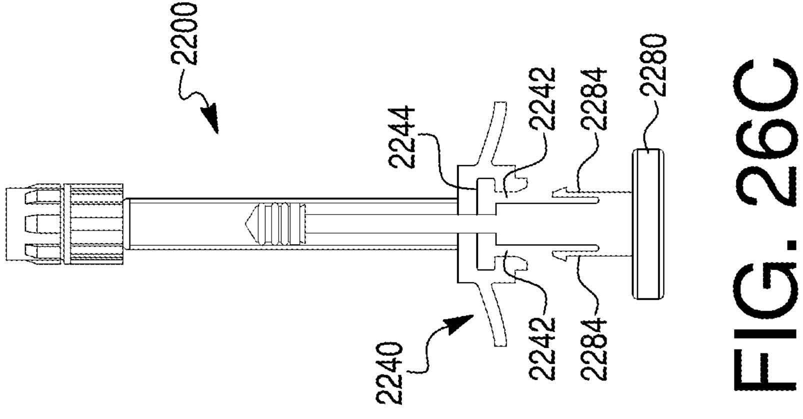

FIGS. 26A-26E depict a delivery device 2200 having further variations on dosage control components. For example, device 2200 includes a plunger rod 2280 with one or more clips 2284, each of which may be configured to slide distally into a channel 2242 of a flange piece 2240 and, once having slid distally, to resist sliding proximally out of channel 2242 (e.g., to prevent or resist back-out of plunger rod 2280). Flange piece 2240 may further have a second channel 2244 and a third channel 2246, through which each of clips 2284 may slide in delivery preparation and dosage delivery steps, as has been previously described. Alternately, as shown in FIG. 26B, channel 2242' may have an open proximal end through which a protrusion 2284' may move, allowing for proximal and/or distal movement of a plunger rod 2280 relative to flange piece 2240'. As depicted in FIG. 26C, in a pre-use configuration, clips 2284 may be disposed proximally to channels 2242 of flange piece 2240. In a priming step, plunger rod 2280 may be moved distally into a body of device 2200, until clips 2284 move into channels 2242 and abut a distal end of channels 2242. In a dispensing preparation step, plunger rod 2280 may be rotated relative to flange piece 2240. In a dispensing step, plunger rod 2280 may be moved further distally into a body of device 2200 to dispense a predetermined volume of the drug substance from device 2200.

Figure 26G:
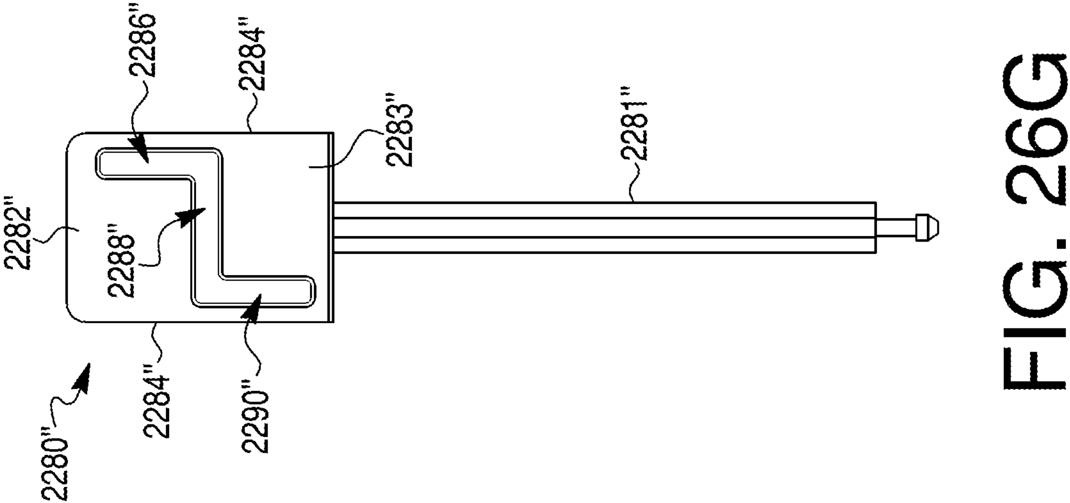
Figure 26F:
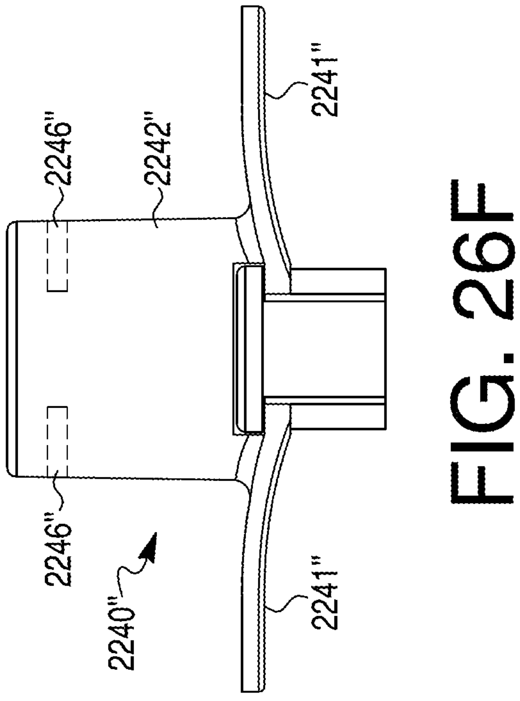

In other embodiments, as shown in FIGS. 26F-26G, a flange piece 2240" may include one or more projections 2246" disposed within a collar 2242". In the present example, collar 2242" may include a pair of projections 2246" extending radially inward from an interior surface of collar 2242" and in opposite directions relative to another. For example, projections 2246" may be disposed approximately 180 degrees away from one another. It should be appreciated that flange piece 2240" may include additional and/or fewer projections 2246" than those shown and described herein without departing from a scope of this disclosure. Flange piece 2240" may be configured to engage a plunger rod 2080" in response to plunger rod 2280" receiving projections 2246".

As seen in FIG. 26G, a plunger rod 2280" may include an actuation member 2284" defined by a proximal end 2282" and a distal end 2283". Plunger rod 2280" may include a series of channels along opposing sides of actuation member 2284", such as, for example, a first channel 2286", a second channel 2288", and a third channel 2290" positioned between proximal end 2282" and distal end 2283". First channel 2286" is offset from third channel 2290" and connected to third channel 2290" by second channel 2288" positioned therebetween. As described in detail below, first channel 2286" may define a longitudinal and axial priming path of plunger rod 2280", second channel 2288" may define a circumferential path of plunger rod 2280", and third channel 2290" may define a longitudinal and axial dose completion path. It should be appreciated that an opposing surface and/or side of actuation member 2284" (not shown) includes a substantially similar series of interconnected first channel 2286", second channel 2288", and third channel 2290" as seen in FIG. 26G. In the present example, first channel 2286" and third channel 2290" may be aligned parallel relative to one another.

First channels 2286", second channels 2288", and third channels 2290" may be sized, shaped, and configured to receive at least one of the pair of projections 2246". With plunger rod 2280" coupled to flange piece 2240", projections 2246" may protrude and slide through first channels 2286", second channels 2288", and third channels 2290" to prime and deliver a dosage from device 2200 (FIG. 26A) as described in detail above. In some embodiments, first channels 2286" may have an open end at proximal end 2282" through which projections 2246" may be received in. In some embodiments, first channels 2286" may have a closed proximal end and projections 2246" may be at least partially flexible and/or deformable such that projections 2246" may be configured to flex radially-outward when being received at the proximal end of first channels 2286". In other embodiments, first channels 2286" may have a sloped, chamfered, and/or tapered end to facilitate guiding projections 2246" toward second channels 2288". In this instance, the sloped end may inhibit retraction (e.g., proximal movement) of plunger rod 2280" relative to flange piece 2240". A longitudinal length of first channels 2286" may define an axial priming path (e.g., an amount or extent priming) that is configured to facilitate proximal and/or distal movement of plunger rod 2280" relative to flange piece 2240". For example, projections 2246" may be disposed at a proximal end of first channels 2286" and proximally of second channels 2288" when device 2200 is in an assembly state. In a priming step, plunger rod 2280" may move distally relative to flange piece 2240" until projections 2246" are positioned within second channels 2288" and at a distal end of first channels 2286". Second channels 2288" may define a circumferential path of plunger rod 2280".

In a dispensing preparation step, plunger rod 2280" may be rotated relative to flange piece 2240" to translate projections 2246" laterally through the circumferential path of second channels 2288" and toward a dose completion path defined by third channels 2290". In some embodiments, plunger rod 2280" and/or flange piece 2240" may be configured to generate a user feedback (e.g., tactile, audible, visual, etc.) when device 1050 is in the dispensing preparation step. In a dispensing step, plunger rod 2280" may move distally into a body of device 2200 to dispense a controlled volume of substance by translating projections 2246" through third channels 2290". A longitudinal length of third channels 2290" may define a dosage delivery path (e.g., a dosage amount). It should be appreciated that the axial priming path (length of first channels 2286") may vary relative to the dosage delivery path (length of third channels 2290"). In other embodiments, plunger rod 2280" may include additional and/or fewer channels along actuation member 2284" (e.g., corresponding to a quantity of projections 2246" on flange piece 2240"), or have various other relative channel configurations, than those shown and described herein.

Figure 27C:
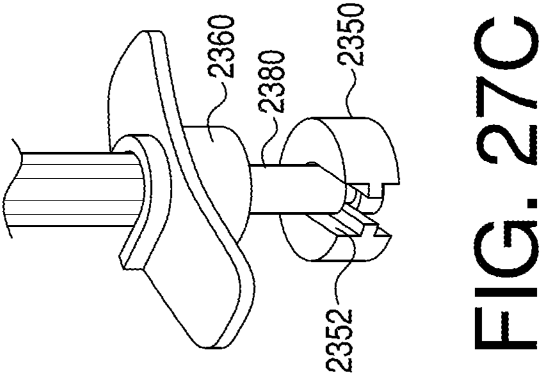
FIGS. 27A-27H depict a further exemplary delivery device and method of using said delivery device, according to aspects of the present disclosure.
Figure 27B:
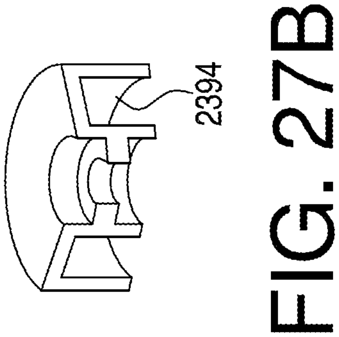
Figure 27A:
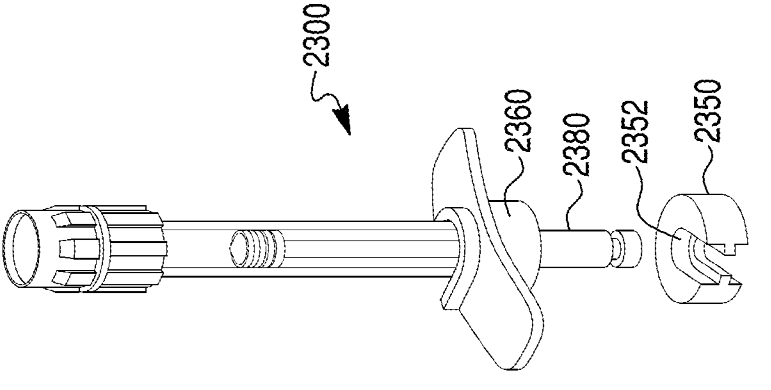
Figures 27D, 27E, 27F:
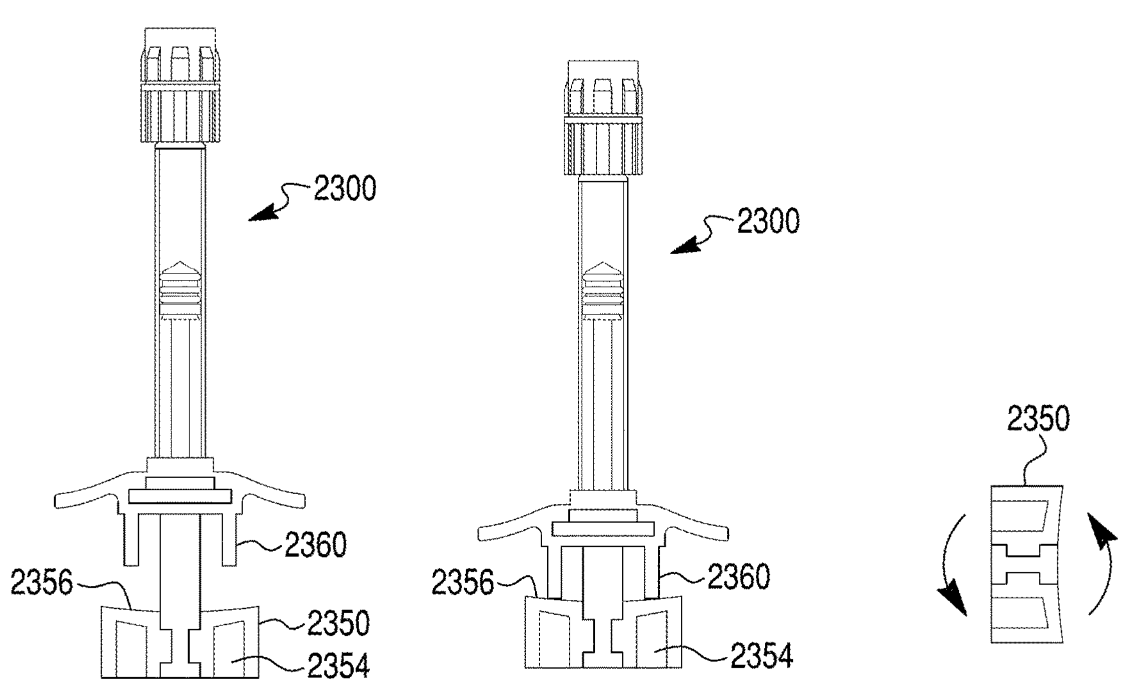
Figures 27G, 27H:
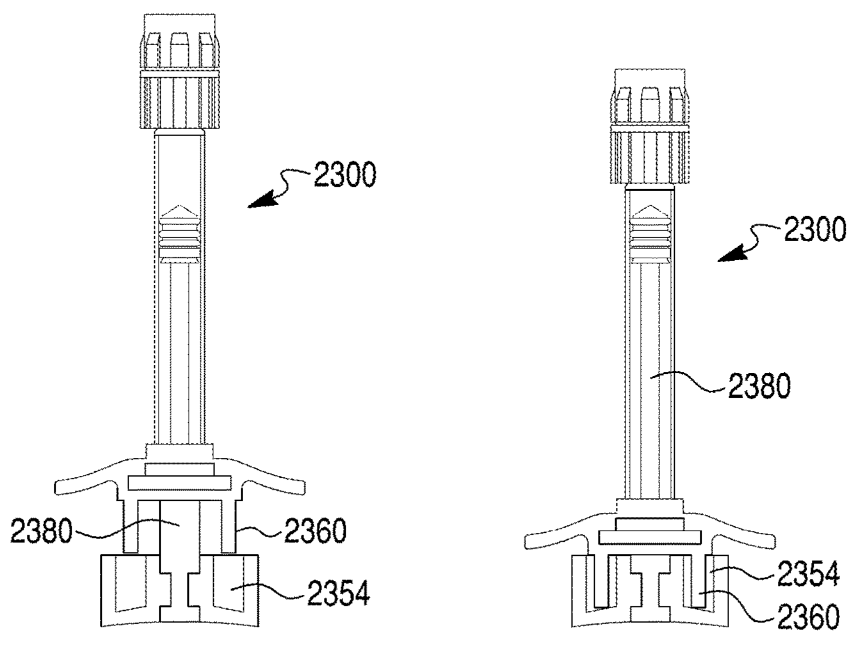

FIGS. 27A-27H depict an exemplary delivery device 2300 and method of using delivery device 2300. An actuation portion 2350 may also serve as a blocking component of device 2300. Actuation portion 2350 may be slidably coupled to plunger rod 2380 in two configurations, via a channel 2352. As depicted in FIG. 27B, one side of actuation portion 2350 may include a channel 2354. A depth of channel 2354 may correspond to a distance that a plunger rod may move to dispense a predetermined volume of a drug substance once device 2300 has been primed. As depicted in FIG. 27C and FIG. 27D, in a pre-use configuration, actuation portion 2350 may be assembled onto plunger rod 2380 such that a flat side of actuation portion 2350 faces a collar 2360 of device 2300. In a priming step, actuation portion 2350 may be used to move plunger rod 2380 distally until the flat side 2356 of actuation portion 2350 abuts a proximal side of collar 2360. To prepare for a dosage delivery step, actuation portion 2350 may be removed from plunger rod 2380, and may be rotated or flipped and reassembled with plunger rod 2380 such that channel 2354 faces collar 2360, as depicted in FIGS. 27F and 27G. In a dosage delivery step, actuation portion 2350 may be used to push plunger rod 2380 further distally, until a proximal end of collar 2360 abuts an inner end of channel 2354. This movement of plunger rod 2380 may be sufficient to dispense a predetermined dose of a drug substance from device 2300.

Figure 28C:
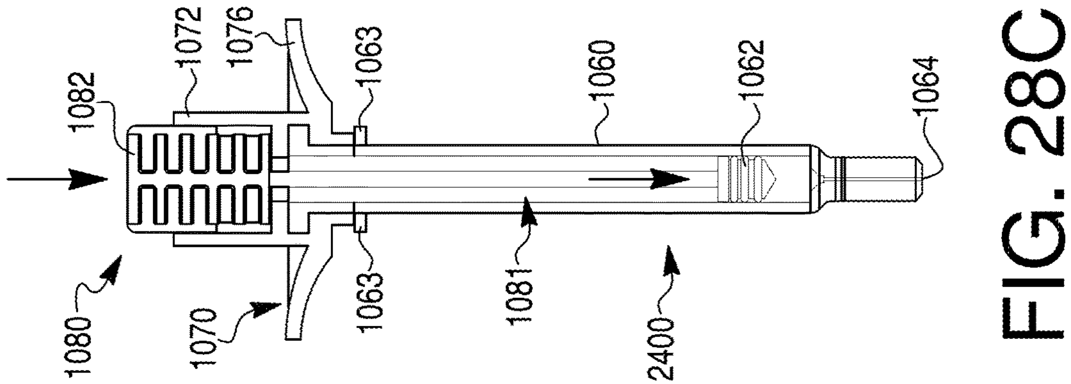
FIGS. 28A-28Z depict further exemplary delivery devices and methods of using said delivery devices, according to aspects of the present disclosure.
Figure 28B:
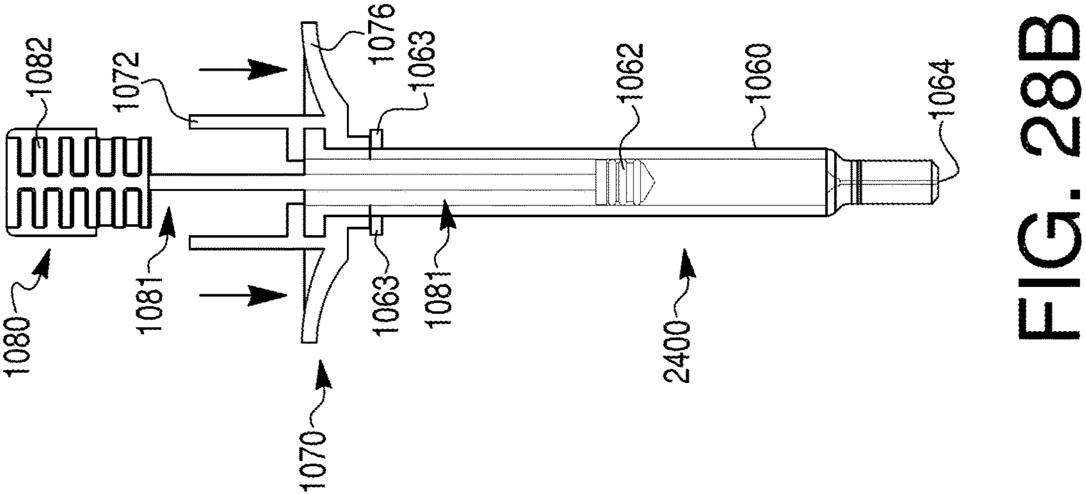
Figure 28A:
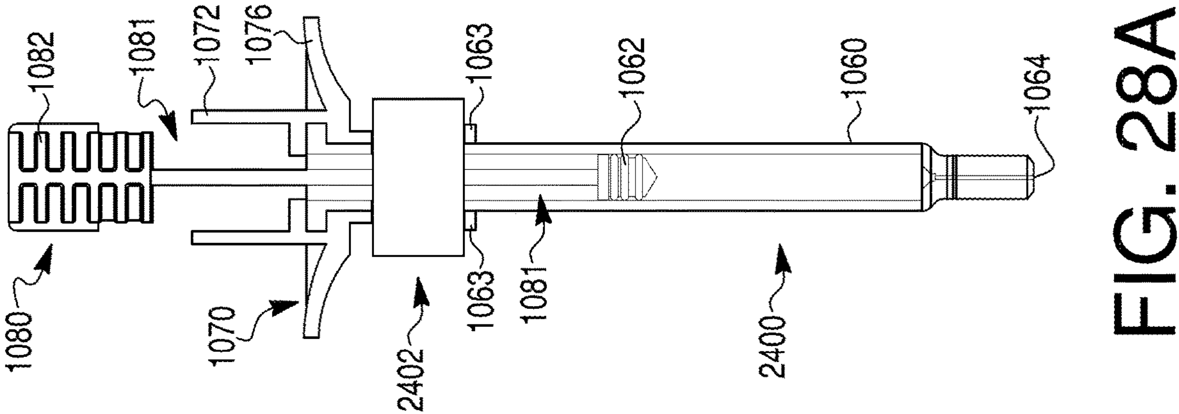

FIGS. 28A-28C depict an exemplary delivery device 2400 and method of using delivery device 2400. Delivery device 2400 may include substantially similar features as those shown and described above such that like reference numerals are used to identify like components. As shown in FIG. 28A, delivery device 2400 may include a removable clip 2402 coupled to body 1060 at a position distal to flange piece 1070. Removable clip 2402 may be an obstruction and/or blocking component configured to inhibit movement of flange piece 1070 relative to body 1060. Removable clip 2402 is selectively removable such that removable clip 2402 may be configured to disengage body 1060 in response to manual actuation of removable clip 2402.

By way of illustrative example, removable clip 2402 may have a body that wraps about an exterior of body 1060 and is configured to selectively deform (e.g., break, tear, etc.) upon application of a force thereto to decouple removable clip 2402 from body 1060. In other examples, removable clip 2402 may have a flexible body that is configured to bend in response to a radially-outward force being applied thereto, thereby disengaging removable clip 2402 from body 1060. By way of further example, removable clip 2402 may have a body that is configured to selectively transition between a closed configuration encapsulating a circumference of body 1060 therein and an open configuration permitting removal of body 1060 from the body of removable clip 2402. Removable clip 2402 may include various other suitable sizes, shapes, and/or configurations than those shown and described herein without departing from a scope of the present disclosure.

Delivery device 2400 may include a radial wall 1063 extending laterally outward from an exterior of body 1060, thereby forming an obstruction along body 1060. As seen in FIG. 28A, radial wall 1063 may be configured to inhibit distal translation of removable clip 2402 along body 1060. In some embodiments, radial wall 1063 may be an add-component attached to body 1060, while in other embodiments, radial wall 1063 may be integrally formed onto body 1060. Referring now to FIG. 28B, flange piece 1070 and plunger rod 1080 may be configured to translate distally along body 1060 to prime delivery device 2400 upon removal of removable clip 2402 from body 1060. In this instance, plunger rod 1080 may remain stationary relative to flange piece 1070, as the combined assembly of flange piece 1070 and plunger rod 1080 moves relative to body 1060. In other embodiments, plunger rod 1080 may remain stationary as flange piece 1070 translates distally along body 1060 to prime delivery device 2400. For example, at least a portion of flange piece 1070 may extend into body 1060 (e.g., and behind stopper 1062) when priming device 2400. In this instance, plunger rod 1080 may be translated separately to deliver a dosage from delivery device 2400.

With flange piece 1070 translated from a proximal position (FIG. 28A) to a distal position (FIG. 28B), delivery device 2400 may be in a primed position. It should be appreciated that body 1060 may be configured to limit movement by flange piece 1070 to a defined distance based on a location of radial wall 1063, which may correspond to a priming distance of delivery device 2400. Accordingly, a priming distance of delivery device 2400 may be controlled by adjusting a range of movement of flange piece 1070 along body 1060.

As seen in FIG. 28C, plunger rod 1080 may be translated distally relative to body 1060 in response to applying a distally-directed force onto actuation portion 1082. In this instance, stem 1081 may move relative to flange piece 1070, thereby causing stopper 1062 to move within body 1060 to deliver a dose. It should be appreciated that an extent that plunger rod 1080 translates relative to flange piece 1070 may define a dosage delivery distance of delivery device 2400. The dosage delivery distance may be controlled based on a gap formed between collar 1072 and actuation portion 1082.

Figure 28F:
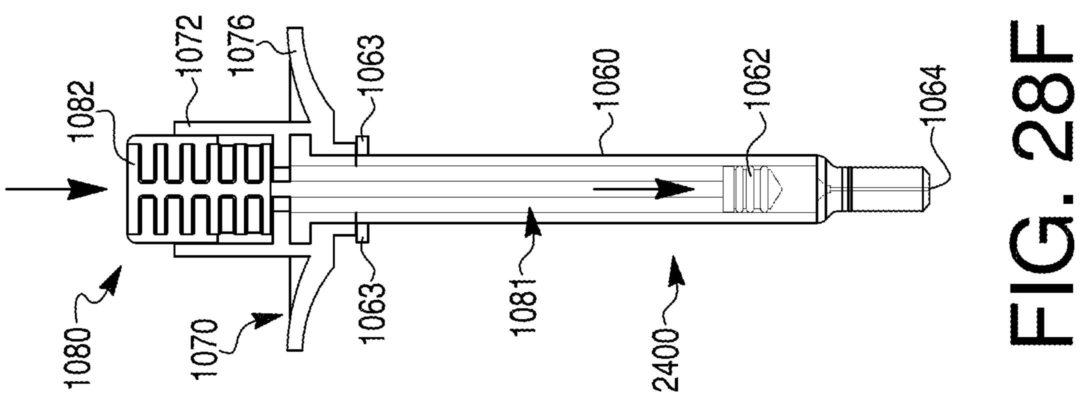
Figure 28E:
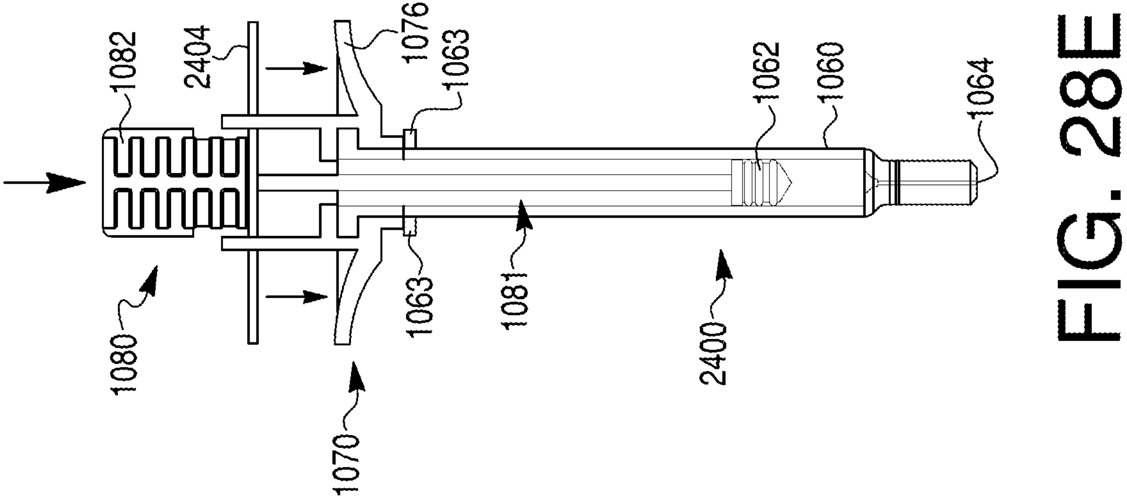
Figure 28D:
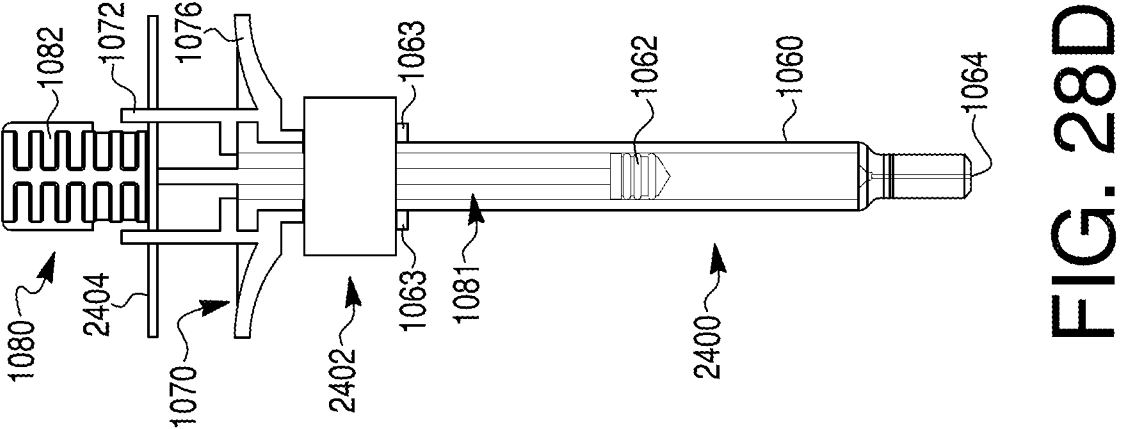

In other embodiments, as seen in FIGS. 28D-28F, delivery device 2400 may further include a locking component, such as, for example, a removable rod 2404 coupled to flange piece 1070. Referring specifically to FIG. 28D, removable rod 2404 may be received through a proximal end of collar 1072, such as, for example, through one or more lateral apertures (not shown) formed through collar 1072. Removable rod 2404 may be configured to inhibit movement of plunger rod 1080 relative to flange piece 1070, such as, for example, preventing receipt of actuation portion 1082 into collar 1072. Removable rod 2404 may be selectively removable and configured to disengage collar 1072 upon manual actuation of removable rod 2404. It should be appreciated that delivery device 2400 may include various other locking components in addition to and/or in lieu of removable rod 2404, such as, for example, a pin, a tab, a bar, and the like.

For example, referring now to FIG. 28E, flange piece 1070 and plunger rod 1080 (e.g., stem 1081 and actuation portion 1082) may be configured to translate distally along body 1060 to prime delivery device 2400 in response to removal of removable clip 2402 from body 1060. Plunger rod 1080 may remain stationary relative to flange piece 1070 as the assembly of flange piece 1070 and plunger rod 1080 moves relative to body 1060. With flange piece 1070 translated from a proximal position (FIG. 28D) to a distal position (FIG. 28E), delivery device 2400 may be in a primed position. It should be appreciated that body 1060 may be configured to limit movement by flange piece 1070 to a defined distance based on a location of radial wall 1063 along body 1060, which may correspond to a priming distance of delivery device 2400.

As seen in FIG. 28F, removable rod 2404 may be disengaged from collar 1072 such that plunger rod 1080 is no longer inhibited from moving distally relative to flange piece 1070. Actuation portion 1082 may be translated into collar 1072 to move stem 1081 and stopper 1062 within body 1060 to deliver a dose. An extent that plunger rod 1080 translates relative to flange piece 1070 may define a dosage delivery distance of delivery device 2400.

Figure 28I:
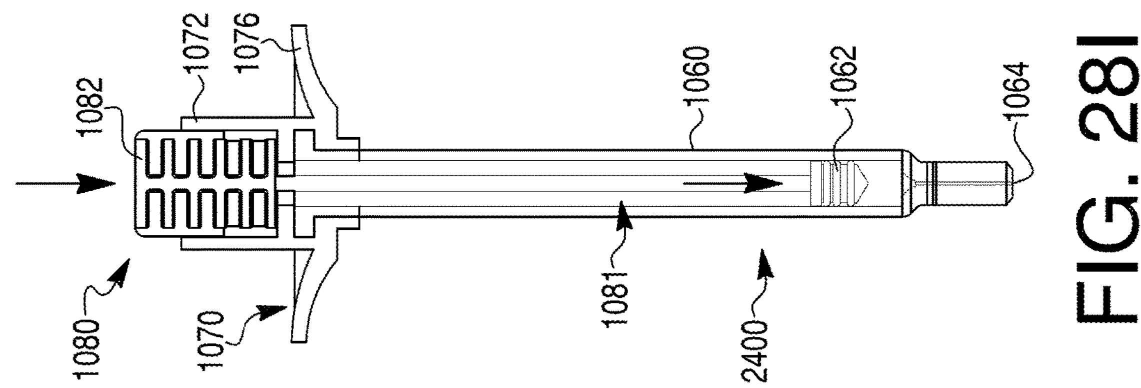
Figure 28H:
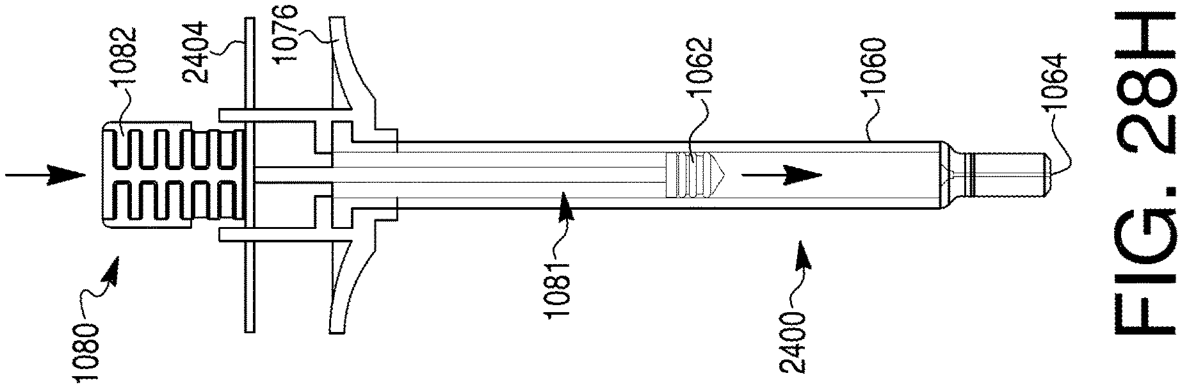
Figure 28G:
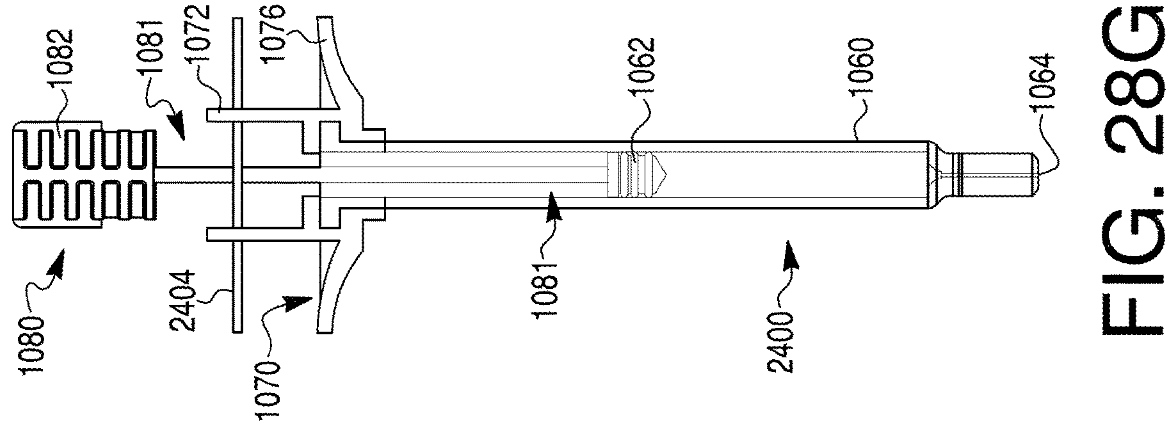

In other embodiments, as seen in FIGS. 28G-281, removable clip 2402 may be omitted entirely such that delivery device 2400 may include a single obstruction and/or blocking component, i.e., rod 2404. In this instance, flange piece 1070 may be fixed relative to body 1060. With actuation portion 1082 positioned proximally of rod 2404, delivery device 2400 may be primed in response to plunger rod 1080 translating distally toward flange piece 1070 until encountering rod 2402. It should be appreciated that flange piece 1070 and/or rod 2404 may be configured to inhibit distal translation of plunger rod 1080 relative thereto absent an application of a distally-directed force thereto. In other examples, delivery device 2400 may include a blocking component positioned between actuation portion 1082 and rod 2404 (e.g., removable clip 2404) to inhibit distal movement of plunger rod 1080.

Accordingly, a priming distance of delivery device 2400 may be defined by a distance between the distal end of actuation portion 1082 and rod 2404 when delivery device 2400 is in an assembled, pre-primed state (FIG. 28G). With actuation portion 1082 engaged against rod 2402, as seen in FIG. 28H, delivery device 2400 may be in a primed state. Rod 2402 may be removed from collar 1072 to thereby allow further translation of plunger rod 1080 distally relative to flange piece 1070. As shown in FIG. 28I, a dose may be delivered from delivery device 2400 in response to collar 1072 receiving actuation portion 1082. It should be appreciated that a longitudinal offset of a distal end of actuation portion 1082 and an inner surface of collar 1072 may be determinative to a dosage delivery distance. Accordingly, an extent (e.g., the dosage delivery distance) that plunger rod 1080 translates relative to flange piece 1070 may define a volume of dosage delivered by delivery device 2400.

Figure 28L:
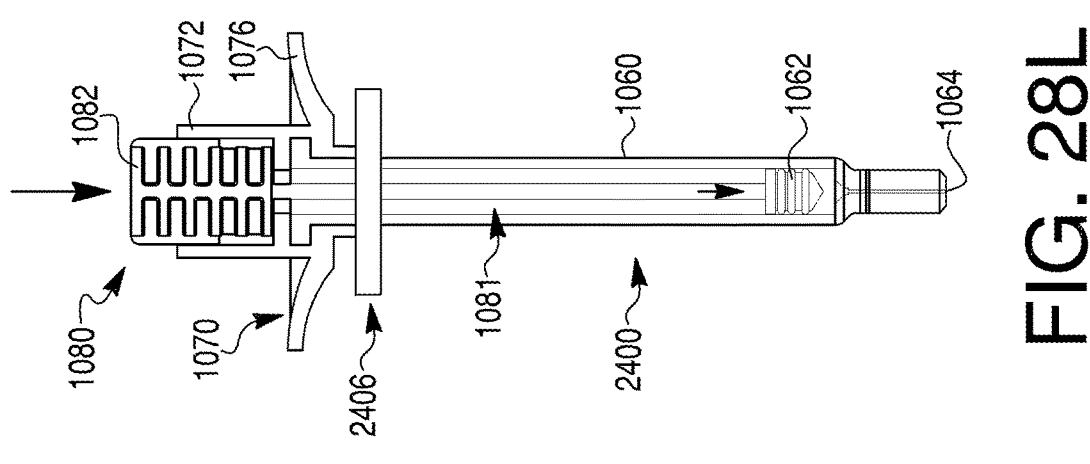
Figure 28K:
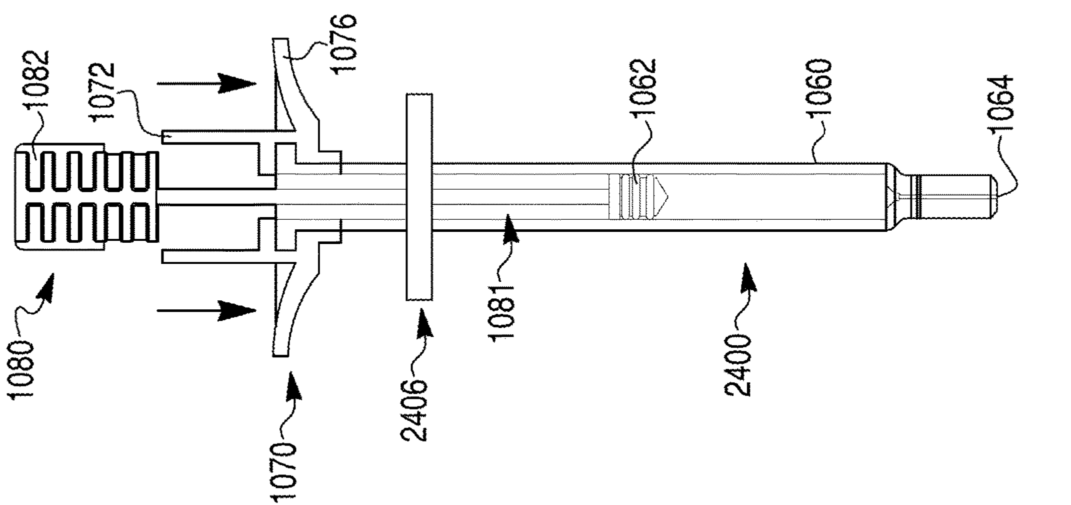
Figure 28J:
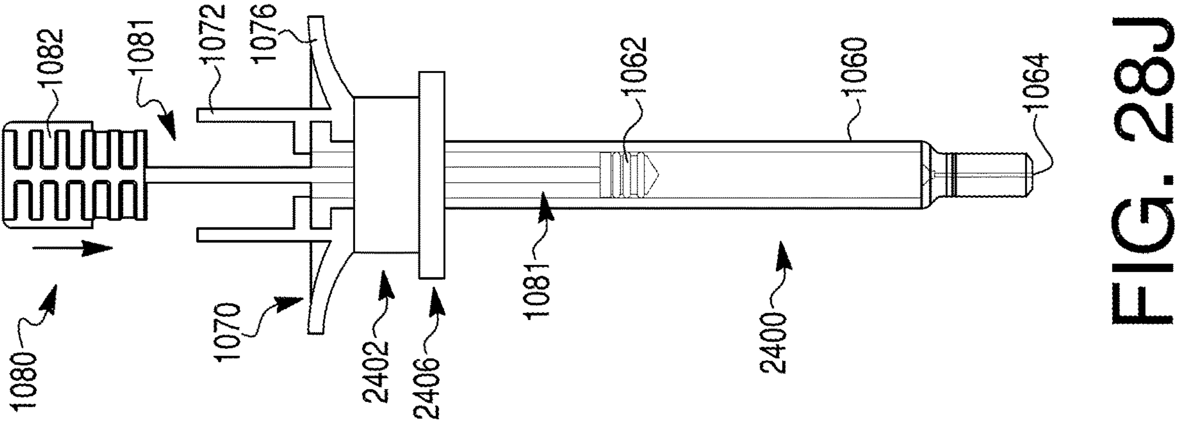

In further embodiments, as shown in FIGS. 28J-28L, delivery device 2400 may include a fixed clip 2406 attached to body 1060 at a location relatively distal of removable clip 2402. Fixed clip 2406 may be an obstruction and/or blocking component positioned in contact with removable clip 2402 such that fixed clip 2406 may be configured to inhibit movement of removable clip 2402 along body 1060. With flange piece 1070 positioned proximally of removable clip 2402, fixed clip 2406 may be further configured to inhibit movement of flange piece 1070 when removable clip 2402 is positioned therebetween.

Referring now to FIG. 28K, flange piece 1070 may be configured to translate distally along body 1060 to prime delivery device 2400 upon removing removable clip 2402 from body 1060. In this instance, plunger rod 1080 may remain stationary relative to flange piece 1070 as the assembly of plunger rod 1080 and flange piece 1070 moves toward fixed clip 2406. With flange piece 1070 translated from a proximal position (FIG. 28J) to a distal position (FIG. 28K) engaged against fixed clip 2406, delivery device 2400 may be in a primed position. It should be appreciated that body 1060 may be configured to limit movement by flange piece 1070 to a defined distance, which may correspond to a priming distance of delivery device 2400.

As seen in FIG. 28L, plunger rod 1080 may be translated distally relative to body 1060 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may define a dosage delivery distance of delivery device 2400. The dosage delivery distance may be controlled based on a position of fixed clip 2406 along body 1060.

Figure 28O:
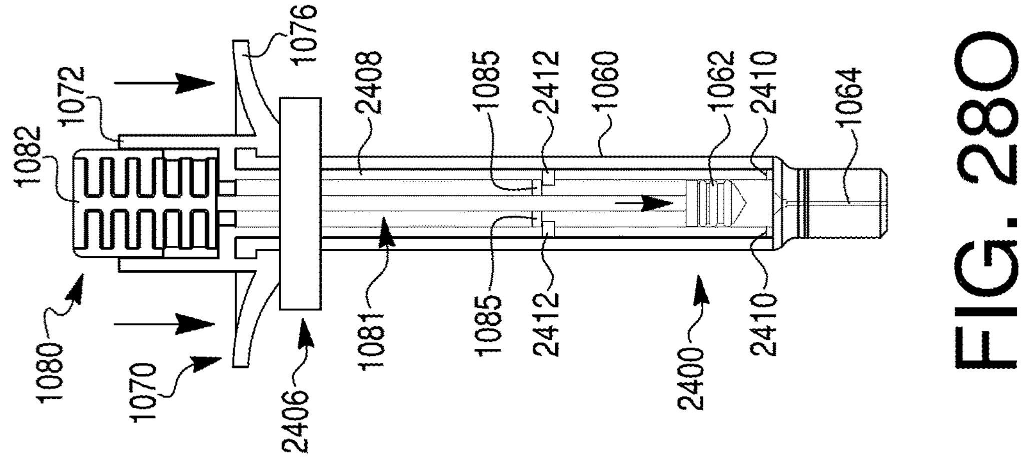
Figure 28N:
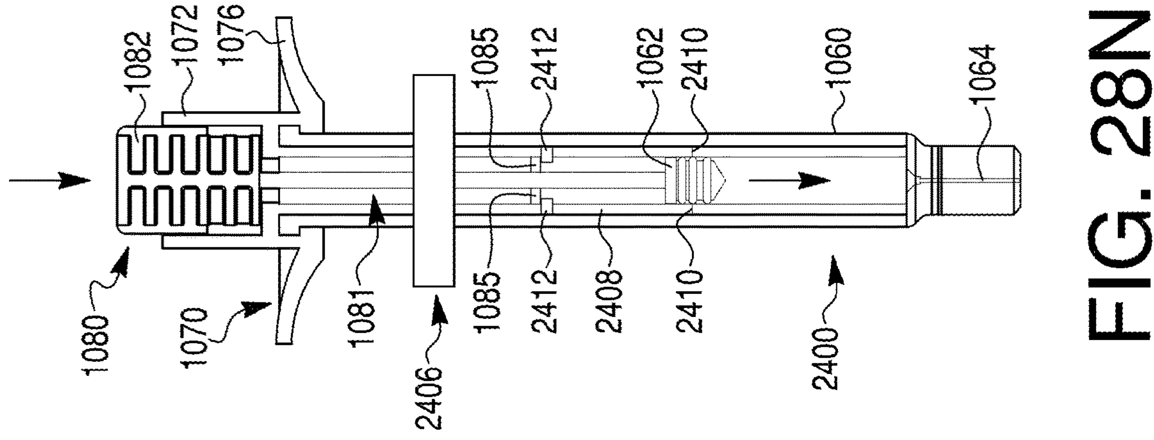
Figure 28M:
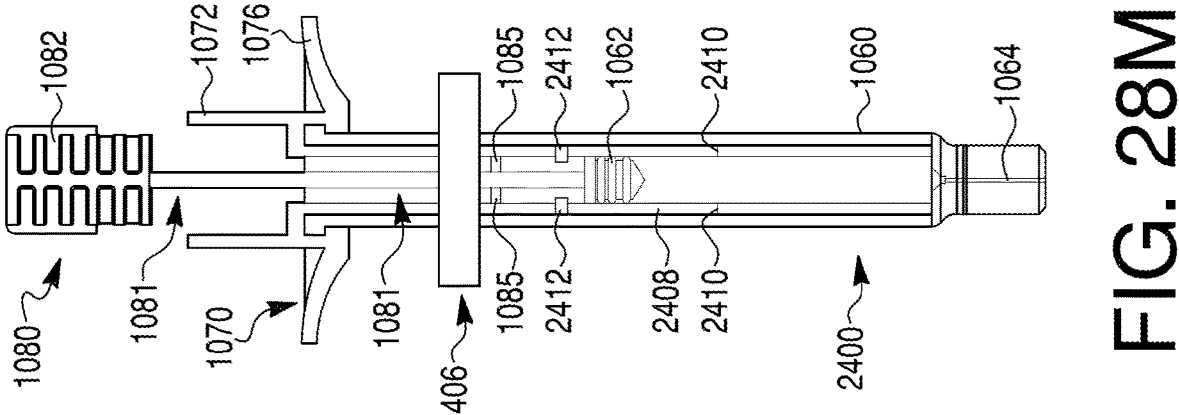

In further embodiments, delivery device 2400 may include a sleeve 2408 extending distally from flange piece 1070, as shown in FIG. 28M. Sleeve 2408 may be attached to a distal end of flange piece 1070 and/or be integral with flange piece 1070, thereby forming a unitary structure. Sleeve 2408 may be disposed within body 1060 and include a distal end 2410. Sleeve 2408 may define a lumen that is sized and shaped to receive stem 1081 when plunger rod 1080 is coupled to flange piece 1070. As described in further detail herein, sleeve 2408 may be configured to move within a lumen of body 1060 in response to flange piece 1070 translating along an exterior of body 1060.

Sleeve 2408 may further include a locking component, such as, for example, a second protrusion 2412 formed along an interior surface of sleeve 2408 such that second protrusion 2412 extends at least partially into the lumen defined by sleeve 2408. In the embodiment, second protrusion 2412 is positioned relatively proximal of distal end 2410. In other embodiments, sleeve 2408 may include various other suitable locking components in lieu of second protrusion 2412, such as, for example, an opening sized, shaped, and configured to receive protrusion 1085.

Referring specifically to FIG. 28M, protrusion 1085 may extend radially outward from stem 1081 and positioned proximally relative to second protrusion 2412 when plunger rod 1080 is received through flange piece 1070 and sleeve 2408. To prime delivery device 2400, plunger rod 1080 may be translated distally relative to flange piece 1070 and sleeve 2408 until protrusion 1085 contacts second protrusion 2412. It should be appreciated that an extent that plunger rod 1080 translates relative to sleeve 2408 may define a priming distance of delivery device 2400. The priming distance may be controlled based on a position of protrusion 1085 and second protrusion 2412 relative to one another.

With protrusion 1085 engaged against second protrusion 2412 and a distal end of actuation portion 1082 received against an inner surface of collar 1072, plunger rod 1080 may be coupled to sleeve 2408 and delivery device 2400 may be in a primed state, as shown in FIG. 28N. Actuation portion 1082 may be fully received within collar 1072 and stem 1081 may be locked onto sleeve 2408. Accordingly, further translation of plunger rod 1080 may provide translation of flange piece 1070 and sleeve 2408 relative to body 1060. For example, as seen in FIG. 28O, plunger rod 1080 and flange piece 1070 may be translated distally relative to body 1060 in response to applying a distally-directed force onto actuation portion 1082. Stem 1081 may move relative to body 1060, causing stopper 1062 to move within body 1060 to deliver a dose.

Distal end 2410 may translate toward expulsion end 1064 as plunger rod 1080 and flange piece 1070 move distally until encountering fixed clip 2406. It should be appreciated that an extent that plunger rod 1080 and flange piece 1070 translate may define a dosage delivery distance of delivery device 2400. The dosage delivery distance may be controlled based on a position of fixed clip 2406 along body 1060.

In other embodiments, as seen in FIGS. 28P-28Q, delivery device 2400 may include an obstruction and/or blocking component in the form of a pull tab 2420. Pull tab 2420 may include a body 2422 having a circular-cross section defining a center opening 2424. Body 2422 may be formed of various flexible materials, including, for example, plastic, rubber, and the like. As described in further detail herein, pull tab 2420 may be frangible and/or deformable in response to an application of force onto body 2422. Pull tab 2420 may further include a graspable feature 2426 extending outwardly from body 2422 and configured to facilitate manual actuation of pull tab 2420. As seen in FIG. 28P, graspable feature 2426 may be integrally formed with body 2422 such that applying a radially-outward force (e.g., a pulling force) onto graspable feature 2426 may cause body 2422 to deform (e.g., tear, break, etc.), as shown in FIG. 28Q.

Referring now to FIG. 28R, pull tab 2420 may be secured to flange piece 1070 along a proximal end of collar 1072. Pull tab 2420 may be disposed over collar 1072 such that flange piece 1070 is separated from actuation portion 1082 by pull tab 2420 positioned therebetween. Stem 1081 may be received through center opening 2424 and into collar 1072 when body 2422 is attached to collar 1072. Pull tab 2420 may be configured to inhibit translation of actuation portion 1082 into collar 1072. A thickness and/or width of body 2422 may be sized such that a diameter of center opening 2424 is smaller than a diameter of actuation portion 1082 to block actuation portion 1082 from passing through pull tab 2420.

Figure 28T:
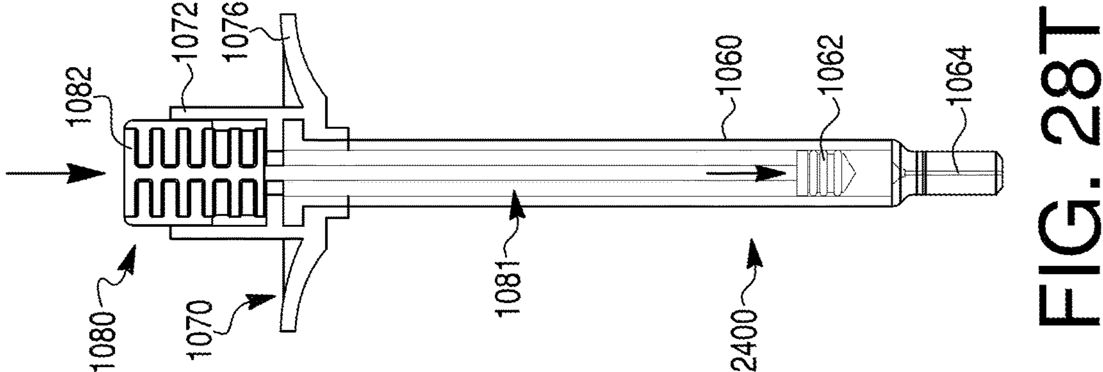
Figure 28S:
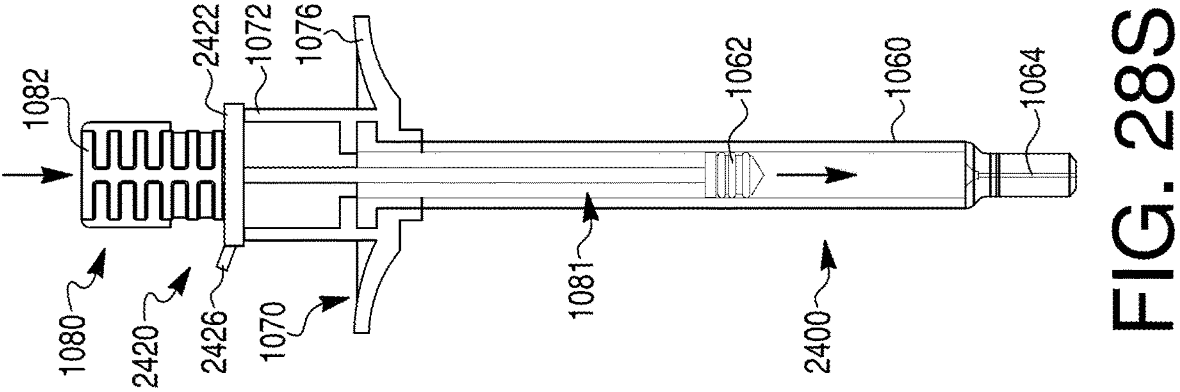

Delivery device 2400 may be primed in response to translating plunger rod 1080 distally relative to flange piece 1070 until encountering body 2422, as seen in FIG. 28S. It should be appreciated that an extent plunger rod 1080 translates relative to flange piece 1070 may correspond to a priming distance of delivery device 2400. The priming distance may be controlled based on a thickness of body 2422, thereby varying a relative distance between actuation portion 1082 and collar 1072. With actuation portion 1082 engaged against body 2422, graspable feature 2426 may be actuated to remove (e.g., break, tear, pull, etc.) pull tab 2420 from collar 1072. In this instance, body 2422 may be deformed (see FIG. 28Q) and disengaged from flange piece 1070, thereby permitting further translation of plunger rod 1080 distally relative to flange piece 1070.

As seen in FIG. 28T, actuation portion 1082 may be received within collar 1072 in response to applying a distally-directed force onto actuation portion 1082. Stem 1081 may move relative to body 1060, causing stopper 1062 to move within body 1060 to deliver a dose. It should be appreciated that an extent that plunger rod 1080 translates relative to collar 1072 may correspond to a dosage delivery distance of delivery device 2400. The dosage delivery distance may be controlled based on a thickness of pull tab 2420, thereby varying a relative distance between actuation portion 1082 and a distal (e.g., bottom) end of collar 1072.

In further embodiments, as shown in FIGS. 28U-28X, delivery device 2400 may include a removable cap 2430 coupled to plunger rod 1080. Removable cap 2430 may include a body 2432 defining a cavity 2434 that is sized and shaped to receive at least a portion of plunger rod 1080 therein (e.g., actuation portion 1082). Removable cap 2430 may include an opening along a bottom (e.g., distal) wall of body 2342 for receiving stem 1081. In some embodiments, removable cap 2430 may be attached to actuation portion 1082, while in other embodiments body 2342 may be directly coupled to stem 1081. Removable cap 2340 may be an obstruction and/or blocking component configured to increase a cross-sectional profile of actuation portion 1082 to inhibit movement of plunger rod 1080 relative to flange piece 1070, and more specifically to prevent translation of actuation portion 1082 into collar 1072.

Figures 28U, 28V, 28X:
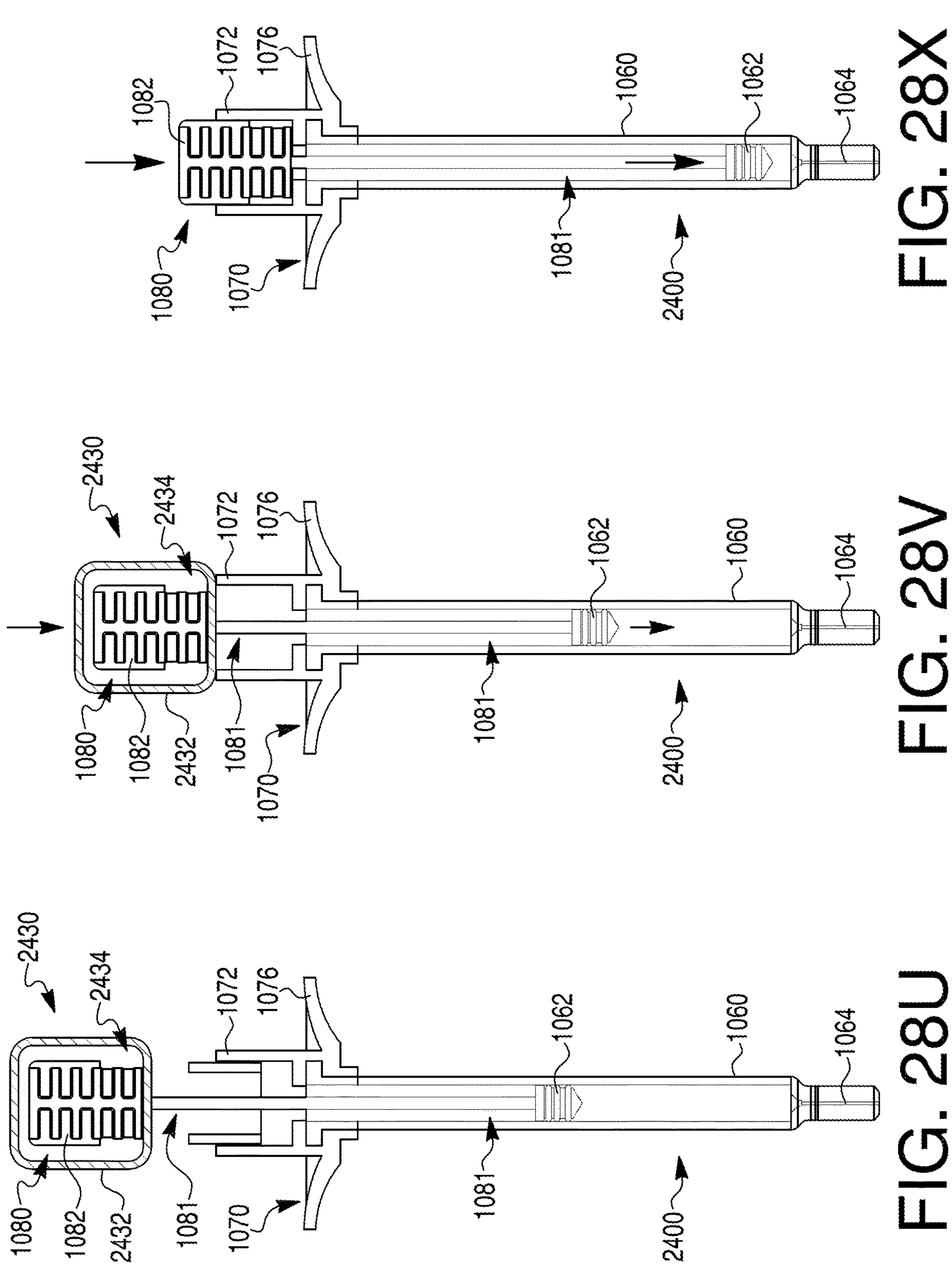

Referring now to FIG. 28V, plunger rod 1080 may be configured to translate distally relative to flange piece 1070 to prime delivery device 2400 until a bottom wall of body 2432 encounters a proximal end of collar 1072. Removable cap 2430 may inhibit actuation portion 1082 from being received within collar 1072 due to at least a portion of body 2342 being disposed between actuation portion 1082 and collar 1072. With plunger rod 1080 translated from a proximal position (FIG. 28U) to a distal position (FIG. 28V) with body 2432 engaged against collar 1072, delivery device 2400 may be in a primed position. It should be appreciated that an extent that plunger rod 1080 translates relative to flange piece 1070 may correspond to a priming distance of delivery device 2400. The priming distance may be controlled based on a size of removable cap 2430 and/or a position of removable cap 2430 relative to plunger rod 1080. For example, in other embodiments, a bottom wall of body 2432 may be secured to a proximal portion of stem 1081 positioned relatively distal of actuation portion 1082. In this instance, a priming distance of delivery device 2400 may be reduced relative to that shown and described herein as body 2432 may be positioned in closer proximity to collar 1072. Accordingly, plunger rod 1080 may be required to move a smaller distance for removable cap 2430 to encounter collar 1072.

As seen in FIG. 28X, removable cap 2430 may be detached from plunger rod 1080 such that actuation portion 1082 may be exposed from body 2432. Plunger rod 1080 may be translated distally relative to body 1060 and received within collar 1072 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may correspond to a dosage delivery distance of delivery device 2400. The dosage delivery distance may be controlled based on an attachment of removable cap 2430 relative to actuation portion 1082 and/or stem 1081 as described above. Further, a depth of collar 1072 may be determinative of the dosage delivery distance such that a size of collar 1072 may be adjusted accordingly to form various suitable dosage delivery distances.

For example, attaching removable cap 2430 such that a distal wall of removable cap 2430 is positioned flush against a distal end of actuation portion 1082 may increase a relative priming distance of delivery device 2400 by providing a longer separation between removable cap 2430 and collar 1072. Accordingly, the attachment position of removable cap 2430 may correspond to a smaller dosage delivery distance upon translating actuation portion 1082 into collar 1072 after removal of removable cap 2420. Alternatively, attaching removable cap 2430 such that the distal wall of removable cap 2430 is positioned distally from the distal end of actuation portion 1082 may decrease a relative priming distance, thereby providing a greater dosage delivery distance as actuation portion 1082 may require further longitudinal translation to be fully received within collar 1072. It should be appreciated that a size and/or shape of removable cap 2430 may vary to accommodate the various attachment positions described above.

Figure 28Z:
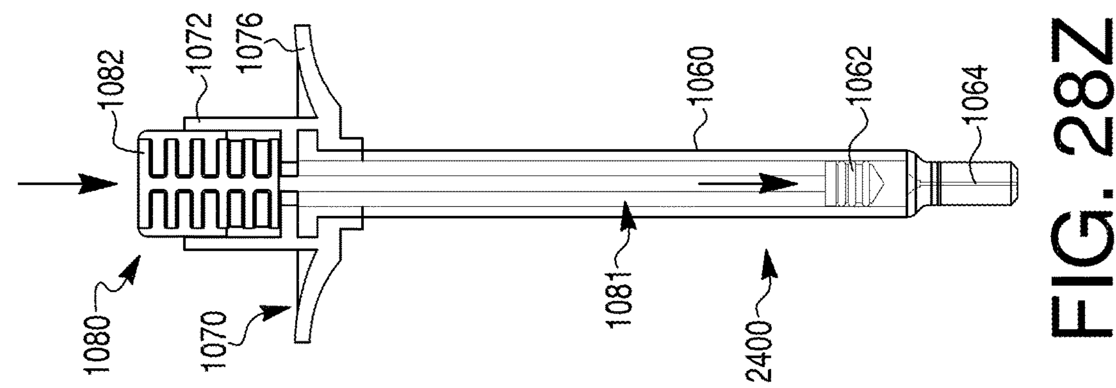

In some embodiments, as shown in FIGS. 28W-28Z, delivery device 2400 may include one or more tabs 2440 secured to plunger rod 1080, such as, for example, along actuation portion 1082, stem 1081, and/or various other portions of plunger rod 1080. In the example, delivery device 2400 includes a pair of tabs 2440 extending radially outward from a distal end of actuation portion 1082. Tabs 2440 may be an obstruction and/or blocking component configured to increase a cross-sectional profile of actuation portion 1082 to inhibit movement of plunger rod 1080 relative to flange piece 1070, and more specifically to inhibit translation of actuation portion 1082 into collar 1072. In some embodiments, tabs 2440 may be selectively removable from actuation portion 1082 upon an application of force thereto. In other embodiments, tabs 2440 may be compressible and configured to be pushed into actuation portion 1082 in response to an application of force thereto. In either instance, tabs 2440 may be configured to transition actuation portion 1082 from an expanded profile (FIGS. 28W-28Y) to a compressed profile (FIG. 28Z).

Figure 28Y:
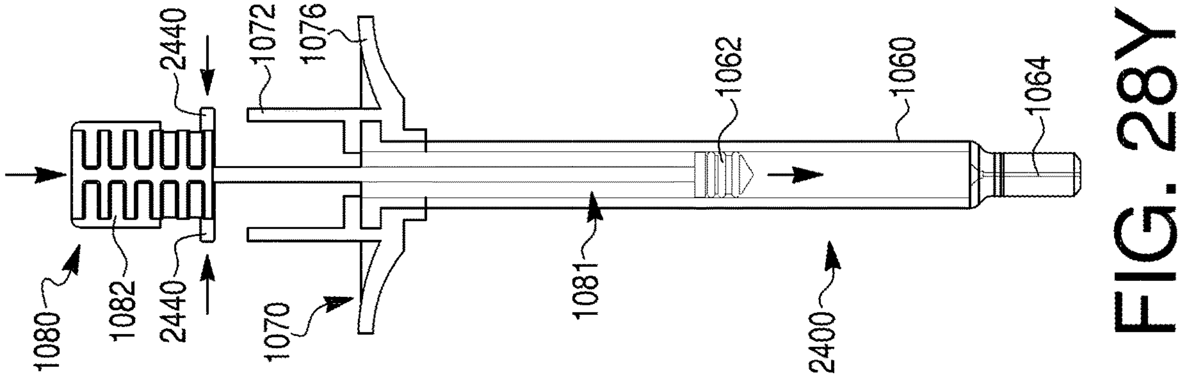
Figure 28W:
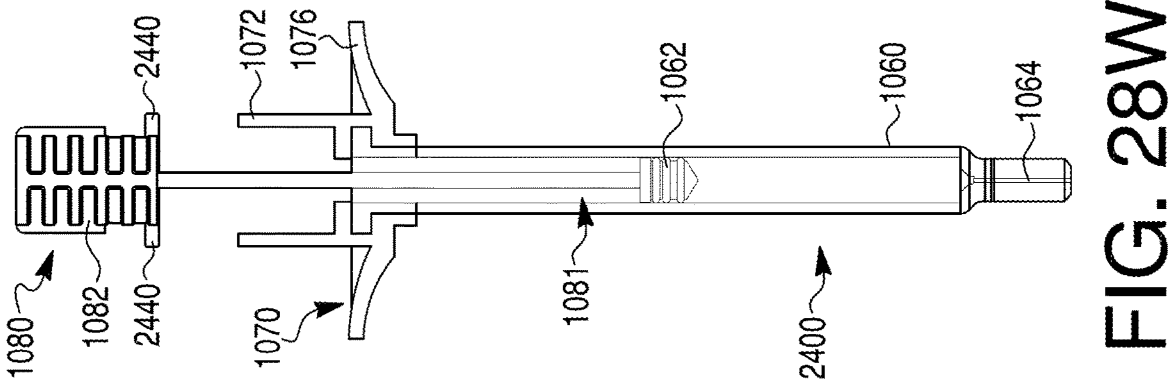

Referring now to FIG. 28Y, plunger rod 1080 may be configured to translate distally relative to flange piece 1070 to prime delivery device 2400 until tabs 2440 encounter a proximal end of collar 1072. Tabs 2440 may inhibit collar 1072 receiving actuation portion 1082 therein. With plunger rod 1080 translated from a proximal position (FIG. 28W) to a distal position (FIG. 28Y) with tabs 2440 engaged against collar 1072, delivery device 2400 may be in a primed position. It should be appreciated that an extent that plunger rod 1080 translates relative to flange piece 1070 may correspond to a priming distance of delivery device 2400.

The priming distance may be controlled based on a size (e.g., thickness, width, height, etc.) of tabs 2440 and/or a position of tabs 2440 relative to plunger rod 1080. For example, in other embodiments, the pair of tabs 2440 may be secured to an intermediate and/or proximal portion of actuation portion 1082, or alternatively along stem 1081. In this instance, a priming distance of delivery device 2400 may be increased and/or decreased, respectively, relative to that shown and described herein.

As seen in FIG. 28Z, tabs 2440 may be compressed into actuation portion 1082 by collar 1072 applying an inward, pushing force thereto (or alternatively decoupled from actuation portion 1082 by applying an outward, pulling force, a rotating snapping force, or the like) such that actuation portion 1082 may form a smaller cross-sectional profile. Plunger rod 1080 may be translated distally relative to body 1060 and received within collar 1072 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may correspond to a dosage delivery distance of delivery device 2400. As described above, the dosage delivery distance may be controlled based on a position of tabs 2440 relative to actuation portion 1082, a size (e.g., longitudinal depth) of collar 1072, and the like. For example, a relative position of tabs 2440 that increases a priming distance of delivery device 2400 may correspond to a smaller dosage delivery distance, and a position of tabs 2440 that corresponds to a reduced priming distance may provide a greater dosage delivery distance. In other examples, plunger rod 1080 may include a second set of tabs (not shown) along actuation portion 1082 which may define a dosage delivery distance based on a relative position of the tabs relative to tabs 2440.

Figures 29A, 29B, 29C:
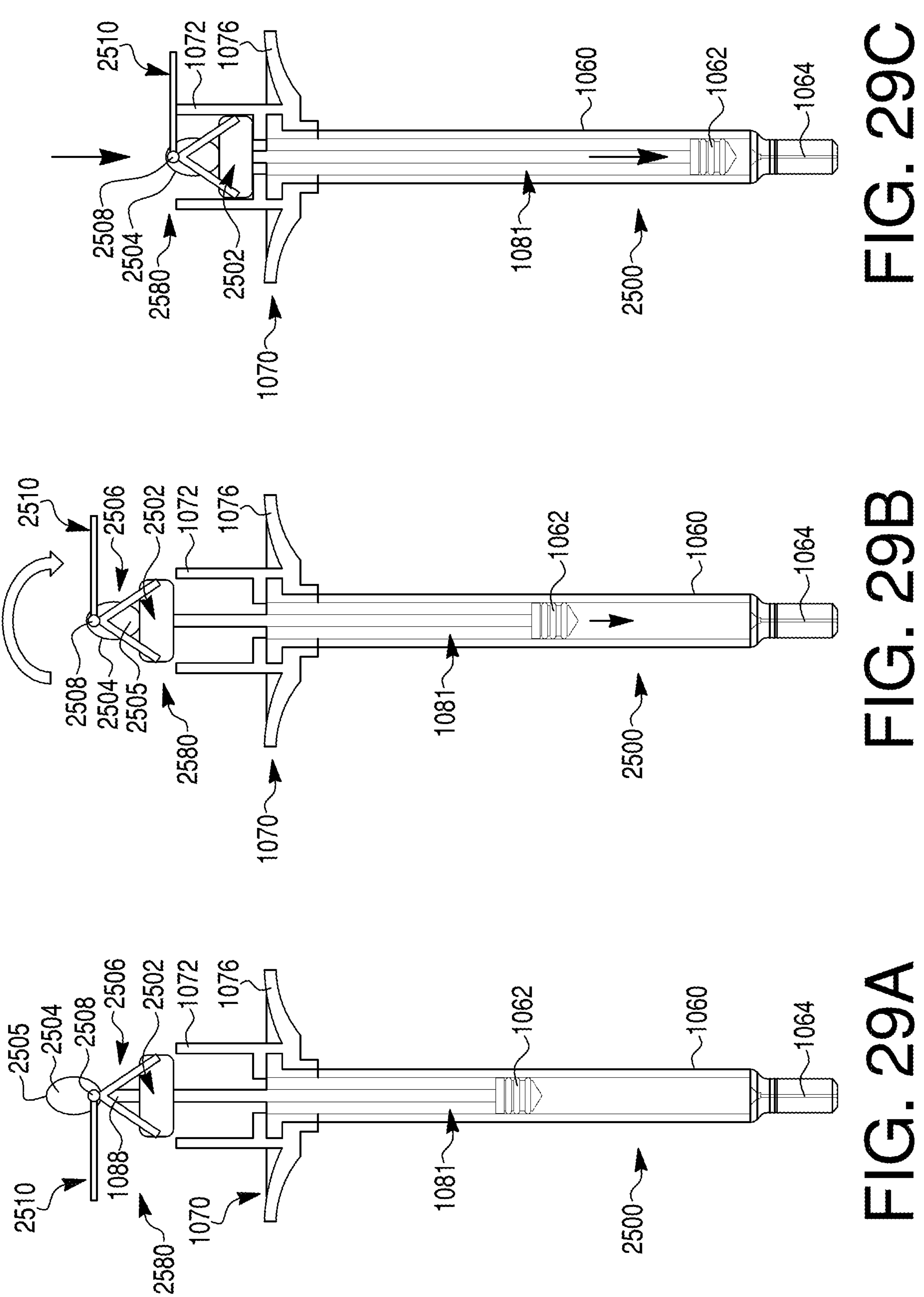
FIGS. 29A-29C depict a further exemplary delivery device and method of using said delivery device, according to aspects of the present disclosure.

FIGS. 29A-29C depict an exemplary delivery device 2500 and method of using delivery device 2500. Delivery device 2500 may include substantially similar features as those shown and described above such that like reference numerals are used to identify like components. As shown in FIG. 29A, delivery device 2500 may include a plunger rod 2580 comprising a first actuation portion 2502, a second actuation portion 2504, and a cam lever 2510. First actuation portion 2502 may be coupled to second actuation portion 2504 by one or more arms 2506. In the example, a pair of arms 2506 may be fixed to first actuation portion 2502 along a first end of arms 2506, and arms 2506 may be further coupled to second actuation portion 2504 at a second end of arms 2506 that is opposite of the first end. Second actuation portion 2504 may be a rotatable element including a proximal end 2505 and an opposing distal end having a joint 2508. The pair of arms 2506 may be coupled to the distal end of second actuation portion 2504 at joint 2508.

It should be understood that, when in a ready position as seen in FIG. 29A, second actuation portion 2504 may be oriented such that joint 2508 is positioned proximate to first actuation portion 2502 relative to proximal end 2505. A proximal end 1088 of stem 1081 may be positioned adjacent to joint 2508 at a distal end of second actuation portion 2504. For example, proximal end 1088 may be in contact with and/or abut against the distal end of second actuation portion 2504. In some embodiments, stem 1081 may extend through a center of first actuation portion 2502 and/or be positioned alongside first actuation portion 2502. Second actuation portion 2504 may be configured to move relative to first actuation portion 2502 and about joint 2508. Cam lever 2510 may be coupled to second actuation portion 2504 at joint 2508 and configured to move (e.g., rotate, pivot, translate, etc.) second actuation portion 2504 relative to first actuation portion 2502. Accordingly, it should be appreciated that second actuation portion 2504 may be configured to move stem 1081 relative to body 1060 in response to cam lever 2510 moving second actuation portion 2504 relative to first actuation portion 2502.

For example, referring to FIG. 29A, cam lever 2510 may be actuated by rotating cam lever 2510 about joint 2508, thereby causing second actuation portion 2504 to rotate about joint 2508. Proximal end 2505 may be moved toward first actuation portion 2502 in response to second actuation portion 2504 rotating about joint 2508. In this instance, proximal end 2505 may be moved toward first actuation portion 2502. With proximal end 2505 moved from a proximal position (FIG. 29A) to a distal position (FIG. 29B), proximal end 1088 may be pushed distally, thereby translating stem 1081 relative to body 1060 to prime delivery device 2500. Stated differently, rotation of cam lever 2510 and/or second actuation portion 2504 relative to first actuation portion 2502 may prime delivery device 2500 by forcing stem 1081 distally.

It should be appreciated that a travel length of proximal end 2505 toward first actuation portion 2502 may correspond to a priming distance of delivery device 2500. In other words, a priming distance of delivery device 2500 may be controlled by a longitudinal length of second actuation portion 2504 between proximal end 2505 and joint 2508. In some embodiments, first actuation portion 2502, arms 2506, and/or cam lever 2510 may be to inhibit further rotation of second actuation portion 2504 after plunger rod 2580 is moved from the ready position (FIG. 29A) to the primed position (FIG. 29B).

As seen in FIG. 29C, plunger rod 2580 may be translated distally relative to body 1060 in response to applying a distally-directed force onto first actuation portion 2502 and second actuation portion 2504. In this instance, cam lever 2510 may be depressed (e.g., pushed and/or pulled) distally to move first actuation portion 2502 and second actuation portion 2504 toward flange piece 1070 until encountering a proximal end of collar 1072. Stem 1081 may move relative to collar 1072 thereby causing stopper 1062 to move within body 1060 to deliver a dose. It should be appreciated that an extent of translation of plunger rod 2580 relative to flange piece 1070 may correspond to a dosage delivery distance of delivery device 2500. The dosage delivery distance may be controlled based on a gap formed between collar 1072 and cam lever 2510.

Figure 31:
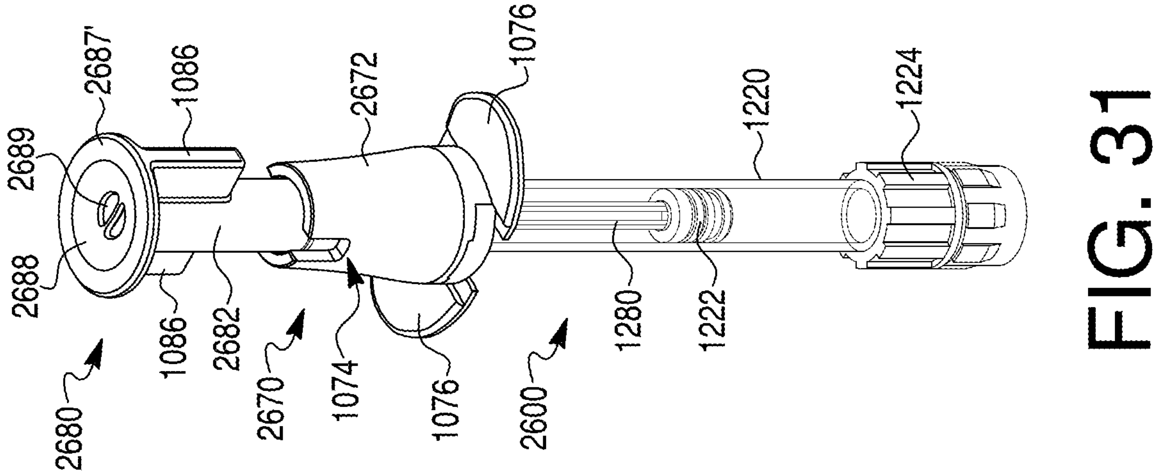
FIGS. 30-31 depict a further exemplary delivery device and method of using said delivery device, according to aspects of the present disclosure.
Figure 30:
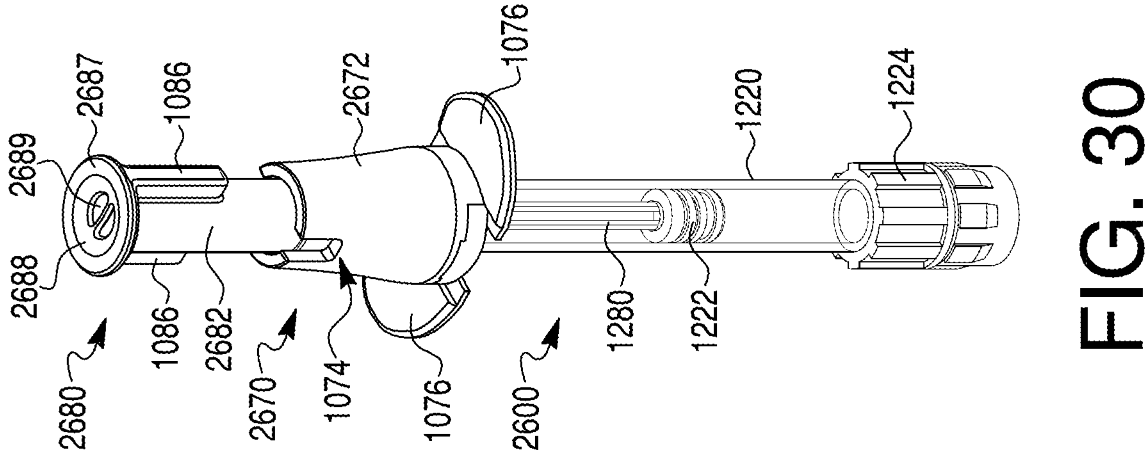

FIGS. 30-31 depict an exemplary delivery device 2600 that may include substantially similar features as those shown and described above such that like reference numerals are used to identify like components. Delivery device 2600 may include a flange piece 2670, a plunger rod 2680, and body 1220. Flange piece 2670 may include a tapered collar 2672 having a varying size and/or shape between a distal end and a proximal end. In the example, tapered collar 2672 may have a greater cross-sectional profile (e.g., diameter) along a distal end adjacent to flanges 1076 than at a proximal end adjacent to slots 1074. Tapered collar 2672 may be configured to minimize an overall profile and/or weight of delivery device 2600 by minimizing a configuration of flange piece 2670. In some embodiments, flanges 1076 may have a reduced length to facilitate enhanced control and maneuverability of flange piece 2670.

Plunger rod 2680 may include an actuation portion 2682 having a cross-sectional profile (e.g., diameter) that is relatively smaller than tapered collar 2672 to facilitate receipt of actuation portion 2682 therethrough. Accordingly, actuation portion 2682 may be similarly configured to minimize an overall profile and/or weight of delivery device 2600 by minimizing a configuration of actuation portion 2682. Further, plunger rod 2680 may omit inclusion of a textured and/or ribbed surface along actuation portion 2682 to simplify an exterior appearance of plunger rod 2680.

Referring specifically to FIG. 30, actuation portion 2682 may further include a proximal end having an outer ring 2687, an inner surface 2688, and one or more openings 2689 formed through inner surface 2688. In the example, inner surface 2688 may be disposed within outer ring 2687 and may have an angled profile that is sloped radially-inward toward the one or more openings 2689. Inner surface 2688 may be configured to define an interface for actuating plunger rod 2680 (e.g., applying a distally-directed force onto actuation portion 2682 by a finger of a user). Although plunger rod 2680 is shown as including a pair of openings 2689, it should be appreciated that in other embodiments additional and/or fewer openings 2689 may be included on inner surface 2688.

In some embodiments, as seen in FIG. 31, plunger rod 2680 may include an outer ring 2687' having a width that defines an outer surface disposed about inner surface 2688. For example, an outer surface of outer ring 2687' may be angled inwardly toward inner surface 2688 and openings 2689 and/or be transverse relative to inner surface 2688. In the present example, outer ring 2687' defines a planar outer surface that is substantially perpendicular to a longitudinal length of actuation portion 2682. The enhanced width of outer ring 2687' may provide additional surface area for a user of device 1050 to contact when actuating plunger rod 2680. It should be appreciated that a width of outer ring 2687' may be greater and/or less than that shown and described herein without departing from a scope of this disclosure.

Figure 33:
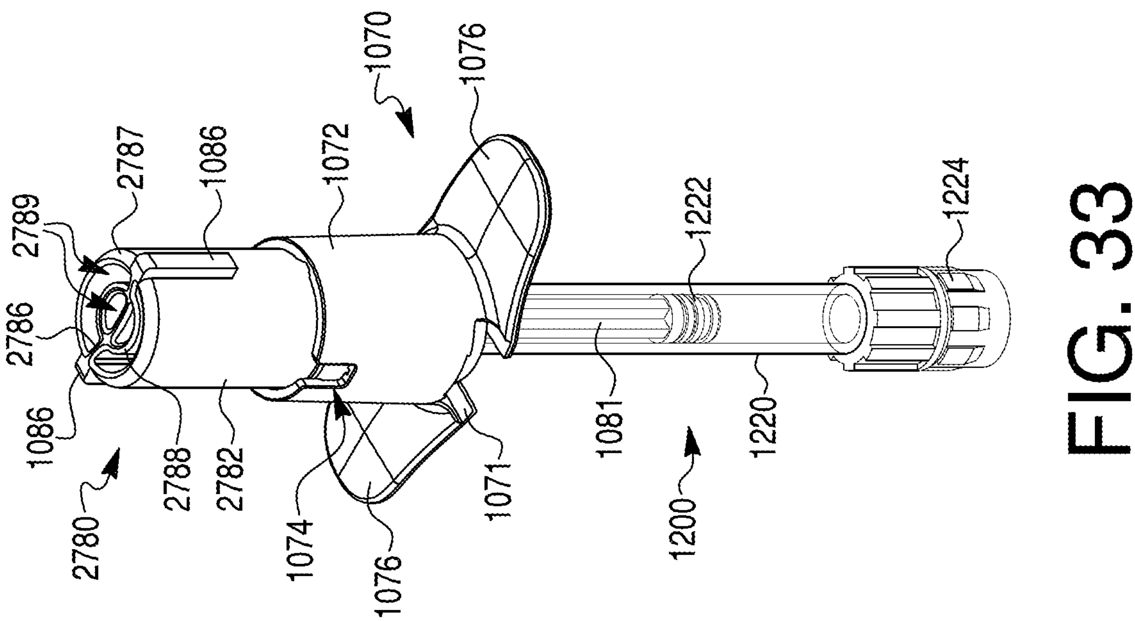
FIGS. 32-33 depict a further exemplary delivery device and method of using said delivery device, according to aspects of the present disclosure.
Figure 32:
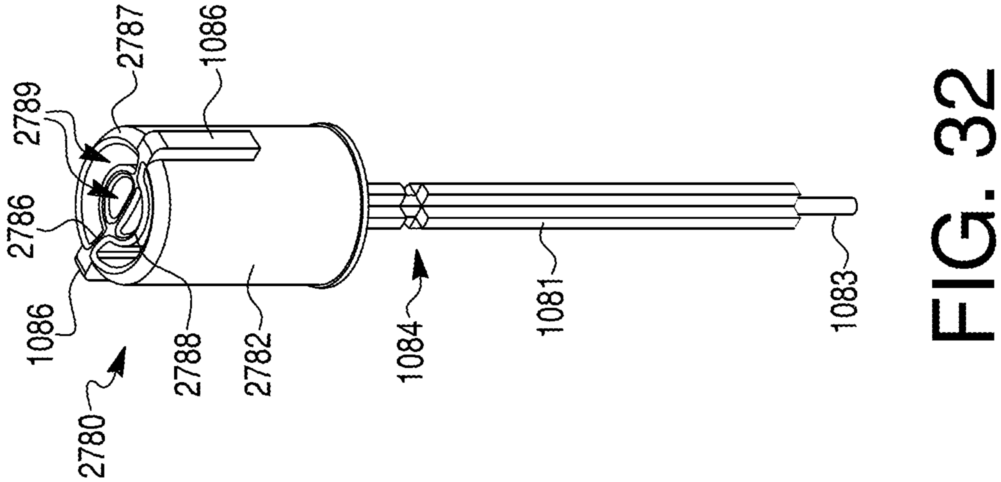

FIGS. 32-33 depict an exemplary plunger rod 2780 that may include substantially similar features as plunger rod 1080 shown and described above such that like reference numerals are used to identify like components. Plunger rod 2780 may include an actuation portion 2782 having a proximal end defined by an outer ring 2787, an inner ring 2788, and one or more openings 2789. In the example, inner ring 2788 may be disposed within outer ring 2787 and may define at least one opening 2789. Outer ring 2787 may further define at least one opening 2789 positioned radially outward of inner ring 2788. One or more of openings 2789 may minimize an overall weight of plunger rod 2780, enhance a molding manufacturing ability of plunger rod 2780 by providing nominal wall thicknesses for actuation portion 2782, and more. Additionally, actuation portion 2782 may include a lateral ledge 2786 extending across a width of the distal end and aligned with protrusions 1086. Lateral edge 2786 may bifurcate the one or more openings 2789 defined by outer ring 2787 and inner ring 2788. Lateral edge 2786 may be collinear with protrusions 1086 to provide visual alignment and/or identification of protrusions 1086 to a user of plunger rod 2780.

As seen in FIG. 33, with plunger rod 2780 received within flange piece 1070 and body 1220, lateral edge 2786 may be configured to enhance an identification of movement by plunger rod 2780 relative to flange piece 1070 from a perspective proximal of device 1200. For example, lateral ledge 2786 may facilitate identifying a relative position of protrusions 1086 to slots 1074 from a perspective proximal to actuation portion 2782 during use of device 1200. In some embodiments, plunger rod 2780 may omit a textured and/or ribbed surface along actuation portion 2782 to simplify an exterior appearance of plunger rod 2780.

Figures 34, 35:
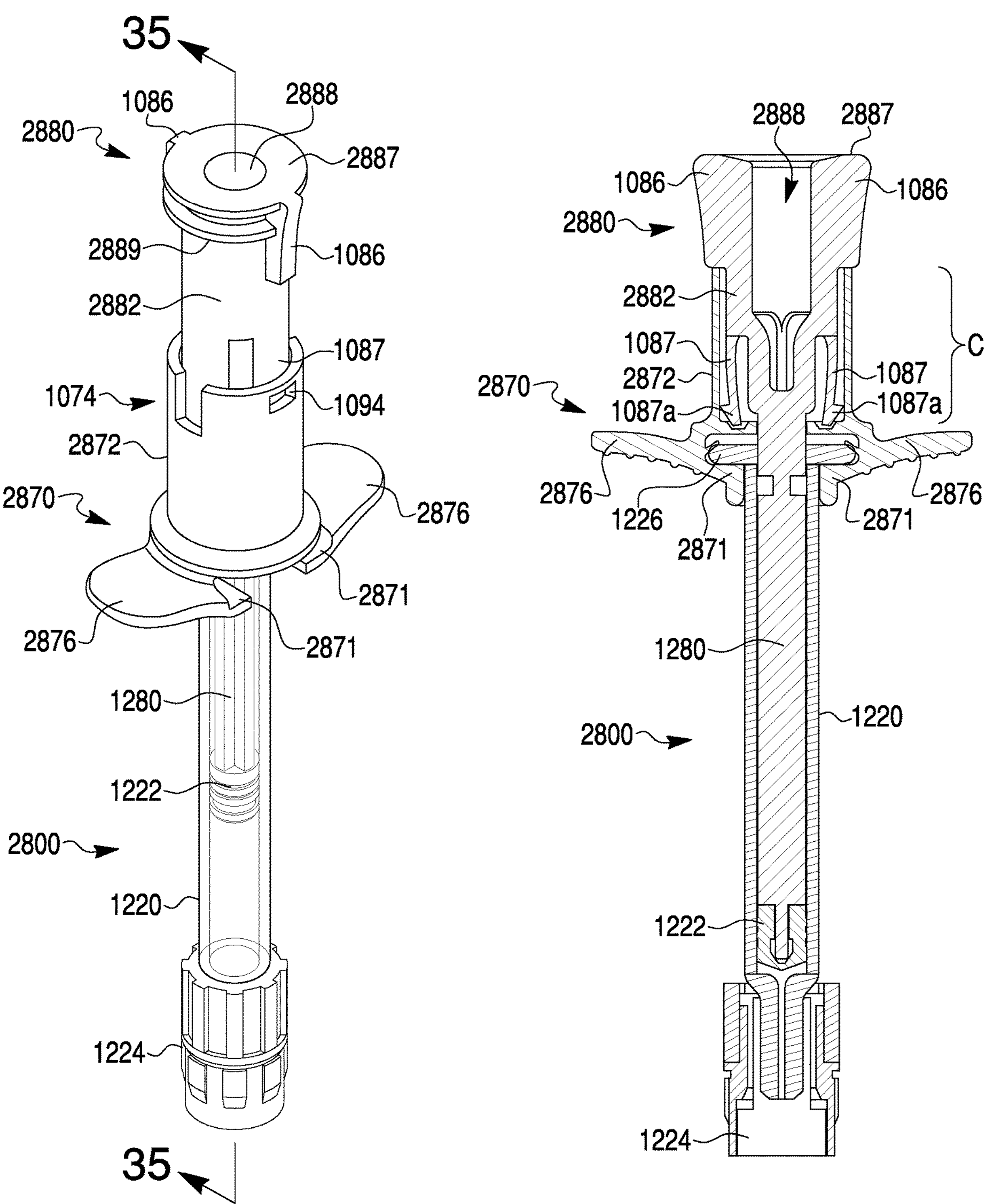

FIG. 34 depicts another exemplary delivery device 2800 in accordance with an example of this disclosure. Delivery device 2800 may include substantially similar features as delivery device 1050 and delivery device 1200 shown and described above such that like reference numerals are used to identify like components. Delivery device 2800 may include a flange piece 2870, a plunger rod 2880, and body 1220. Flange piece 2870 may have a collar 2872 and a pair of flanges 2876 extending laterally outward from collar 2872. Collar 2872 may have a narrowed profile, such as, for example, relative to collar 1072. Additionally, flanges 2876 may have a shortened length relative to flanges 1076. Accordingly, flange piece 2870 of the present example may generally have a narrowed profile. Flange piece 2870 may further include a lip 2871 that may slide under or otherwise receive body flange 1226 (FIG. 35). Lip 2871 may be configured to hold flange piece 2870 in place by slidably coupling flange piece 2870 to body 1220. As described in further detail below, lip 2871 may be made of a flexible or semi-flexible material capable of forming a snap-fit connection with body flange 1226.

Plunger rod 2880 may include an actuation portion 2882 having one or more protrusions 1086 along a proximal end and one or more extensions 1087 along a distal end. Actuation portion 2882 may have a diameter that is generally smaller than actuation portion 1082 shown and described above. Accordingly, it should be appreciated that plunger rod 2880 and flange piece 2870 may collectively form a narrowed profile relative to an assembly of plunger rod 1080 and flange piece 1070. By providing a reduced profile, delivery device 2800 may be configured to provide a user enhanced control and maneuverability of plunger rod 2880 and flange piece 2870 during use of delivery device 2800.

In the embodiment, protrusions 1086 may have a curvature configured to enhance a grip, comfort, and/or ergonomics of plunger rod 2880 for a user of delivery device 2800. A curvature of protrusions 1086 may have a concave exterior configuration that taper inwardly along a distal portion of protrusions. A proximal end of actuation portion 2882 may further include a first ring 2887, an opening 2888, and a second ring 2889 positioned distally relative to first ring 2887. First ring 2887 may define a proximal interface of actuation portion 2882 and opening 2888 may be positioned at a center of first ring 2887. The proximal interface defined by first ring 2887 may be angled toward opening 2888 such that a proximal end of actuation portion 2882 may be sloped radially inward. In some embodiments, first ring 2887 may be sized, shaped, and configured to facilitate actuation of plunger rod 2880 by defining a finger pad for receiving a finger of a user. Opening 2888 may be configured to maintain a nominal wall thickness of actuation portion 2882 to facilitate molding of plunger rod 2880 during a manufacturing process of delivery device 2800. Openings 2888 may further minimize an overall weight of plunger rod 2880.

Still referring to FIG. 34, second ring 2889 may extend radially outward from an exterior surface of actuation portion 2882 and is positioned adjacent to first ring 2887. Second ring 2889 may be configured to form a graspable feature along actuation portion 2882 to enhance control of plunger rod 2880, such as, for example, when rotating plunger rod 2880. First ring 2887 may have a greater diameter than actuation portion 2882 such that the finger pad formed by first ring 2887 may have a greater cross-sectional profile than actuation portion 2882. In some embodiments, second ring 2889 may include a diameter greater than actuation portion 2882 and substantially similar to first ring 2887. Plunger rod 2880 may omit inclusion of a textured and/or ribbed surface along actuation portion 2882 to simplify an appearance of plunger rod 2880.

As seen in FIG. 35, actuation portion 2882 may be sized to have a predetermined length C between a distal end of protrusion 1086 and hook or clip shaped part 1087*a* of extensions 1087. In some embodiments, predetermined length C may be sized in accordance with a type and/or size of a syringe cap used with delivery device 2800 (e.g., Ompi Alba ITC, Ompi Alba OVS, Gerresheimer TELL, silicone-free syringes, etc.). For example, predetermined length C may be decreased and/or increased according to a lower and/or higher fill volume requirement, respectively, determined based on the syringe cap. Further, predetermined length C may be sized to provide a complete stroke of plunger rod 2880 into flange piece 2870 to ensure a complete dosage is delivered by delivery device 2800. The predetermined length C may be further adjusted to provide one of a plurality of suitable dosage delivery distances for delivery device 2800. Flange piece 2870 may include additional features and/or components configured to allow for a complete stroke of plunger rod 2880.

Figure 36:
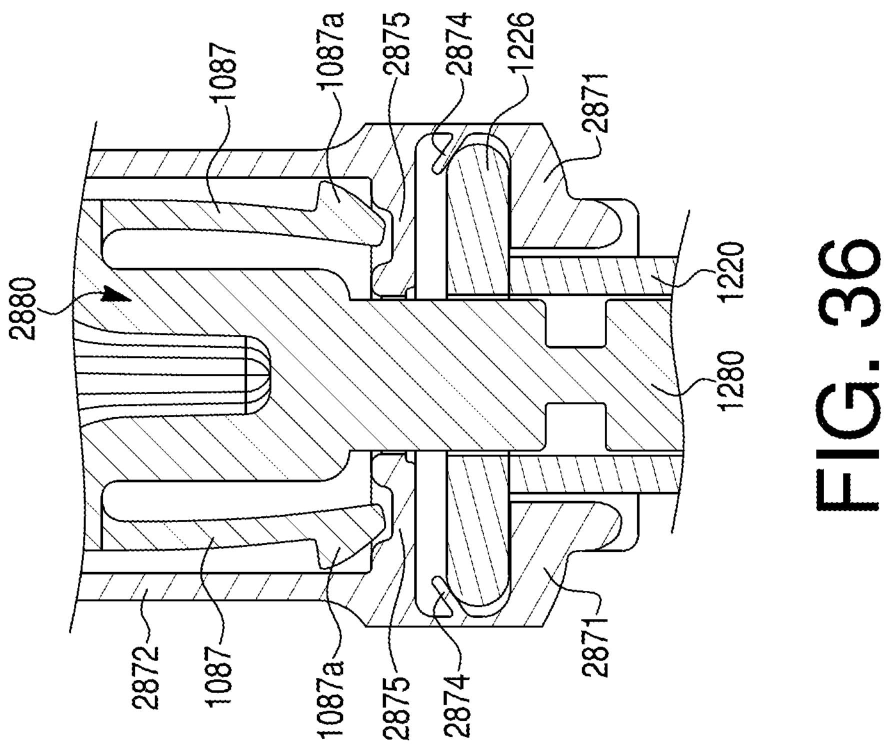

For example, referring now to FIG. 36, flange piece 2870 may include one or more indents 2875 formed along a proximally-facing and distally-located (bottom) surface of collar 2872. Indent 2875 may be sized and/or shaped to form a recessed surface into the bottom surface of collar 2872. Indent 2875 may be configured to facilitate receipt of plunger rod 2880 into flange piece 2870 to allow for a complete stroke. Stated differently, indent 2875 may provide an increased space and/or clearance within collar 2872 to receive one or more components of plunger rod 2880, such as, for example, hook or clip shaped part 1087*a* of extensions 1087.

In the present example, delivery device 2800 may be configured to deliver a complete dose upon the pair of protrusions 1086 contacting a distal end (the bottom) of slots 1074. The pair of extensions 1087 may be positioned adjacent to (but not in contact with) a bottom surface of collar 2872 when protrusions 1086 contact the distal end of slots 1074. That is, in some embodiments, extensions 1087 may positioned proximal to the bottom surface of collar 2872 such that extensions 1087 do not contact the bottom surface when plunger rod 2880 has bottomed out and/or when a complete dose has been delivered from delivery device 2800. By forming a depression along the bottom surface of collar 2872, indent 2875 may allow actuation portion 2882 to translate distally relative to collar 2872 to complete a full stroke of plunger rod 2880 without extensions 1087 engaging or contacting the bottom surface of collar 2872. In some embodiments, extensions 1087 may bend inwardly toward indent 2875 upon hook or clip shaped parts 1087*a* encountering the bottom surface of collar 2872, thereby guiding hook or clip shaped parts 1087*a* into indent 2875. It should be appreciated that an increased space formed by indent 2875 may ensure extensions 1087 are not prevented from contacting the bottom surface of collar 2872 to complete the full stroke of plunger rod 2880 and/or to deliver a complete dose.

Still referring to FIG. 36, flange piece 2870 may further include one or more ribs 2874 configured to engage body flange 1226 when body 1220 is coupled to flange piece 2870. The one or more ribs 2874 may be positioned adjacent to lip 2871, such as, for example, distally of the bottom surface of collar 2872 and proximally of lip 2871. In some embodiments, ribs 2874 may extend radially inward from an inner sidewall of flange piece 2870, while in other embodiments ribs 2874 may extend outwardly from an inner top wall of flange piece 2870. In the present example, ribs 2874 may extend radially inward at an angle relative to the inner sidewall of flange piece 2870. It should be appreciated that ribs 2874 may be positioned and/or extend from various other suitable locations, and at various other suitable angles, within flange piece 2870 for engaging body flange 1226.

In the embodiment, ribs 2876 may be formed of a flexible and/or semi-flexible material (e.g., plastic, rubber, etc.) and configured to interact with body flange 1226 upon receipt of body 1220 within flange piece 2870. By way of illustrative example, ribs 2874 may be configured to flex and/or bend proximally toward a bottom surface of collar 2872 in response to lip 2871 receiving body flange 1226. Ribs 2874 may be operable to secure body flange 1226 to flange piece 2870 by applying a distally-directed force thereto. Accordingly, ribs 2874 may secure a position (e.g., longitudinal, rotational, etc.) of body 1220 relative to flange piece 2870 by engaging a top/proximal surface of body flange 1226 as lip 2871 engages a bottom surface of body flange 1226. In other embodiments, additional and/or fewer ribs 2874 may be included for inhibiting movement of body flange 1226 and/or body 1220 relative to flange piece 2870.

Figure 37:
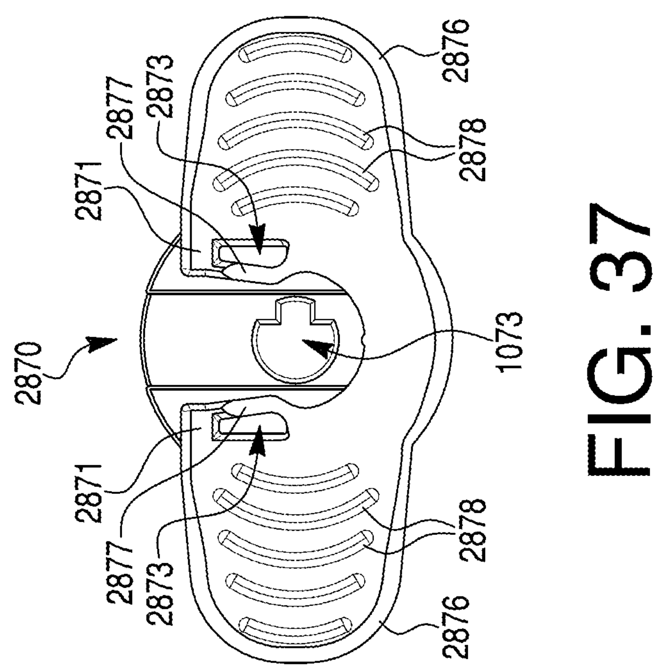

Referring now to FIG. 37, flange piece 2870 may include a textured and/or patterned interface 2878 along a bottom, distally-facing surface of flanges 2876. Textured interface 2878 may include one or more protrusions, depressions, and/or various other features forming at least one of a plurality of patterns to enhance a grip, control, and/or ergonomics of flange piece 2870. In the example, textured interface 2878 includes a plurality of semi-circular protrusions of varying sizes. As shown in FIG. 37, each interface 2878 may be concave when viewed from a radial center of flange 2876. However, in alternate embodiments, one or more interface 2878 may be convex when viewed from the radial center of flange 2876. As described in further detail below, textured interface 2878 may include various other designs, features, and/or patterns along the bottom surface (see FIGS. 41A-41D) of flanges 2876. Flange piece 2870 may further include a pair of movable tabs 2877 positioned adjacent to lip 2871 and along opposing sides of opening 1073. Movable tabs 2877 may be formed of a flexible and/or semi-flexible material and may be configured to move relative to collar 2872 and/or flanges 2876 in response to a force being applied thereto (e.g., by body 1220).

Each movable tab 2877 may define an opening 2873 disposed between movable tab 2877 and flange 2876. Accordingly, movable tabs 2877 may be separated from flanges 2876 by opening 2873 formed therebetween. Openings 2873 may provide a gap and/or clearance space to accommodate lateral movement of movable tabs 2877 upon receiving a radially-outward directed force. For example, movable tabs 2877 may be deflected radially outward toward flanges 2876 in response to flange piece 2870 receiving body 1220 through opening 1073, thereby changing a size and/or shape of openings 2873. In this instance, movable tabs 2877 may bend outwardly away from opening 1073 until body flange 1226 is received by lip 2871. Movable tabs 2877 may be configured to bend inwardly toward body 1220 to return to an original configuration upon lip 2871 fully receiving body flange 1226 therein. In some embodiments, movable tabs 2877 may bend toward body 1220 to a substantially originally configuration such that movable tabs 2877 may remain at least partially compressed against body 1220 to inhibit movement of body 1220 relative to flange piece 2870 to allow pressure to be continually applied onto body 1220 to prevent slippage.

Still referring to FIG. 37, movable tabs 2877 may be configured to apply a radially-inward directed force onto body 1220 (e.g., with a radially-inward directed material bias), thereby forming a snap-fit connection between flange piece 2870 and body 1220. Additionally, movable tabs 2877 may maintain body 1220 in a stabilized and fixed position relative to flange piece 2870, thereby coupling flange piece 2870 to body 1220. It should be appreciated that openings 2873 may be included between movable tabs 2877 and flanges 2876 to decrease a required force to couple body 1200 to flange piece 2870. For example, openings 2873 may be operable to reduce a force necessary to snap body 1200 into flange piece 2870 by a minimum force ranging from about 15 Newton to about 25 Newton, compared to a design omitting openings 2873.

Figure 38B:
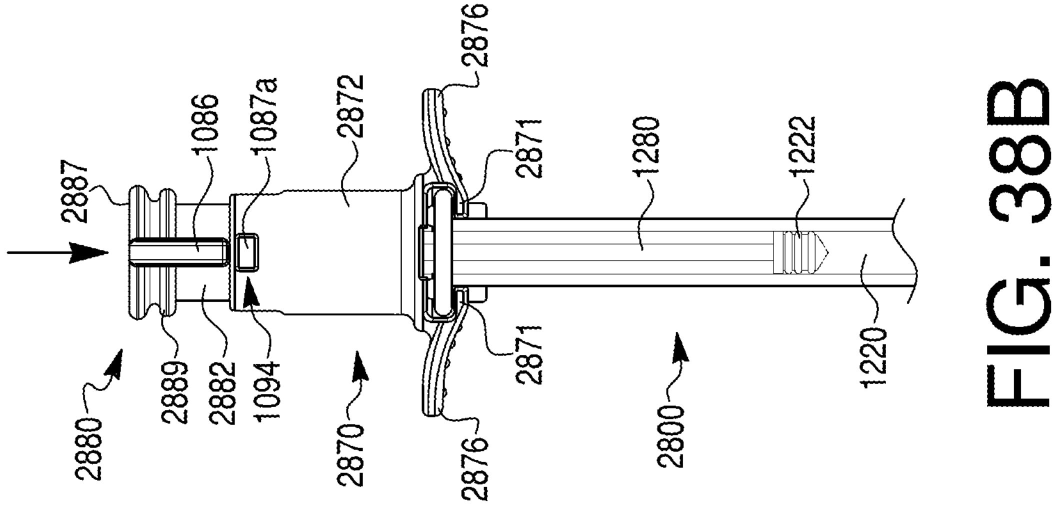
Figure 38A:
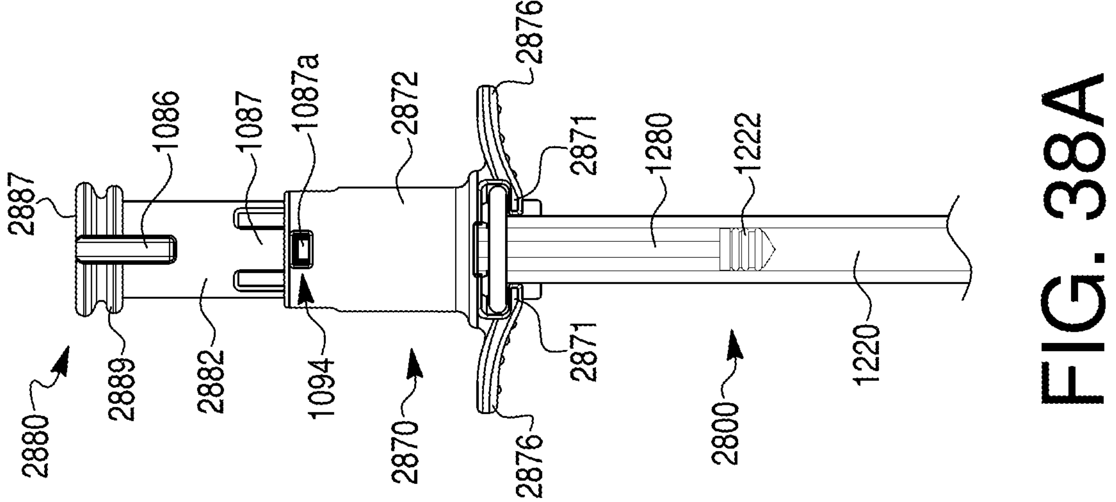

FIGS. 38A-40C show an illustrative method of using delivery device 2800. As seen in FIG. 38A, delivery device 2800 may be preassembled with a distal portion of actuation portion 2882 received within collar 2872 and extensions 1087 received within and coupled to openings 1094. With extensions 1087 coupled to collar 2872 via openings 1094, it should be appreciated that flange piece 2870 may inhibit proximal retraction of actuation portion 2882. Accordingly, disassembly of plunger rod 2880 from flange piece 2870 may be prevented. In this instance, delivery device 2800 may be primed by distally translating plunger rod 2880 into flange piece 2870.

As seen in FIG. 38B, actuation portion 2882 may be translated distally relative to flange piece 2870 until protrusions 1086 encounter a proximal end of collar 2872. Plunger rod 2880 may complete a priming process of delivery device 2800 upon protrusions engaging and/or abutting collar 2872. It should be appreciated that an extent that plunger rod 2880 translates distally relative to flange piece 2870 may correspond to a priming distance of delivery device 2800. The priming distance may be controlled based on a longitudinal length of protrusions 1086 and/or extensions 1087, thereby varying a relative distance between the proximal end of collar 2872 and a distal end of protrusions 1086.

Figure 38D:
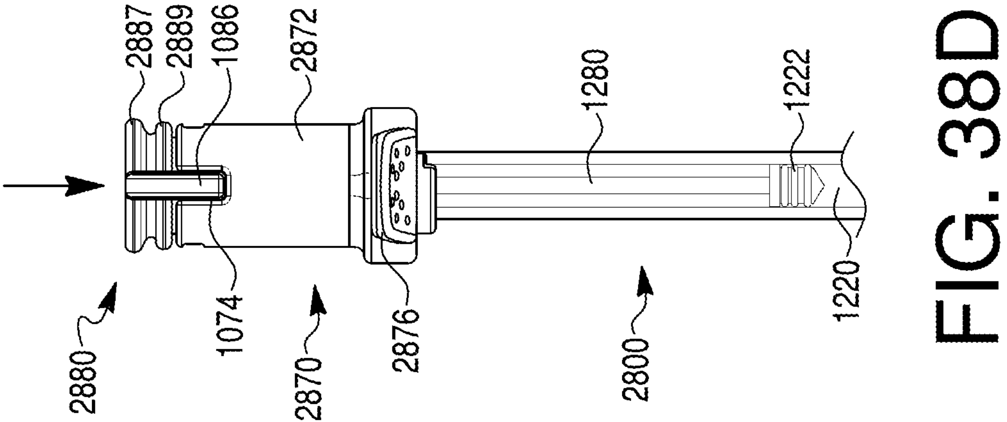
Figure 38C:
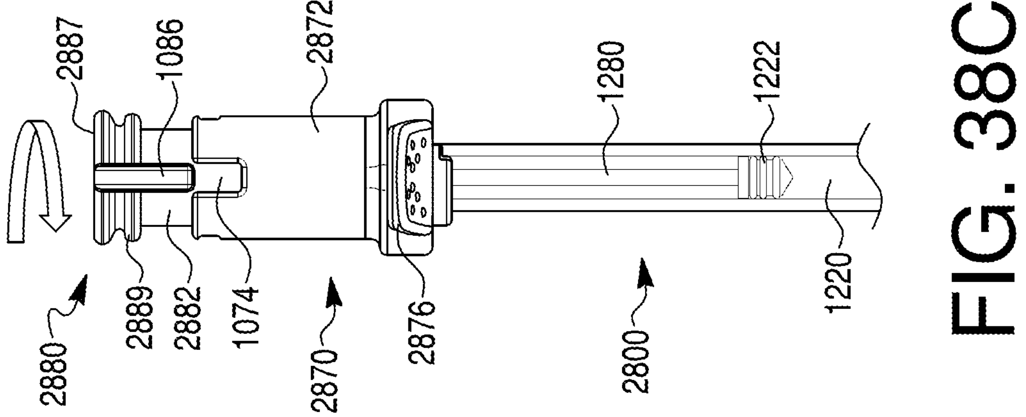
Figure 39A:
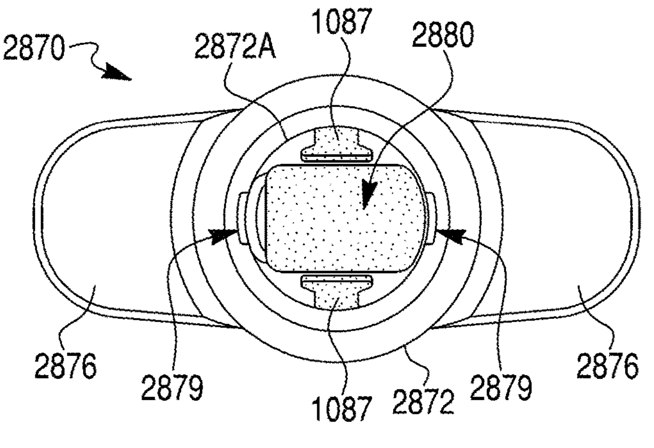
Figure 39D:
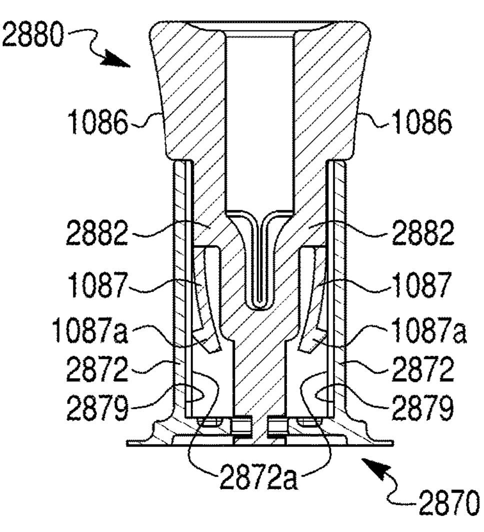
Figure 39B:
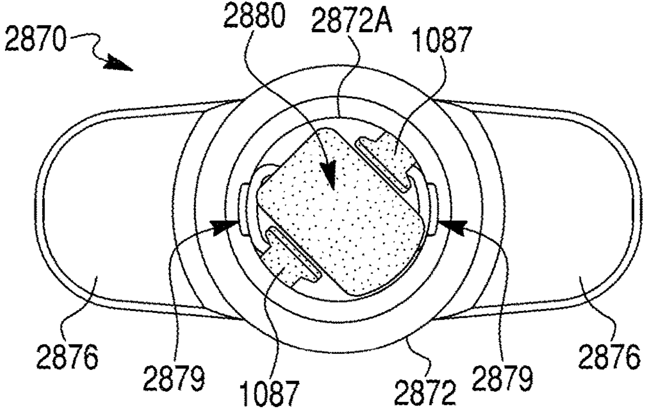

As shown in FIG. 38C, flange piece 2870 may be rotated relative to plunger rod 2880, or vice versa, to move protrusions 1086 relative to collar 2872 until arriving into radial and longitudinal alignment with slots 1074. Referring to FIGS. 39A-39B, extensions 1087 may contact an interior surface 2872A of collar 2872 as plunger rod 2880 rotates relative to flange piece 2870. As seen in FIG. 39D, with hook or clip shaped part 1087*a* engaged against interior surface 2872A, extensions 1087 may be deflected radially-inward by collar 2872 until plunger rod 2880 is rotated to align extensions 1087 with internal grooves 2879 of flange piece

Figure 39C:
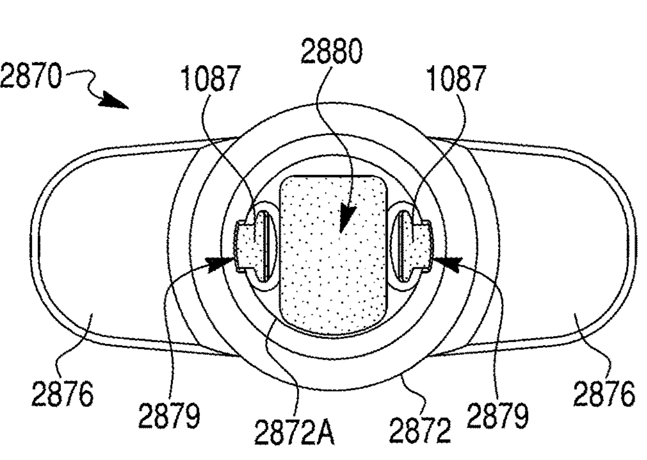
Figure 39E:
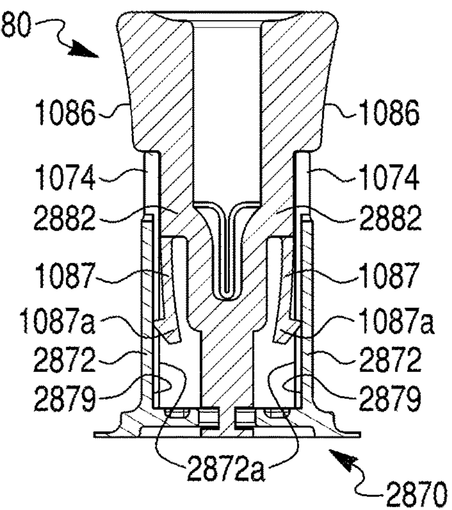

2870. Internal grooves 2879 may define recesses formed along interior surface 2872A. As seen in FIG. 39C and FIG. 39E, internal grooves 2879 may be sized and shaped to receive extensions 1087 therein. It should be appreciated that collar 2872 may have a greater diameter at internal grooves 2879 than along interior surface 2872A such that extensions 1087 are configured to expand radially-outward from a compressed configuration (FIGS. 39A-39B and FIG. 39D) to an expanded configuration (FIG. 39C and FIG. 39E) when extensions 1087 are moved into radial alignment with internal grooves 2879.

Stated differently, extensions 1087 may be transitioned to a relaxed state when received within internal grooves 2879 due to the additional space provided by internal grooves 2879, as seen in FIG. 39E. In some instances, a feedback (e.g., tactile, auditory, etc.) may be generated in response to extensions 1087 being received within internal grooves 2879. Delivery device 2800 may be positioned in a dosage delivery state such that further actuation of plunger rod 2880 may provide a dose delivery. In some embodiments, flange piece 2870 may be operable to generate a user feedback (e.g., tactile, audible, etc.) upon rotating plunger rod 2880 relative to flange piece 2870 to prime delivery device 2800.

As described in detail above and as seen in FIGS. 40A-40C, opening 1073 may have a semi-circular shape with one or more edges 2873 extending into opening 1073. With plunger rod 2880 coupled to flange piece 2870, stem 1280 may be received through opening 1073. Stem 1280 may include a rounded sidewall 2884 that is configured to interact with the one or more edges 2873 as plunger rod 2880 rotates relative to collar 2872. For example, rounded sidewall 2884 may define a semi-circular end along stem 1280 that may contact edges 2873 when plunger rod 2880 is moved from the primed position (FIG. 38B) to the dosage delivery position (FIG. 38C). As described in detail above (FIGS. 4K-4X), it should be appreciated that stem 1280 may have various suitable shapes and/or configurations for facilitating movement (e.g., rotation) of plunger rod 2880 relative to flange piece 2870.

Referring now to FIG. 38D, with protrusions 1086 aligned with slots 1074, actuation portion 2880 may be translated distally relative to collar 2872 to complete a full stroke of plunger rod 2880 in response to applying a distally-directed force onto actuation portion 2882. In this instance, stem 1280 may move relative to flange piece 2870, thereby causing stopper 1222 to move within body 1220 to deliver a dosage. In this instance, protrusions 1086 may be received within slots 1074 and second ring 2889 may be positioned proximate to a proximal end of collar 2872. In other words, in some embodiments, second ring 2889 does not contact the proximal end of collar 2872. Further, as described in greater detail above, indents 2875 may receive extensions 1087 (FIG. 36) therein when completing a full stroke of plunger rod 2880. It should be appreciated that an extent that plunger rod 2880 translates relative to flange piece 2870 may define a dosage delivery distance of delivery device 2800. The dosage delivery distance may be controlled based on a longitudinal length of protrusions 1086 relative to actuation portion 2882 and/or a depth of slots 1074 relative to collar 2872.

As seen in FIGS. 41A-41D, delivery device 2800 may include various other flange pieces 2870 having at least one of a plurality of textured interfaces on flanges 2876. As merely an illustrative example, as seen in FIG. 41A, an alternative exemplary flange piece 2870A may include a textured interface 2878A on flanges 2876 comprising a plurality of circular protrusions and/or depressions arranged in an annular array relative to one another. As seen in FIG. 41B, another exemplary flange piece 2870B may include a textured interface 2878B comprising an ornamental design, such as a snowflake, on each flange 2876. FIG. 41C shows an exemplary flange piece 2870C including a textured interface 2878C on flanges 2876 comprising a plurality of circular protrusions and/or depressions arranged in an irregular pattern relative to one another.

By way of further example, referring now to FIG. 41D, a flange piece 2870D may include a textured interface 2878D comprising a plurality of diamond-shaped protrusions and/or apertures positioned in a grid-like arrangement along flanges 2876. It should be understood that the various textured interfaces shown and described herein may be configured to enhance a grip, control, aesthetic, and/or ergonomics of the flange piece. It should further be appreciated that the textured interfaces shown and described herein are merely illustrative such that various other suitable patterns, textures, and/or features may be included on the flange pieces without departing from a scope of this disclosure.

Components of the devices described herein may be designed and/or suited for manufacture in one or more ways. In some embodiments, for example, components of the devices described herein (e.g., device 1050, device 1200, device 1300, device 1400, device 2400, device 2500, device 2600, device 2800, etc.) may be suitable for manufacture via, e.g., injection molding, 3-dimensional printing, or machining. In one embodiment, for example, components of device 1050 may be particularly suited for manufacture via injection molding. For example, in some existing devices, molding is not suitable for high volume production, resulting in the use of 3-dimensional printing. In some embodiments, while manufacturing tolerances may be tighter with molding techniques than with 3-dimensional printing techniques, devices formed by 3-dimensional printing do not have the same level of precision as devices formed by molding. Precision may be particularly important for devices of the present disclosure, for example, those devices used for vitreous injections at volumes of 100 μL or less.

Accordingly, it should be appreciated that devices of the present disclosure described herein may be designed to store predefined volumes of therapeutic agent that may be suitable for vitreous (IVT) injections, such as, for example, 100 μL or less. In some embodiments, the devices described herein may be designed for injection of certain volumes of vitreous based on an intended use of the device in a particular procedure. For example, devices of the present disclosure may be configured to store a volume of vitreous of about 65 μL to about 75 μL for high dose aflibercept procedures; about 95 μL to about 105 μL for Mini Trap procedures; and/or about 5 μL to about 15 μL for Retinopathy of Prematurity (ROP).

Devices of the present disclosure may be further configured to store relatively greater volumes of vitreous for injection based on a degree of myopia, such as about 3 milliliters, 4 milliliters, and greater. Additionally, the devices described herein may be designed for injection of larger volumes of vitreous based on an intended procedure, such as, about 3 ml to about 6 ml of silicone or gas for tamponade post vitrectomy. It should be appreciated that the devices of the present disclosure may be designed to inject various other volumes of vitreous relative to other procedures, such as, Diabetic Eye Disease, post-injection noninfectious Endophthalmitis, Neovascular (Wet) Age-related Macular Degeneration (AMD), Macular Edema following Retinal Vein Occlusion (RVO), Diabetic Macular Edema (DME), and Diabetic Retinopathy (DR).

Devices of the present disclosure are operable to provide accurate measurements in delivering large volumes of vitreous with high precision by minimizing instances of user error in improperly setting a dose line. As described in detail above, the various designs and configurations of the one or more components of the devices described herein (e.g., a plunger rod, a flange piece, etc.) may provide dosage precision by controlling a priming distance and a dosage delivery distance of the device, thereby removing user determination in setting the device at each respective configuration.

Features enumerated above have been described within the context of particular embodiments. However, as one of ordinary skill in the art would understand, features and aspects of each embodiment may be combined, added to other embodiments, subtracted from an embodiment, etc. in any manner suitable to assist with controlled preparation and/or delivery of a drug.

Aspects of the embodiments disclosed herein are described with respect to priming drug delivery devices and removing excess air bubbles from within drug delivery devices, and some embodiments disclosed herein are described as being particular types of drug delivery devices (e.g., pre-filled syringes). Aspects of the present disclosure may also be employed and/or found in other types of drug delivery devices (e.g., fillable syringes, pipettes, and the like). For example, devices having features according to the present disclosure may provide more precise means for transferring a volume of a drug substance or other fluid from one container to another, such as from a vial to a syringe. The precision in fluid transfer afforded by embodiments disclosed herein may reduce or minimize unwanted overfilling and/or decrease wastage of a drug substance.

While a number of embodiments are presented herein, multiple variations on such embodiments, and combinations of elements from one or more embodiments, are possible and are contemplated to be within the scope of the present disclosure. Moreover, those skilled in the art will appreciate that the conception upon which this disclosure is based may readily be used as a basis for designing other devices, methods, and systems for carrying out the several purposes of the present disclosure.

What is claimed is:

1. A drug delivery device, comprising:

a body;

a flange coupled to the body, the flange including a channel defined by an interior surface and a groove formed in the interior surface; and a plunger rod coupled to the flange, the plunger rod including a proximal end and an extension extending distally from the proximal end;

wherein the extension is configured to compress radially-inwards and engage the interior surface as the plunger rod moves relative to the flange by a first stroke, the groove is configured to receive the extension and the extension is configured to expand radially-outwards as the plunger rod rotates relative to the flange, and the extension is configured to engage the groove of the flange as the plunger rod moves relative to the flange by a second stroke.

2. The drug delivery device of claim 1, wherein the plunger rod is positioned relative to the flange such that the extension is radially misaligned with the groove when the plunger rod is coupled to the flange in a first position.

3. The drug delivery device of claim 2, wherein the plunger rod is positioned relative to the flange such that the extension is radially aligned with the groove when the plunger rod is coupled to the flange in a second position.

4. The drug delivery device of claim 3, wherein the plunger rod is configured to move from the first position to the second position.

5. The drug delivery device of claim 4, wherein the extension is compressed radially-inward to a compressed state when in the first position.

6. The drug delivery device of claim 4, wherein the flange includes an opening formed along the interior surface of the flange; and wherein the opening is configured to receive the extension when the plunger rod is coupled to the flange prior to moving to the first position.

7. The drug delivery device of claim 6, wherein the flange is configured to inhibit proximal and rotational movement of the plunger rod relative to the channel when the extension is received in the opening;

wherein the extension is configured to exit the opening when the plunger rod moves distally relative to the flange towards the first position.

8. The drug delivery device of claim 4, wherein the flange includes an indent formed along a bottom wall of the flange; and wherein the indent is configured to receive the extension when the plunger rod moves distally relative to the flange from the second position to a third position.

9. The drug delivery device of claim 8, wherein the extension is positioned proximal to the indent when the plunger rod is in one of the first position or the second position.

10. The drug delivery device of claim 8, wherein the indent defines a depression along the bottom wall of the flange, wherein the depression is sized such that the extension does not contact the bottom wall when the plunger rod moves to the third position.

11. The drug delivery device of claim 8, wherein the flange is configured to at least partially compress the extension radially-inward towards the indent upon the plunger rod moving to the third position.

12. The drug delivery device of claim 1, wherein the flange is configured to inhibit proximal movement of the plunger rod relative to the channel when the groove receives the extension;

wherein the proximal end of the plunger rod is fixed within the flange when the extension is disposed within the groove.

13. The drug delivery device of claim 1, wherein the drug delivery device is configured to generate a user feedback in response to the groove receiving the extension.

14. A drug delivery device, comprising:

a body storing a dose of medicament;

a flange coupled to the body, the flange including a sidewall, a channel defined by the sidewall, and a pair of grooves formed along an interior of the sidewall; and a plunger rod coupled to the flange and at least partially disposed within the body, the plunger rod including a proximal end and a pair of extensions extending distally from the proximal end;

wherein the plunger rod is configured to prime the drug delivery device by moving a first stroke relative to the flange, thereby positioning the pair of extensions against the sidewall; and wherein the plunger rod is configured to prepare the drug delivery device for delivering the dose of medicament by rotating relative to the flange, thereby generating a user feedback as the pair of extensions expand radially-outward from a compressed state to an extended state upon engaging the pair of grooves.

15. The drug delivery device of claim 14, wherein the plunger rod is positioned relative to the flange such that the pair of extensions are radially misaligned with the pair of grooves when the plunger rod moves the first stroke, and the pair of extensions are radially aligned with the pair of grooves when the plunger rod is rotated relative to the flange.

16. The drug delivery device of claim 14, wherein the plunger rod includes a protrusion extending radially-outward from an exterior of the proximal end, and the flange includes a slot formed along the sidewall; and wherein, when the protrusion is misaligned with the slot, the flange restricts distal movement of the plunger rod through the channel to a first position, and when the protrusion is aligned with the slot, the flange restricts distal movement of the plunger rod through the channel to a second position when the protrusion abuts against the slot, the second position being positioned distal to the first position.

17. The drug delivery device of claim 14, wherein the flange includes a cavity, a pair of ribs that extend into the cavity, and a pair of moveable tabs that extend into the channel; and wherein the pair of ribs is configured to engage a top flange of the body and the pair of moveable tabs is configured to engage a shaft of the body, thereby coupling the flange to the body.

18. A drug delivery device, comprising:

a body;

a flange coupled to the body, the flange including a collar having a channel and a pair of grooves positioned along opposite sides of the channel; and a plunger rod coupled to the flange with the channel configured to accept the plunger rod, the plunger rod including a proximal portion and a pair of extensions extending distally from opposite sides of the proximal portion;

wherein the plunger rod is longitudinally moveable and rotatable relative to the flange, wherein the plunger rod is configured to:

move distally relative to the flange by an initial stroke to prime the drug delivery device, wherein the pair of extensions are radially misaligned with and positioned outside of the pair of grooves as the plunger rod moves the initial stroke;

rotate relative to the flange to prepare the drug delivery device for delivering a dose of medicament from the body, wherein the pair of extensions radially align with and contact the pair of grooves, thereby generating an audible feedback, as the plunger rod rotates relative to the flange; and move distally relative to the flange by a final stroke to deliver the dose of medicament from the drug delivery device, wherein the pair of extensions are maintained inside and in contact with the pair of grooves as the plunger rod moves the final stroke.

19. The drug delivery device of claim 18, wherein the plunger rod includes a pair of protrusions extending radially-outward from the proximal portion, and the flange includes a pair of slots formed on a proximal end of the collar; and wherein the flange restricts distal movement of the plunger rod through the channel to a first position when the pair of protrusions are misaligned with the pair of slots, and restricts distal movement of the plunger rod through the channel to a second position that is distal to the first position when the pair of protrusions are aligned with and received in the pair of slots.

20. The drug delivery device of claim 18, wherein the flange is configured to inhibit proximal movement of the plunger rod relative to the channel when the pair of grooves receive the pair of extensions.

21. The drug delivery device of claim 18, wherein the body includes a medicament that is configured to treat an eye disorder.

22. The drug delivery device of claim 21, wherein the medicament includes an anti-VEGF agent, and the eye disorder includes an angiogenic eye disorder.

23. The drug delivery device of claim 22, wherein the anti-VEGF agent is aflibercept.

24. The drug delivery device of claim 23, wherein, in response to the flange controlling movement of the plunger rod relative to the body, the drug delivery device is configured to administer a volume of less than 75 μl of aflibercept to an eye of a patient.

25. The drug delivery device of claim 24, wherein the injection of aflibercept has a concentration of at least 8 mg.

* * * * *